US012181474B2

(12) United States Patent
Schulte et al.

(10) Patent No.: US 12,181,474 B2
(45) Date of Patent: Dec. 31, 2024

(54) BIOMARKERS FOR THE DIAGNOSIS OF INVASIVE FUNGAL INFECTIONS

(71) Applicant: B.R.A.H.M.S GmbH, Hennigsdorf (DE)

(72) Inventors: Janin Schulte, Hennigsdorf (DE); Anne Incamps, Saint Victor la Coste (FR); Markus Alexander Weigand, Wettenberg (DE); Thorsten Brenner, Mörlenbach (DE)

(73) Assignee: B.R.A.H.M.S GmbH, Hennigsdorf (DE)

( * ) Notice: Subject to any disclaimer, the term of this patent is extended or adjusted under 35 U.S.C. 154(b) by 931 days.

(21) Appl. No.: 17/059,918

(22) PCT Filed: May 31, 2019

(86) PCT No.: PCT/EP2019/064198
§ 371 (c)(1),
(2) Date: Nov. 30, 2020

(87) PCT Pub. No.: WO2019/229241
PCT Pub. Date: Dec. 5, 2019

(65) Prior Publication Data

US 2021/0349089 A1 Nov. 11, 2021

(30) Foreign Application Priority Data

Jun. 1, 2018 (EP) .................................... 18175538

(51) Int. Cl.
*G01N 33/569* (2006.01)
*G01N 33/68* (2006.01)

(52) U.S. Cl.
CPC ... *G01N 33/56961* (2013.01); *G01N 33/6848* (2013.01); *G01N 2333/4704* (2013.01);
(Continued)

(58) Field of Classification Search
CPC ......... G01N 33/56961; G01N 33/6893; G01N 33/53; G01N 33/6648; G01N 2333/4704;
(Continued)

(56) References Cited

U.S. PATENT DOCUMENTS

2010/0035289 A1 2/2010 Bergmann et al.
2015/0011017 A1 1/2015 Bergmann et al.
(Continued)

FOREIGN PATENT DOCUMENTS

EP 3803396 B1 1/2023
WO WO-2005107791 A1 * 11/2005 ......... A61K 31/7048

OTHER PUBLICATIONS

Rodland et al., (BMC Infectious Diseases 144(2012) (Year: 2012).*
(Continued)

*Primary Examiner* — Jana A Hines
(74) *Attorney, Agent, or Firm* — Klarquist Sparkman, LLP; Susan Alpert Siegel; Gregory K. Scott

(57) ABSTRACT

The present invention relates to a method for the diagnosis, prognosis, risk assessment, risk stratification, monitoring, therapy guidance and/or therapy control of a fungal infection, in particular invasive fungal infections (IFI) and/or the ruling in or ruling out of an fungal infection and/or the differential diagnosis of a fungal colonization vs. an invasive fungal infection in a subject, wherein in particular the subject has an increased risk of getting or having a fungal infection and/or the subject is in a critical disease state, particularly has an existing infection and/or a state of sepsis, particularly a septic shock. The method of the invention comprises determining the level of at least one marker selected from the group of ICAM1, AHSG, CPN1, FABP1, HRG, PIGR, RAP1A, THBS1, VCL, ET-1. Furthermore, the
(Continued)

invention relates to a diagnostic assay and a kit for carrying out the method.

23 Claims, 56 Drawing Sheets

Specification includes a Sequence Listing.

(52) U.S. Cl.
CPC ................ *G01N 2333/4728* (2013.01); *G01N 2333/5754* (2013.01); *G01N 2333/585* (2013.01); *G01N 2333/70525* (2013.01); *G01N 2333/70535* (2013.01); *G01N 2333/948* (2013.01); *G01N 2800/26* (2013.01)

(58) Field of Classification Search
CPC ... G01N 2333/4728; G01N 2333/5754; G01N 2333/585; G01N 2333/70525; G01N 2333/70535; G01N 2333/948; G01N 2800/26
See application file for complete search history.

(56) References Cited

U.S. PATENT DOCUMENTS

| | | | | |
|---|---|---|---|---|
| 2016/0041153 A1* | 2/2016 | Brown | G01N 33/5308 | 436/501 |
| 2016/0194715 A1* | 7/2016 | Zaas | G01N 33/56961 | 506/9 |

OTHER PUBLICATIONS

Denning et al., (European Respiratory Journal 2016 47: 45-68); (Year: 2016).*

Miglietta et al., (Infez Med. Sep. 2015;23(3):230-7). (Year: 2015).*

Decker et al., "Immune-response patterns and next generation sequencing diagnostics for the detection of Mycoses in patients with septic shock-results of a combined clinical and experimental investigation," *International Journal of Molecular Sciences* 18(8): 1796, 32 pages (Aug. 18, 2017).

Elmorsy et al., "Sinus aspirates in chronic rhinosinusitis: fungal colonization of paranasal sinuses, evaluation of ICAM-1 and IL-8 and studying of immunological effect of long-term macrolide therapy," *Rhinology* 48(3): 312-317 (Aug. 31, 2010).

Gonzalez et al., "Expression of adhesion molecules in lungs of mice infected with *Paracoccidioides brasiliensis* conidia," *Microbes and Infection* 7(4): 666-673 (e-Pub Apr. 2, 2005).

International Search Report and Written Opinion from parent PCT Application No. PCT/EP2019/064198, 24 pages (mailed Aug. 27, 2019).

Kidane et al., "Computational approaches for discovery of common immunomodulators in fungal infections: towards broad-spectrum immunotherapeutic interventions," *BMC Microbiology* 13(1): 244, 15 pages (Oct. 7, 2013).

Röland et al., "Systemic biomarkers of inflammation and haemostasis in patients with chronic necrotizing pulmonary aspergillosis," *BMC Infectious Diseases* 12:144, 6 pages (Jun. 25, 2012).

Xing et al., "Thrombospondin-1 production regulates the inflammatory cytokine secretion in THP-1 Cells through NF-κB signaling pathway," *Inflammation* 40(5): 1606-1621 (Jun. 20, 2017).

Decker et al., "Immune-response patterns and next generation sequencing diagnostics for the detection of mycoses in patients with septic shock—Results of a combined clinical and experimental investigation," *International Journal of Molecular Sciences* 18(8):1796 (31 pages), Aug. 18, 2017.

Heylen et al., "Acute invasive pulmonary aspergillosis: clinical presentation and treatment," *Semin Respir Crit Care Med* 45:69-87 (e-Pub Jan. 11, 2024).

Johnson et al., "Use of antifungal combination therapy: agents, order, and timing," *Curr Fungal Infect Rep*. 4(2): 87-95 (May 1, 2010).

Kousha et al., "Pulmonary aspergillosis: a clinical review," *Eur. Respir. Rev*. 20(121): 156-174 (2011).

Yokomura et al., "Role of Intercellular Adhesion Molecule 1 in Acute Lung Injury Induced by Candidemia," *Experimental Lung Research* 27(5):417-431, Jul. 2001.

* cited by examiner

[Figure 1]
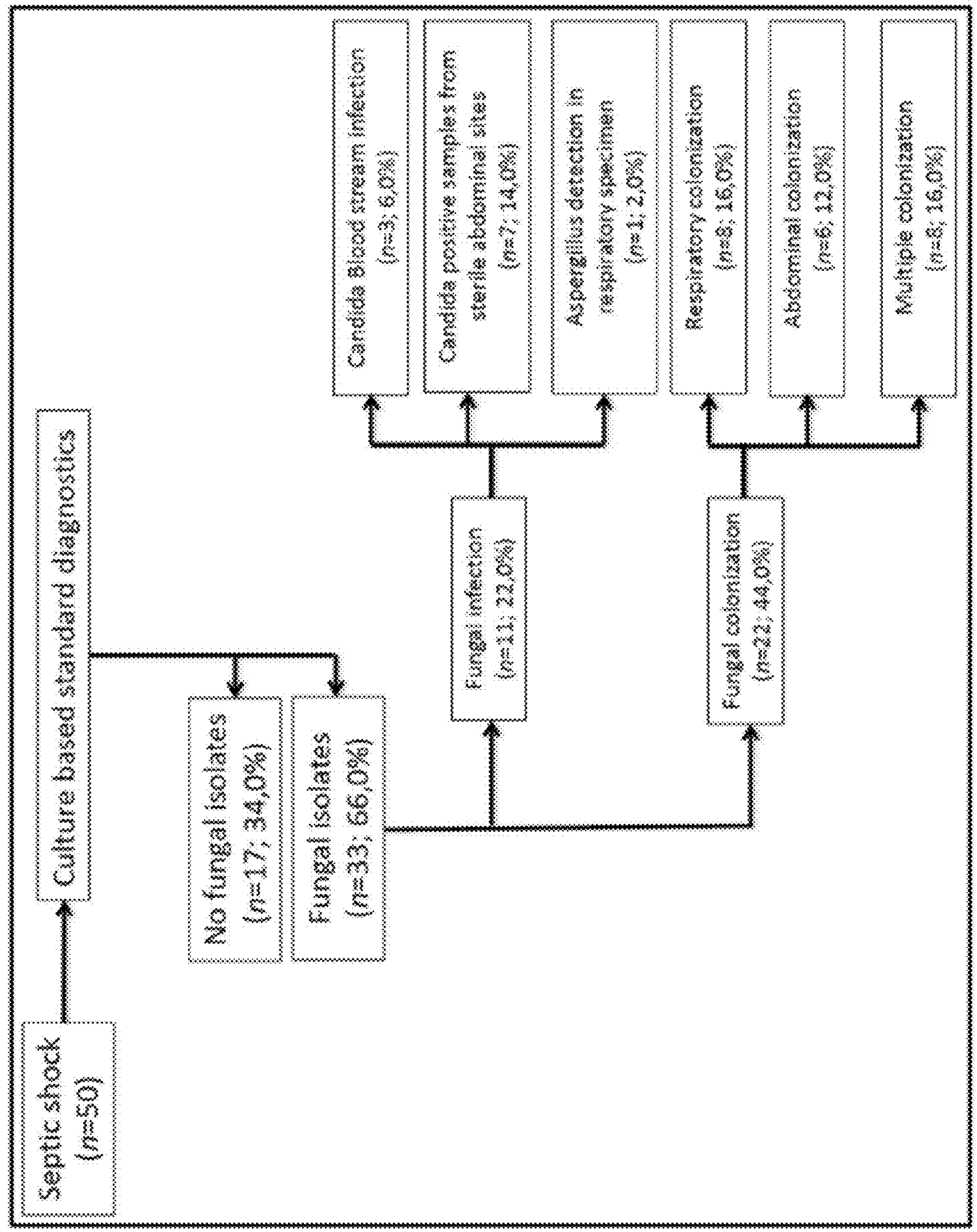

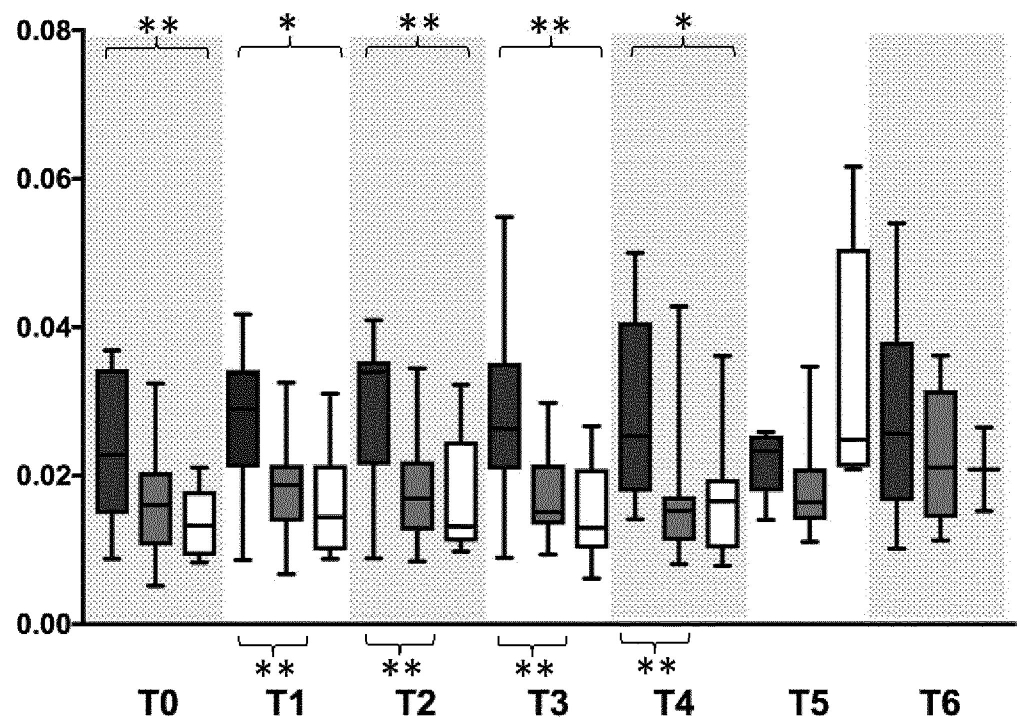
[Figure 2.1A]
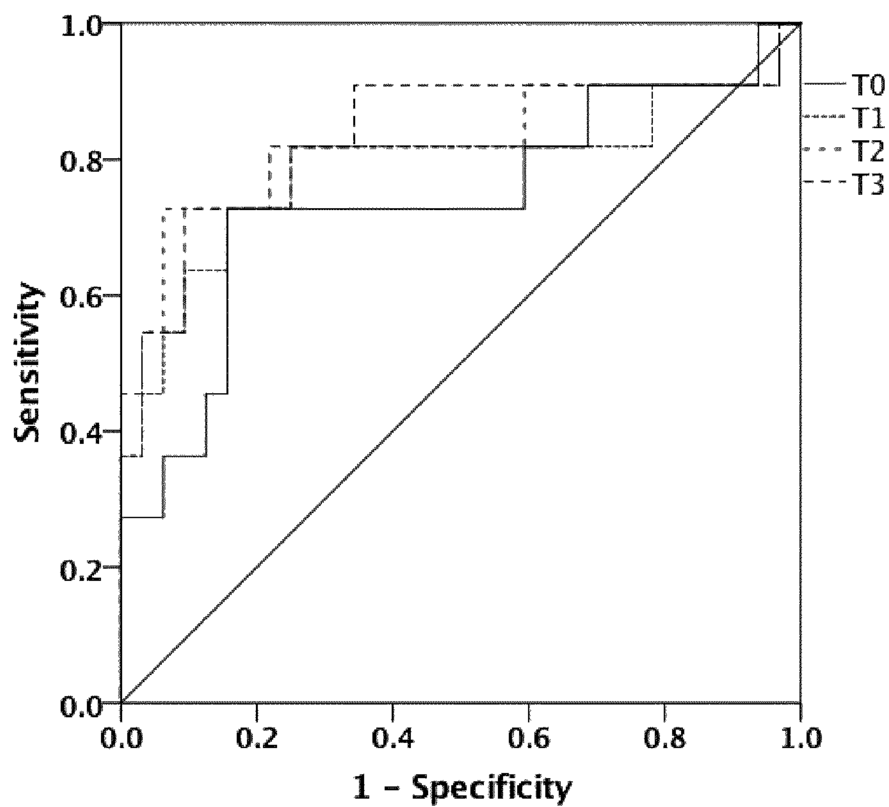
[Figure 2.1B]

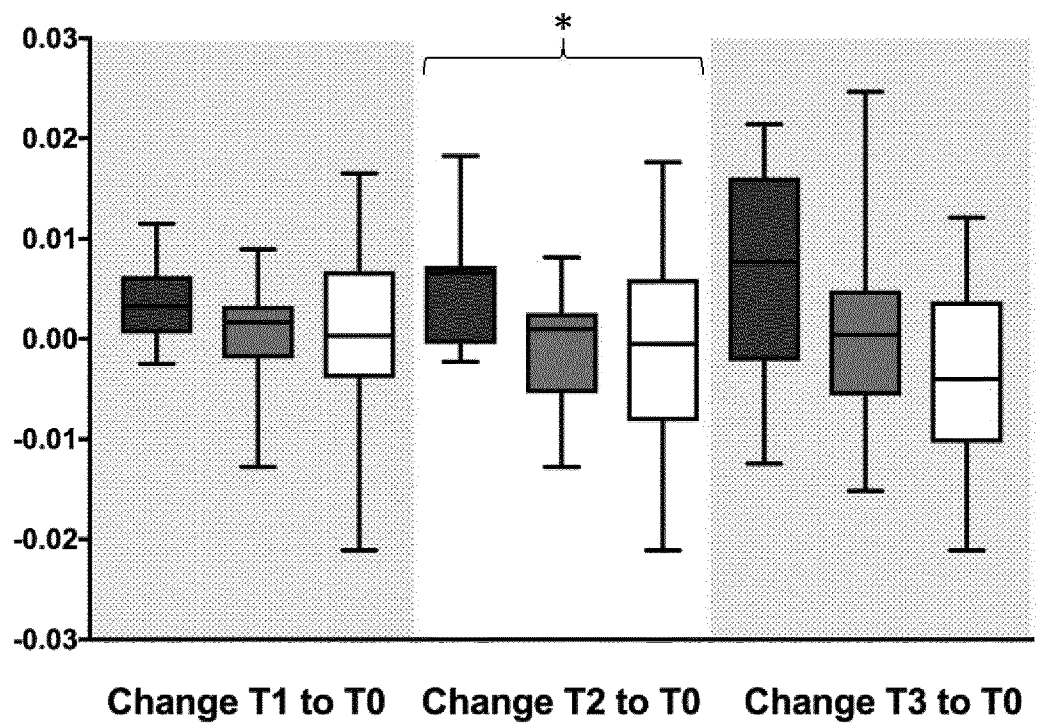
[Figure 2.1C]
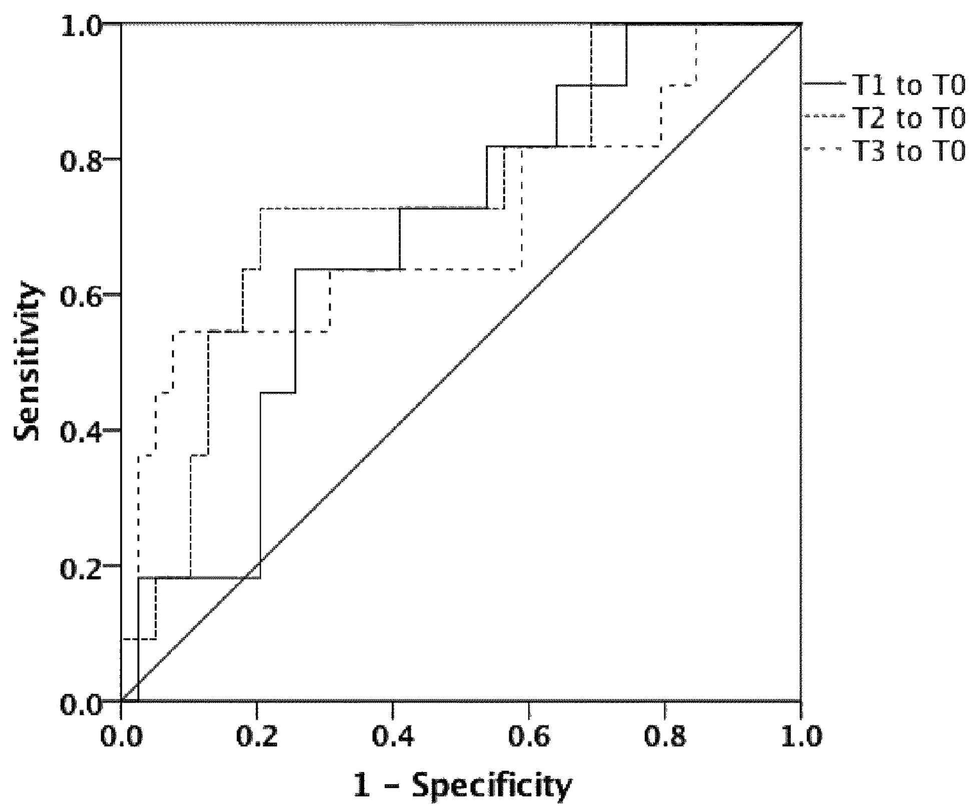
[Figure 2.2]

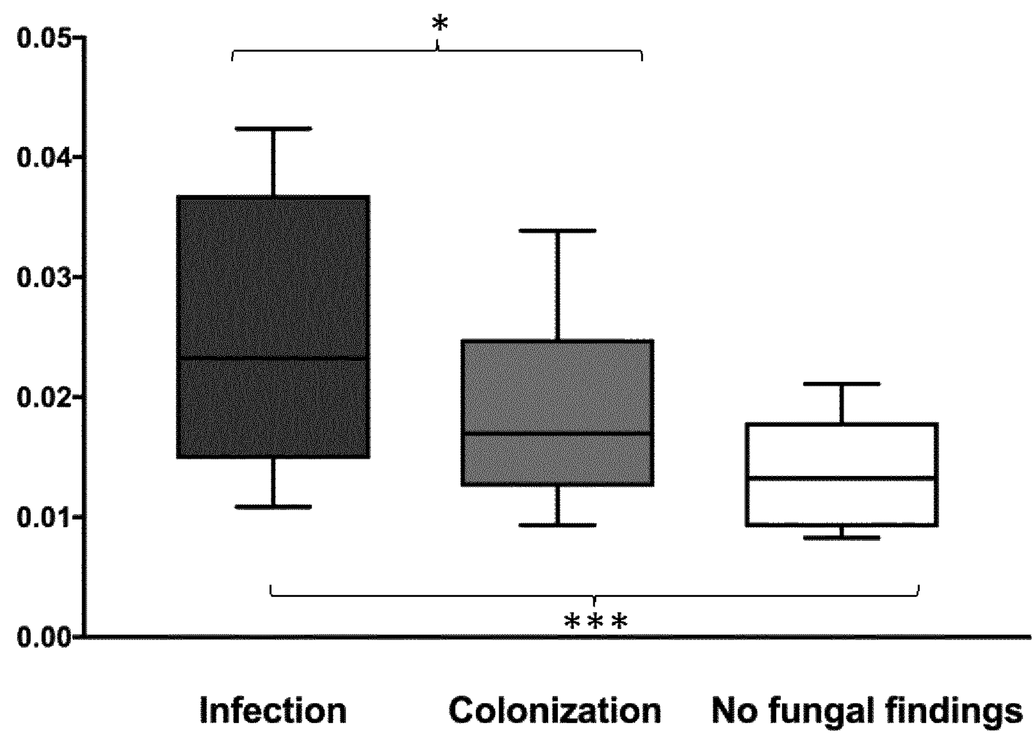
[Figure 2.3]
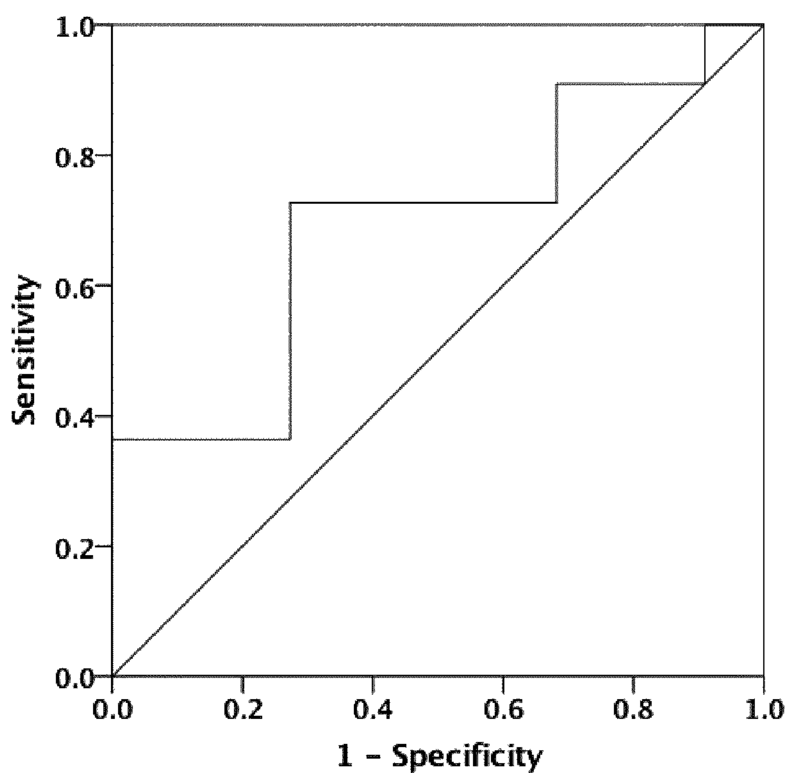
[Figure 2.4]

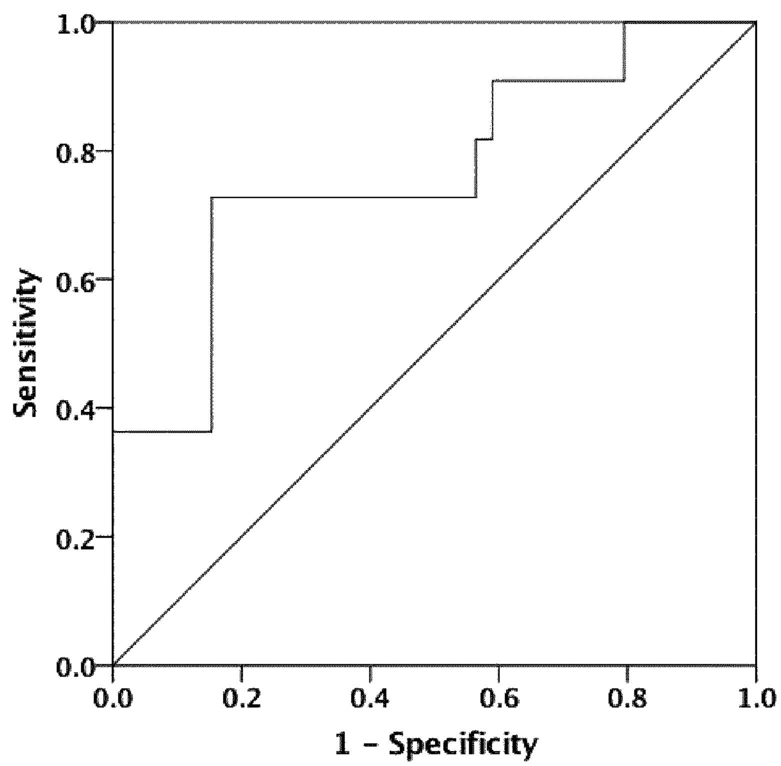
[Figure 2.5]
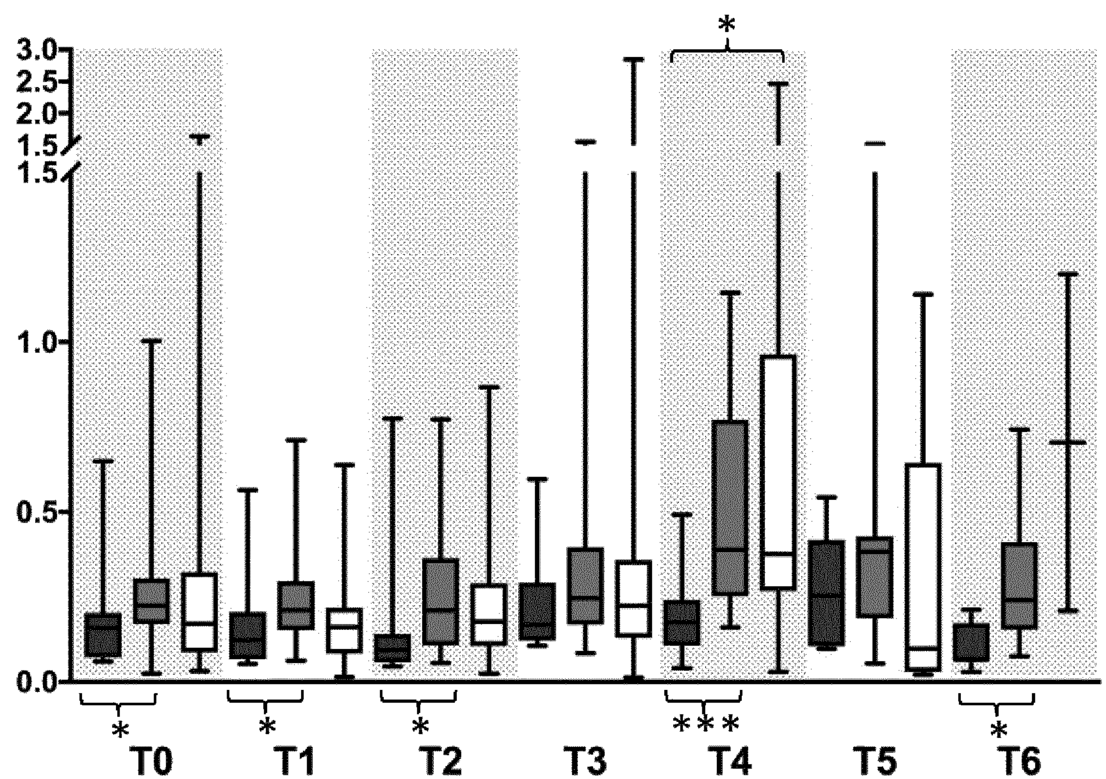
[Figure 3A]

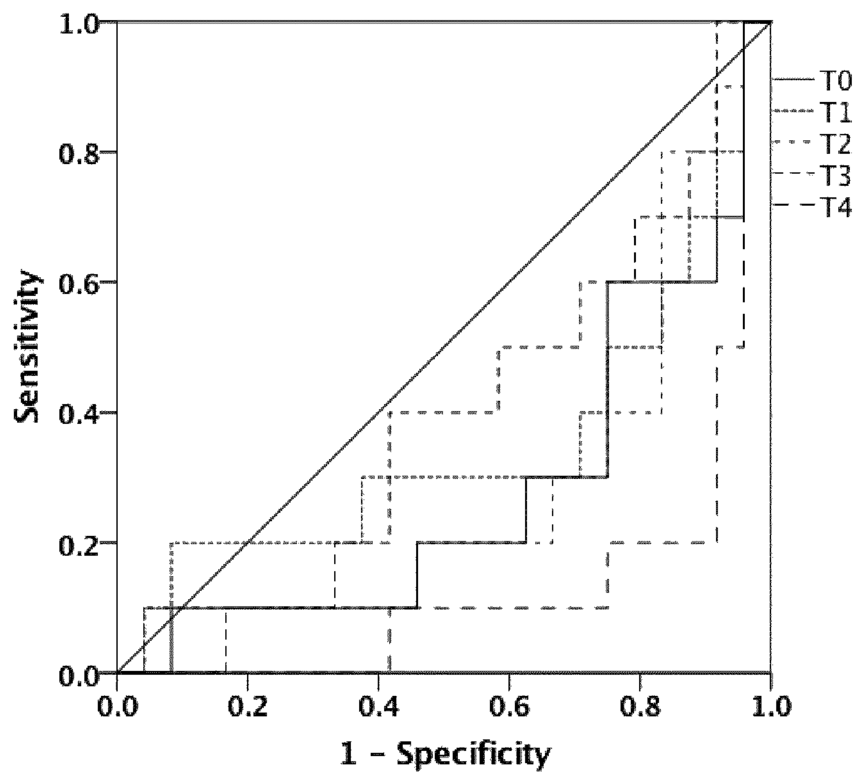
[Figure 3B]
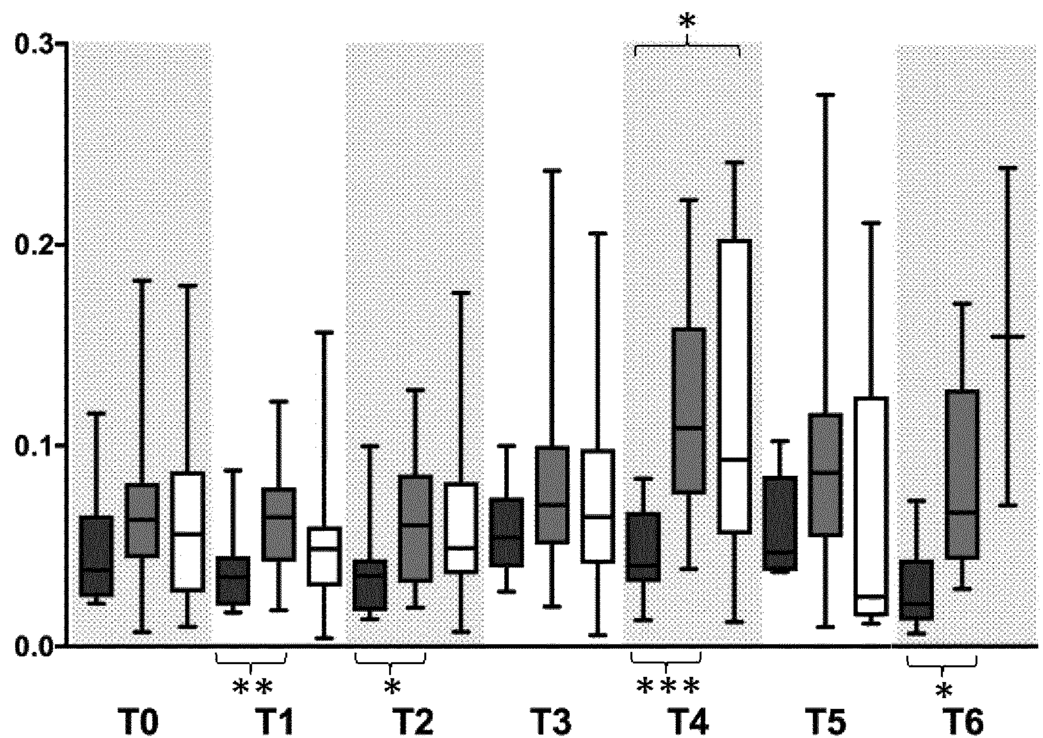
[Figure 4.1A]

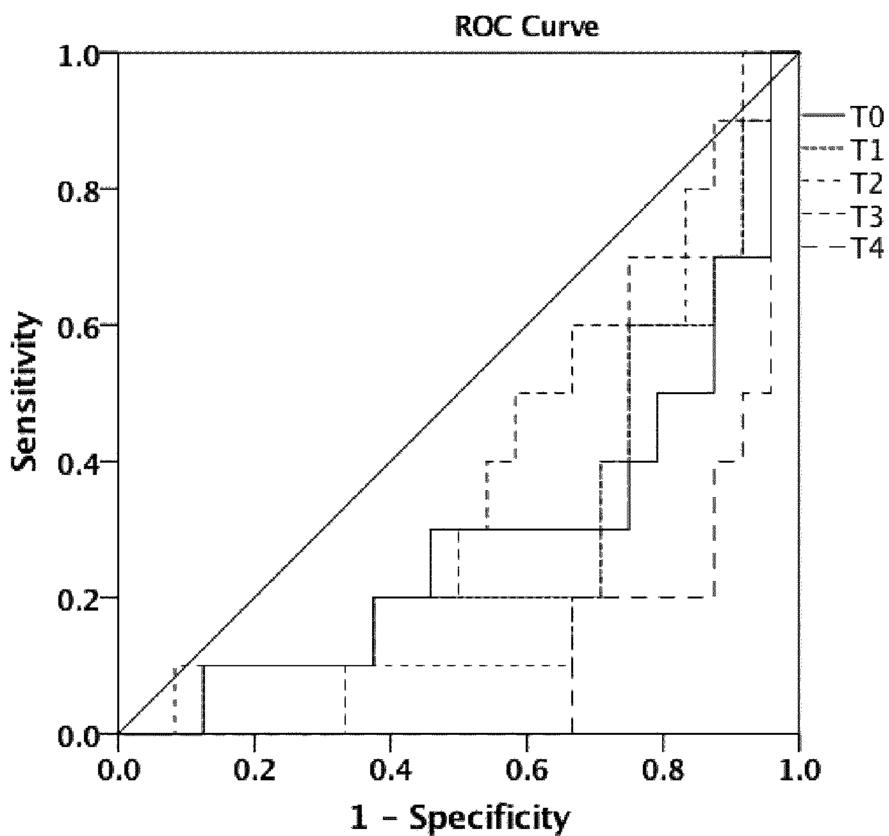
[Figure 4.1B]
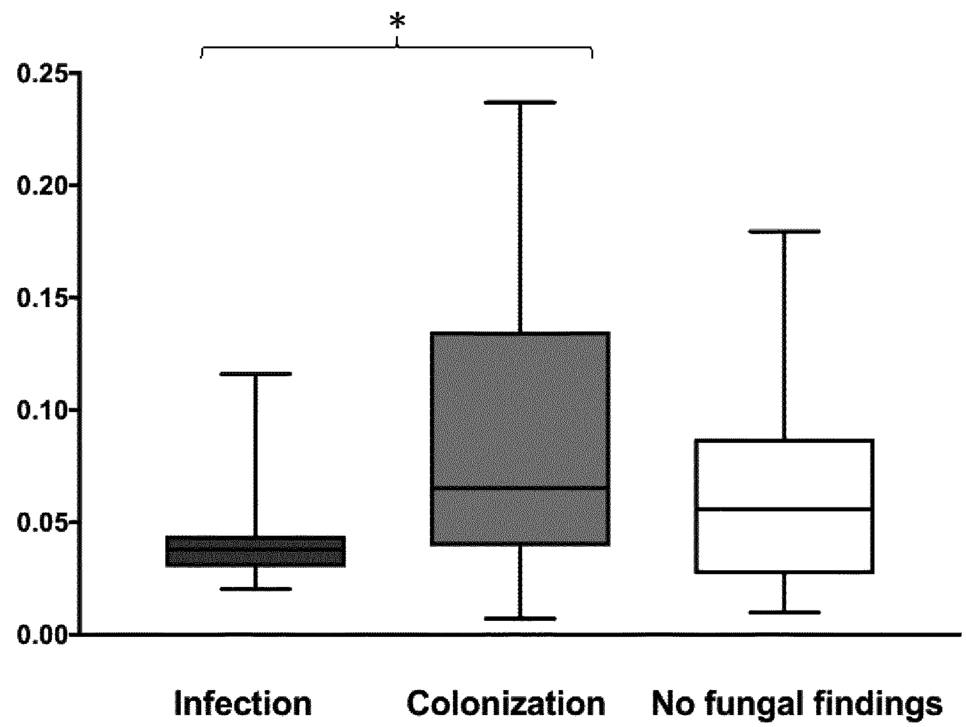
[Figure 4.2]

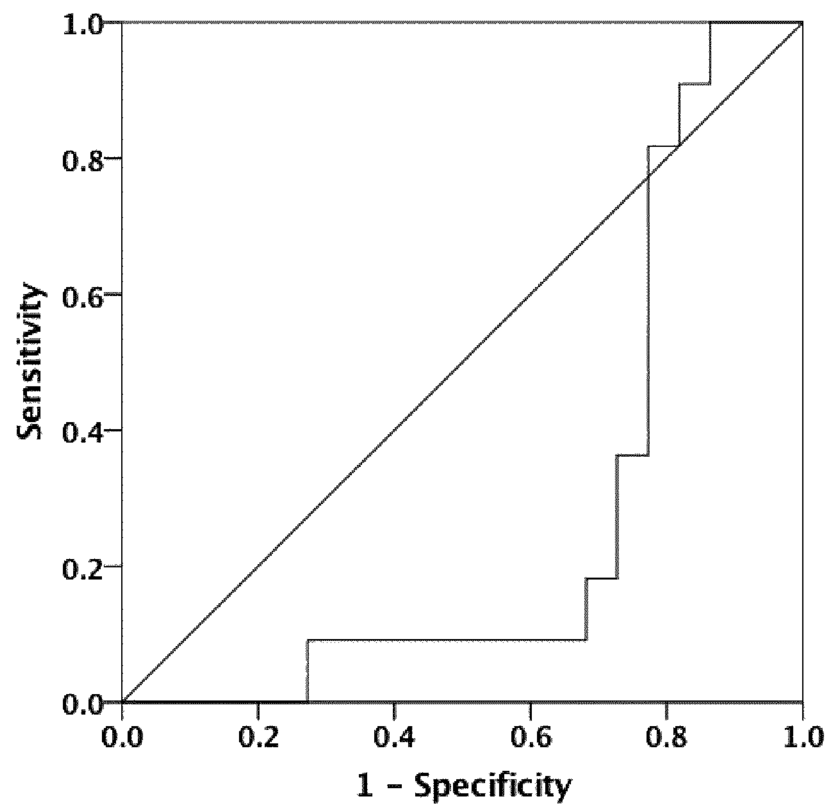
[Figure 4.3]
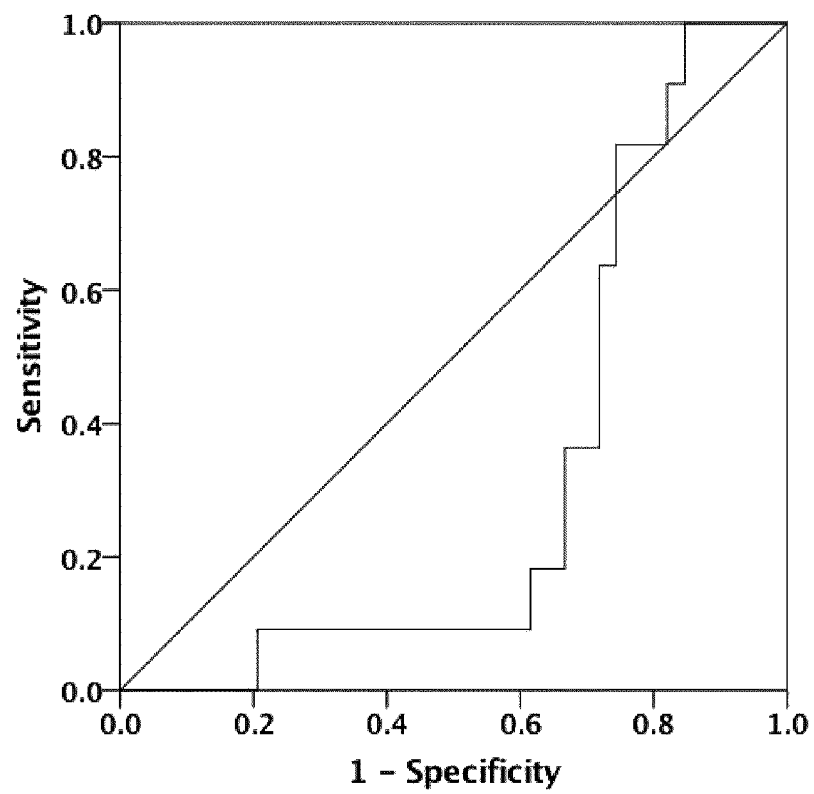
[Figure 4.4]

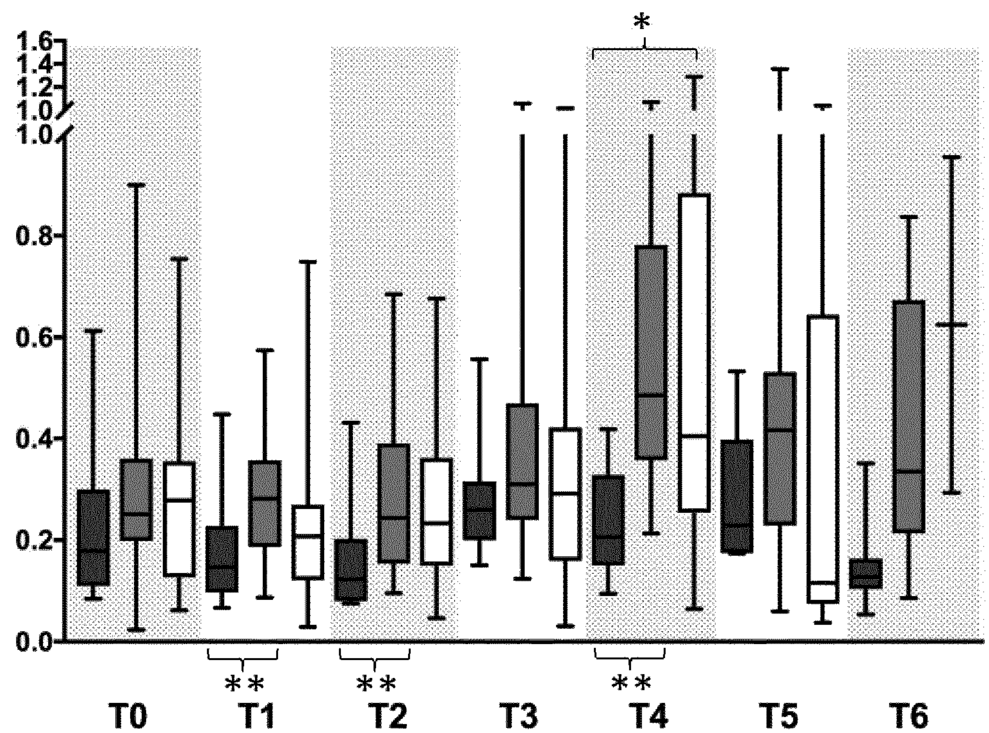
[Figure 5.1A]
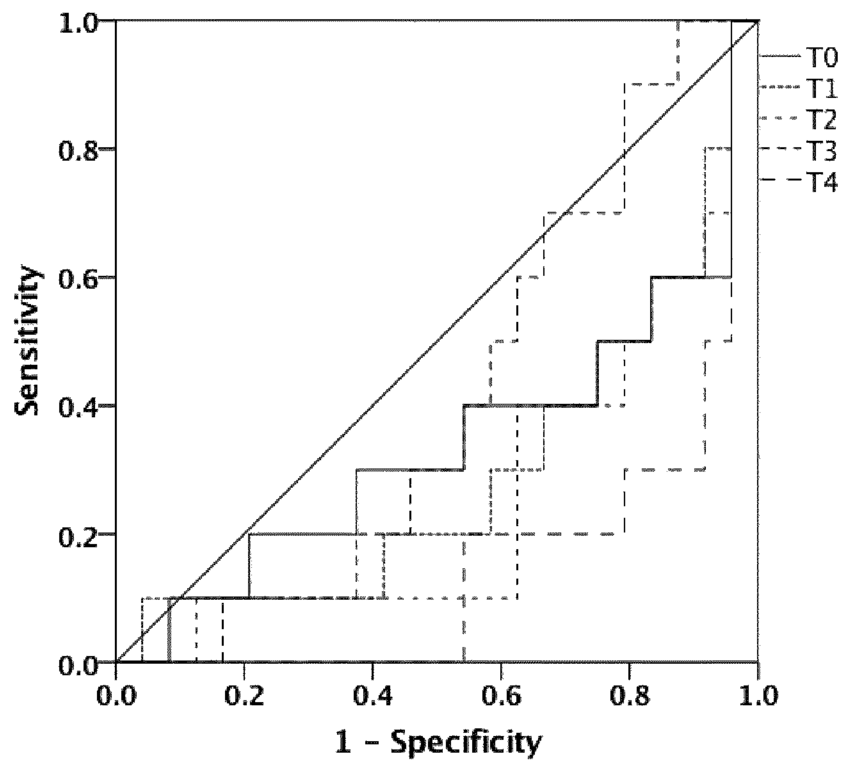
[Figure 5.1B]

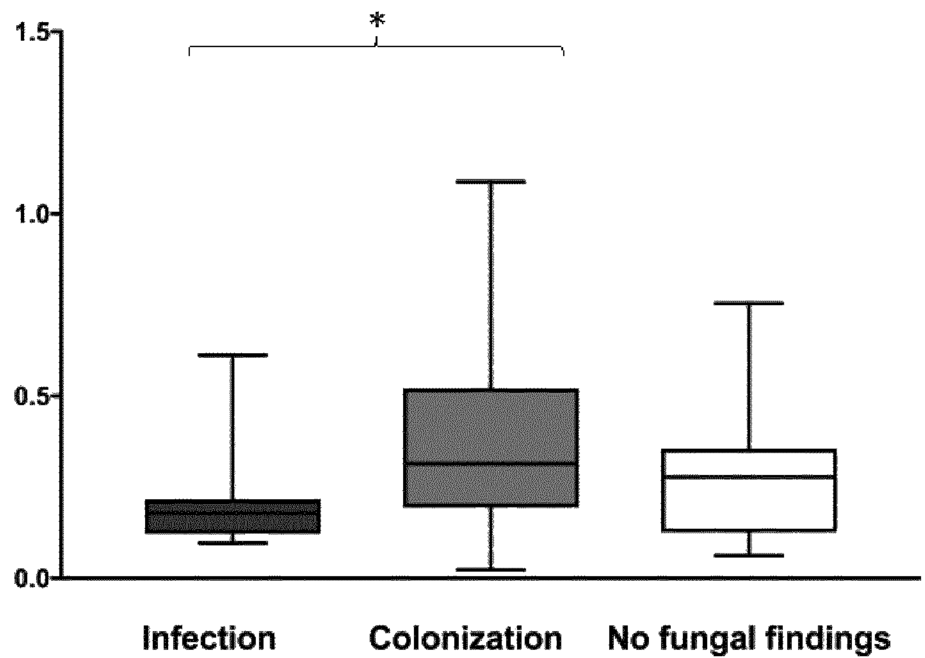
[Figure 5.2]
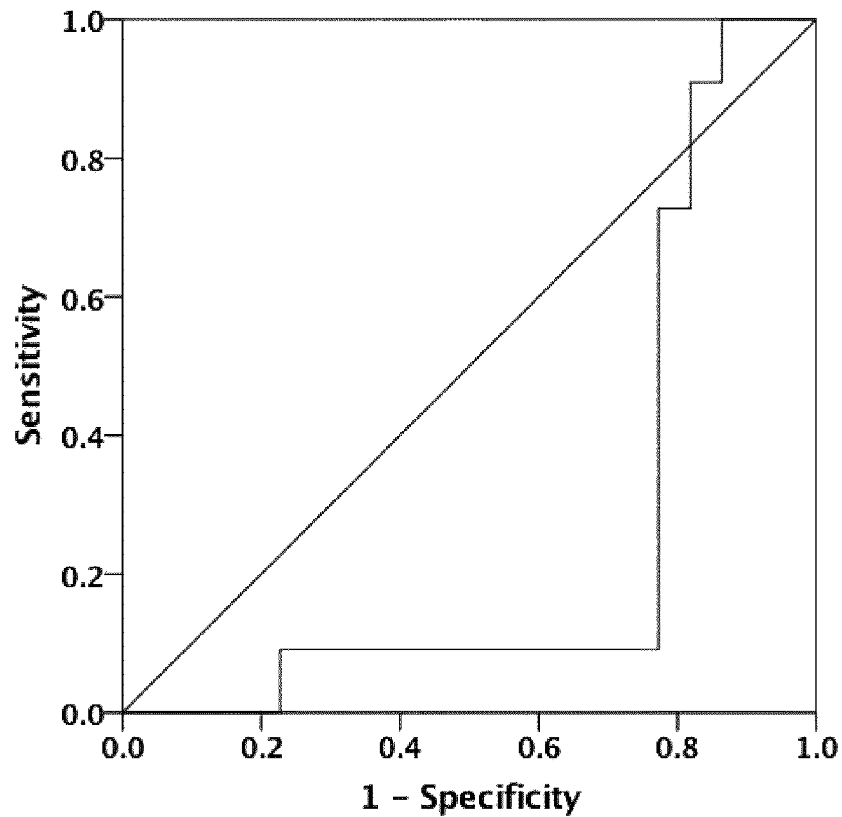
[Figure 5.3]

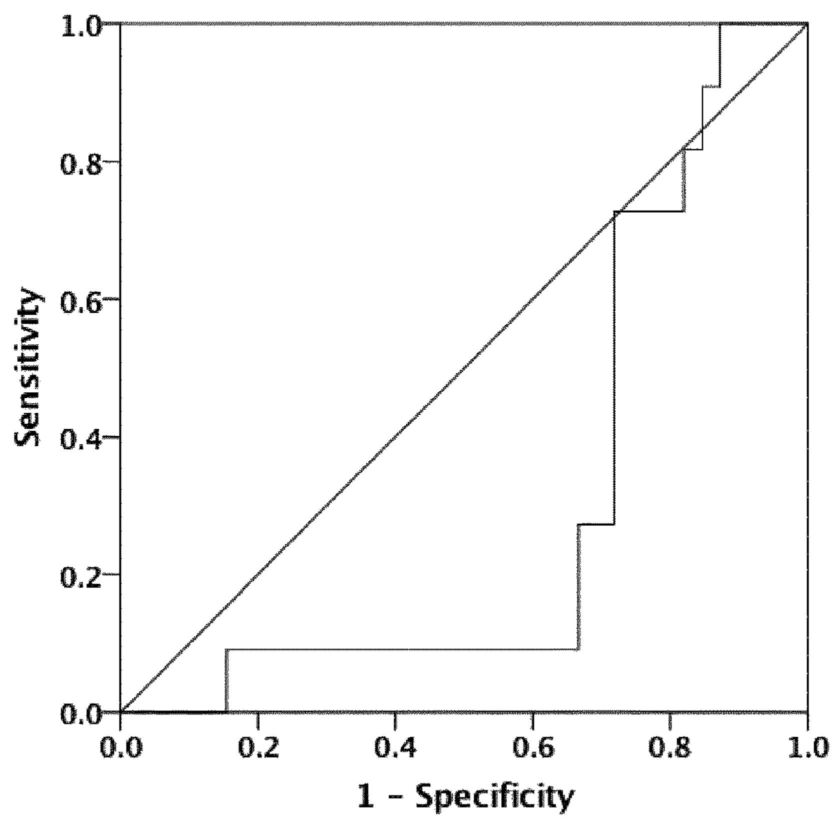
[Figure 5.4]
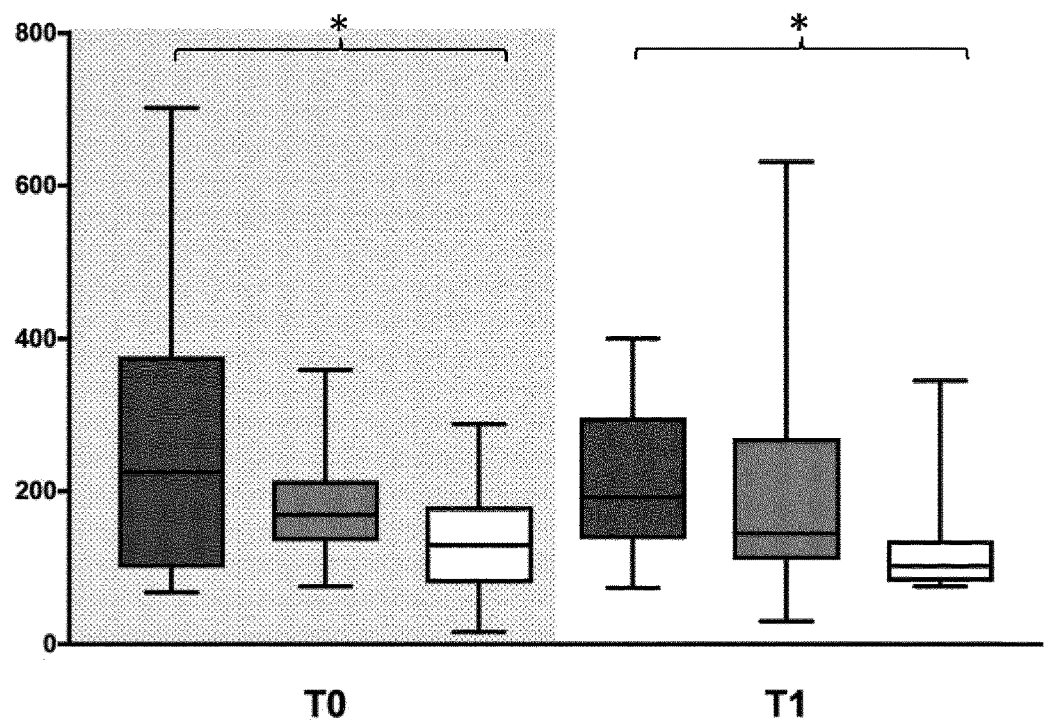
[Figure 6A]

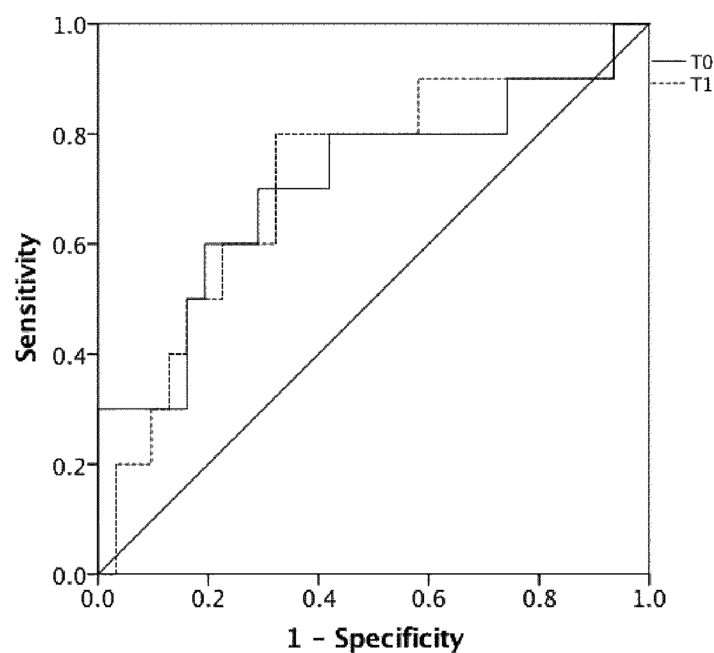
[Figure 6B]

[Figure 7A]
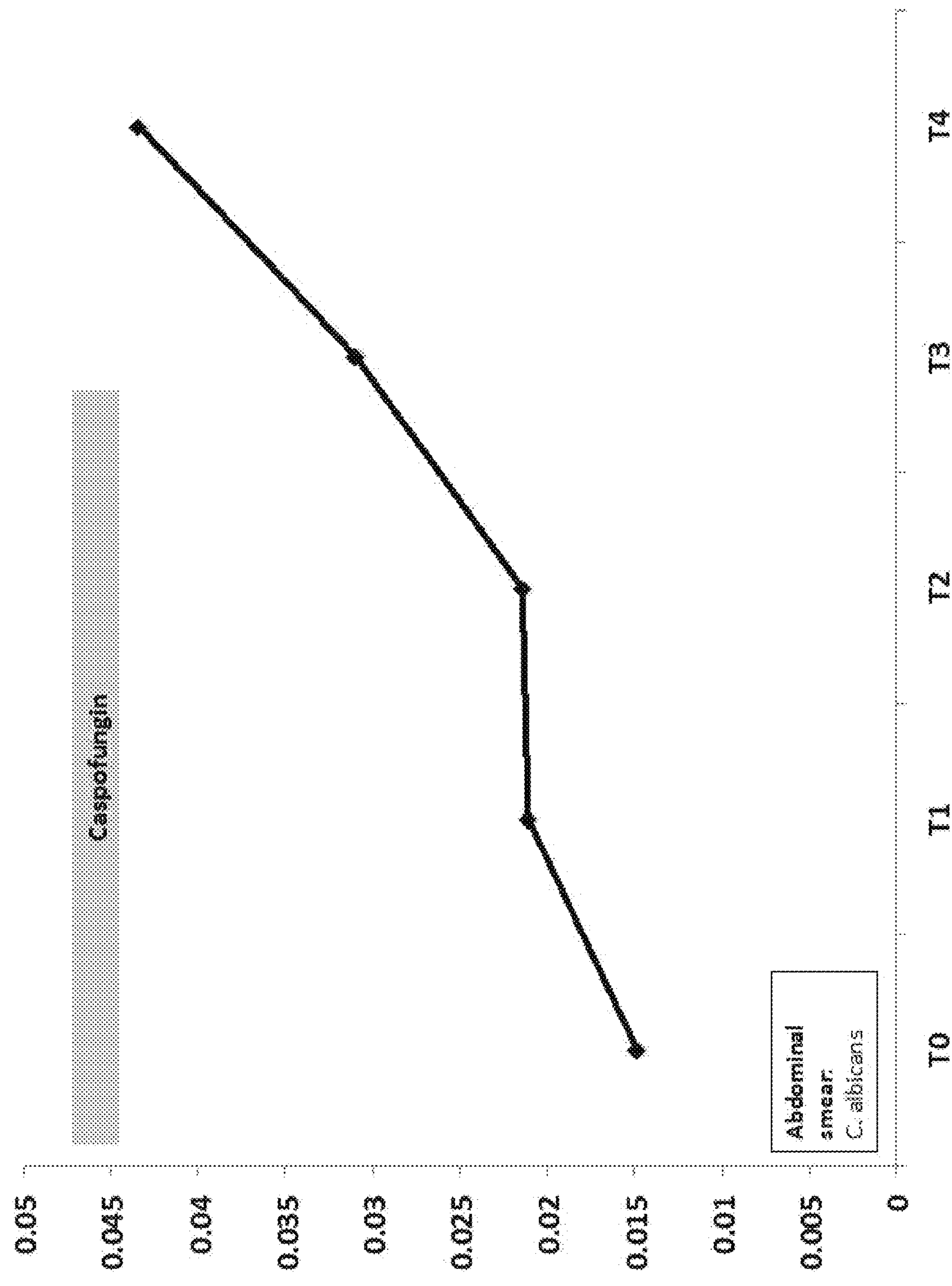

[Figure 7B]
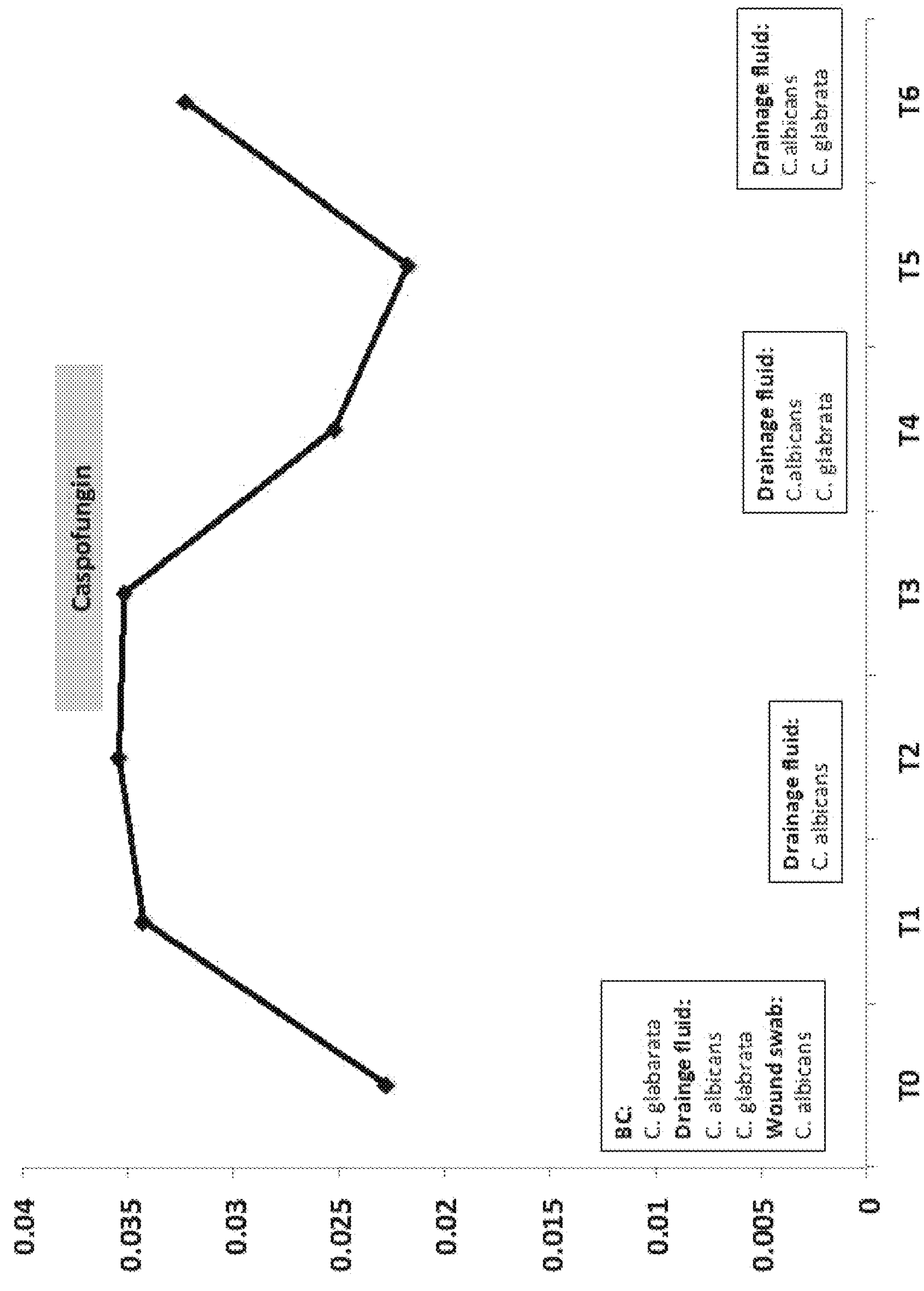

[Figure 7C]
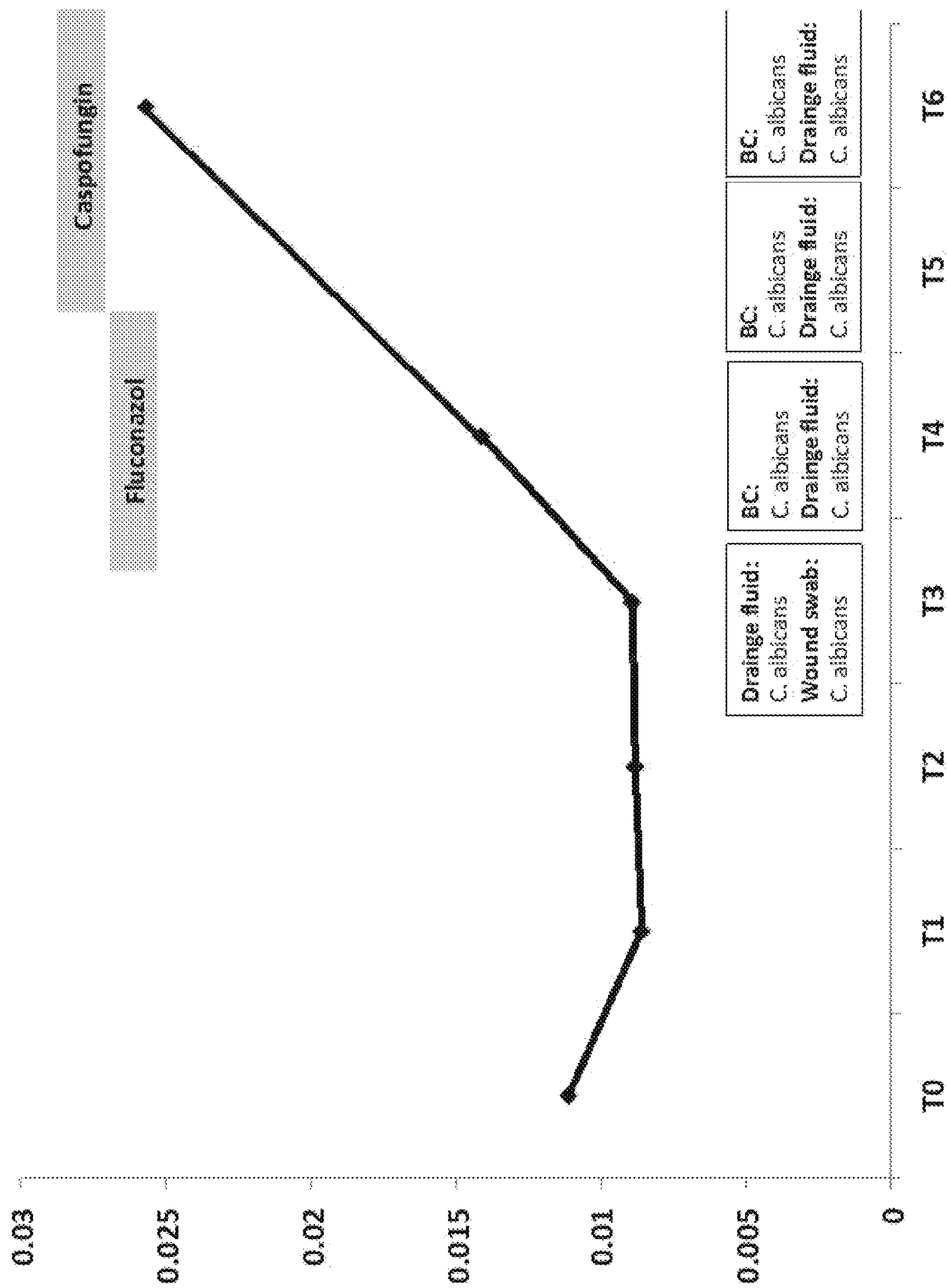

[Figure 7D]
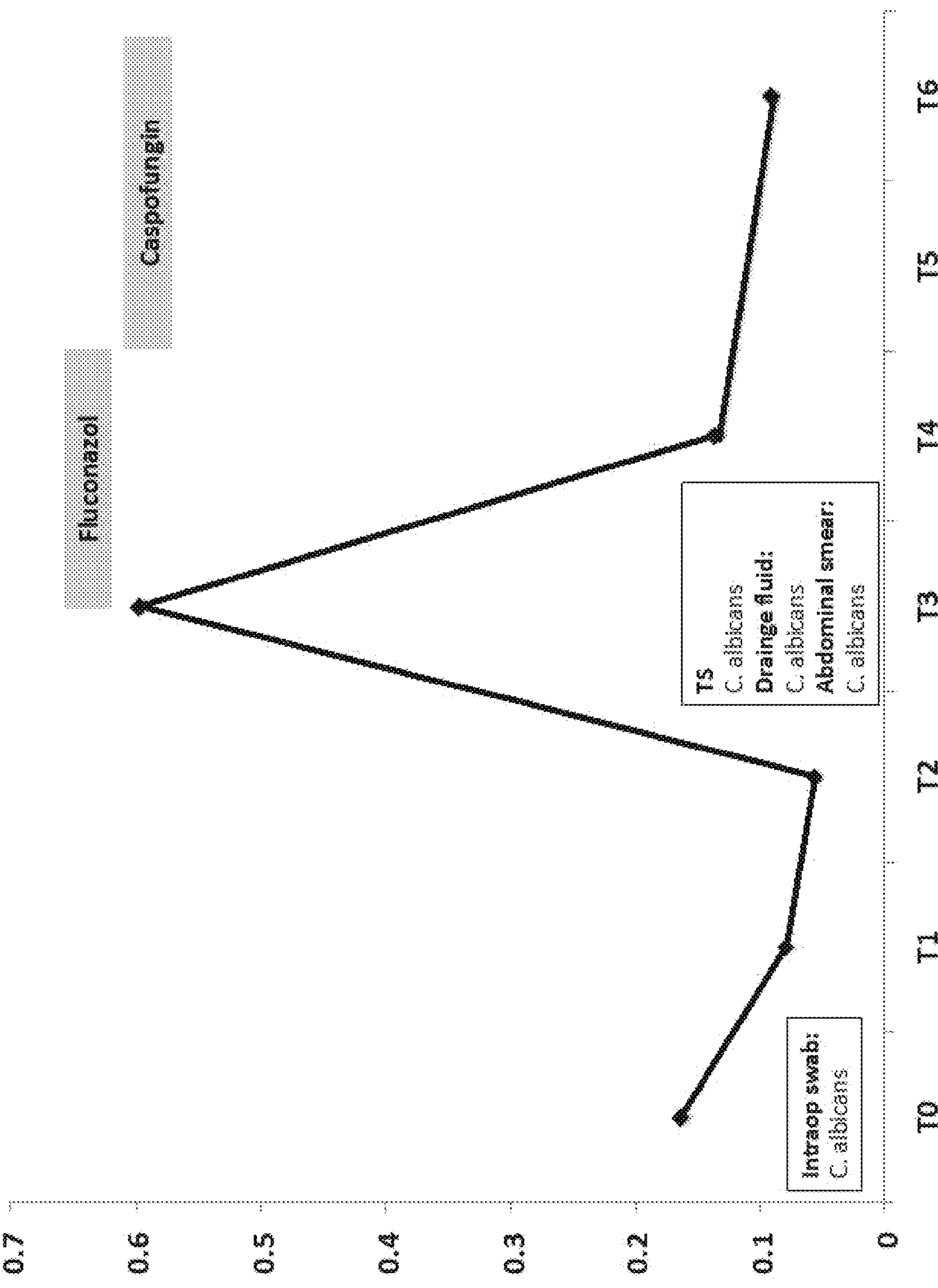

[Figure 7E]
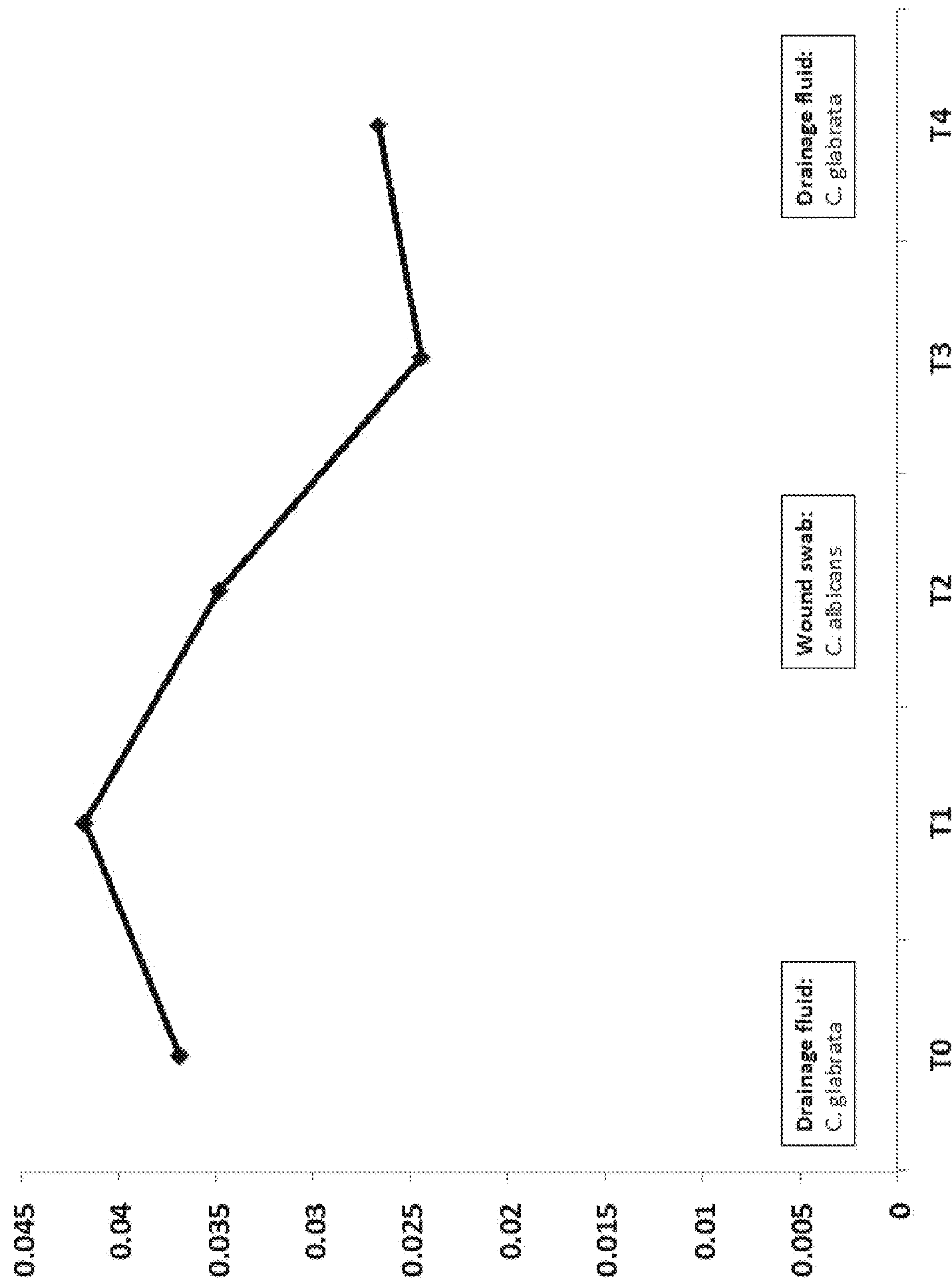

[Figure 7F]
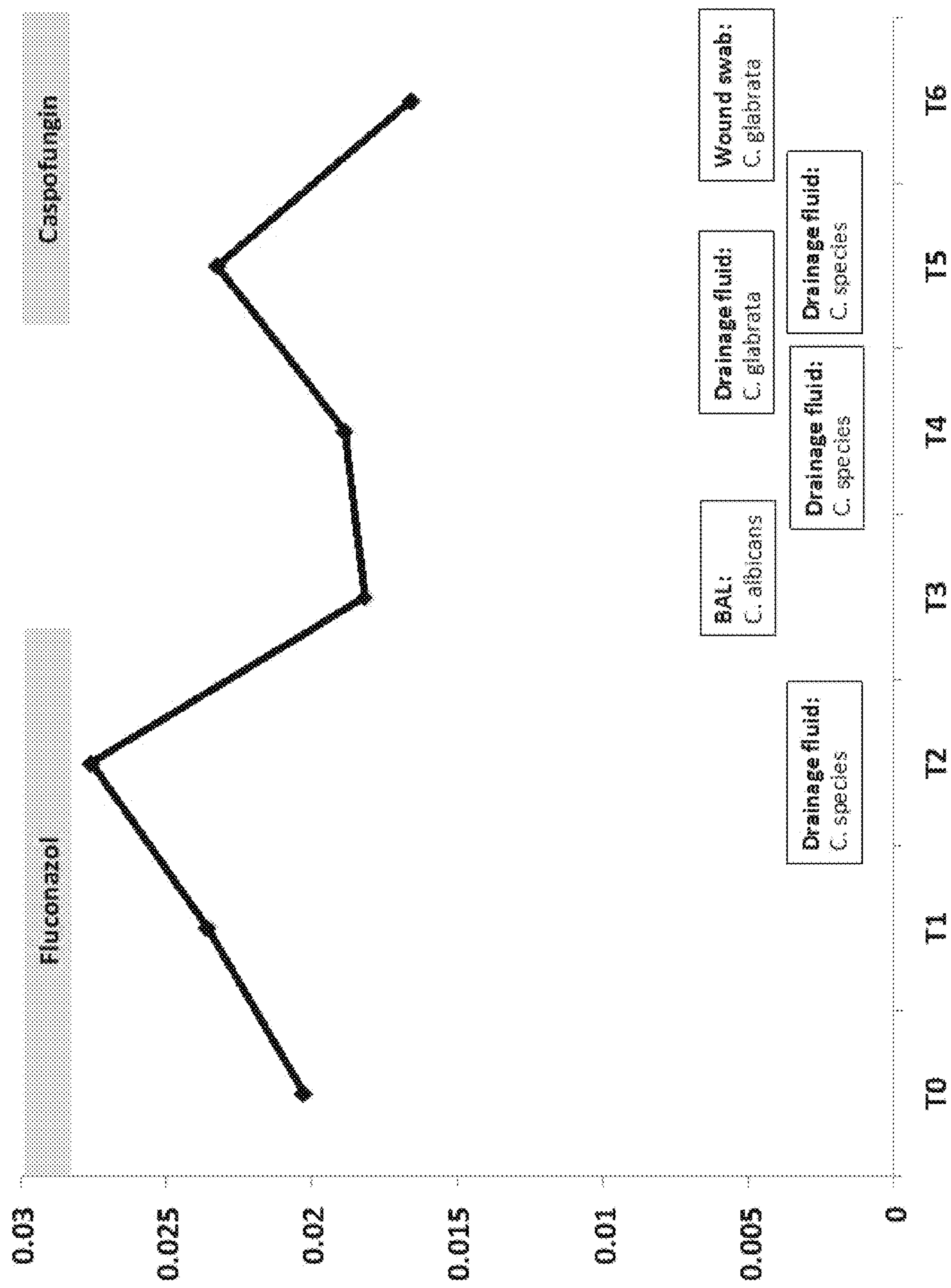

[Figure 7G]
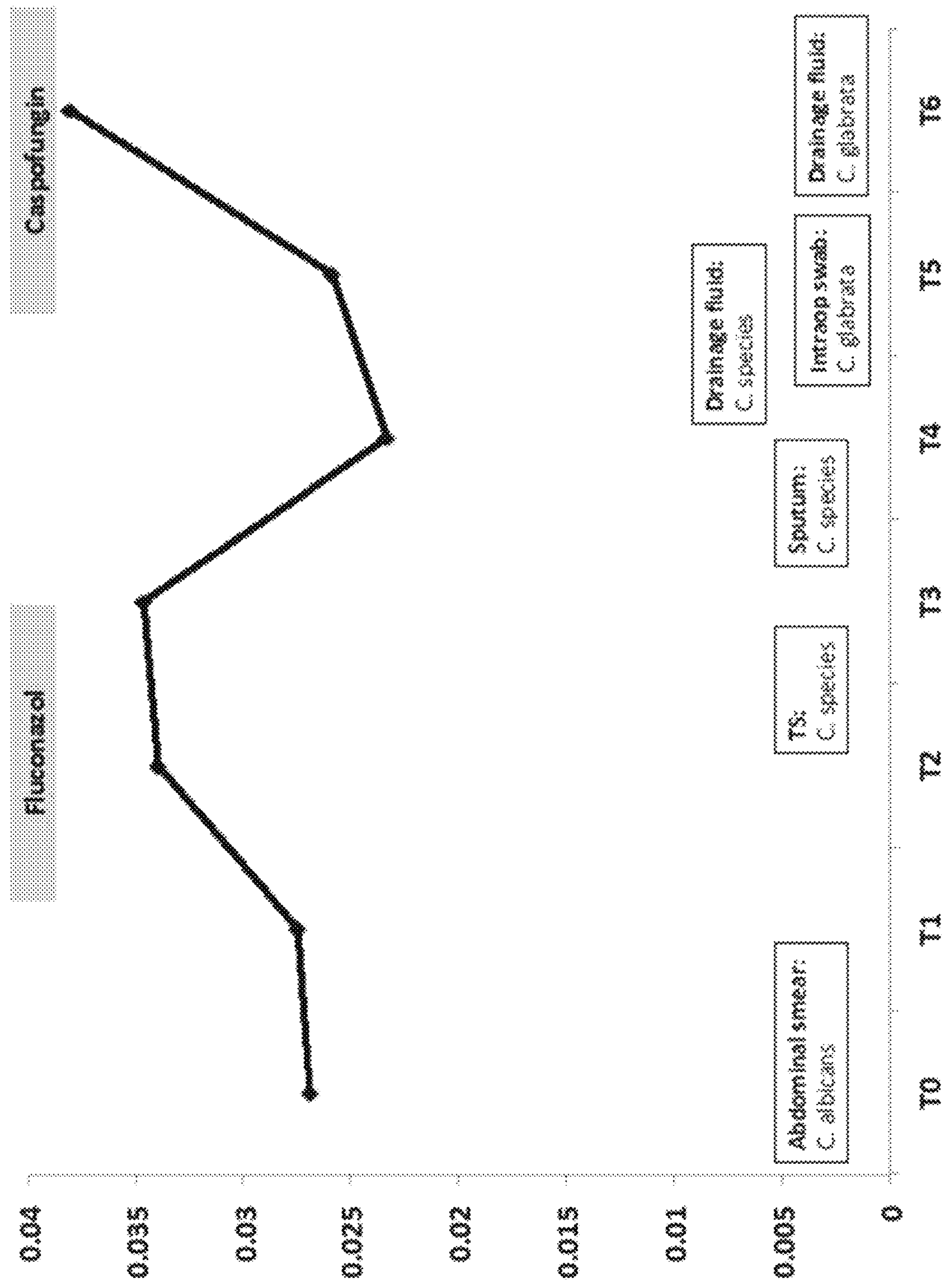

[Figure 7H]
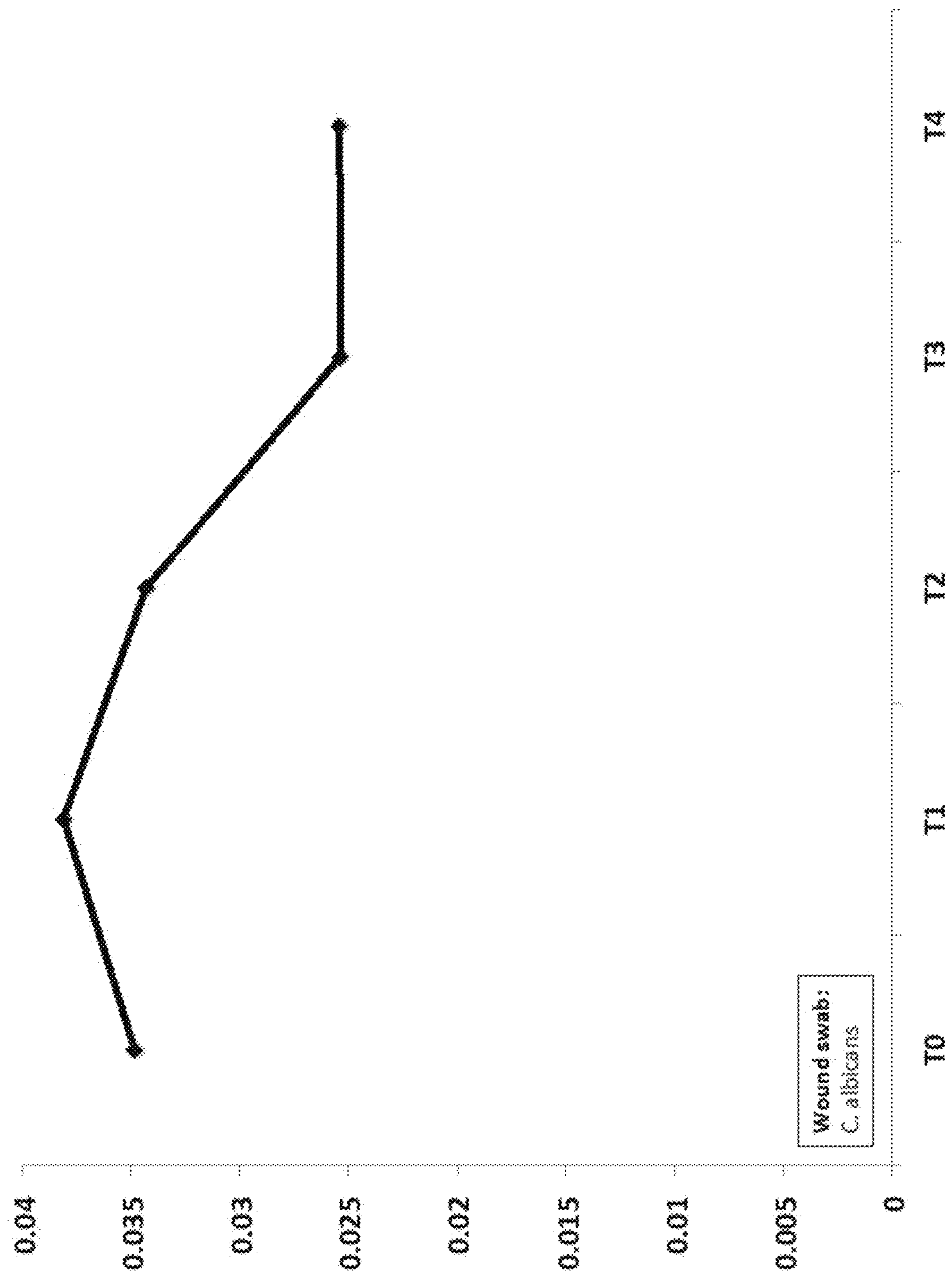

[Figure 7I]
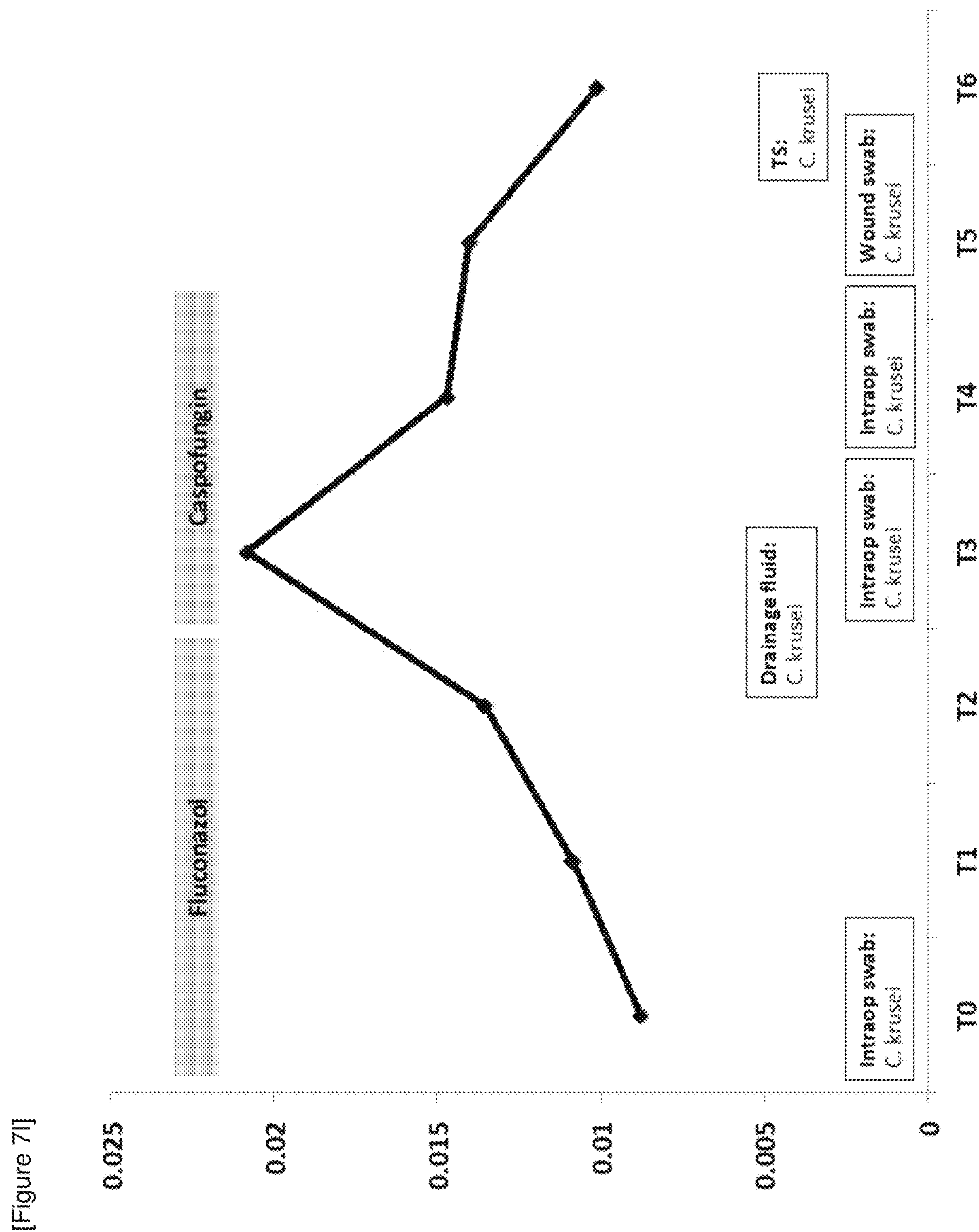

[Figure 7J]
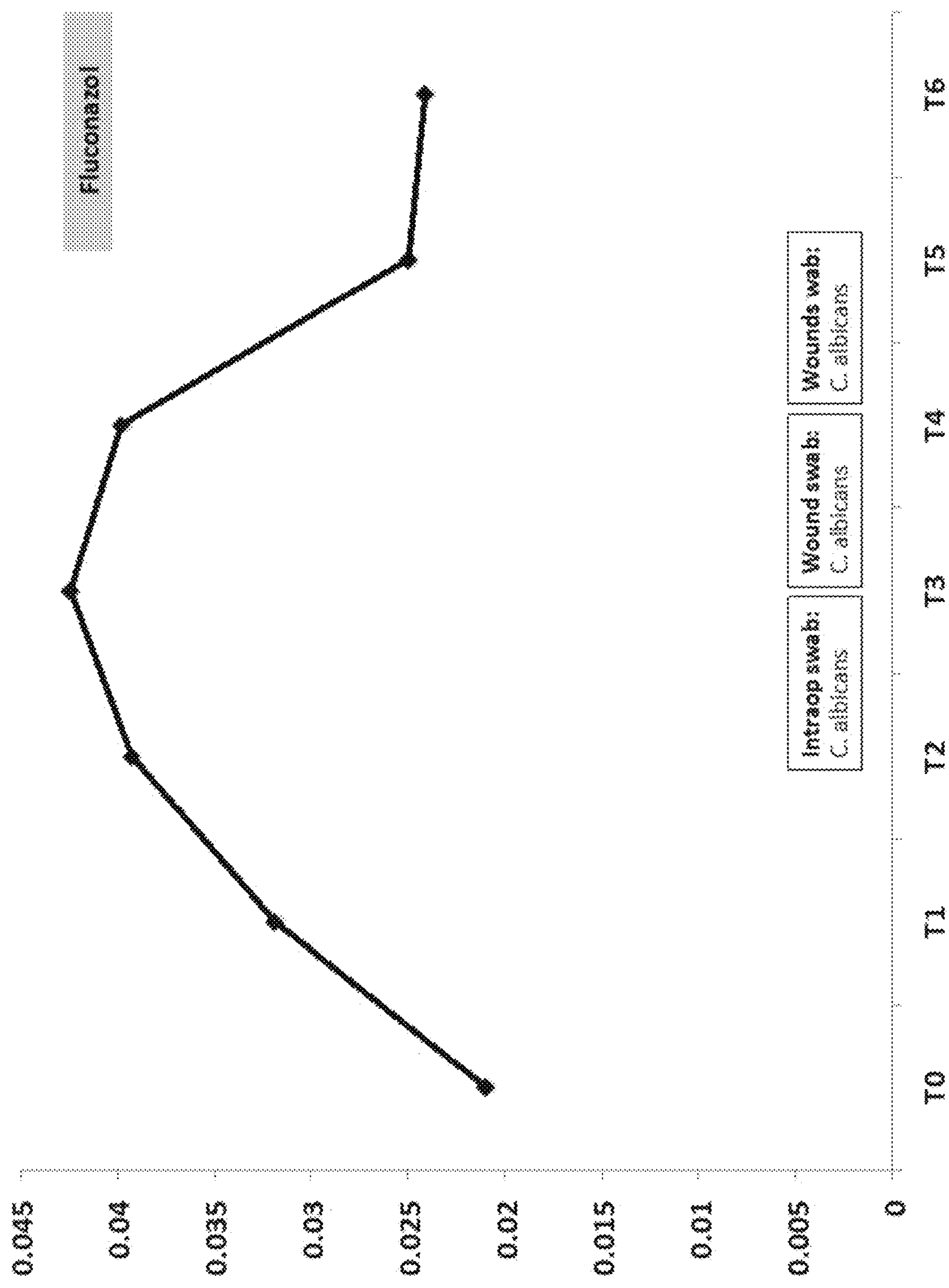

[Figure 7K]
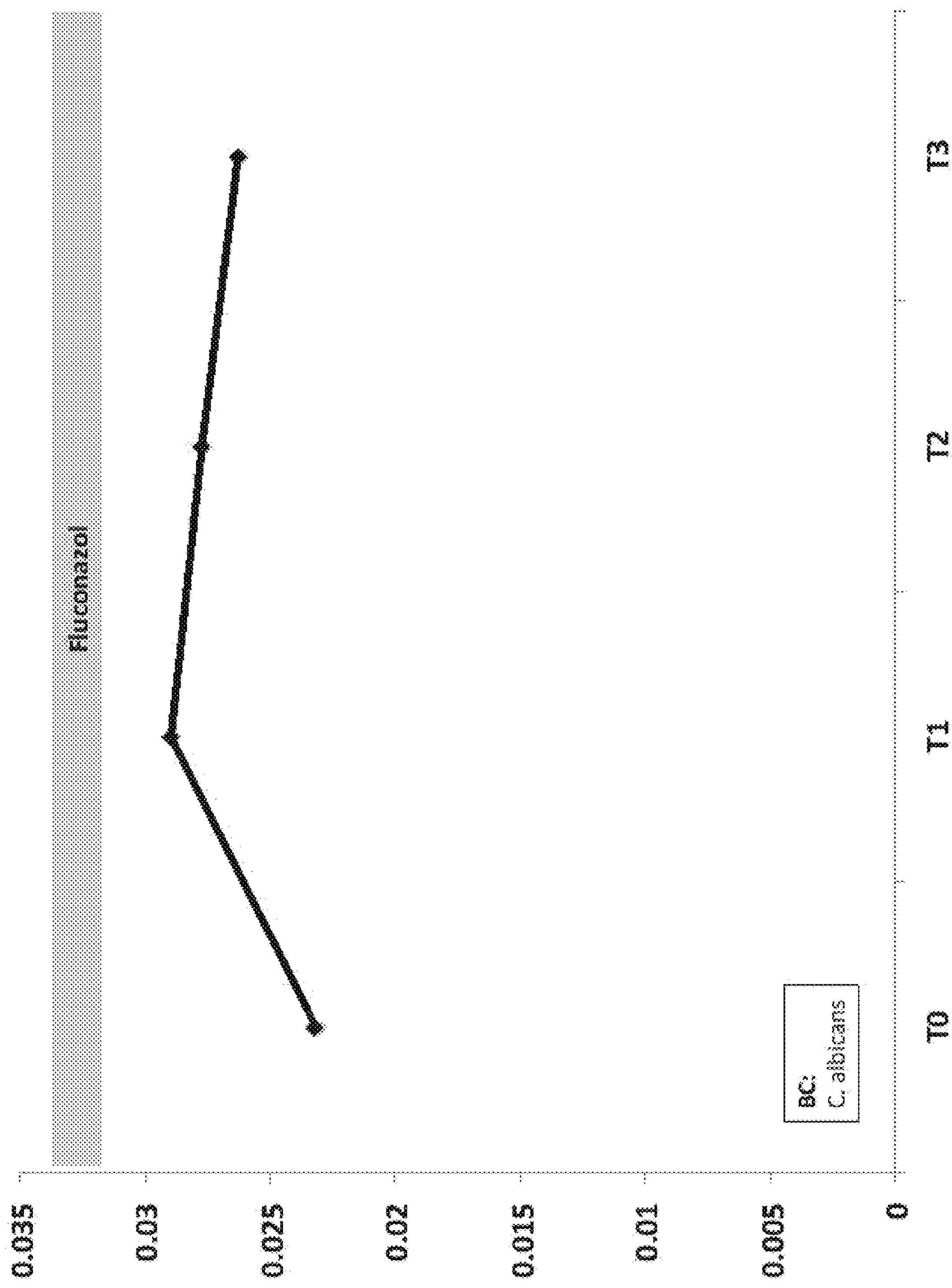

[Figure 8A]
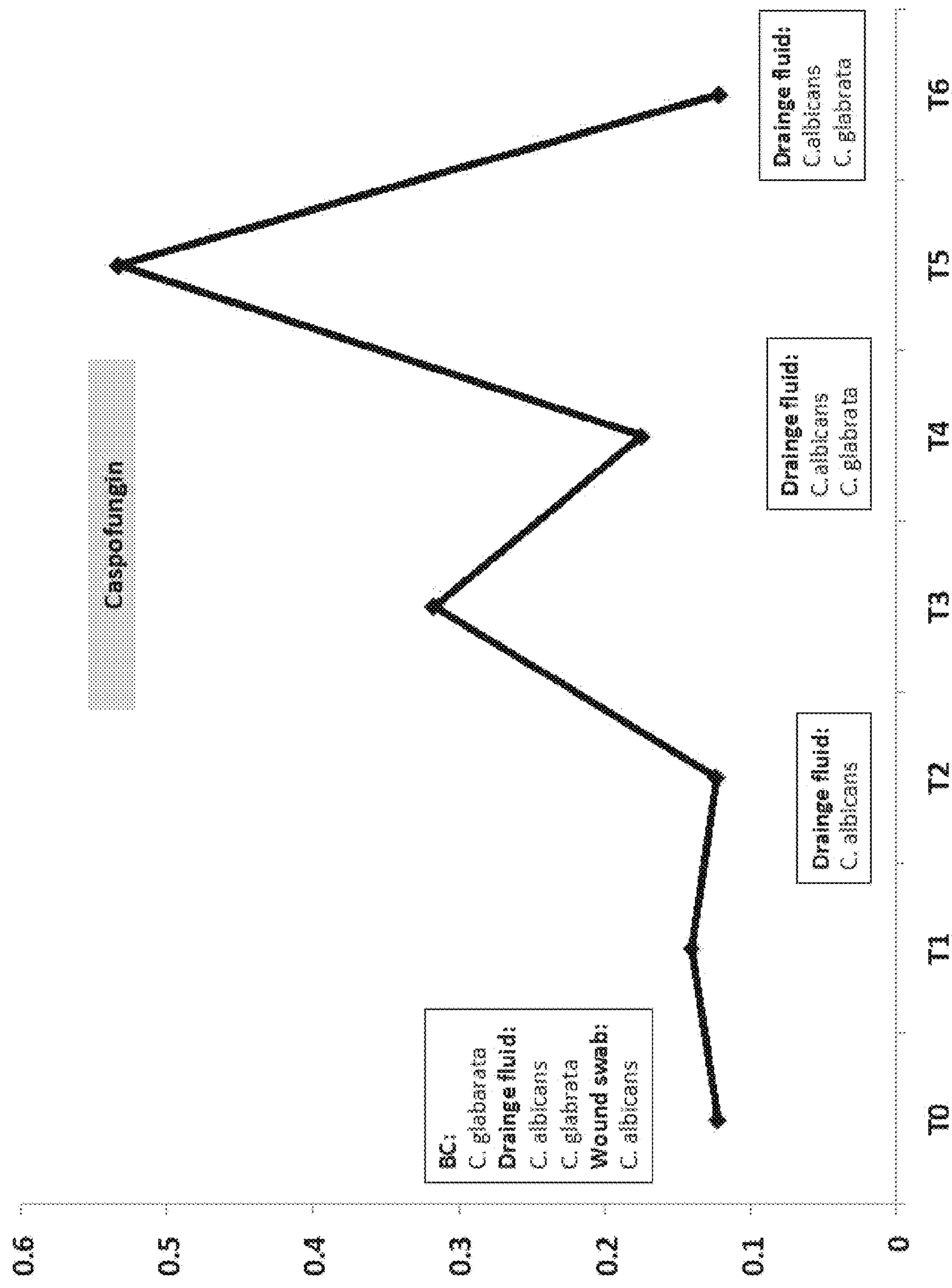

[Figure 8B]
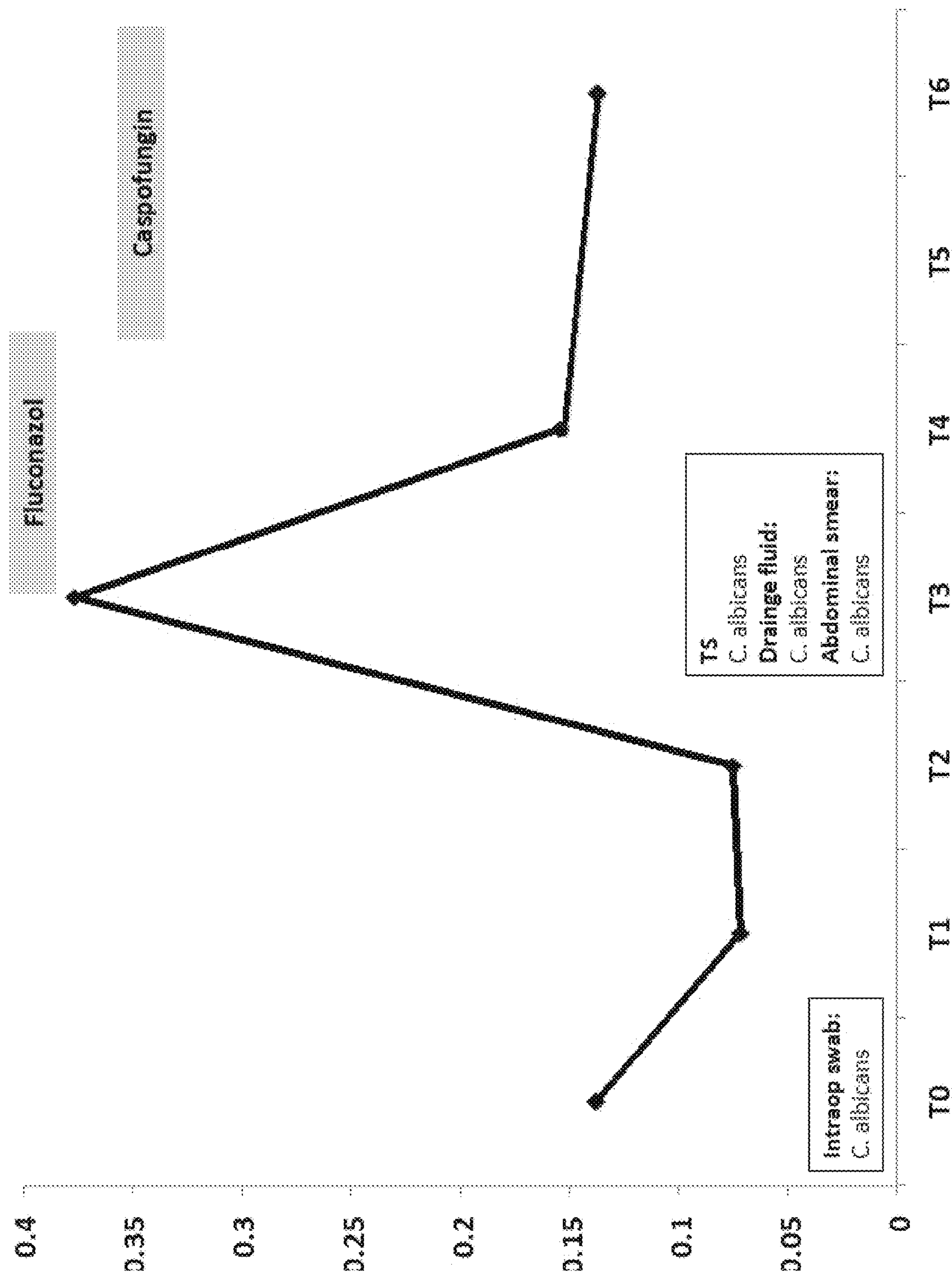

[Figure 8C]
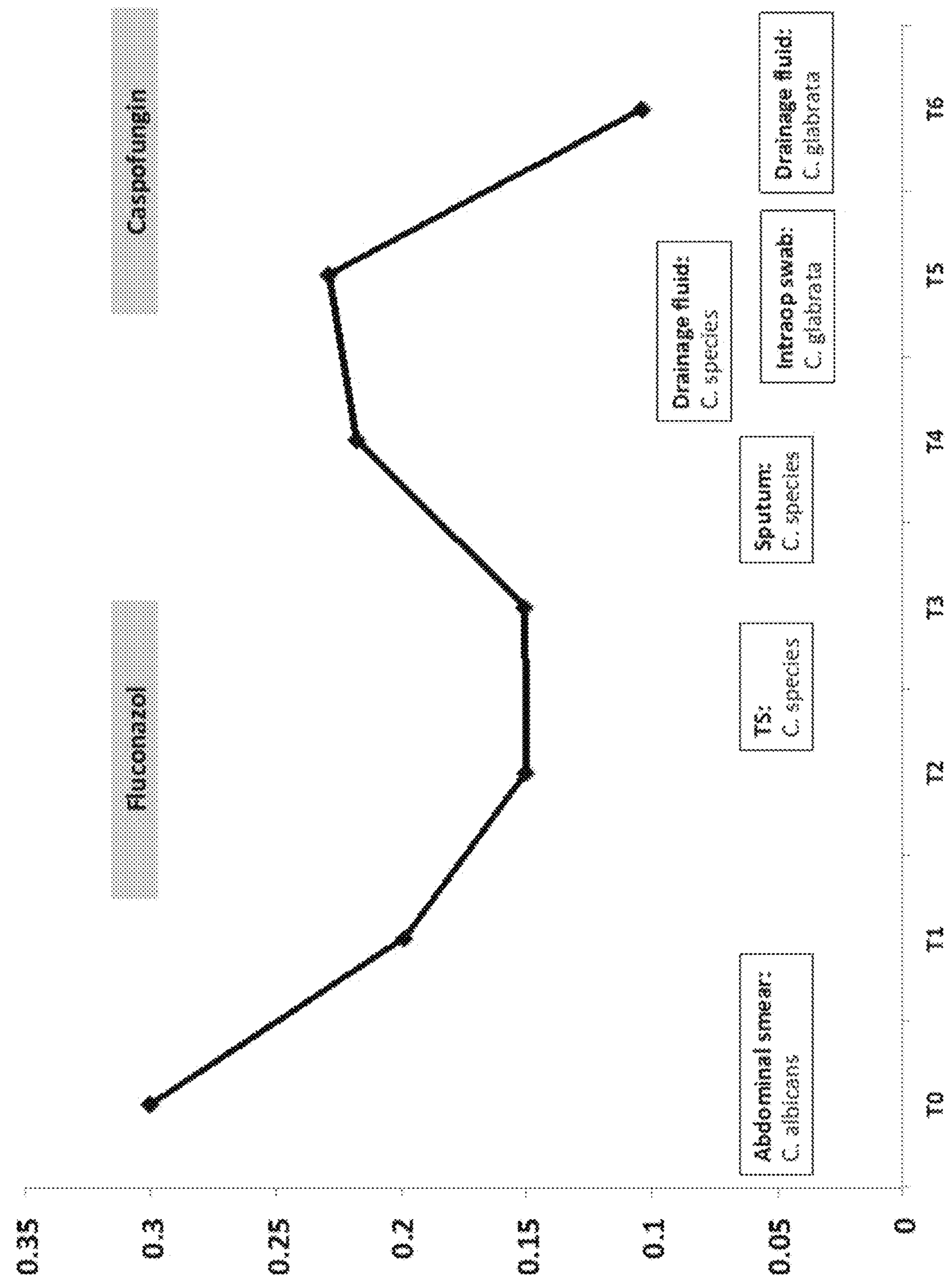

[Figure 8D]
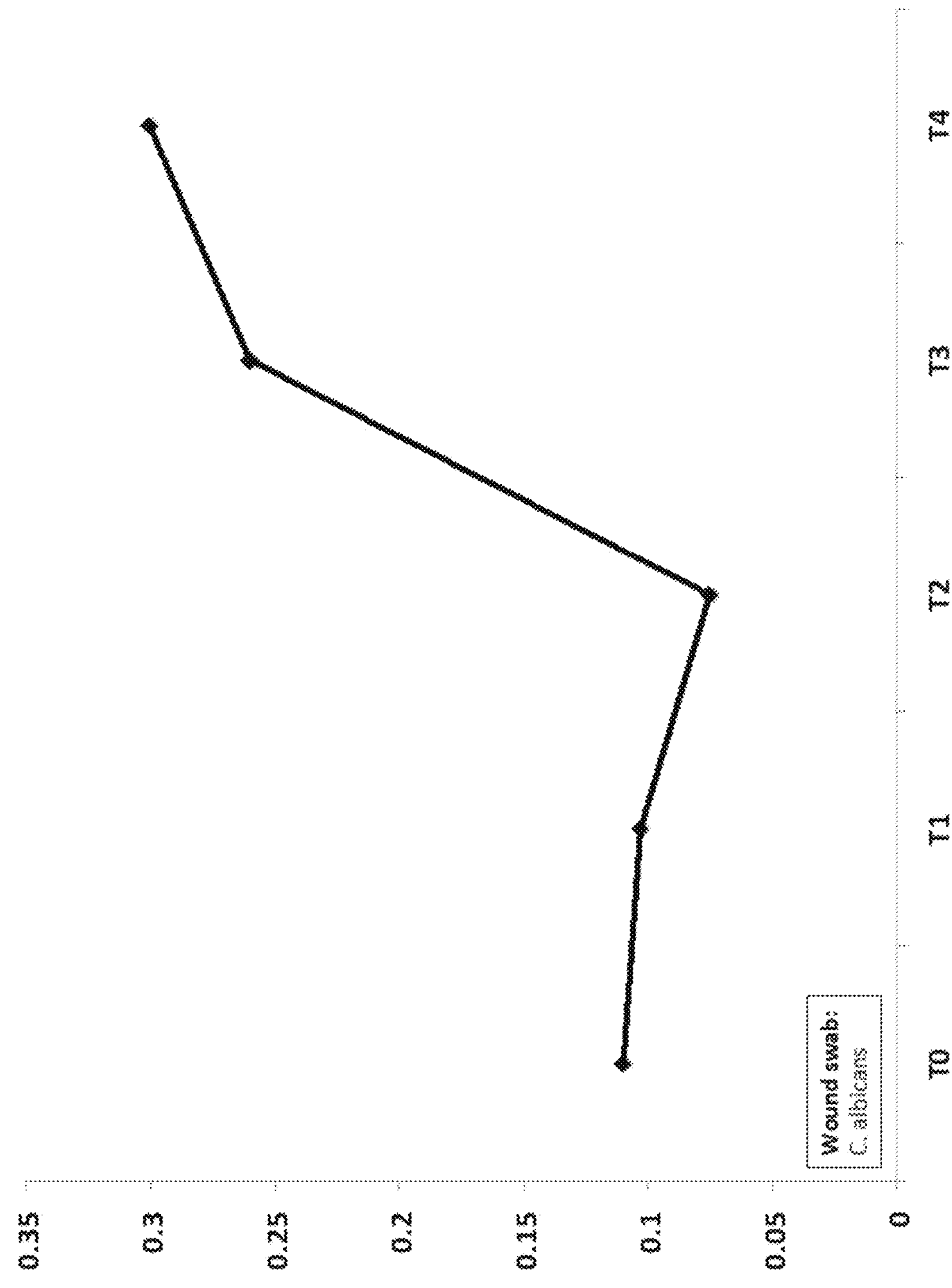

[Figure 8E]
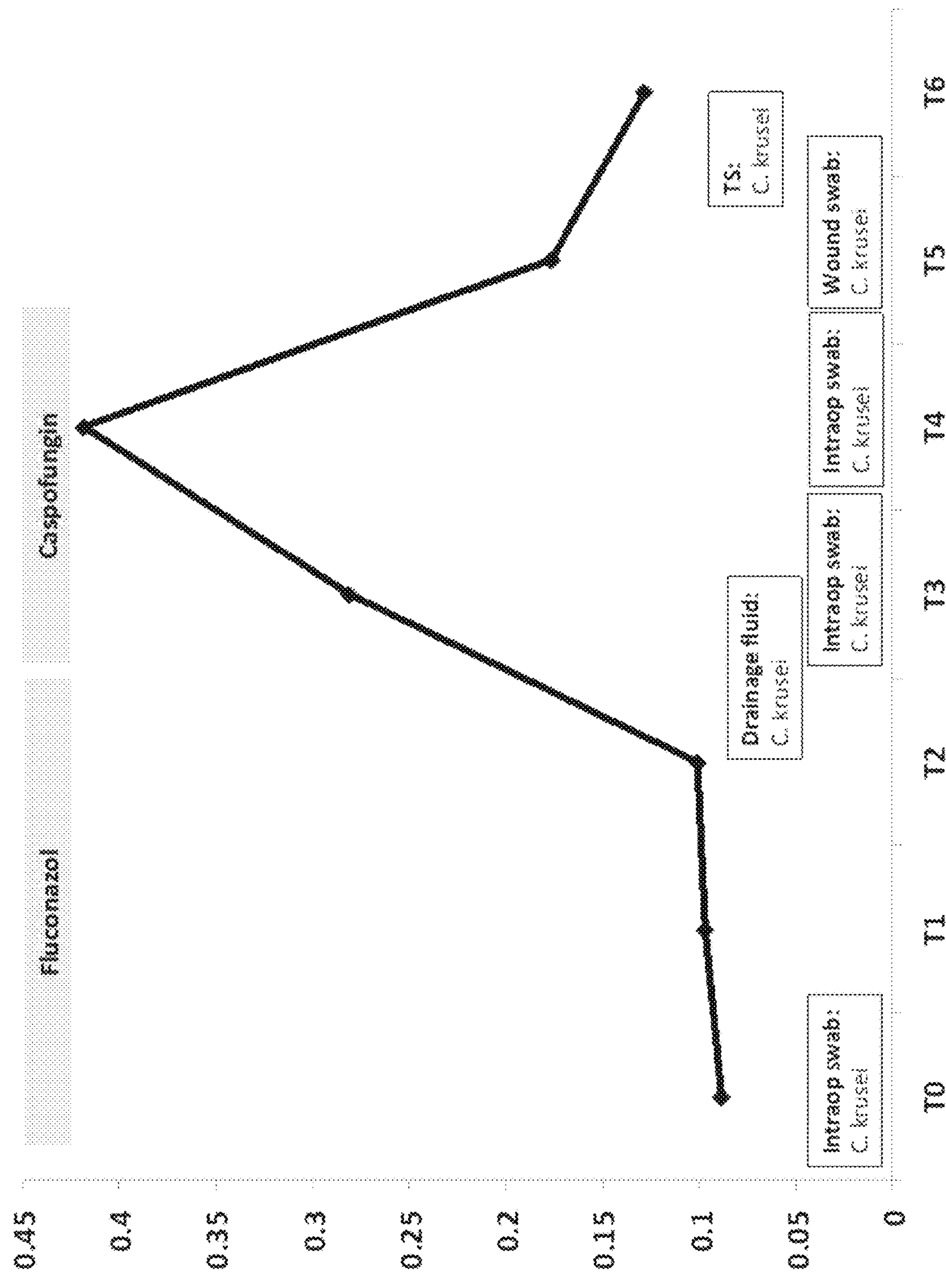

[Figure 9A]
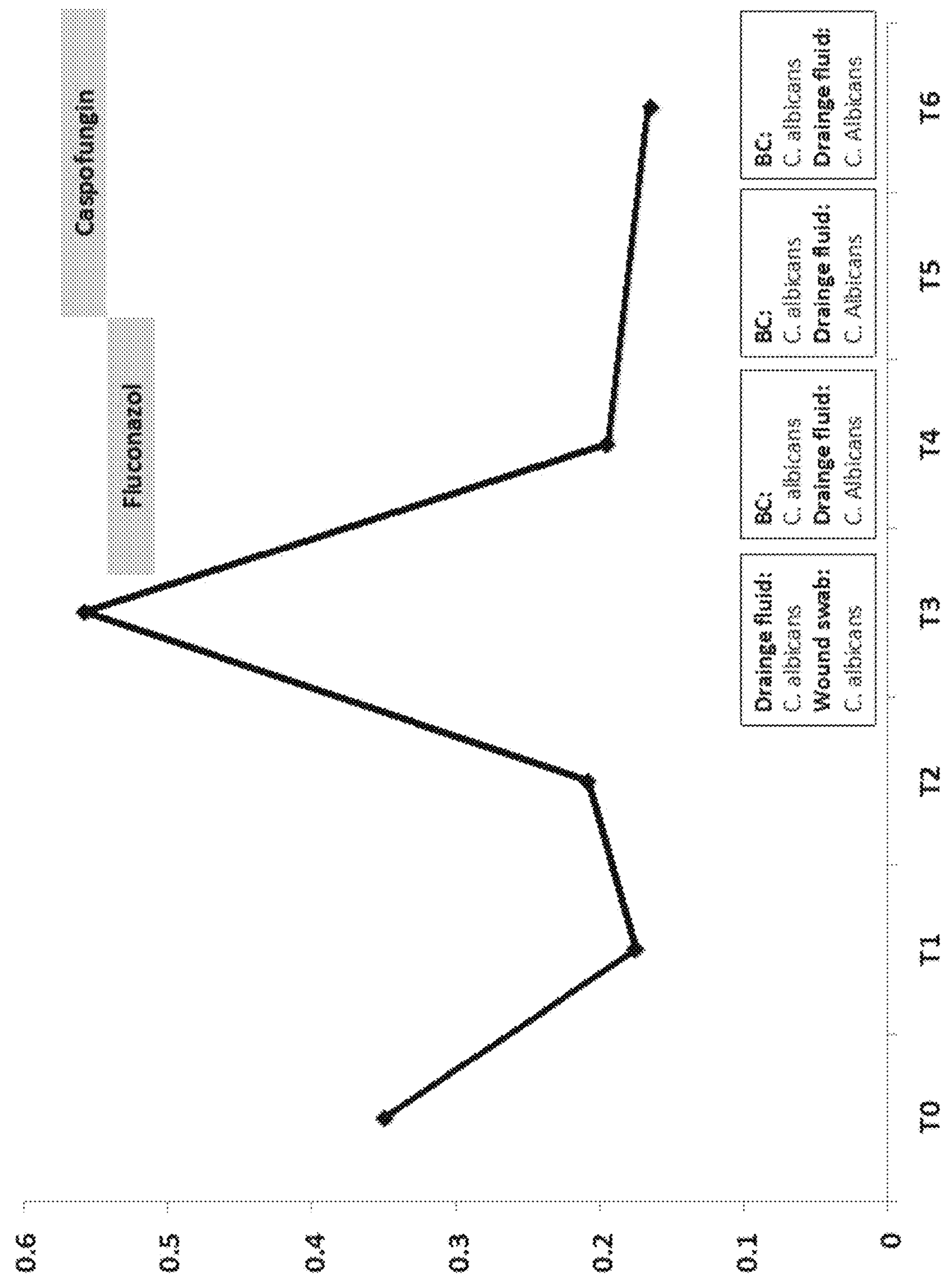

[Figure 9B]
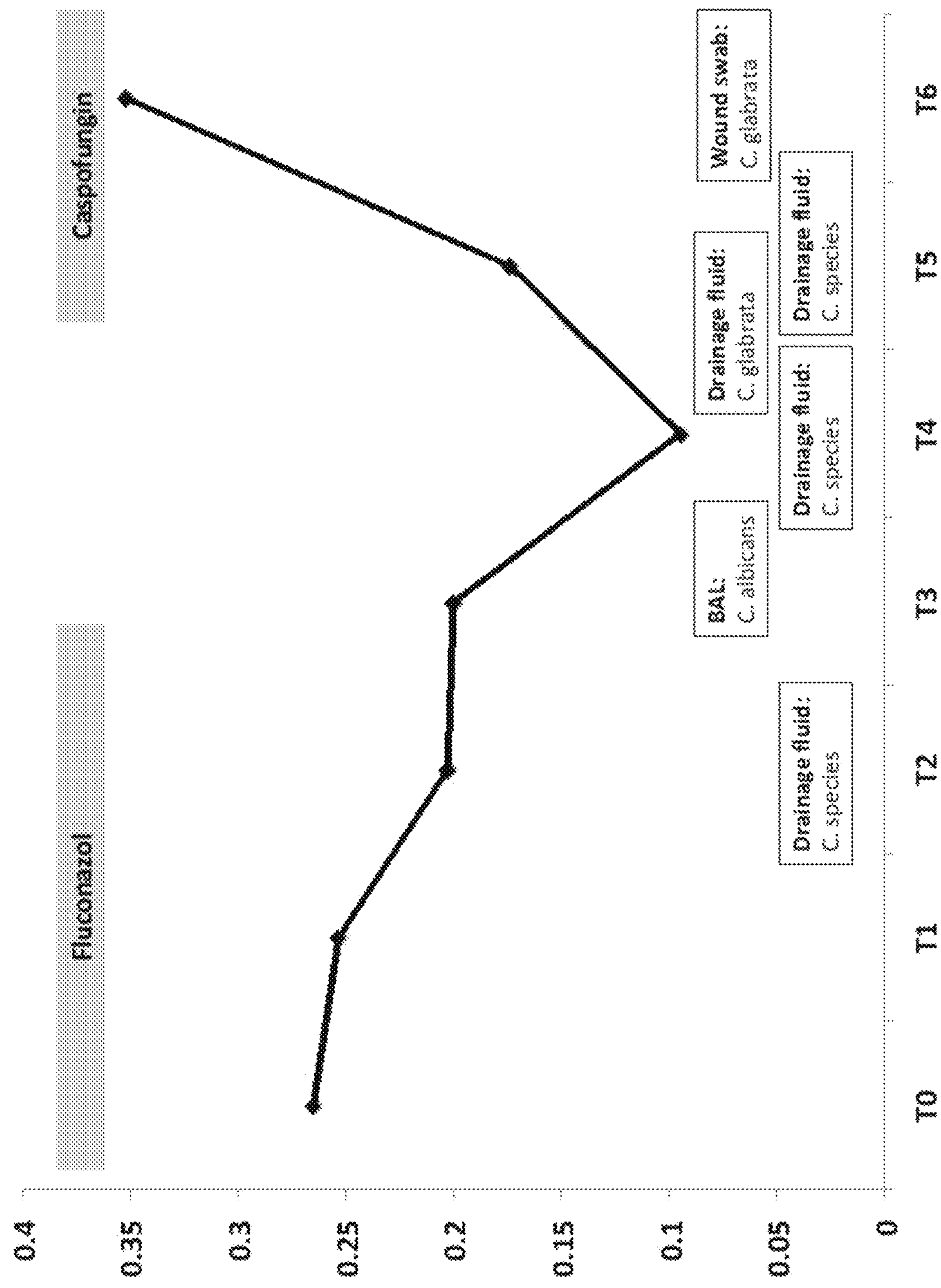

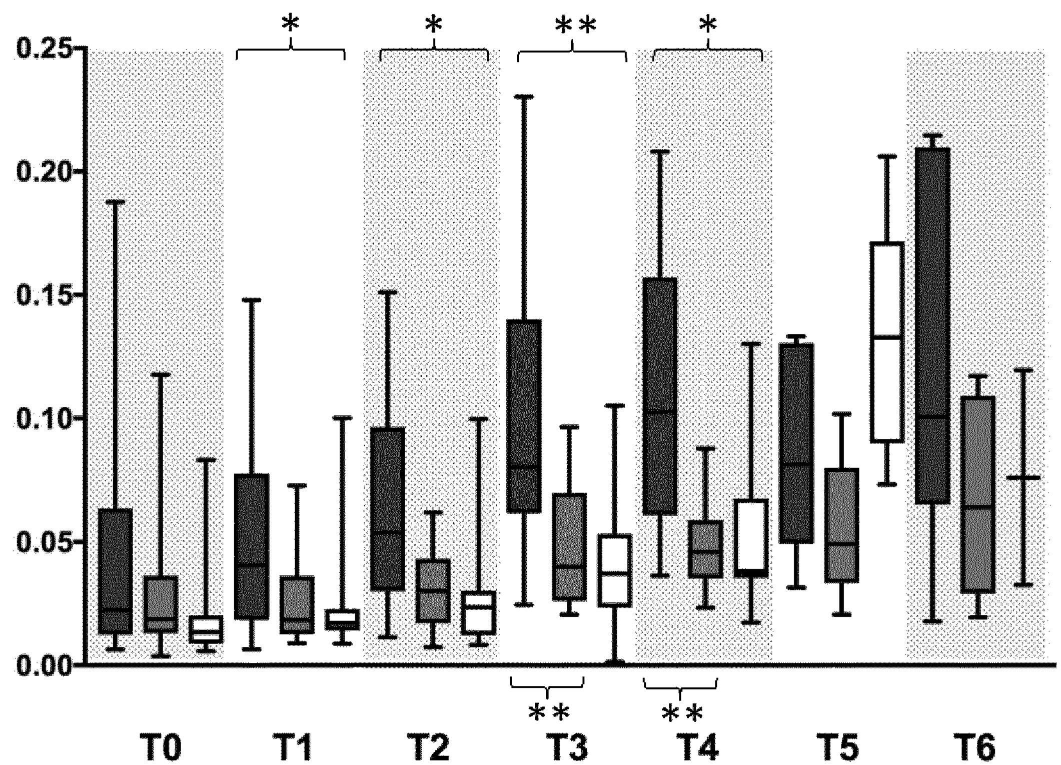
[Figure 10.1A]
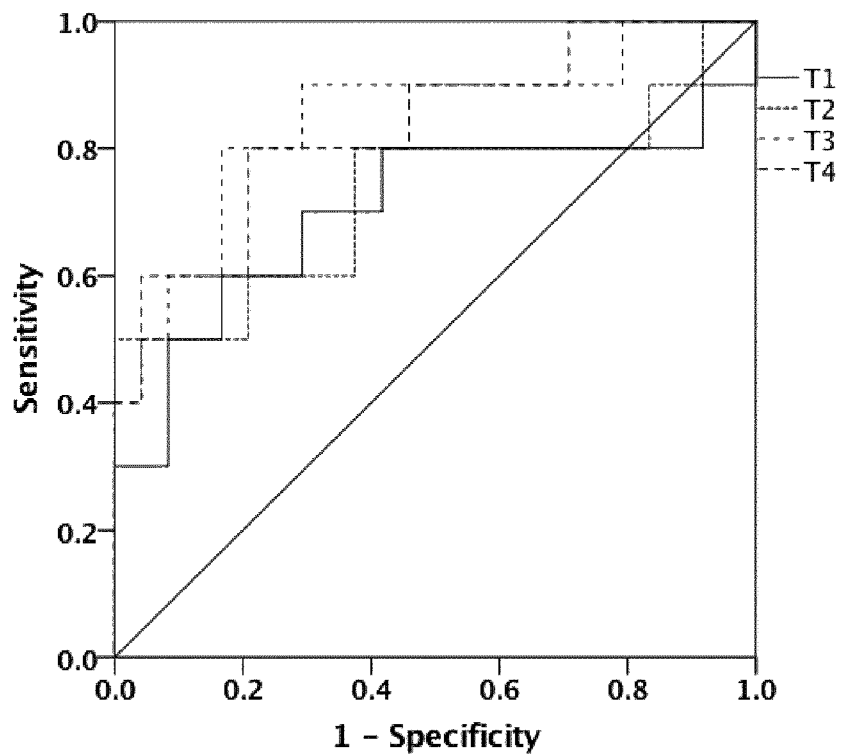
[Figure 10.1B]

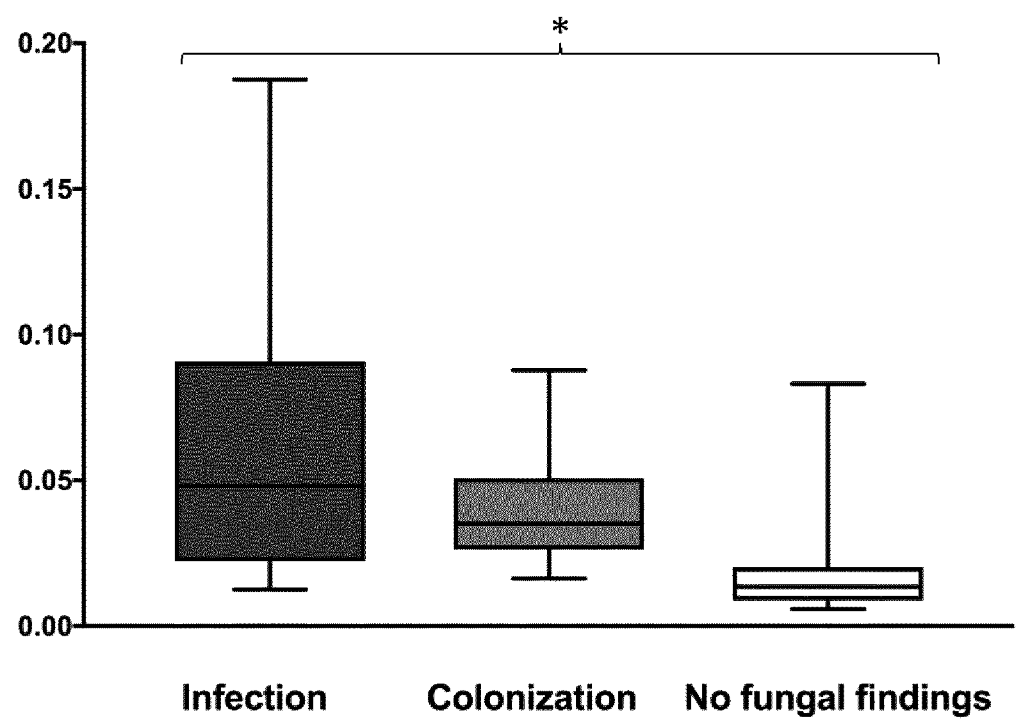
[Figure 10.2]
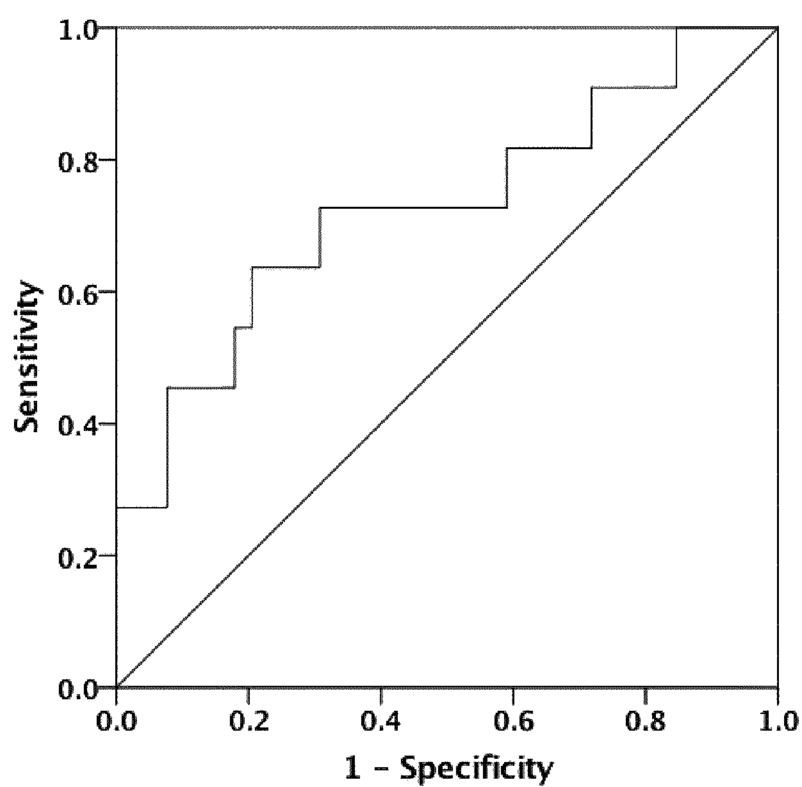
[Figure 10.3]

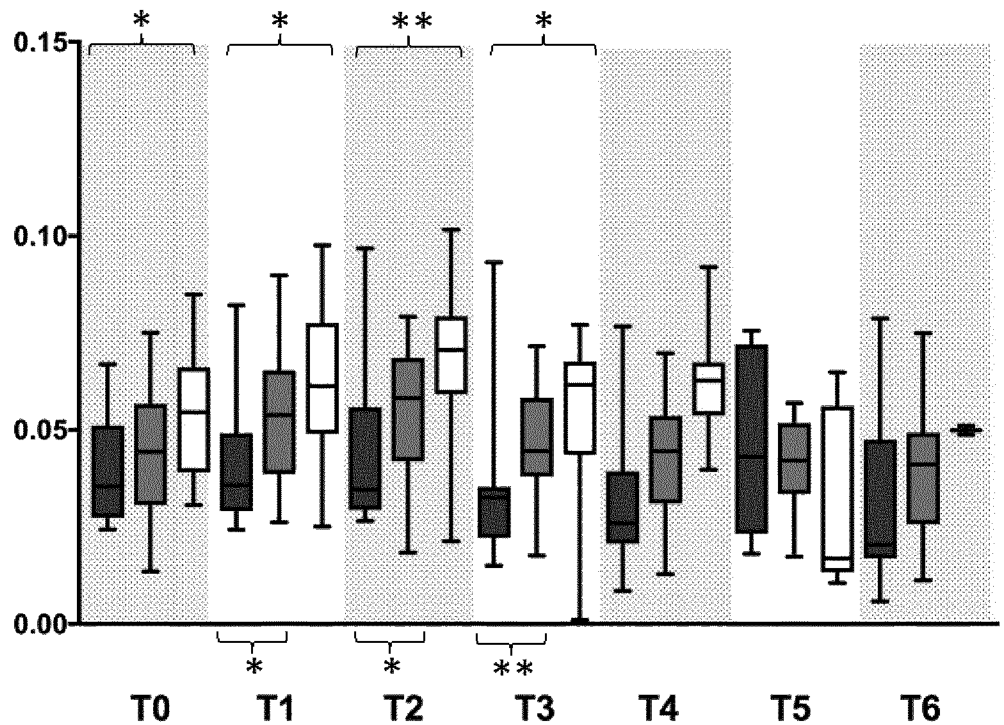
[Figure 11.1A]
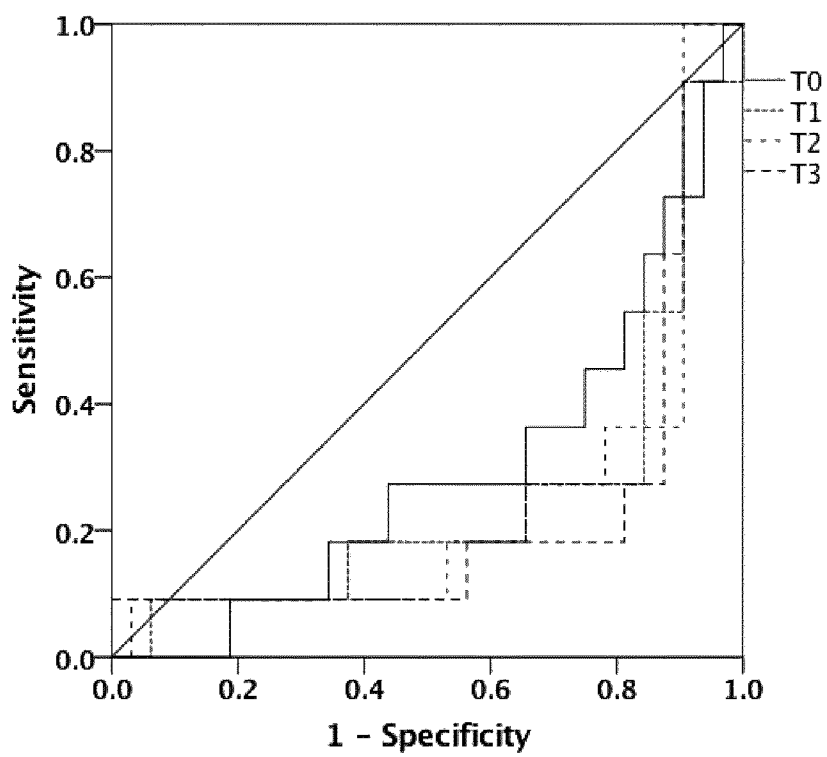
[Figure 11.1B]

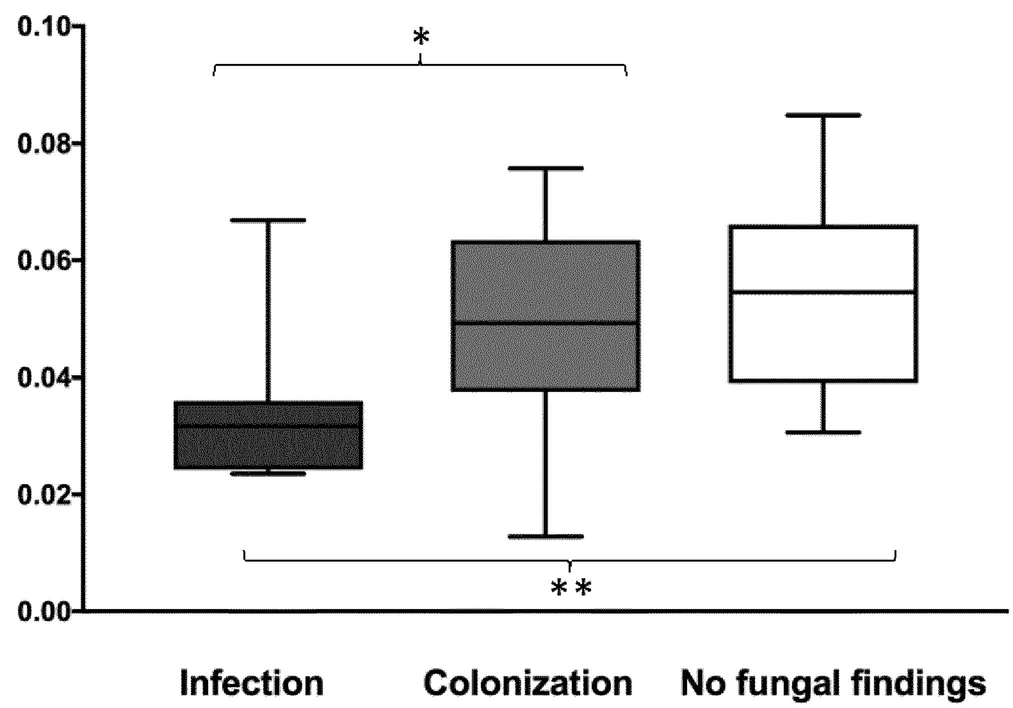
[Figure 11.2]
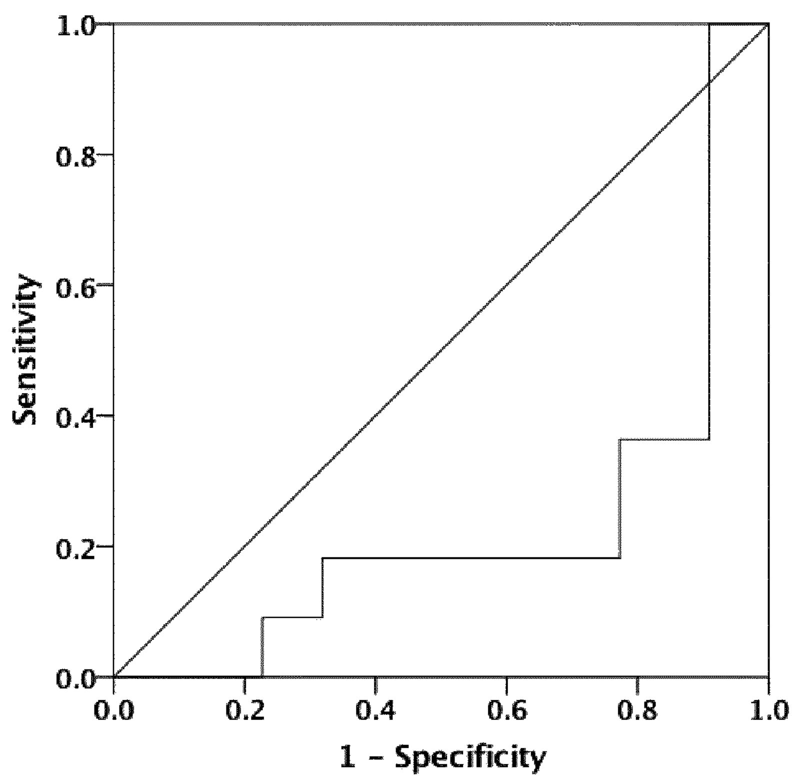
[Figure 11.3]

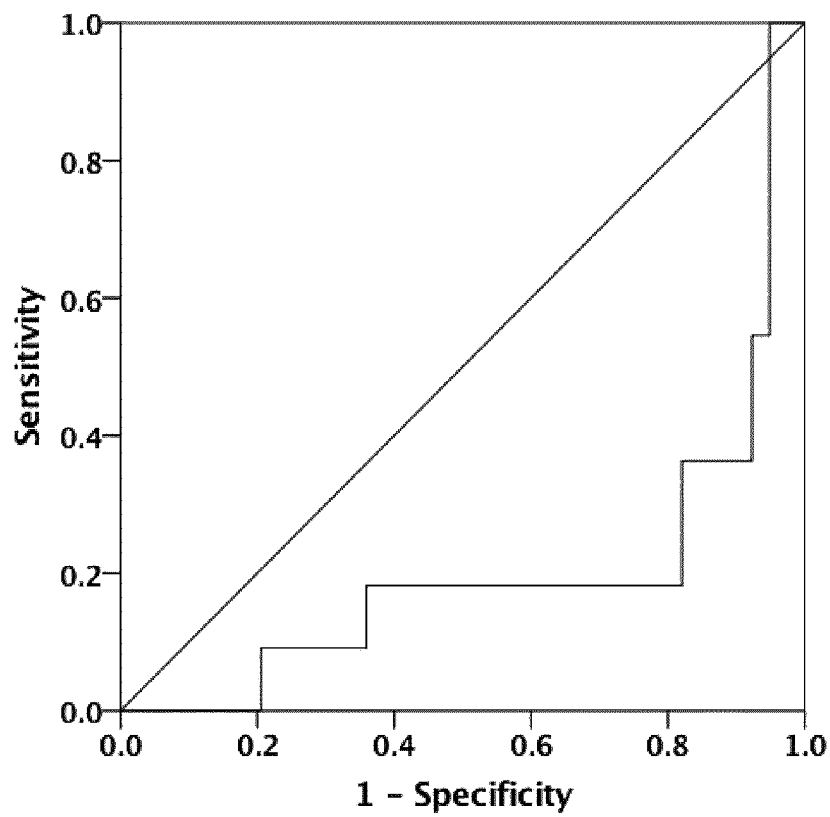
[Figure 11.4]
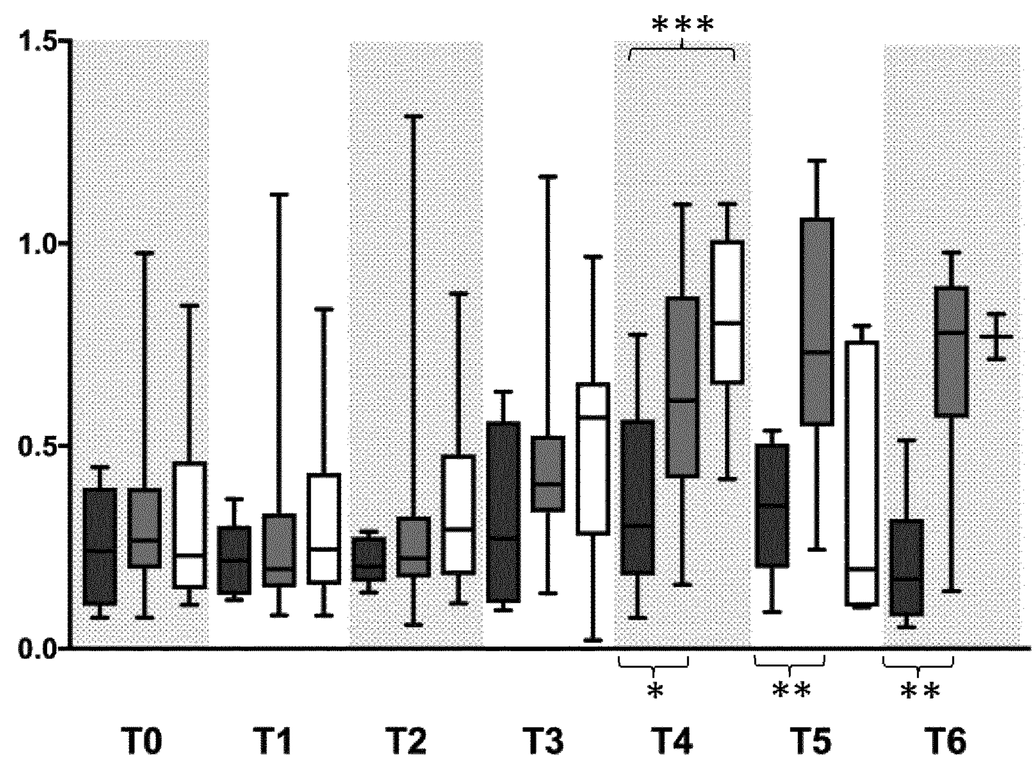
[Figure 12A]

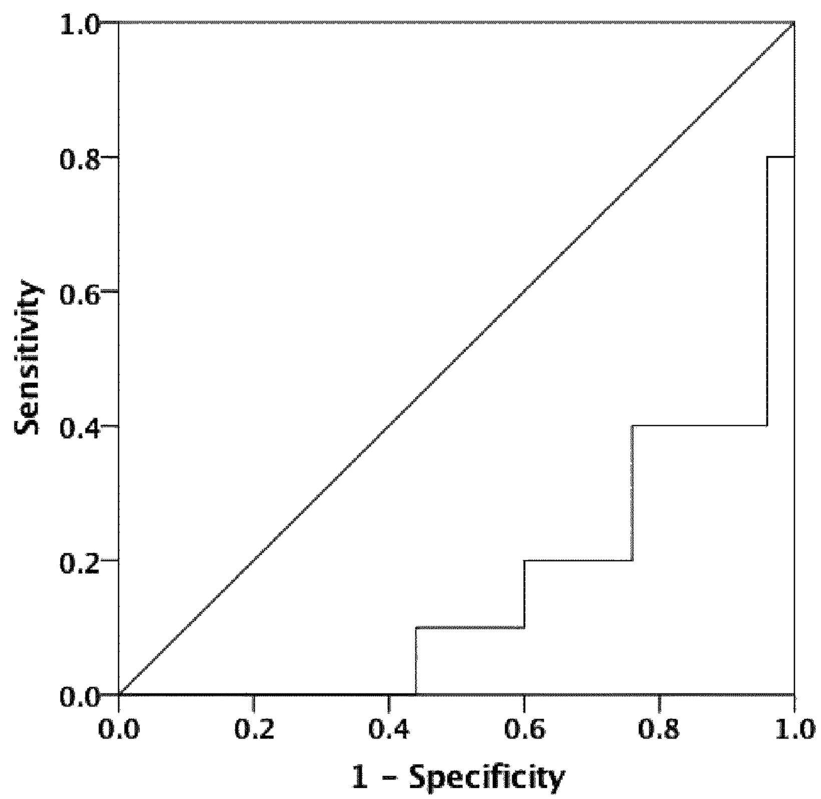
[Figure 12B]
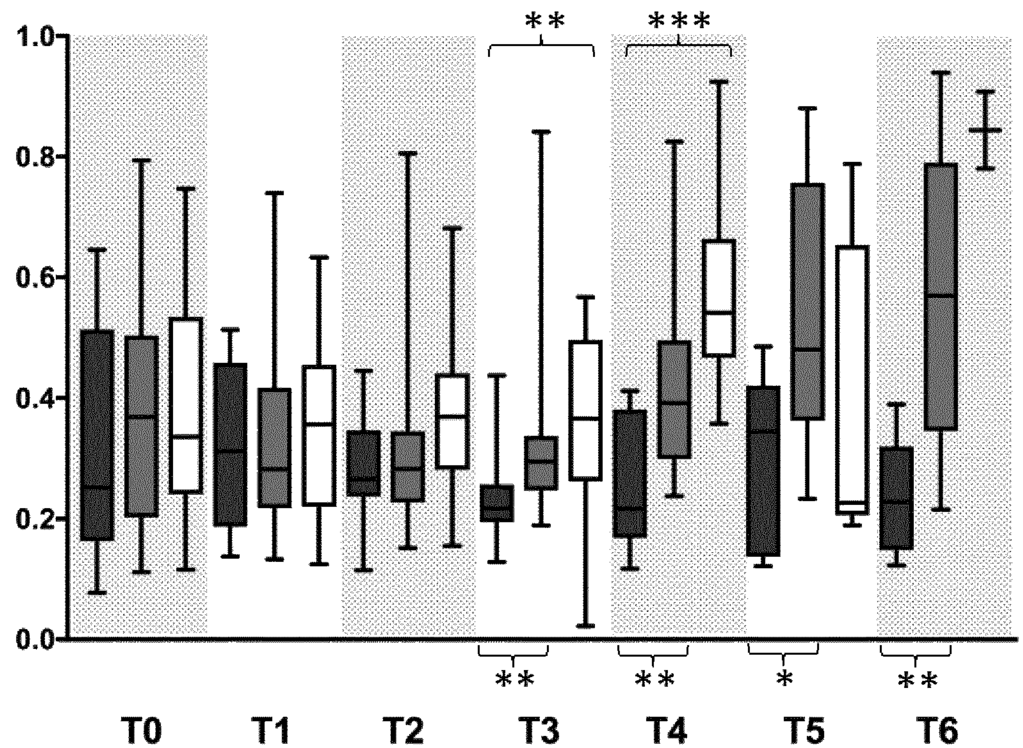
[Figure 13A]

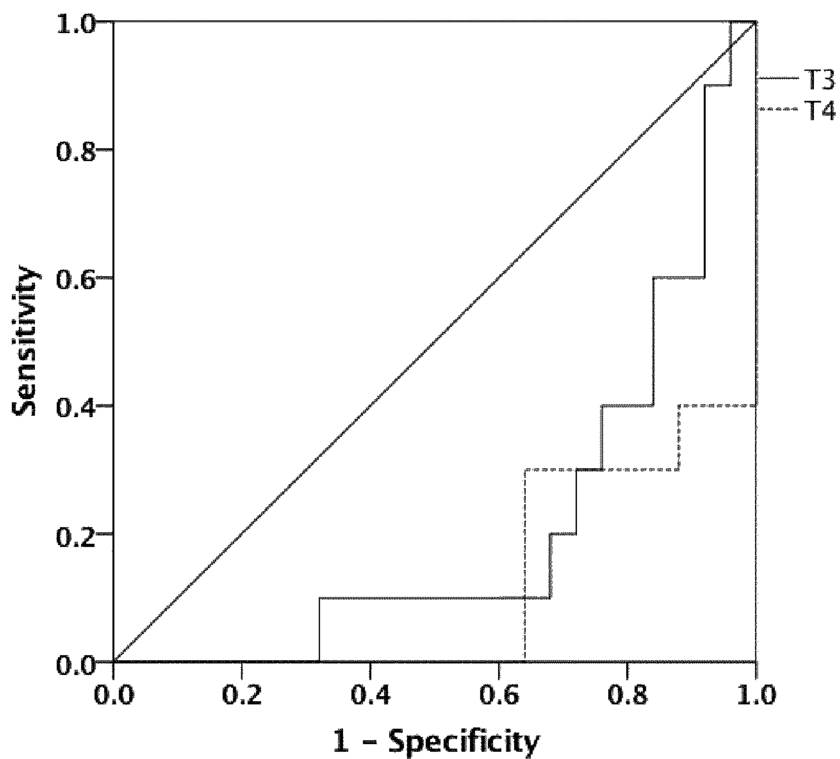
[Figure 13B]
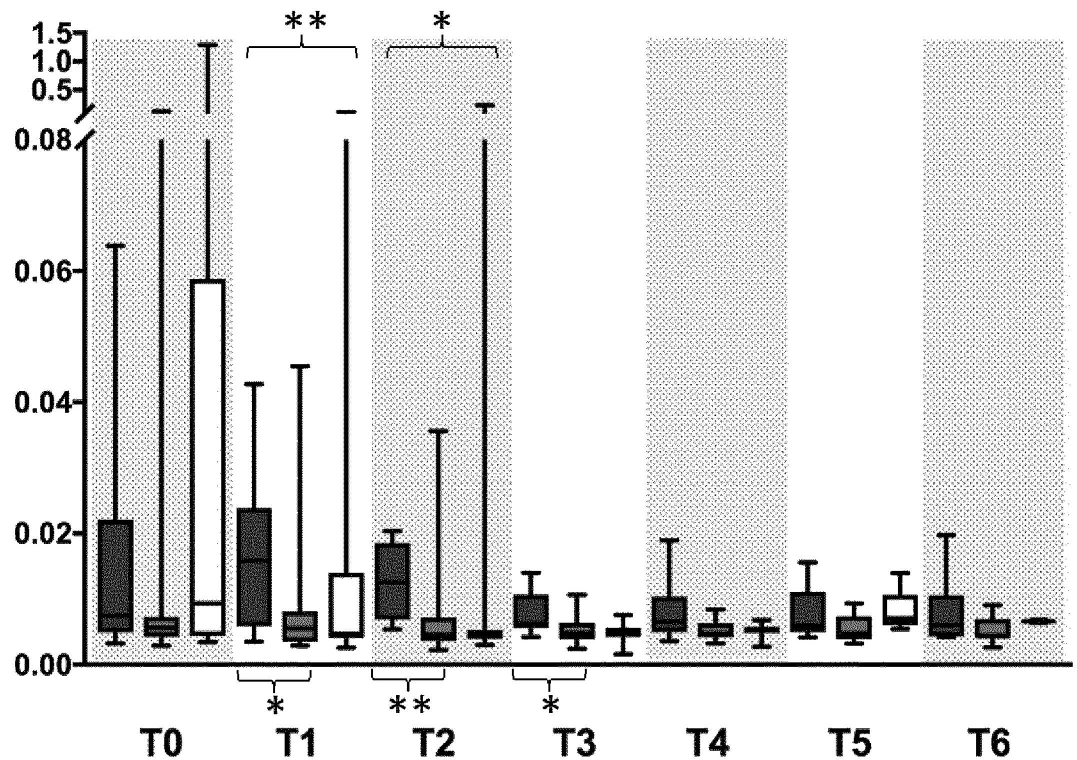
[Figure 14A]

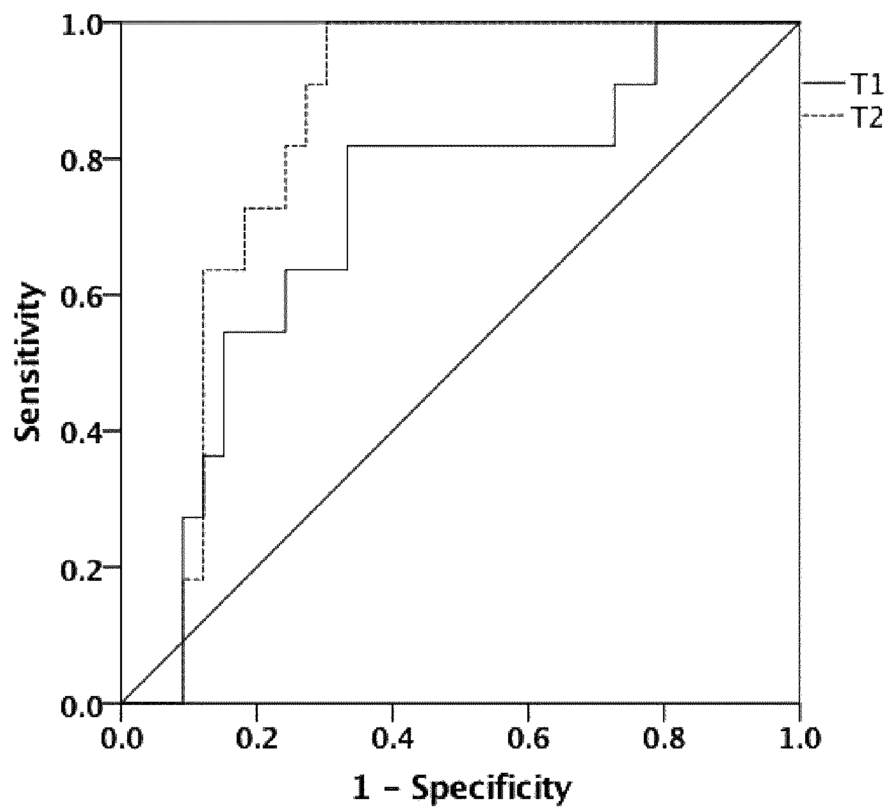
[Figure 14B]
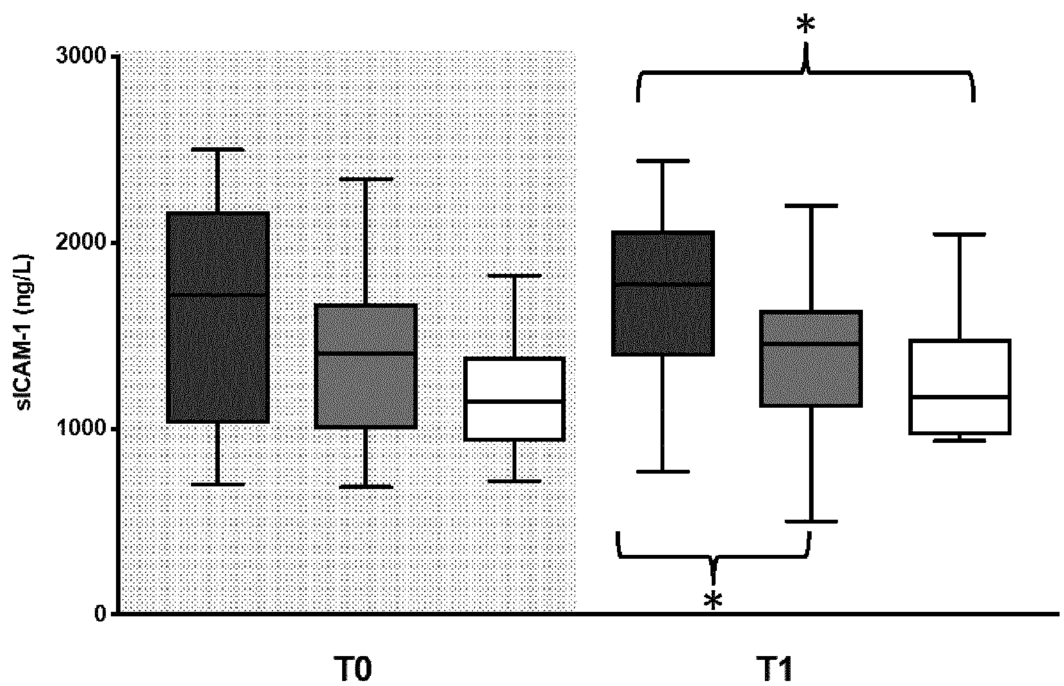
[Figure 15A]

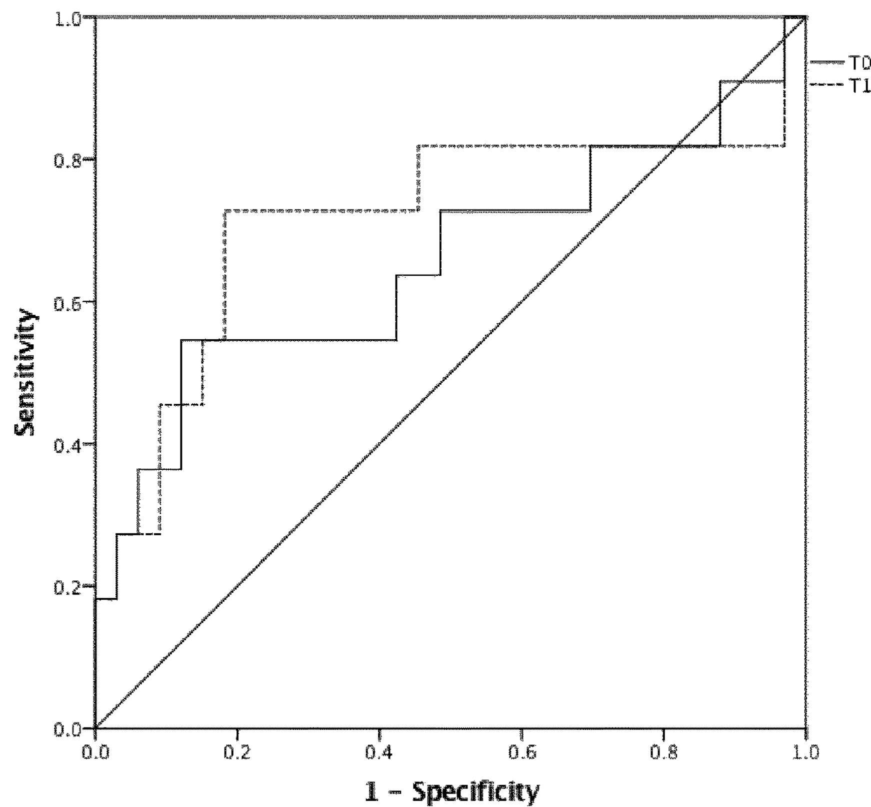
[Figure 15B]
PCT solo
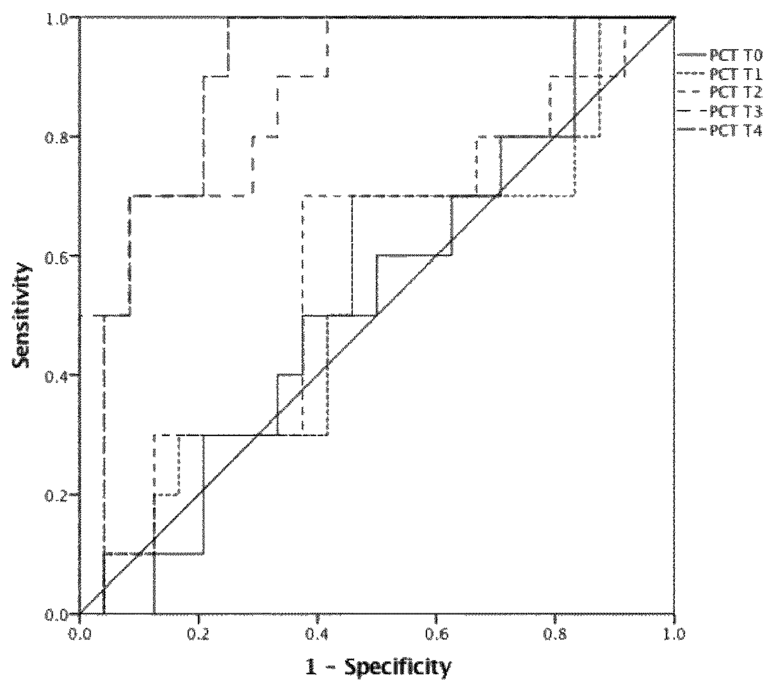
[Figure 16]

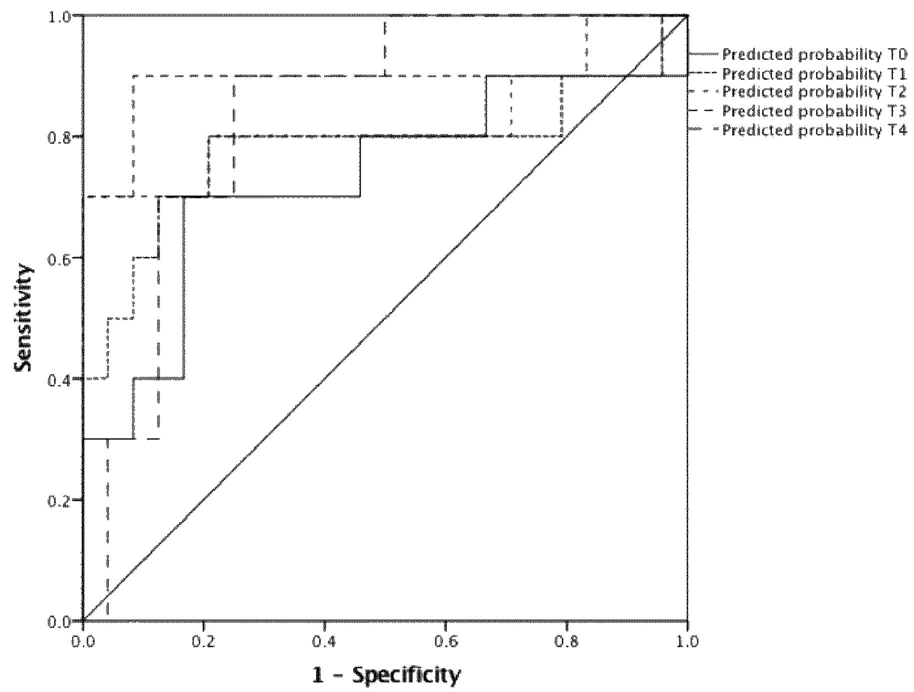
[Figure 17]
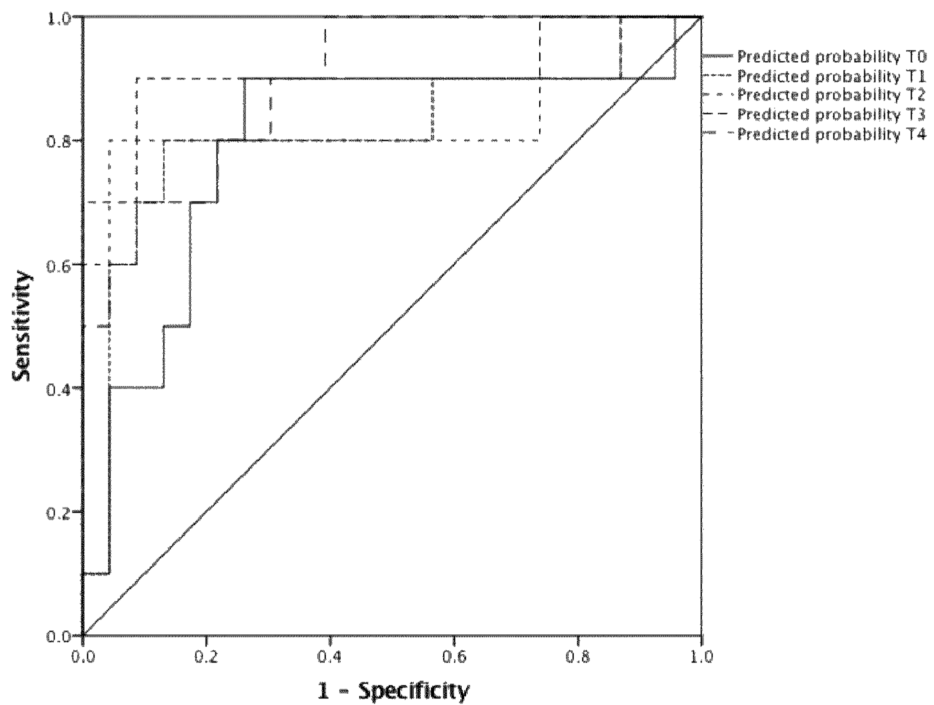
[Figure 18]

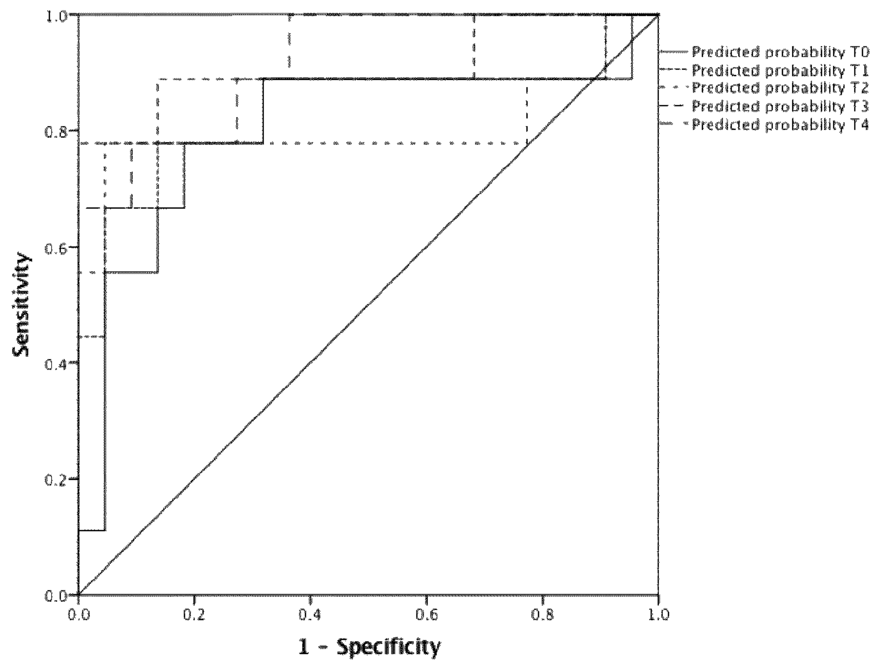
[Figure 19]
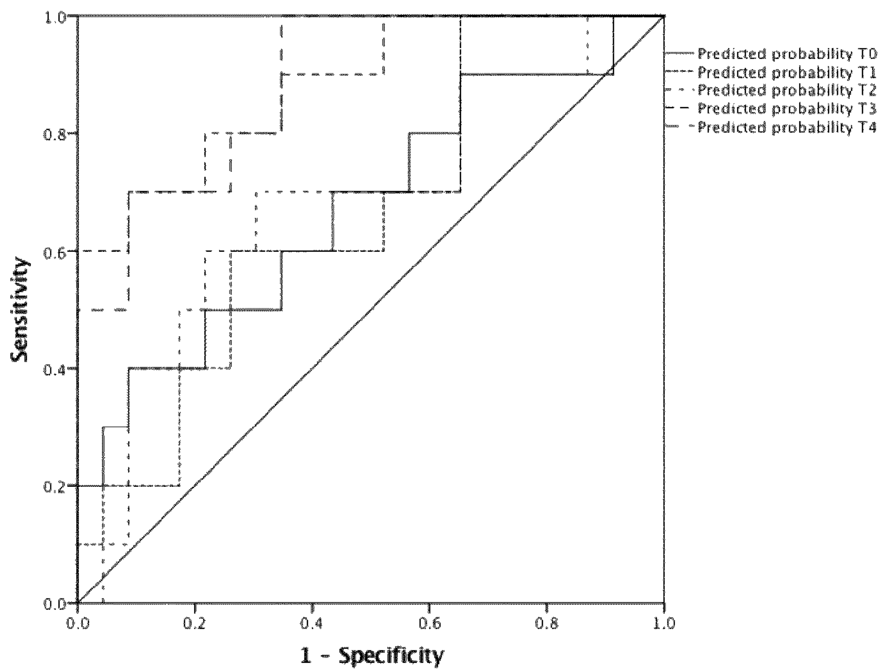
[Figure 20]

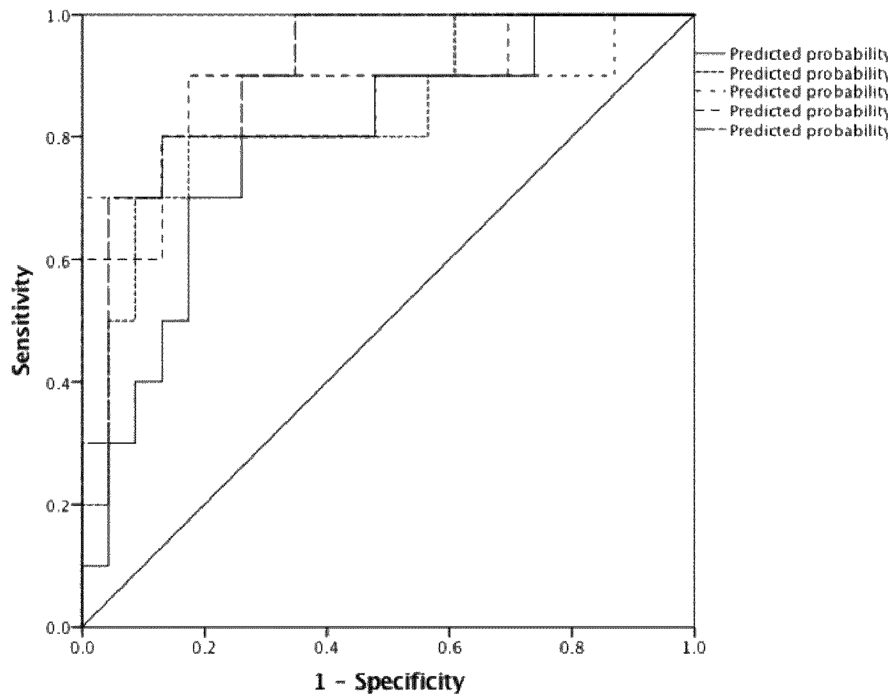
[Figure 21]
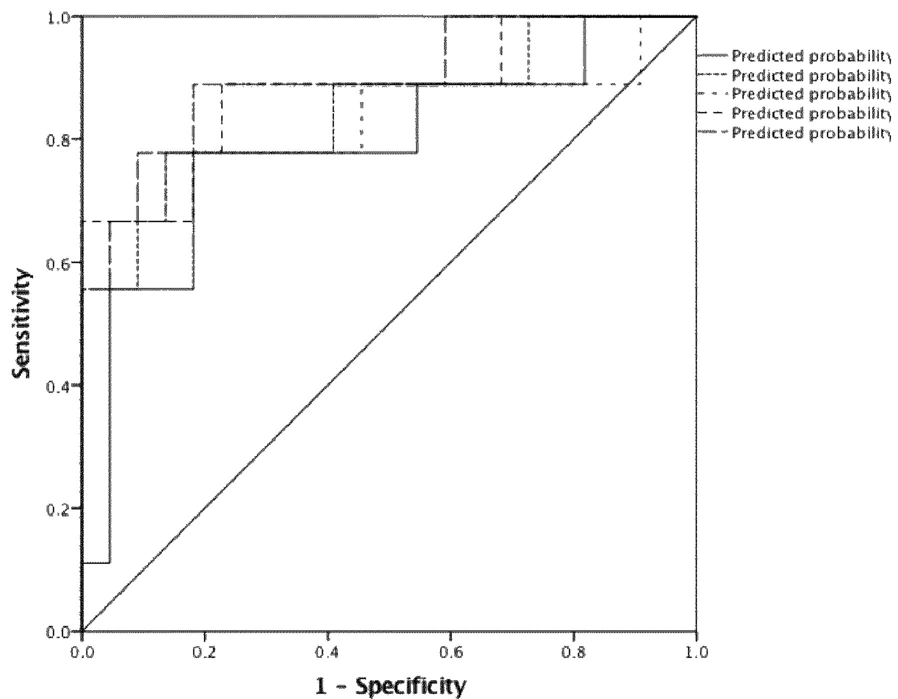
[Figure 22]

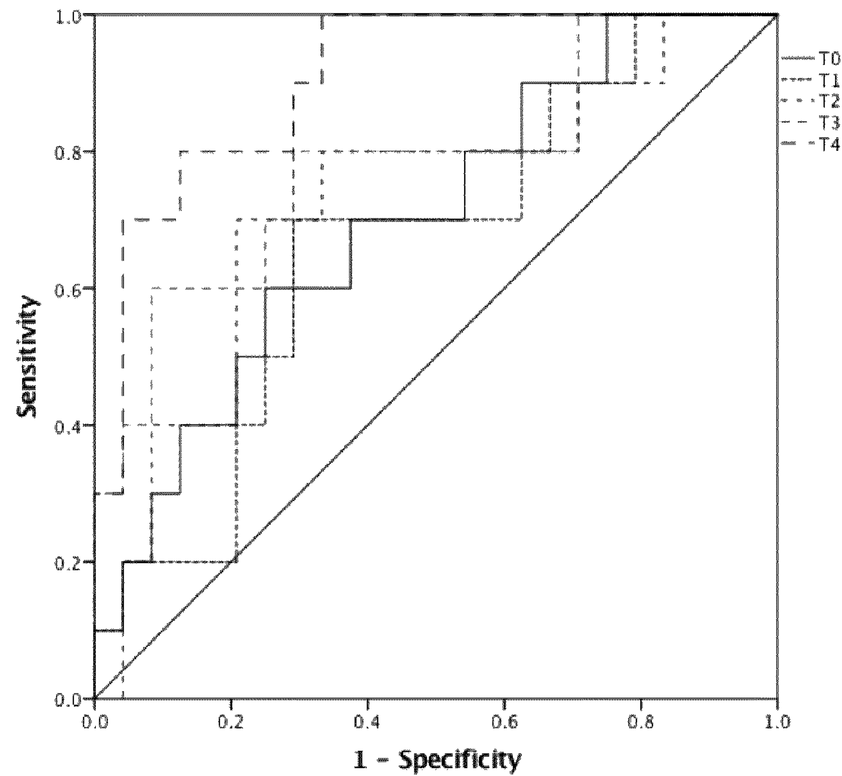
[Figure 23]
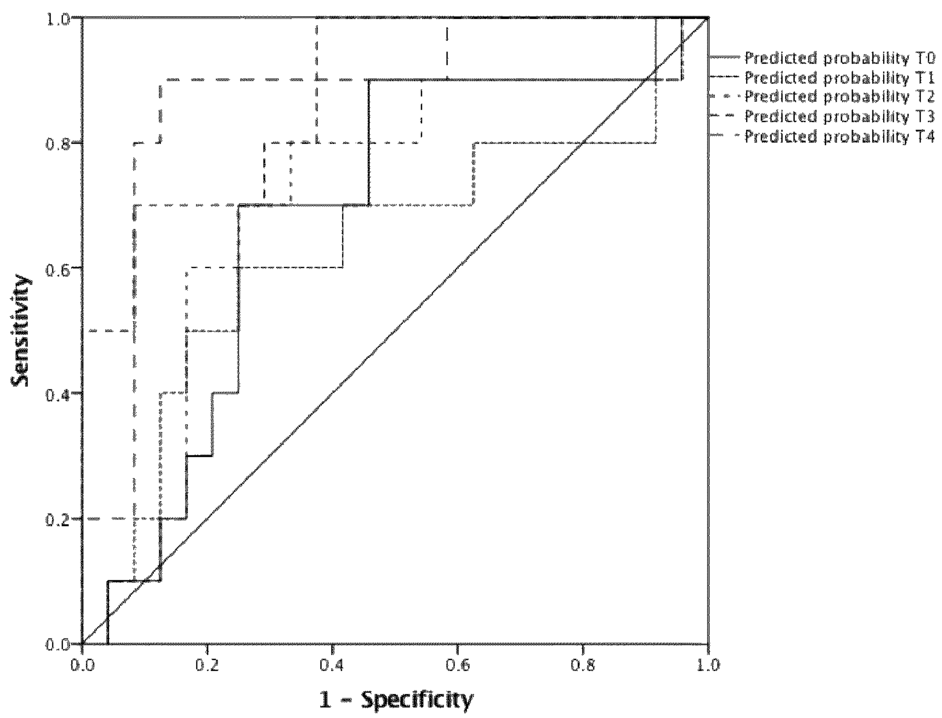
[Figure 24]

ADM+THBP
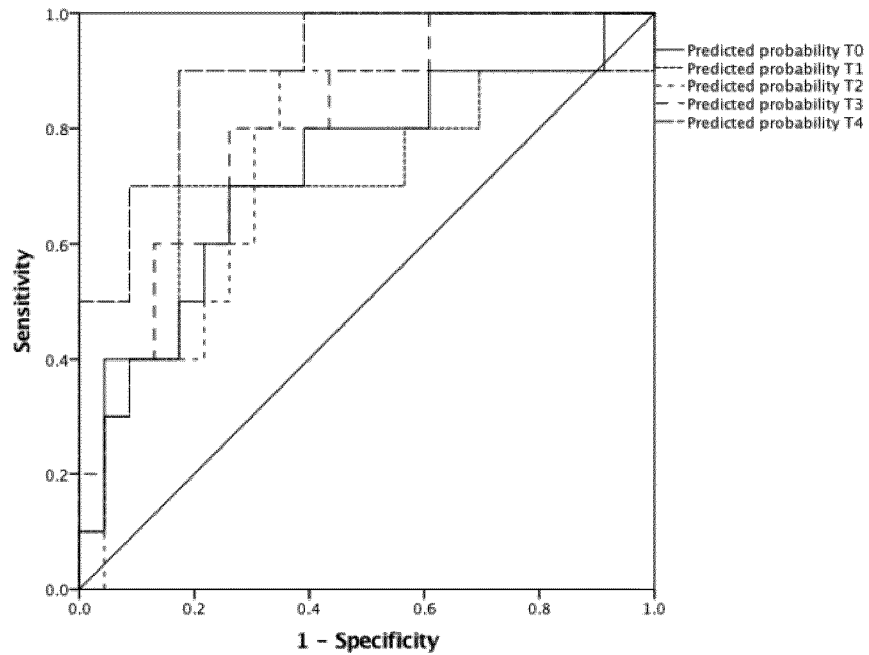
[Figure 25]
PCT+ADM+THBP
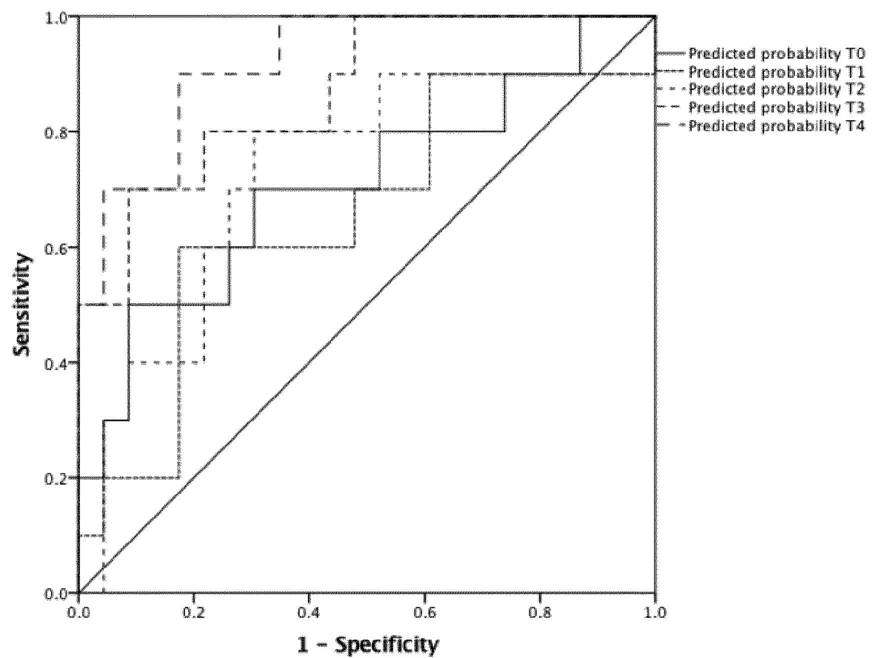
[Figure 26]

PCT+VCL
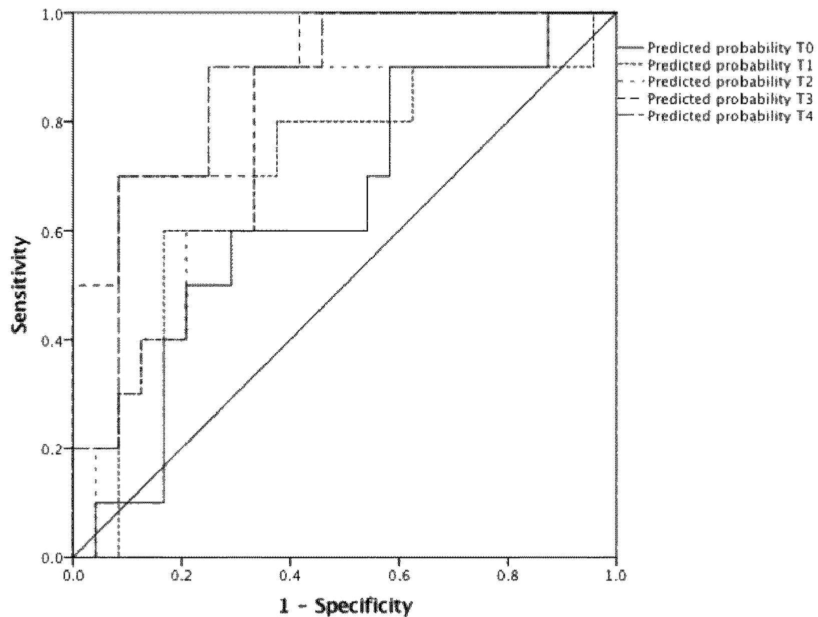
[Figure 27]
ADM+VCL
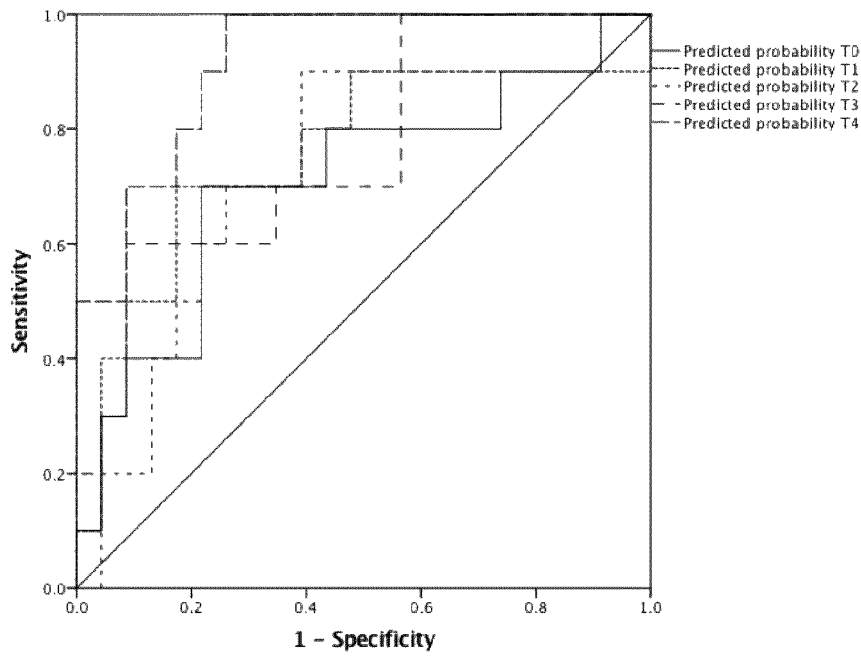
[Figure 28]

ADM+VCL+PCT
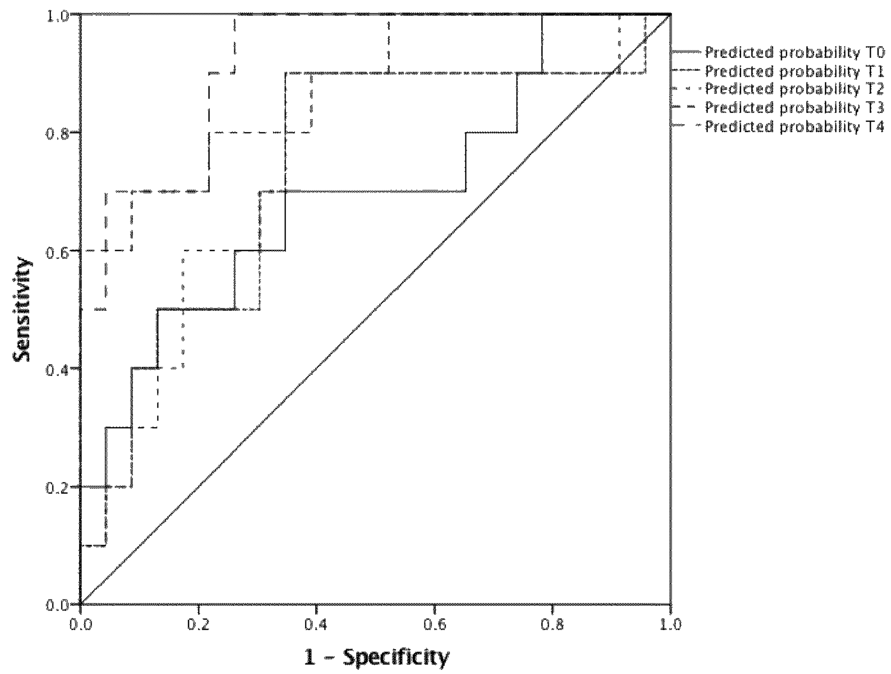
[Figure 29]
ICAM1+THBP
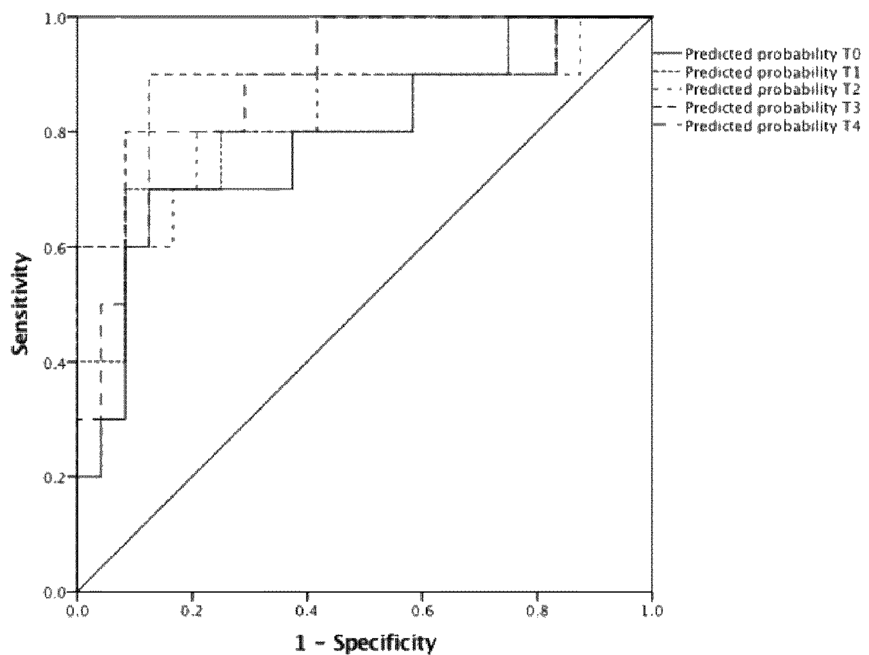
[Figure 30]

ICAM1+VCL
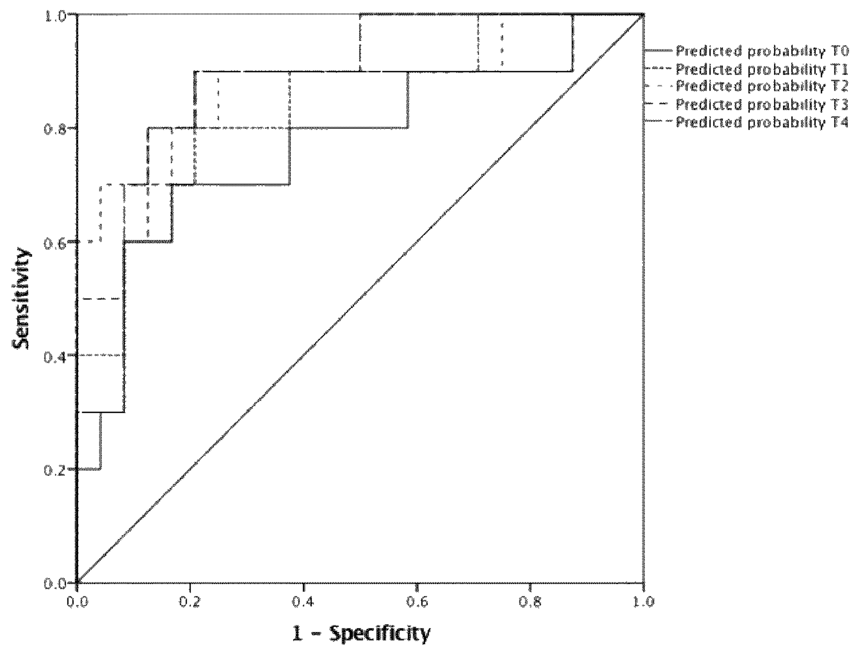
[Figure 31]
ICAM1+THBSP+VCL
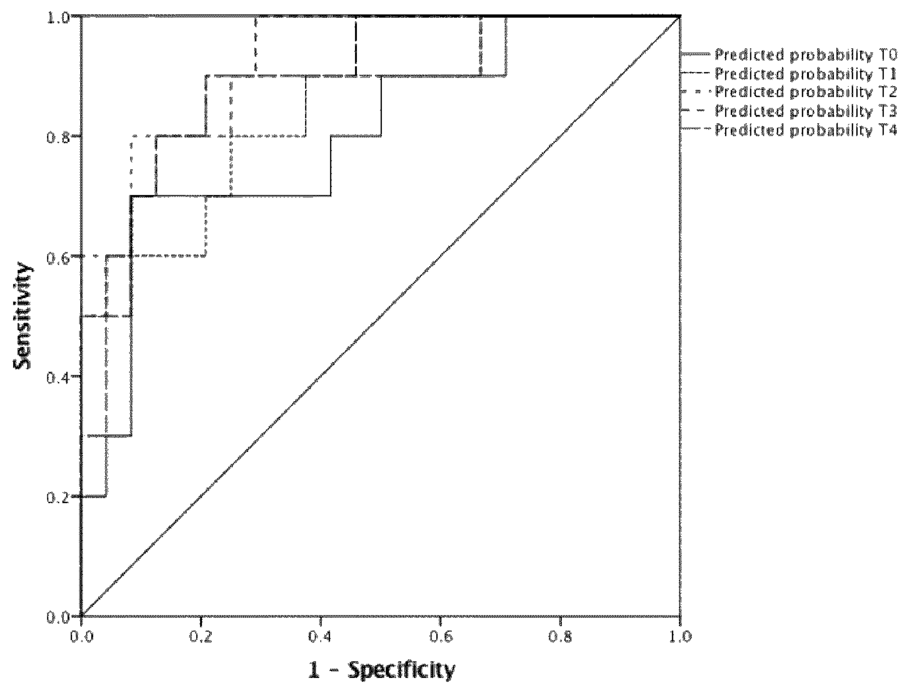
[Figure 32]

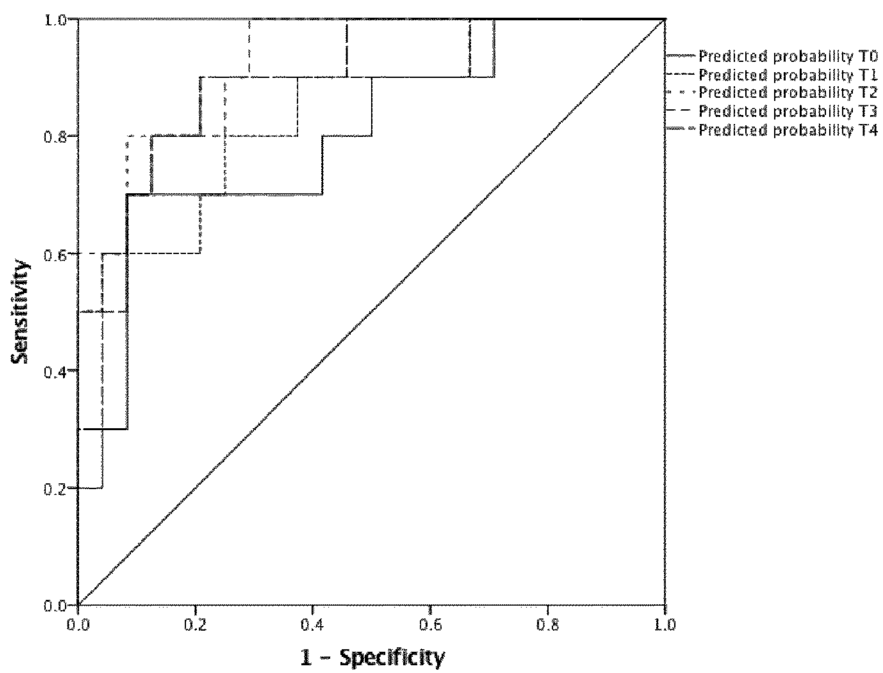
[Figure 33]
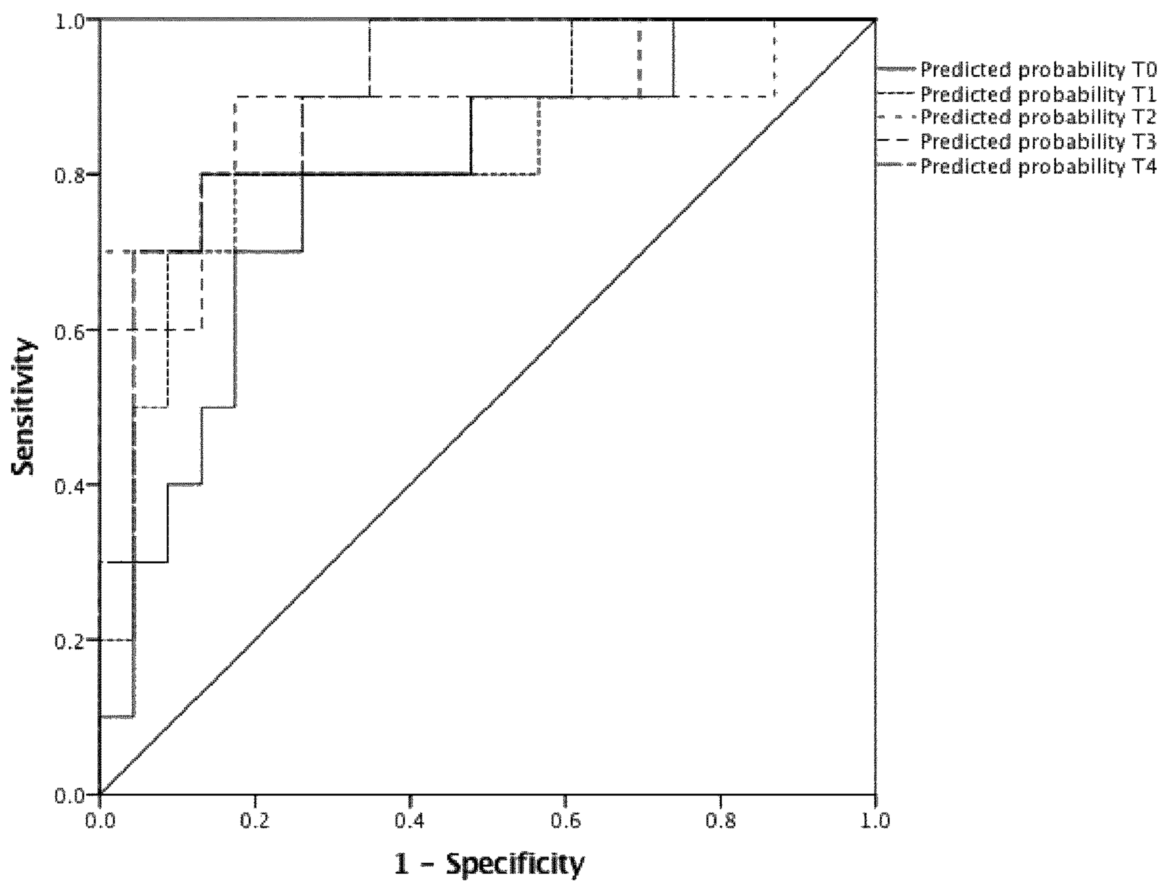
[Figure 34]

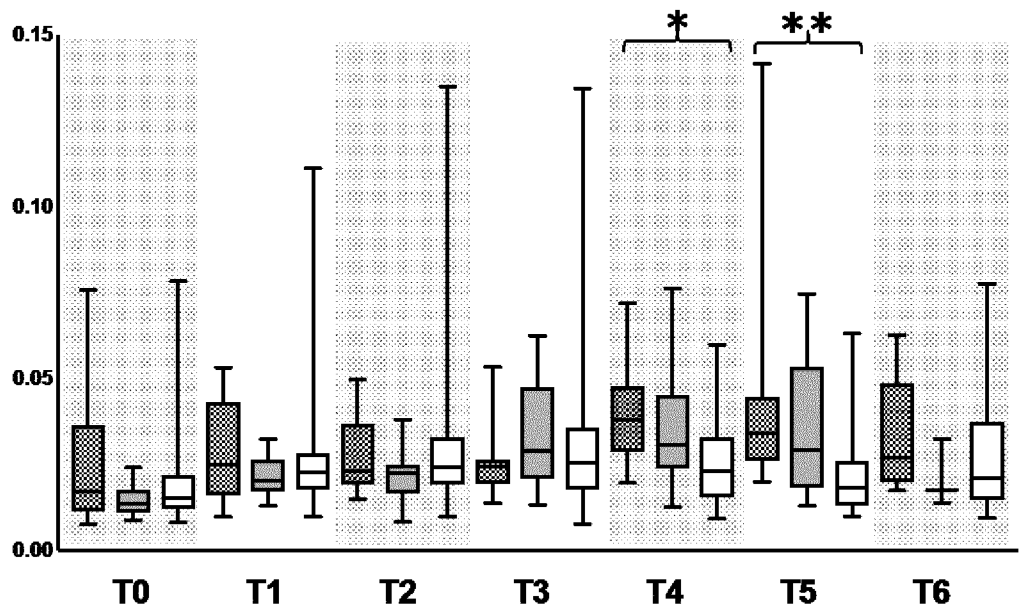
[Figure 35.1 A]
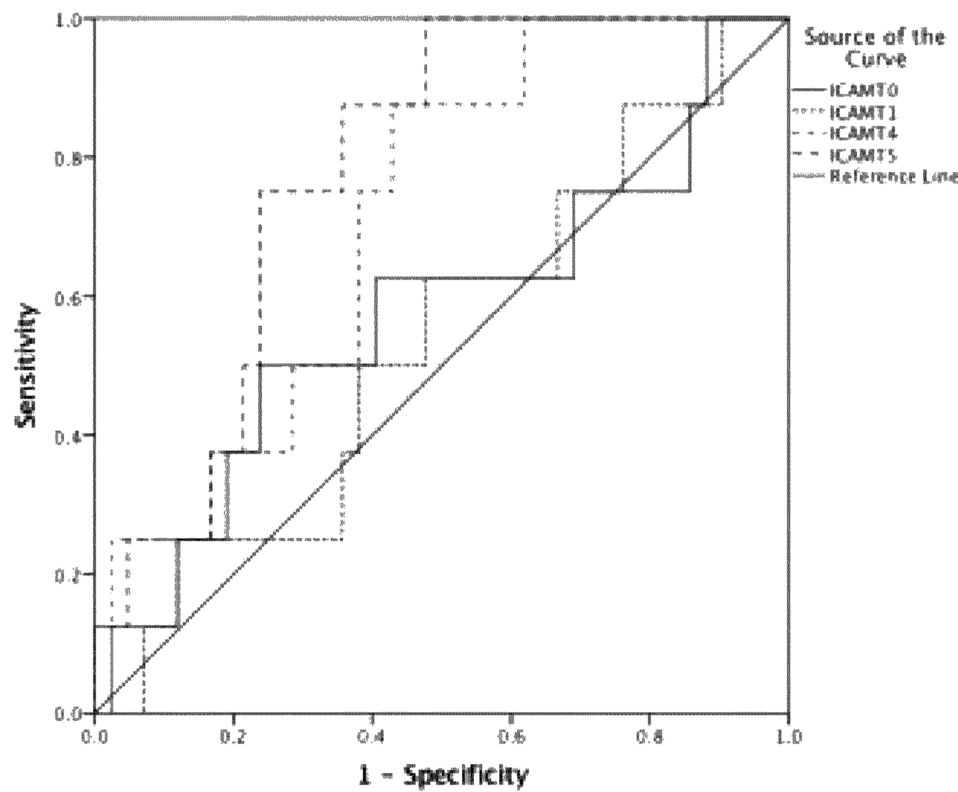
[Figure 35.1 B]

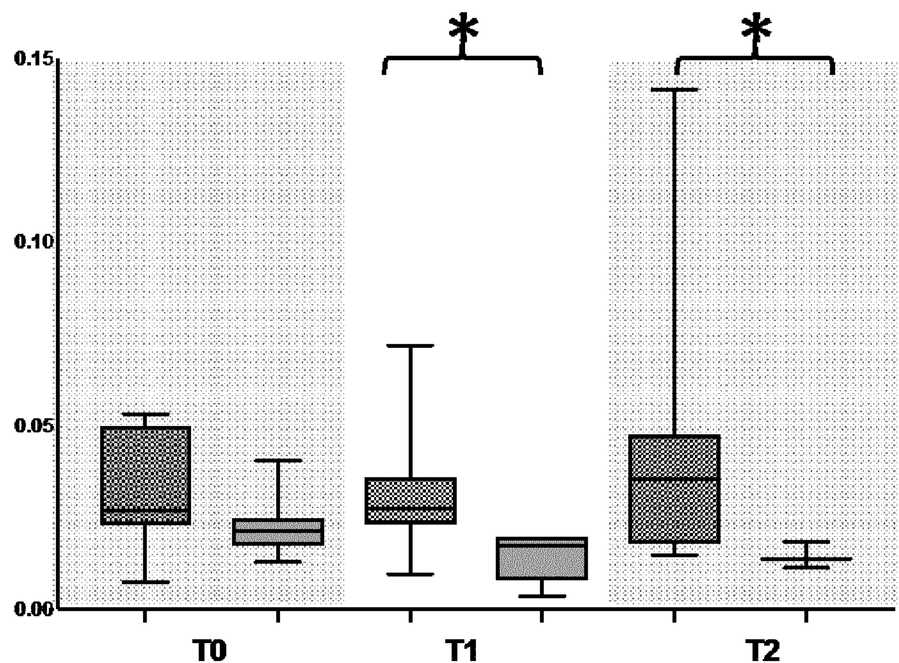
[Figure 35.2 A]
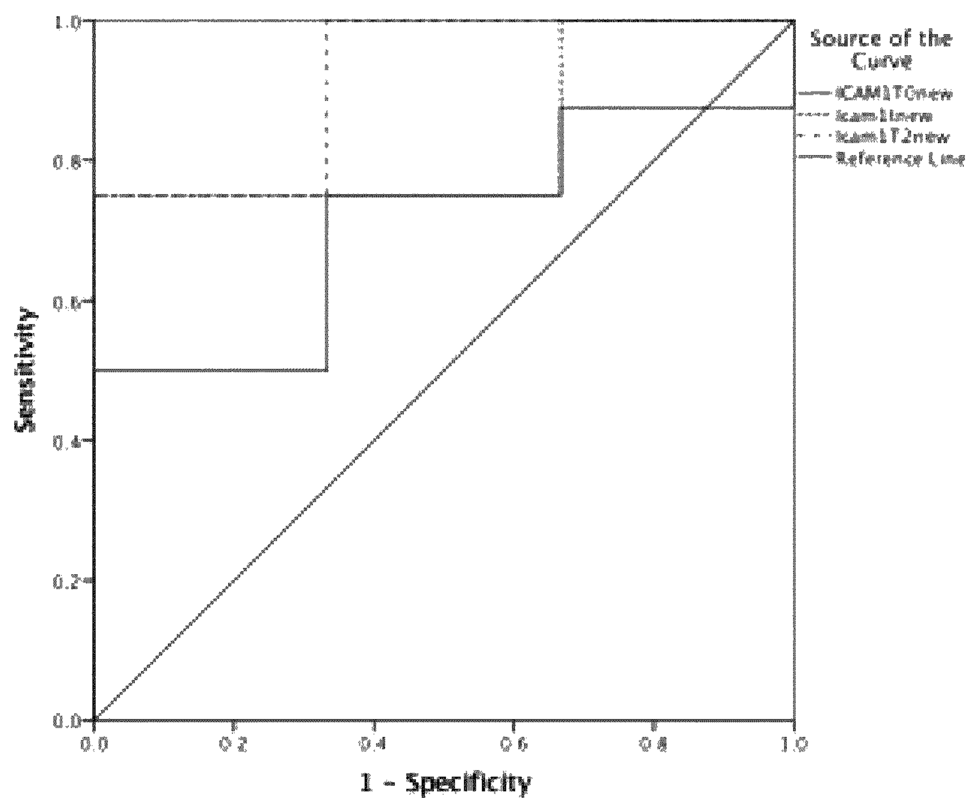
[Figure 35.2B]

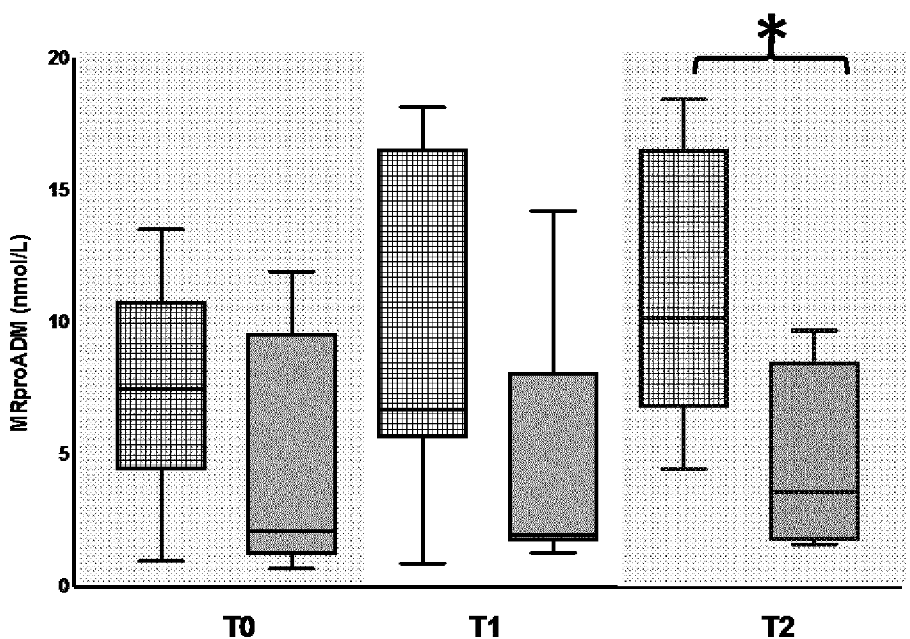
[Figure 36A]
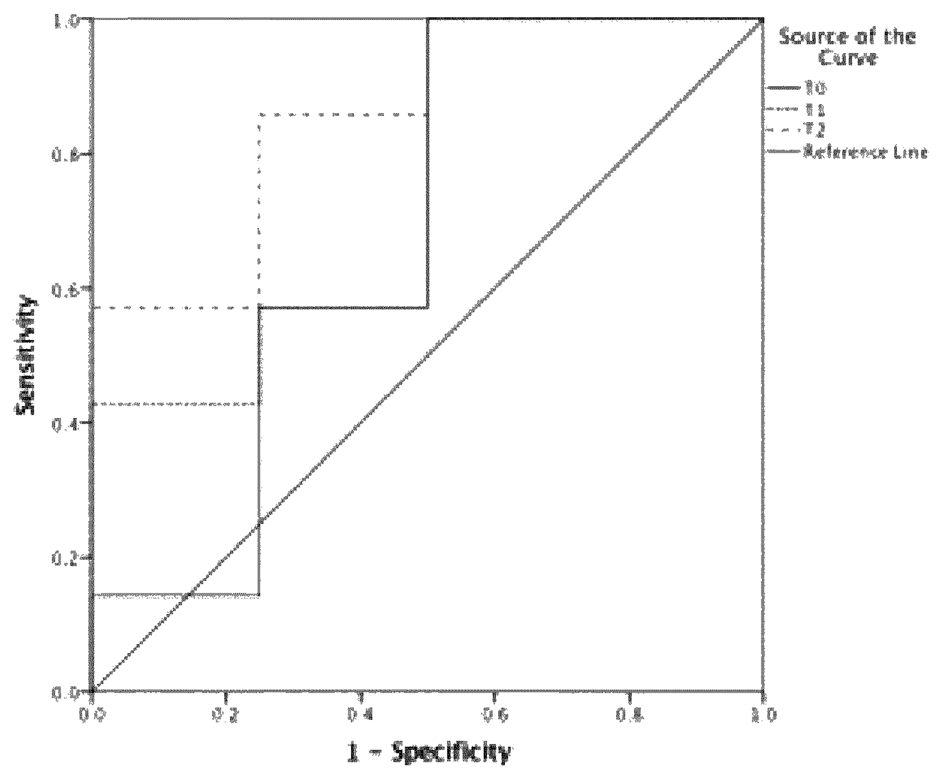
[Figure 36B]

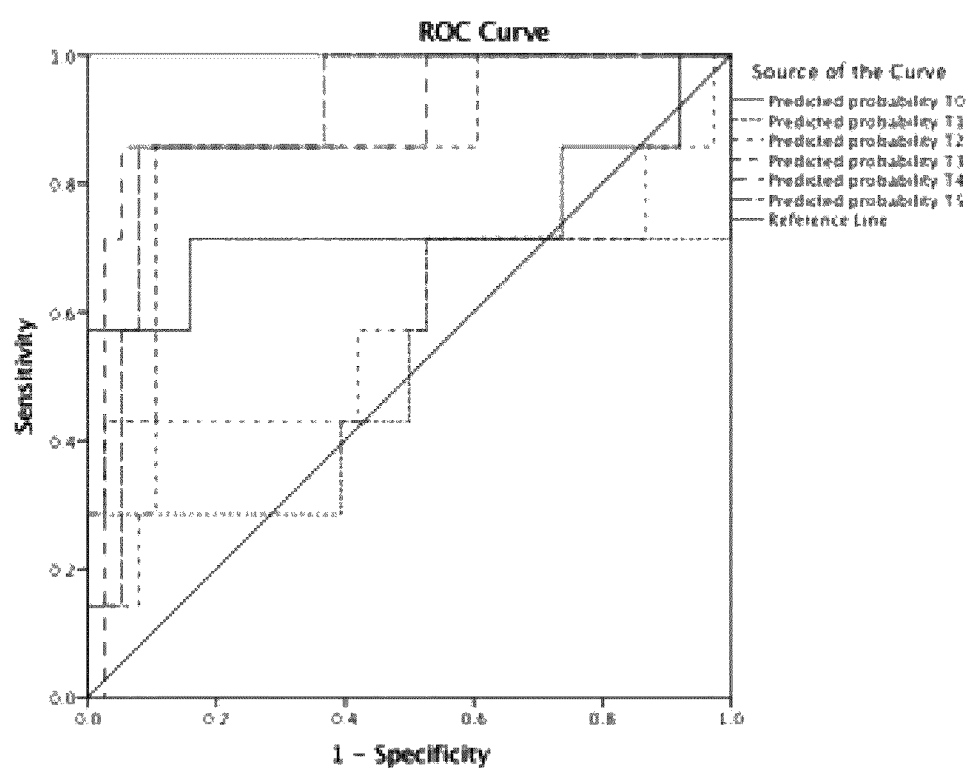
[Figure 37]

[Figure 38A]
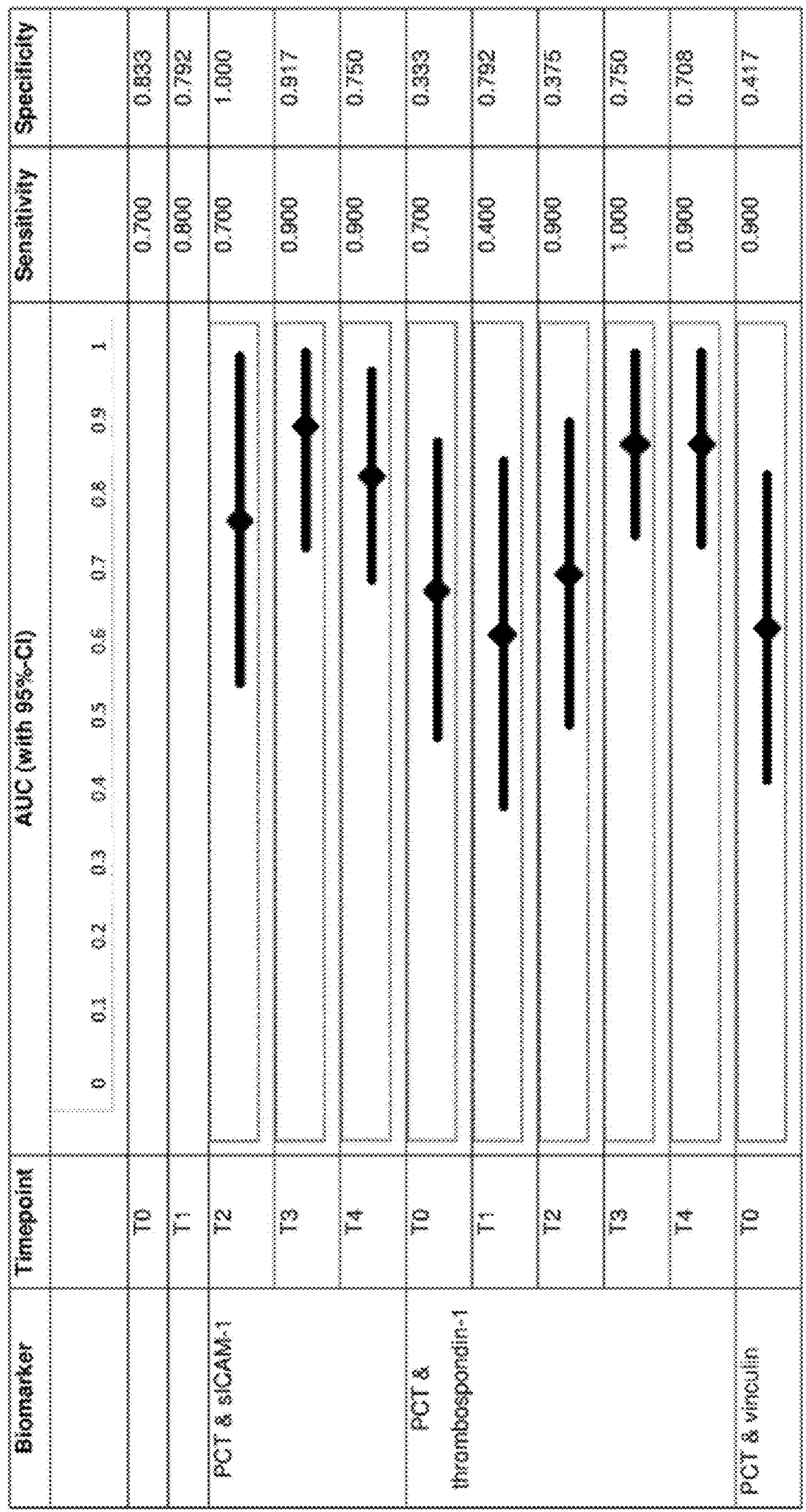
| Biomarker | Timepoint | AUC (with 95%-CI) | Sensitivity | Specificity |
|---|---|---|---|---|
| | | 0 0.1 0.2 0.3 0.4 0.5 0.6 0.7 0.8 0.9 1 | | |
| | T0 | | 0.700 | 0.833 |
| | T1 | | 0.800 | 0.792 |
| PCT & sICAM-1 | T2 | | 0.700 | 1.000 |
| | T3 | | 0.900 | 0.917 |
| | T4 | | 0.900 | 0.750 |
| PCT & thrombospondin-1 | T0 | | 0.700 | 0.333 |
| | T1 | | 0.400 | 0.792 |
| | T2 | | 0.900 | 0.375 |
| | T3 | | 1.000 | 0.750 |
| | T4 | | 0.900 | 0.708 |
| PCT & vinculin | T0 | | 0.900 | 0.417 |

[Figure 38B]
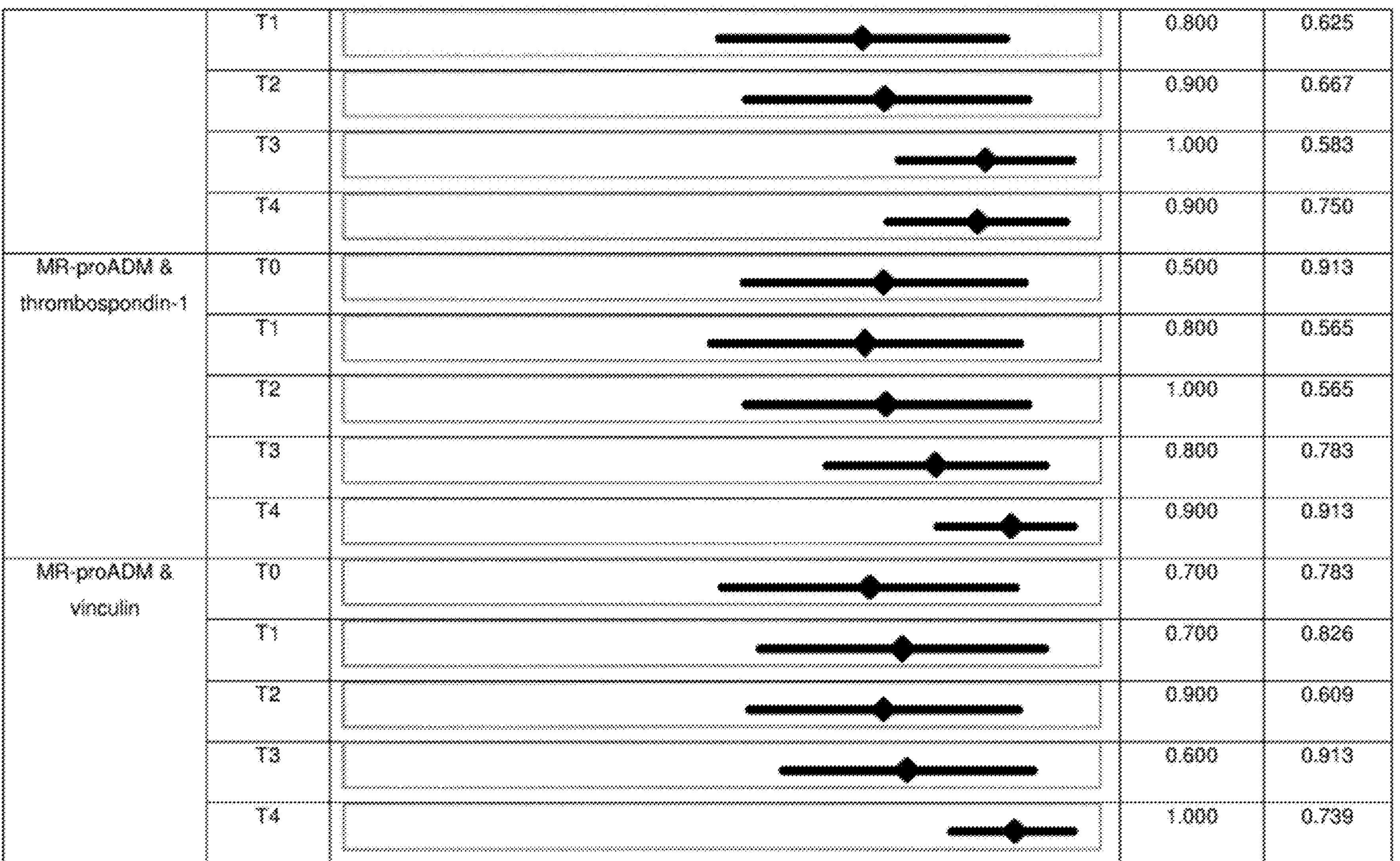

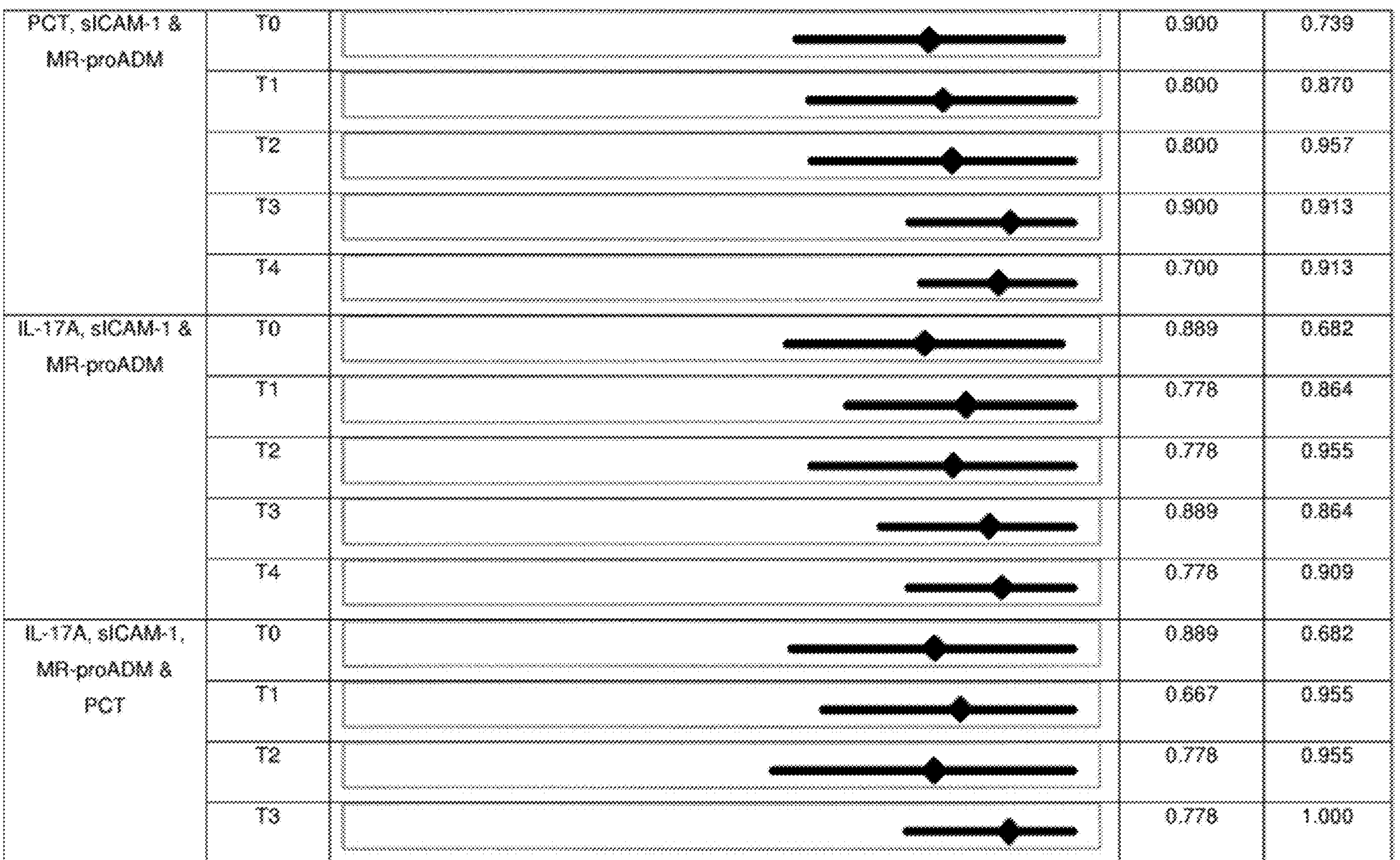
[Figure 38C]
PCT, sICAM-1 & MR-proADM
T0 0.900 0.739
T1 0.800 0.870
T2 0.800 0.957
T3 0.900 0.913
T4 0.700 0.913
IL-17A, sICAM-1 & MR-proADM
T0 0.889 0.682
T1 0.778 0.864
T2 0.778 0.955
T3 0.889 0.864
T4 0.778 0.909
IL-17A, sICAM-1, MR-proADM & PCT
T0 0.889 0.682
T1 0.667 0.955
T2 0.778 0.955
T3 0.778 1.000

BIOMARKERS FOR THE DIAGNOSIS OF INVASIVE FUNGAL INFECTIONS

CROSS REFERENCE TO RELATED APPLICATIONS

This is the U.S. National Stage of International Application No. PCT/EP2019/064198, filed May 31, 2019, which claims the benefit of European Application No. 18175538.0, filed Jun. 1, 2018.

The present invention relates to a method for the diagnosis, prognosis, risk assessment, risk stratification, monitoring, therapy guidance and/or therapy control of a fungal infection, in particular invasive fungal infections (IFI) (synonym: invasive fungal diseases (IFD)) and/or the ruling in or ruling out of an invasive fungal infection and/or the differentiation of a fungal colonization vs. an invasive fungal infection in a subject. The method is particularly useful when the subject has an increased risk of getting or having a fungal infection and/or the subject is in a critical disease state, particularly has an existing bacterial or viral infection and/or a state of sepsis, particularly a septic shock.

The invention relates to a method that comprises determining the level of at least one marker or a partial peptide or fragment thereof from the group of ICAM1, AHSG, CPN1, FABP1, HRG, PIGR, RAP1, THBS1, VCL and ET-1. Furthermore, the invention relates to a diagnostic assay and a kit for carrying out the method.

BACKGROUND OF THE INVENTION

Invasive fungal infections (IFI) have alarming mortality rates (e.g. up to 90% mortality in invasive aspergillosis), not least because of a delay in diagnosis and appropriate therapeutic actions.

The term IFI or IFD is used only to characterize systemic, generalized, deep-seated, visceral and severe, life-threatening fungal infections and/or a multifocal infection, in contrast to superficial, local, particularly unifocal, benign, self-limiting fungal presence.

According to the present invention, the term "severe infection" refers to a fungal infection that can be differentiated from non-severe fungal infections, e.g., by using scoring systems known in the art. These scoring systems are used, e.g., in the decision whether an antifungal treatment should be initiated or not. For example, the so-called "*Candida* score" is obtained in order to assist clinicians to select patients who will benefit from early antifungal administration (Léon et al., Crit Care Med 2006 14(3): 730-736). Thereby, the *Candida* score takes into account relevant risk factors of candidiasis, for example, but not limited to factors including length of ICU stay, patient category, surgery on ICU admission, total parenteral nutrition, extra renal depuration procedures, unifocal or multifocal colonization, and severe sepsis. The discrimination of severe versus non-severe fungal infection based on the *Candida* score can then be evaluated by the area under the receiver operating characteristics (ROC) curve and the 95% confidence interval. A cut-off value which is dependent from the sensitivity and specificity in the validation set of the ROC analysis can be selected in order to differentiate between severe and non-severe infections.

In principle, one has therefore to differentiate between a mere colonization and an invasive fungal infection (IFI) with quite different clinical manifestations and consequences (Hof H., Int. J. Infect. Dis. 2010 14(6): e458-e459).

The incidence of severe fungal infections is growing with the increasing number of elderly and immunocompromised patients (e.g. transplant recipients, patients with hematologic malignancy, HIV, patients using steroids and antibiotics) which have a higher risk of getting severe fungal infections, especially IFI. Another or additive problem is the occurrence of mixed infections e.g. patients with primary bacterial or viral infection and at least a second invasion of pathogenic agents e.g. fungal agents, that can dramatically shift from a manageable infection into a serious and complex multi-infection with negative consequences regarding outcome and mortality risk. Clinicians often have the problem to diagnose a fungal infection. An additional problem can be the onset of a second infection that can be critical for immune compromised patients with a risk of getting infections, especially fungal infections, but also immune-competent patients, having a normal functional immune system. An improved management of these groups of patients, especially the differentiation of uncritical colonization and pathogenic serious nosocomial or iatrogenic as well as natural fungal infections is needed. Moreover, an effective therapy monitoring or therapeutic guidance is essential to avoid an overtreatment or wrong focus in patient management regarding uncritical colonization that is not easy to distinguish with the known testing methods like polymerase chain reaction (PCR) techniques or other pathogen-specific detections.

Current diagnostic techniques such as fungal cultures, pathogen specific detection e.g. by determining β-D-glucan or (galacto)mannan or imaging (computed tomography, chest X-ray) are time-consuming, not broadly available and/or lack accuracy making invasive fungal infections one of the most frequently missed diagnoses that can consequently imply serious outcome, in particular in the intensive care unit (ICU) or in patients with a risk of getting serious fungal infections, especially invasive fungal infections. Especially in patients suffering from fungemia, diagnostic weaknesses may contribute substantially to this alarming mortality. Only a small part of affected patients show positive blood-cultures and fungal growth on culture media is known to be very slow. Accordingly, several studies have shown, that IFI/IFD are the most frequently missed diagnoses in critically ill patients (Combes A. et al. Arch Intern Med. 2004 164:389-392). Hence, often a life-saving antifungal therapy is either missed, or initiated with a minimum delay of 2 to 3 days (Abe M. et al et al. Clin Microbiol Infect. 2016 22:576). Such a delay is known to be associated with a bad outcome, especially an increased mortality.

Therefore, there is a need for presenting a reliable diagnosis of IFI/IFD, or for undertaking (risk) stratification, particularly with regard to further clinical decisions and, in particular, with regard to the degree of severity of fungal infections, in particular IFI/IFD associated with sepsis or septic shock.

In summary, there is a clear medical need to improve the challenging diagnosis of invasive fungal infections for early initiation of antifungal treatment and its monitoring.

Although, the group of fungal infected patients seems to be small, the number of IFI/IFD is growing up due to an increasing number of immunocompromised patients, a more aggressive surgical therapy in older patients with relevant co-morbidities and an increasing number of patients suffering from oncologic diseases (Bassetti M. et al. BMC Infect Dis. 2006 6:21). Within this context different fungal species seem to be most relevant: *Candida* spp. (*C. albicans, C. glabrata, C. krusei*), *Aspergillum* ssp. (*A. fumigatus*), *Saccharomyces* spp. (*S. cerevisiae*), *Hansenula* spp. (*H.*

*anomala*), *Diplodocus* spp. (*D. capitatus*), *Mucor* spp., *Rhizopus* spp. (*R. microspores*), *Scedosporium* spp., *Trichosporon* spp. (*T. asahii*), Zygomycosis, *Fusarium* spp., *Cryptococcus* spp. (Lichtenstern et al. Mycoses. 2015 58:399-407; Low et al. FI000 Medicine Reports. 2011 3:14; Badiee et al. Indian J of Med Res. 2014 February 139(2); Muskett et al. Critical Care. 2011, 15:R287; Patterson T. Transactions of the American clinical and climatological association. 2011 vol. 122; Shahzad et al. Mol Med Ther. 2012 1:1; Zaragoza et al. Adv Sepsis. 2008 6(3)).

Sepsis-associated mortality in patients suffering from IFI/IFD is known to be high, amounting up to 42% for *Candida* spp. and even much higher for *Aspergillus* spp. (Shorr A F et al. (. Crit Care Med. 2009 37:2519-2526; Trof R J et al. Intensive Care Med. 2007 33:1694-1703).

Sepsis is generally caused by a dysregulated host response to infection (Singer M. et al. Jama. 2016 315:801-81), is most frequently caused by bacteria, whereas fungal or viral infections are less common (Eggimann P. et al. Lancet Infect Dis. 2003 3:685-702). Accordingly, fungemia is only present in 3% of unselected sepsis cases (Eggimann (supra)). Contrariwise, fungi are one of the most isolated species recovered from abdominal foci in peritonitis and numerous patients develop fungal colonization during their hospital stay (Eggimann (supra)).

ICAM1, THBS1, CPN1, PIGR, HRG, AHSG, ET-1 and PCT are already known in the field of infection (WO2013083781; Kidane Y H et al. BMC Microbiol 2013; Orozco A S et al. Infect Immun 2000; Martin-Manso G et al. PLoS One 2012; Rydengard V et al. PLoS Pathog 2008; Toyotome T et al. Int J Med Microbiol. 2012), but are not revealed for the improved diagnosis, differentiation, risk assessment, monitoring and therapeutic guidance in fungal infections, especially for the differentiation of harmless fungal colonization or non-fungal infection with serious fungal infections, especially invasive fungal infections. The present invention shows surprising findings of the biomarkers for the clinical use.

DESCRIPTION OF THE INVENTION

The invention relates to an improved diagnosis, risk assessment, therapeutic guidance and monitoring of severe fungal infections, in particular invasive fungal infections as well as the differentiation of non-critical fungal colonization or non-fungal infection with serious invasive fungal infections. The method of the invention is based on the detection of intercellular adhesion molecule 1 (ICAM1), alpha-2-HS-glycoprotein (AHSG), carboxypeptidase N catalytic chain 1 (CPN1), fatty-acid binding protein 1 (FABP1), histidine rich glycoprotein (HRG), polymeric immunoglobulin receptor (PIGR), ras-related protein 1 (RAP1), thrombospondin-1 (THBS1), vinculin (VCL) and/or endothelin 1 (ET-1) in a sample of the subject to be assessed. ICAM1, AHSG, CPN1, FABP1, HRG, PIGR, RAP1, THBS1, VCL and ET-1 are herein referred as the biomarkers of the present invention. ICAM1 is the preferred biomarker used herein in all aspects of the invention.

[1] Hence, in one aspect, the invention relates to a method for the diagnosis, prognosis, risk assessment and/or therapy monitoring of a fungal infection in a subject, comprising the step of determining the level of at least one biomarker selected from the group consisting of ICAM1, AHSG, CPN1, FABP1, HRG, PIGR, RAP1, THBS1, VCL and ET-1 in a sample of said subject, wherein said level of the at least one biomarker is indicative for the presence, the risk of getting, severity and/or type of fungal infection in said subject. [2] The invention also relates to a method of [1], wherein the method is for the diagnosis of an invasive fungal infection in a subject, comprising the step of determining the level of at least one biomarker selected from the group consisting of ICAM1, AHSG, CPN1, FABP1, HRG, PIGR, RAP1, THBS1, VCL and ET-1 In a sample of said subject, wherein said level of the at least one biomarker is indicative for an invasive fungal infection in said subject, in particular as opposed to a fungal colonization or no fungal infection;

Thus, in one aspect, the invention relates to a method for the diagnosis of an invasive fungal infection in a subject, comprising the step of determining the level of at least one biomarker selected from the group consisting of ICAM1, AHSG, CPN1, FABP1, HRG, PIGR, RAP1, THBS1, VCL and ET-1 in a sample of said subject, wherein said level of the at least one biomarker is indicative for an invasive fungal infection in said subject, particularly as opposed to a fungal colonization or no fungal infection. [3] The invention also relates to a method of [1], wherein the method is for assessing whether a subject is in a need and/or the adjustment of an anti-fungal treatment, wherein the method comprises the step of determining the level of at least one biomarker selected from the group consisting of ICAM1, AHSG, CPN1, FABP1, HRG, PIGR, RAP1, THBS1, VCL and ET-1 or fragments thereof in a sample of said subject, wherein the level of the at least one biomarker is indicative of a need of said subject to receive anti-fungal treatment.

Thus, in one aspect, the invention relates to a method for assessing whether a subject is in a need and/or the adjustment of an anti-fungal treatment, wherein the method comprises the step of determining the level of at least one biomarker selected from the group consisting of ICAM1, AHSG, CPN1, FABP1, HRG, PIGR, RAP1, THBS1, VCL and ET-1 or fragments thereof in a sample of said subject, wherein the level of the at least one biomarker is indicative of a need of said subject to receive anti-fungal treatment. The treatment may comprise the administration of one or more anti-fungal agents. Herein, the invasive fungal infection is most preferably a systemic fungal infection, in particular a fungemia as will be outlined below in more detail.

Hence, the present invention also relates to an antifungal agent for use in treating an invasive fungal infection in a subject, wherein said antifungal agent is administered to said subject if an invasive fungal infection has been diagnosed or predicted in said subject by a method according to the invention. Similarly, the present invention relates to a method of treating or preventing an invasive fungal infection comprising (I) determining whether the subject to be treated is in need of a treatment with an anti-fungal agent using a diagnostic method according to the invention and (ii) if the subject is determined to require such treatment, administering an antifungal agent to said subject.

In the present invention, new host response biomarkers have been tested by immunoassay techniques and exemplarily shown by mass spectrometry (MS) In serial plasma samples of septic shock patients. The present invention is particularly useful for subjects that are at risk of getting or having an invasive fungal infection for instance in septic patients or patients after transplantation of fluid or solid tissue, in particular liver transplant patients. The present examples show the validity of the invention in different subgroups of patients with risk of getting a serious fungal infection. The method of the invention can be generally used in patients with an increased risk of getting a serious fungal infection, in particular an invasive fungal infection. The biomarkers ICAM1, AHSG, CPN1, FABP1, HRG, PIGR, RAP1, THBS1, VCL and ET-1 demonstrate diagnostic potential for early and accurate differentiation between invasive fungal infections on one hand and fungal colonization and/or no fungal infections on the other hand. It is also surprising, that the diagnostic value could be further improved by a combination of further biomarkers or parameters associated with infectious disease and deterioration of general condition, especially for monitoring of patients, especially with risk of getting a fungal infection or having a fungal infection or risk of getting or having a mixed infection and the therapeutic guidance.

An early and specific diagnosis of invasive fungal infections by these new biomarkers enables timely initiation of life-saving antifungal therapy. Similarly, the biomarkers of the present invention allow ruling-out serious (invasive) fungal infection and enable cessation of prophylactic antifungal treatment with its potential adverse effects (toxicity to the patient, drug-resistance) where possible.

The biomarkers of the present invention also allow ruling-in serious fungal (invasive) infection and are indicative for the need of anti-fungal drug administration with its potential to reduce the risk of getting adverse events or reduce the mortality risk. The assessment of patients can be improved by combining the biomarkers of the present invention with further known markers or parameters for detecting fungal infections e.g. fungal culture, detection methods for fungal specific epitopes but are not very effective or inappropriate to differentiate between a fungal colonization and a serious invasive fungal infection.

Hence, in one aspect, the present invention relates to a method for in vitro diagnosis, prognosis, differentiation, monitoring, therapeutic guidance and/or risk stratification of fungal infections, in particular IFI/IFD associated with sepsis or septic shock, wherein a determination of at least one biomarker selected from the group consisting of ICAM1, AHSG, CPN1, FABP1, HRG, PIGR, RAP1, THBS1, VCL and ET-1 (or combination thereof, i.e. a panel or cluster of biomarkers), is carried out in a sample from a patient to be examined. In a particular aspect, the determination of ICAM1 (either alone or as part of a marker panel or marker cluster), is carried out in a sample from a patient to be examined.

The determination of the levels of the biomarkers of the present invention can also be performed by detecting respective fragments or precursors (e.g. in the case of ET-1: proET-1) or—where applicable—fragments of the precursors of the biomarkers. In the case of RAP1 including RAP1A, RAP1B and RAPBL (RAP "B-like"), several variants exist which can all be detected in the context of the present invention.

In the following exemplary amino acid sequences for the biomarkers of the present invention are given: ICAM1 (SEQ ID NO:1), AHSG (SEQ ID NO:2), CPN1 (SEQ ID NO:3), FABP1 (SEQ ID NO:4), HRG (SEQ ID NO:5), PIGR (SEQ ID NO:6), RAP1 (as RAP1A SEQ ID NO:7), RAP1B (SEQ ID NO: 8) or RAP1BL (SEQ ID NO: 9)), THBS1 (as isoform 1 (SEQ ID NO:10) or isoform 2 SEQ ID NO: 11)), VCL (as isoform 1 (SEQ ID NO:12), isoform 2 (SEQ ID NO: 13) or isoform 3 (SEQ ID NO: 14)) or ET-1 (as pre-pro-ET-1 (SEQ ID NO:15), pro-ET-1 (SEQ ID NO 16), ET-1 (SEQ ID NO: 17), CT-ET-1 (SEQ ID NO: 18) or Big-ET-1 (SEQ ID NO: 19)). The biomarkers of the present invention and fragments thereof do not necessarily need to have the exact sequences given in these exemplary SEQ ID NOs because of normal variability within patients genome and expressions patterns in human blood (Whitney et al. PNAS. 2003 100(4):1896-1901). Hence, also biomarkers having at least 90%, at least 95%, at least 97%, at least 98% or at least 99% identity are biomarkers according to the present invention. Therefore, whenever biomarkers of the present invention are mentioned herein, also distinct fragments thereof (having at least a length of 6 amino acid residues, preferably at least a length of 12 amino acid residues) can be detected and determined for the diagnostic and prognostic purposes of the present invention. Such fragments may be measured in quantitative selected reaction monitoring (SRM) assays by LC-MS/MS technology (TSQ Quantiva mass spectrometer (MS); ThermoFisher Scientific). Examples of amino acids of such fragments of the markers ICAM1, AHSG, CPN1, FABP1, HRG, PIGR, RAP1, THBS1, VCL are provided by the underlined SEQ ID NOs 1 to 14 and by SEQ ID NOs 21 to 29 (selected reaction monitoring (SRM) peptide of ICAM1 (SEQ ID NO: 21), SRM peptide of AHSG (SEQ ID NO: 22), SRM peptide of CPN1 (SEQ ID NO: 23), SRM peptide of FABP1 (SEQ ID NO: 24), SRM peptide of HRG (SEQ ID NO: 25), SRM peptide of PIGR (SEQ ID NO: 26), SRM peptide of RAP1 (SEQ ID NO: 27), SRM peptide of THBS1 (SEQ ID NO: 28) and SRM peptide of VCL (SEQ ID NO: 29).

For the reasons discussed herein above, it is particularly advantageous that a reliable diagnosis, prognosis and/or risk stratification can take place by means of the method according to the invention. The method according to the invention allows clinical decisions that lead to a more rapid diagnosis of fungal infections in critically ill patients. The method according to the invention allows clinical decisions that lead to a more rapid diagnosis of the IFI/IFD, in particular IFI/IFD associated with sepsis or septic shock. Such clinical decisions may also lead to further treatment using medications for the therapy or prophylaxis of the IFI/IFD, in particular IFI/IFD associated with sepsis or septic shock.

Appropriate treatment requires early diagnosis and differentiation of IFI/IFD, in particular IFI/IFD associated with sepsis or septic shock. Since clinical symptoms in IFI/IFD are unspecific and recent diagnostic tools for the detection of fungal pathogens are associated with relevant weaknesses, the differentiation and delineation from other infectious diseases caused by e.g. bacterial or viral pathogens, as well as the identification of IFI/IFD, e.g. IFI/IFD associated with sepsis or septic shock are essential. The difficulty is the identification of a fungal pathogen and/or the ruling out of a fungal pathogen, because clinical symptoms are unspecific (e.g. comparable to non-fungal based infections like bacteria or virus). The current diagnostic tools incl. clinical microbiology are associated with relevant weaknesses.

Such clinical decisions enabled by the present invention allow the therapy by means of medications for the treatment or prevention of IFI/IFD, in particular IFI/IFD associated with patients at risk of having or getting a fungal infection, such as patients with sepsis or septic shock or immunocompromised patients such as patients after transplantation e.g. liver transplantation. In such therapy at least one antifungal agent is used, like polyene antifungal drugs (e.g. (liposomal) amphotericin B), echinocandins (e.g. caspofungin, anidulafungin, micafungin), azole antifungal drugs (e.g. fluconazole, itraconazole, posaconazole, voriconazole), allylamine and morpholine antifungal drugs, antimetabolite antifungal drugs (e.g. 5-fluorocytosine) as well as other known anti-fungal substances or variants and/or combinations thereof.

In another preferred aspect of the method according to the invention, diagnosis, prognosis and/or risk stratification take place for assessing the course of a fungal infection, in particular IFI/IFD in patients being at risk of having or getting a fungal infection, e.g. patients with sepsis or septic shock.

In another aspect of the method according to the invention, the method further comprises the diagnosis and/or risk stratification for the course and/or the severity of a fungal infection, preferably invasive fungal infection, in the sample of the patient as an accompaniment to a therapy; wherein said therapy is adjusted comprising administration of appropriate anti-infectious therapeutic agents, such as common anti-fungal therapeutic agents.

In other words, diagnosis and/or risk stratification take place for the course of IFI/IFD as an accompaniment to therapy and to adjust therapeutic treatment such as for example mechanical ventilation, renal replacement therapy or medications like antifungals, antibiotics, antiviral drugs, statins, chemotherapy or immuno-modulating drugs.

The adjustment of a therapeutic treatment may also include the decision whether the subject's treatment is continued, adapted or stopped. For example, the adjustment of the therapeutic treatment may be whether the subject is kept on the intensive care unit (ICU) or emergency department (ED) or whether it is released. As another example, the adjustment of the therapeutic treatment may be whether the dosage of an anti-fungal treatment is adapted and/or whether the treatment is stopped or whether an additional treatment is initiated over an existing treatment, in particular a change of anti-fungal agent or a combination of different anti-fungal agents.

In the context of the present invention, the level of said biomarker(s) may be determined after the subject is diagnosed of having or getting a fungal infection or the subject is diagnosed to be in a critical disease state and/or after admission of the subject to a medical site, preferably into ICU or hospital.

In this context, the level of said biomarker(s) determined for the diagnosis, prognosis, risk assessment and/or therapy monitoring of a fungal infection in a subject is indicative for the presence, the risk of getting, severity and/or type of fungal infection in said subject by the minimum at least fold change value of the biomarker level compared to control as provided by the fold-changes of the present invention, preferably as provided by the fold-changes values in Tables 2, 8 and 17.

In one aspect, the level of the at least one biomarker may be compared to a reference value of said at least one biomarker, wherein said reference value is derived from the level of the respective biomarker in (a) sample(s) of a reference subject or a population of reference subjects without said invasive fungal infection, and when the biomarker is ICAM1, a level of at least the 1.1 fold is indicative for the presence of an invasive fungal infection and/or differentiation between invasive fungal infection and no invasive fungal infection in the subject; when the biomarker is FABP1, a level of at least the 1.4 fold is indicative for the presence of an invasive fungal infection and/or differentiation between invasive fungal infection and no invasive fungal infection in the subject; when the biomarker is PIGR, a level of at least the 1.3 fold is indicative for the presence of an invasive fungal infection and/or differentiation between invasive fungal infection and no invasive fungal infection in the subject; when the biomarker is ET-1, a level of at least the 1.1 fold is indicative for the presence of an invasive fungal infection and/or differentiation between invasive fungal infection and no invasive fungal infection in the subject; when the biomarker is AHSG, a level of at least the 0.7 fold is indicative of the presence of an invasive fungal infection and/or differentiation between invasive fungal infection and no invasive fungal infection in the subject; when the biomarker is CPN1, a level of at least the 0.9 fold is indicative for the presence of an invasive fungal infection and/or differentiation between invasive fungal infection and no invasive fungal infection in the subject; when the biomarker is HRG, a level of at least the 0.8 fold is indicative of the presence of an invasive fungal infection and/or differentiation between invasive fungal infection and no invasive fungal infection in the subject; when the biomarker is RAP1A, a level of at least the 0.7 fold is indicative of the presence of an invasive fungal infection and/or differentiation between invasive fungal infection and no invasive fungal infection in the subject; when the biomarker is THBS1, a level of at least the 0.98 fold is indicative of the presence of an invasive fungal infection and/or differentiation between invasive fungal infection and no invasive fungal infection in the subject.

In another aspect, the level of the at least one biomarker may be compared to a reference value of said at least one biomarker, wherein said reference value is derived from the level of the respective biomarker in (a) sample(s) of a reference subject or a population of reference subjects which has/have a fungal colonization (but of course no IFI), and, when the biomarker is ICAM1, a level of at least the 1.1 fold is indicative for the presence of an invasive fungal and/or differentiation between (invasive) fungal infection and no invasive fungal infection or fungal colonization infection in the subject; when the biomarker is PIGR, a level of at least the 1.1 fold is indicative for the presence of an invasive fungal infection and/or differentiation between (invasive) fungal infection and no invasive fungal infection or fungal colonization in the subject; when the biomarker is AHSG, a level of at least the 0.7 fold is indicative of the presence of an invasive fungal infection and/or differentiation between (invasive) fungal infection and no invasive fungal infection or fungal colonization in the subject; when the biomarker is CPN1, a level of at least the 0.9 fold is indicative for the presence of an invasive fungal infection and/or differentiation between (invasive) fungal infection and no invasive fungal infection or fungal colonization in the subject; when the biomarker is HRG, a level of at least the 0.7 fold is indicative of the presence of an invasive fungal infection and/or differentiation between (invasive) fungal infection and no invasive fungal infection or fungal colonization in the subject; when the biomarker is RAP1A, a level of at least the 0.7 fold is indicative of the presence of an invasive fungal infection and/or differentiation between (invasive) fungal infection and no invasive fungal infection or fungal colonization in the subject; when the biomarker is THBS1, a level of at least the 0.8 fold is indicative of the presence of an invasive fungal infection and/or differentiation between (invasive) fungal infection and no invasive fungal infection or fungal colonization in the subject; when the biomarker is VCL, a level of at least the 0.9 fold is indicative of the presence of an invasive fungal infection and/or differentiation between (invasive) fungal infection and no invasive fungal infection or fungal colonization in the subject.

In another aspect, the level of the at least one biomarker may be compared to a reference value of said at least one biomarker, wherein said reference value is derived from the level of the respective biomarker in (a) sample(s) of a reference subject or a population of reference subjects without a fungal colonization, and, when the biomarker is ICAM1, a level of at least the 1.1 fold is indicative for the presence of an invasive fungal infection diagnosis and/or differentiation between (invasive) fungal infection and fungal colonization in the subject; when the biomarker is FABP1, a level of at least the 1.1 fold is indicative for the presence of an invasive fungal infection diagnosis and/or differentiation between (invasive) fungal infection and fungal colonization in the subject; when the biomarker is PIGR, a level of at least the 1.1 fold is indicative for the presence of an invasive fungal infection diagnosis and/or differentiation between (invasive) fungal infection and fungal colonization in the subject; when the biomarker is AHSG, a level of at least the 0.9 fold is indicative of the presence of an invasive fungal infection diagnosis and/or differentiation between (invasive) fungal infection and fungal colonization in the subject; when the biomarker is HRG, a level of at least the 0.9 fold is indicative of the presence of an invasive fungal infection diagnosis and/or differentiation between (invasive) fungal infection and fungal colonization in the subject; when the biomarker is RAP1A, a level of at least the 0.8 fold is indicative of the presence of an invasive fungal infection diagnosis and/or differentiation between (invasive) fungal infection and fungal colonization in the subject; when the biomarker is THBS1, a level of at least the 0.9 fold is indicative of the presence of an invasive fungal infection diagnosis and/or differentiation between (invasive) fungal infection and fungal colonization in the subject; when the biomarker is VCL, a level of at least the 0.8 fold is indicative of the presence of an invasive fungal infection diagnosis and/or differentiation between (invasive) fungal infection and fungal colonization in the subject.

In a preferred embodiment of the present invention, the level of said biomarker(s) may for instance be determined between day 0 and 28, preferably between day 0, 1, 2, 7, 14 or 21 and day 28, after the subject is diagnosed of having or getting a fungal infection or the subject is diagnosed to be in a critical disease state and/or after admission of the subject to a medical site such as into an ICU or a hospital. In certain instances, the level of said biomarker may determined between day 0 and day 14 after the subject is first diagnosed of having or getting a fungal infection and/or after the subject is first diagnosed to be in a critical disease state and/or after admission of the subject into a medical site such as an intensive care unit (ICU) or a hospital.

For example in one aspect of the present invention (a) the level of ICAM1 is determined between day 0 and day 14; preferably between day 2 and day 14, more preferably between day 7 and 14 and most preferably on day 7;

(b) the level of CPN1 is determined between day 1 and day 14, preferably on day 1, day 2 and/or day 14, more preferably between day 1 and day 2, most preferably on day 2;

(c) the level of HRG is determined between day 14 and day 28, preferably on day 14 and/or day 28 and more preferably on day 14;

(d) the level of THBS1 is determined between day 14 and day 28; preferably on day 14 and/or day 28, more preferably on day 14;

(e) the level of RAP1 is determined between day 14 and day 28; preferably on day 14 and/or day 28; more preferably on day 14, (f) the level of AHSG is determined between day 14 and day 28, preferably on day 14 and 28 and more preferably on day 14;

(g) the level of VCL is determined between day 1 and day 28, preferably between day 1 and day 14; more preferably on day 1 or day 2 and even more preferably on day 2;

(h) the level of FABP1 is determined between day 7 and day 14, preferably on day 7; and/or (i) the level of ET-1 is determined on day 0;

after the subject is diagnosed of having or getting a fungal infection or the subject is diagnosed to be in a critical disease state and/or after admission of the subject to am medical site such as into ICU or hospital.

In the context of the methods of the present invention, said level of the at least one biomarker may be compared to a reference value of said at least one biomarker, wherein (i) when the biomarker is selected from the group consisting of ICAM1, FABP1, PIGR and ET-1, a level above said reference value in the sample is indicative for the presence of an invasive fungal infection in the subject; or (ii) when the biomarker is selected from the group consisting of AHSG, CPN1, HRG, RAP1, THBS1 and VCL, a level below said reference value in the sample of the subject is indicative for the presence of an invasive fungal infection in the subject.

Typically, said reference value is derived from the level of the respective biomarker in (a) sample(s) of a reference subject or a population of reference subjects without said invasive fungal infection.

Hence, said reference value may be derived from the level of the respective biomarker in (a) sample(s) of a reference subject or a population of reference subjects without a fungal colonization. Alternatively, said reference value may derived from the level of the respective biomarker in (a) sample(s) of a reference subject or a population of reference subjects which has/have a fungal colonization (but of course no IFI). Said reference value may also be derived from the level of the respective biomarker in (a) sample(s) of a healthy reference subject or a population of healthy reference subjects.

The subject to be diagnosed may have previously been diagnosed as having a fungal colonization. In such a situation, the reference level may very well be derived from the level of the respective biomarker in (a) sample(s) of a reference subject or a population of reference subjects which has/have a fungal colonization (but of course no IFI).

In general, as will be explained herein below in more detail, the decisive threshold value selected for the method of the invention (either in terms of absolute biomarker level(s) or expressed as a factor of the reference level), may e.g. depend on the exact purpose of the method, or the reference subject or population of reference subjects selected. As in many diagnostic methods, thresholds or cut-off values normally do not provide an absolute "black and white" separation of subjects. The skilled person is aware that their selection may depend on the balance of false negatives and false positives (i.e. the sensitivity and selectivity of the assay) that is acceptable for a specific purpose. Moreover, absolute threshold values may depend on the measuring method- (e.g. immunoassay vs. other immunoassay or vs. mass spectrometry (MS)). The person skilled in the art knows that a change of the measuring system can implicate different absolute threshold values based e.g. on the use of other assay components or detection systems. In other words, the absolute threshold may depend on the actual assays used. The definition of the optimal threshold can be calculated with the help of specialized software systems. The absolute threshold levels disclosed herein are therefore specific for the underlying systems, however, present the invention is not limited to these values.

In one aspect of the present invention, significant fold changes of the biomarker were determined by multiple comparison analysis performed by one-way analysis of variance (ANOVA) followed by a Dunnett's post hoc test.

In this context, said reference value is derived from the level of the respective biomarker in (a) sample(s) of a subject or a population of subjects without said fungal infection, wherein (a) when the biomarker is ICAM1, a level of at least the 1.1 fold, preferably at least the 1.3 fold, more preferably at least the 1.6 fold, more preferably of at least the 1.7 fold, more preferably at least the 1.9 fold, more preferably at least the 2.3 fold, more preferably at least the 2.8 fold is indicative for the presence of an invasive fungal infection in the subject;

(b) when the biomarker is FABP1, a level of at least the 1.4 fold, more preferably at least the 1.5 fold, more preferably at least the 1.9 fold, more preferably at least the 2.0 fold, more preferably at least the 2.1 fold is indicative for the presence of an invasive fungal infection in the sample of the subject;

(c) when the biomarker is PIGR, a level of at least the 1.3 fold, preferably at least the 1.9 fold, more preferably at least the 2.1 fold, more preferably of at least the 2.8 fold, more preferably at least the 3.5 fold, more preferably at least the 3.6 fold, more preferably at least the 5.7 fold is indicative for the presence of an invasive fungal infection in the subject;

(d) when the biomarker is ET-1, particularly CT-proET-1, a level of at least the 1.1 fold, more preferably at least the 1.7 fold, even more preferably at least the 2.0 fold, even more preferably at least the 3.0 fold; even more preferably at least the 3.5 fold is indicative of the presence of an invasive fungal infection in the subject.

(e) when the biomarker is AHSG, a level of at least the 0.7 fold, preferably at least the 0.6 fold, more preferably at least the 0.4 fold, more preferably at least the 0.3 fold, more preferably at least the 0.1 fold is indicative of the presence of an invasive fungal infection in the subject;

(f) when the biomarker is CPN1, a level of at least the 0.9 fold, more preferably at least the 0.7 fold, more preferably at least the 0.6 fold, more preferably at least the 0.5 fold, more preferably at least the 0.4 fold, more preferably at least the 0.3 fold is indicative for the presence of an invasive fungal infection in the subject;

(g) when the biomarker is HRG, a level of at least the 0.8 fold, preferably at least the 0.7 fold, more preferably at least the 0.4 fold, preferably at least the 0.2 fold, preferably at least the 0.1 fold is indicative of the presence of an invasive fungal infection in the subject;

(h) when the biomarker is RAP1A, a level of at least the 0.9 fold, preferably at least 0.9 fold, more preferably at least the 0.7 fold, more preferably at least the 0.5 fold, even more preferably at least the 0.2 fold, preferably at least the 0.04 fold is indicative of the presence of an invasive fungal infection in the subject;

(i) when the biomarker is THBS1, a level of at least the 0.9 fold, more preferably at least the 0.8 fold, more preferably at least the 0.4 fold, even more preferably at least the 0.2 fold, even more preferably at least the 0.04 fold is indicative of the presence of an invasive fungal infection in the subject.

In one aspect of the present invention, significant fold changes of the biomarker were determined by a non-parametric by Mann-Whitney U test. In another certain aspect of the methods of the present invention, said reference value is derived from the level of the respective biomarker in (a) sample(s) of a subject or a population of subjects without said fungal infection, wherein (a) when the biomarker is ICAM1, a level of at least the 1.5 fold, preferably at least the 1.7 fold, more preferably at least the 2.0 fold, even more preferably of at least the 2.6 fold is indicative for the presence of an invasive fungal infection in the subject;

(b) when the biomarker is FABP1, a level of at least the 1.2 fold, preferably at least the 1.3 fold, more preferably at least the 2.6 fold, more preferably at least the 2.7 fold, more preferably at least the 2.9 fold is indicative for the presence of an invasive fungal infection in the sample of the subject;

(c) when the biomarker is PIGR, a level of at least the 2.2 fold, preferably at least the 2.3 fold, more preferably at least the 2.4 fold, even more preferably of at least the 2.7 fold is indicative for the presence of an invasive fungal infection in the subject;

(d) when the biomarker is AHSG, a level of at least the 0.7 fold, preferably at least the 0.6 fold, more preferably at least the 0.4 fold is indicative of the presence of an invasive fungal infection in the subject;

(e) when the biomarker is CPN1, a level of at least the 0.8 fold, preferably at least the 0.7 fold, more preferably at least the 0.6 fold, more preferably at least the 0.5 fold, more preferably at least the 0.4 fold is indicative for the presence of an invasive fungal infection in the subject;

(f) when the biomarker is HRG, a level of at least the 0.5 fold, preferably at least the 0.2 fold is indicative of the presence of an invasive fungal infection in the subject;

(g) when the biomarker is RAP1, a level of at least the 0.6 fold, preferably at least the 0.5 fold, more preferably at least the 0.4 fold, even more preferably at least the 0.3 fold is indicative of the presence of an invasive fungal infection in the subject;

(h) when the biomarker is THBS1, a level of at least the 0.7 fold, preferably at least the 0.6 fold, more preferably at least the 0.5 fold, even more preferably at least the 0.4 fold, even more preferably at least the 0.3 fold is indicative of the presence of an invasive fungal infection in the subject; or (i) when the biomarker is VCL, a level of at least the 0.5 fold, preferably at least the 0.4 fold is indicative of the presence of an invasive fungal infection in the subject.

Furthermore, the invention relates to a method for diagnosis and/or risk stratification of IFI/IFD, in particular IFI/IFD associated with patients at risk of having or getting a fungal infection, in particular patients with sepsis or septic shock, or to a method for in vitro diagnosis for early or differential diagnosis or prognosis of IFI/IFD, in particular IFI/IFD associated with patients at risk of having or getting a fungal infection, in particular patients with sepsis or septic shock, as explained above, where after occurrence of the symptoms, for example for ICAM1 between day 0 and 14, a mean fold change of at least the 1.1 fold, preferably at least the 1.3 fold, more preferably at least the 1.6 fold, more preferably of at least the 1.7 fold, more preferably at least the 1.9 fold, more preferably at least the 2.3 fold, more preferably at least the 2.8 fold of ICAM1 or a partial peptide or fragment thereof, is/are significant (specific) for the said diagnosis and/or risk stratification.

The term "Diagnosing or diagnosis" according to the present invention includes determining, monitoring, confirmation, subclassification and prediction of the relevant disease, disorder, complication, or risk. "Diagnosis" in the context of the present invention relates to the recognition and (early) detection of a disease or clinical condition in a subject and may also comprise differential diagnosis. The term "diagnosis", thus, in the context of the present invention also comprises differential diagnosis, risk stratification, prognosis, stratification for applying preventive and/or therapeutic measures and/or managements of patients, therapy monitoring, and therapy guidance of a disease or clinical condition. The term diagnosis, according to the invention, may comprise identifying patients having IFI/IFD, in particular IFI/IFD associated with sepsis or septic shock which have a poor prognosis, in order to provide optimal treatment. Diagnosing herein may also mean ruling in IFI/IFD as well as ruling-out IFI/IFD.

Prognosis relates to predicting a disease disorder or complication before other symptoms or markers have become evident or have become significantly altered. Hence, in one aspect, the level of the biomarker is determined a soon as possible, particularly on the same day ("day 0=T0") as the admission of the subject into the ED or ICU in order to provide a prognosis of the further course of the fungal infection.

"Determining" (or measuring or detecting) the level of a marker herein may be performed using a detection method and/or a diagnostic assay as explained.

The term "differentiation", relates to the distinction of two different conditions in a subject e.g. an invasive fungal infection versus an uncritical fungal colonization and/or a non-fungal infection.

"Confirmation" relates to the strengthening or substantiating a diagnosis already performed using other indicators or markers.

"Subclassification" relates to further defining a diagnosis according to different subclasses of the diagnosed disease, disorder, complication or risk, e.g. defining according to mild and severe forms of the disease.

The term "ruling in" relates to a highly specific diagnostic test, meaning the highest, but at least 80% disease probability for a positive test result, in particular with at least 70%, 75%, 80%, 85%, 89%, 90%, 91%, 92%, 92%, 94%, 95% 96%, 98%, 99%, 100% accuracy.

The term "ruling out" relates to a highly sensitive diagnostic test, meaning the lowest, but at least 80% disease probability for a negative test result, in particular with at least 70%, 75%, 80%, 85%, 89%, 90%, 91%, 92%, 92%, 94%, 95% 96%, 98%, 99%, 100% accuracy.

As used herein, the term "risk stratification" may refers to the grouping of subjects into different risk groups according to their further prognosis. Risk stratification also relates to stratification for applying preventive and/or therapeutic measures.

In the method of the present invention, a "ratio", in particular "positive likelihood ratio", "negative likelihood ratio", "odds ratio", or "hazard ratio" may be used as a measure of a test's ability to predict risk or diagnose a disease or a condition such as IFI. In the case of a "positive likelihood ratio", a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a "negative likelihood ratio", a value of 1 indicates that a negative result is equally likely among subjects in both the "diseased" and "control" groups; a value greater than 1 indicates that a negative result is more likely in the test group; and a value less than 1 indicates that a negative result is more likely in the control group. In certain preferred embodiments, markers and/or marker panels are preferably selected to exhibit a positive or negative likelihood ratio of at least about 1.5 or more or about 0.67 or less, more preferably at least about 2 or more or about 0.5 or less, still more preferably at least about 5 or more or about 0.2 or less, even more preferably at least about 10 or more or about 0.1 or less, and most preferably at least about 20 or more or about 0.05 or less. The term "about" in this context refers to +/−5% of a given measurement. In the case of an "odds ratio", a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In certain preferred embodiments, markers and/or marker panels are preferably selected to exhibit an odds ratio of at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less. The term "about" in this context refers to +/−5% of a given measurement. In one instance in the context of the present invention, the "diseased" group is the subjects with an IFI/IFD, whereas the "control" group consists of subjects not having an IFI/1FD. The "control" group may or may not include subjects with a fungal colonization depending on the circumstances. For example, if the subject has been diagnosed with a fungal colonization and is to be assed for the individual risk of getting an IFI/IFD, the non-IFI/IFD "control" group may include or consists of subjects with a fungal colonization.

In the case of a "hazard ratio", a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group. In certain preferred embodiments, markers and/or marker panels are preferably selected to exhibit a hazard ratio of at least about 1.1 or more or about 0.91 or less, more preferably at least about 1.25 or more or about 0.8 or less, still more preferably at least about 1.5 or more or about 0.67 or less, even more preferably at least about 2 or more or about 0.5 or less, and most preferably at least about 2.5 or more or about 0.4 or less. The term "about" in this context refers to +/5% of a given measurement.

In this invention ratios can be calculated by using the measurement results of two different markers (e.g. ICAM1/PCT or ICAM1/ET-1). It includes also the relation of ratios to different time points and/or disease stages.

Monitoring relates to keeping track of an already diagnosed disease, disorder, complication or risk, e.g. to analyse the progression of the disease or the influence of a particular treatment on the progression of disease or disorder.

As used herein, the term "therapy guidance/therapeutic guidance" refers to application of certain therapies or medical interventions as well as change e.g. dosage, drug, time point of the intervention, frequency of monitoring or discontinuation of therapies based on the value of one or more biomarkers and/or clinical parameter and/or clinical scores. It also includes the decision of whether a therapy is initiated at all. Therapy control is an important part of the therapeutic guidance. The therapeutic guidance is related on patients at risk or having an invasive fungal infection with or without an at least second infection e.g. a bacterial infection. Single biomarkers or clinical parameters or scores can be used, but can also be combined with other known markers like PCT for bacterial-(co)infected patients.

The term “anti-fungal therapy” or “anti-fungal treatment” refers to a treatment of a fungal infection using one or more antifungal agent(s). “Antifungal agents” used in an antifungal therapy include, but are not limited to, polyene antifungal drugs (e.g. (liposomal) amphotericin B), echinocandins (e.g. caspofungin, anidulafungin, micafungin), azole antifungal drugs (e.g. fluconazole, itraconazole, posaconazole, voriconazole), allylamine and morpholine antifungal drugs, antimetabolite antifungal drugs (e.g. 5-fluorocytosine) as well as other known anti-fungal substances or variants and/or combinations thereof. As described herein, an aspect of the present invention is a method of treating an invasive fungal infection in a subject caused by at least one fungus by application of one or more antifungal agents for the treatment of infections and preventing the development of invasive fungal infections in patients at a critical disease state and/or at an increased risk of getting or having an invasive fungal infection. Also contemplated by an antifungal therapy as described by the present invention are single as well as co-administration of more than one antifungal agent.

The present invention is particularly useful for avoiding unnecessary or overdosed treatment with an anti-fungal agent. For example, if it is based on the determined marker level(s) of the subject unlikely that the subject will develop an IFI/IFD, the administration of the anti-fungal agent(s) may be deemed unnecessary in order to avoid the agent's side effects.

In one particular aspect, the subject suffers from a mixed infection, i.e. an infection with more than one pathogen, e.g. an IFI/IFD and a bacterial or viral infection at the same time. The term “antibacterial therapy” refers to a treatment of a bacterial infection using one or more antibiotic(s). “Antibiotics” used in an antibacterial therapy refer to antibacterial agents that inhibit the growth of microorganisms without damage to the host. For example, the antibiotic may inhibit cell wall synthesis, protein synthesis, nucleic acid synthesis, or alter cell membrane function. Classes of antibiotics that can be used in an antibacterial therapy include, but are not limited to, macrolides (i.e., erythromycin), penicillins (i.e., nafcillin), cephalosporins (i.e., cefazolin), carbapenems (i.e., imipenem, aztreonam), other beta-lactam antibiotics, beta-lactam inhibitors (i.e., sulbactam), oxalines (i.e. linezolid), aminoglycosides (i.e., gentamicin), chloramphenicol, sulfonamides (i.e., sulfamethoxazole), glycopeptides (i.e., vancomycin), quinolones (i.e., ciprofloxacin), tetracyclines (i.e., minocycline), fusidic acid, trimethoprim, metronidazole, clindamycin, mupirocin, rifamycins (i.e., rifampin), streptogramins (i.e., quinupristin and dalfopristin) lipoprotein (i.e., daptomycin), polyenes (i.e., amphotericin B), azoles (i.e., fluconazole), and echinocandins (i.e., caspofungin acetate). In case of a mixed infection, different markers may be used for therapy guidance or control, e.g. the biomarkers of the invention in combination with PCT as a marker for a bacterial infection.

In one particular aspect, the subject suffers from a mixed infection, i.e. an infection with more than one pathogen, e.g. an IFI/1FD and a bacterial or viral infection at the same time.

In this case, different infection markers and different diagnostic methods e.g. the combination of immunoassays with known detection methods like molecular diagnostics e.g. PCR (polymerase chain reaction) or NGS (Next Generation Sequencing), MS (Mass Spectrometry), Flow Cytometry, imaging techniques e.g. X-ray or tomographies, or microbiological detection methods can be used for an improved diagnosis, therapy guidance or control, e.g. the biomarkers of the invention in combination with PCT as a marker for a bacterial infection and the combination with PCR for the detection of biomarkers or for the detection of pathogens or for the detection of drug resistant pathogens.

In case of a mixed infection, antibacterial therapy may be adjusted including the decision whether the subject's antibacterial therapy is continued, adapted or stopped. As for example, the adjustment of the antibacterial therapy may be whether the dosage of an antibacterial therapy is adapted and/or whether the antibacterial therapy is stopped or whether an additional antibacterial therapy is initiated over an existing antibacterial therapy, in particular a change of an antibiotic or a combination of different antibiotic agents.

The term “therapy control”, refers to the monitoring and/or adjustment of a therapeutic treatment of said subject.

The term “outcome”, refers to the patients end stage of a disorder or disease. A negative outcome can be related to the increased risk of mortality, especially in fungal infections e.g. in mixed infections, in patients with risk of having or getting fungal infections or sepsis, especially at onset of septic shock (day 0=T0), after 1 day (T1), 2 days (T2), 7 days (T3), 14 days (T4), 21 days (T5), 28 days (T6), up to 90 days. Furthermore, a negative outcome can be related to a missing diagnosis, a lack or delay of therapeutic interventions like starting anti-fungal therapy or a missing monitoring (measuring and relating the biomarker values at different time points, but at least more than one time point, especially regularly, meaning all 6 hours, all 12 hours, every day, every second day, every week, every 14 days, very 21 days, every 28 days or at the time point of clinical decision making process or change in the patients clinical situation). The relative outcome is depending on the relative level or median fold change values above or below the median. The outcome relates also in the degree of severity of the disease. The term critical disease state, refers to a condition of a subject with an increased risk of mortality or adverse medical events.

The diagnosis, prognosis, risk assessment, risk stratification, monitoring, therapy guidance and/or therapy control can take place on the basis of the determination of at least one marker or a partial peptide or fragment thereof from the group of ICAM1, AHSG, CPN1, FABP1, HRG, PIGR, RAP1, THBS1, VCL, ET-1 and its amount or level that is present, or a change in amount or level (fold change), as compared with a reference, in at least one patient sample. As used in the methods of the present invention, the diagnosis, prognosis, risk assessment, risk stratification, monitoring, therapy guidance and/or therapy control can take place on the basis of the determination of at least the marker ICAM1 and its amount or level that is present, or a change in amount or level (fold change), as compared with a reference, in at least one sample of the subject.

The term “level” or “amount” in the context of the present invention relates to the concentration (preferably expressed as weight/volume; w/v, or expressed as fold change) of the markers or a meaningful partial peptide or fragment thereof, in the sample taken from a subject, in particular a patient.

As mentioned herein in the context of markers and other peptides (alternative: proteins or peptides), the term “fragment” refers to smaller proteins or peptides derivable from larger proteins or peptides, which hence comprise a partial sequence of the larger protein or peptide. Said fragments are derivable from the larger proteins or peptides by saponification of one or more of its peptide bonds. “Fragments” of the mentioned markers preferably relate to fragments of at least 6 amino acids in length, most preferably at least 12 amino acid residues in length. Such fragments are preferably detectable with immunological assays as described herein.

In one aspect, the reference level may be a cut-off level and/or a mean fold change, wherein when ICAM1, AHSG, CPN1, FABP1, HRG, PIGR, RAP1, THBS1, VCL, and/or ET1 levels above or below (depending on the particular marker as outlined herein) the cut-off level or a particular mean fold change are determined, the assay indicates the presence of an invasive fungal infection. The same applies to the markers that can be determined in addition such as PCT.

With respect to a "fold change", the mean fold change value may be applied analogously to a cutoff value. Fold change is a measure describing how much a quantity changes going from an initial to a final value. In other words, if a certain fold change in the amount of the biomarker of the present invention is detected in relation to a reference level, this fold change value may be indicative of the presence of an invasive fungal infectious disease.

Mean fold changes below 1.0 correspond to a downregulation of a biomarker. Mean fold changes above 1.0 correspond to an upregulation of a biomarker.

Appropriate fold changes can be found in the appended examples; e.g. Table 2 provides values for the differentiation of invasive fungal infection from no fungal infection and Table 17 provides values for the differentiation of invasive fungal infection from fungal colonization and Table 8 provides values for the differentiation of invasive fungal infections vs. no invasive fungal infection or fungal colonization. Useful fold changes include:

- at least 1.1; 1.2; 1.3; 1.4; 1.5; 1.6; 1.7; 1.8; 1.9; 2.0; 2.1; 2.2; 2.3; 2.4; 2.5; 2.6; 2.7; 2.8; 2.9; 3.0; 3; 4; 5; 6; 7; 8; 9; 10; 20; 50; 100 fold change of ICAM1 in invasive fungal infection vs. no fungal infection (isolate), in particular at least 1.1; 1.3; 1.6; 1.7; 1.9; 2.3; 2.8 change of ICAM1;
- at least 1.02; 1.03; 1.1; 1.2; 1.3; 1.4; 1.5; 1.6; 1.7; 1.8; 1.9; 2.0; 2.1; 2.2; 2.3; 2.4; 2.5; 3; 4; 5; 6; 7; 8; 9; 10; 20; 50; 100 fold change of ICAM1 in invasive fungal infection vs. fungal colonization, in particular at least 1.02; 1.03; 1.1; 1.2; 1.3; 1.5; 1.6; 2.1; 2.2; 2.3; 2.5 fold change of ICAM1;
- at least 1.04; 1.1; 1.2; 1.3; 1.4; 1.5; 1.6; 1.7; 1.8; 1.9; 2.0; 2.1; 2.2; 2.3; 2.4; 2.5; 2.6; 3; 4; 5; 6; 7; 8; 9; 10; 20; 50; 100 fold change of ICAM1 in invasive fungal infection vs. fungal colonization and no fungal infection, in particular at least 1.04; 1.1; 1.2; 1.3; 1.5; 1.7; 1.8; 2.0; 2.2; 2.3; 2.5 fold change of ICAM1;
- at least 0.9; 0.8; 0.7; 0.6; 0.5; 0.4; 0.3; 0.2; 0.1 fold change of AHSG in invasive fungal infection vs. no fungal infection, in particular at least 0.7; 0.6; 0.4; 0.3; 0.1 fold change of AHSG;
- at least 0.9; 0.8; 0.7; 0.6; 0.5; 0.4; 0.3; 0.2; 0.1 fold change of AHSG in invasive fungal infection vs. fungal colonization, in particular at least 0.9; 0.8; 0.6; 0.5; 0.4; 0.3; 0.2 fold change of AHSG;
- at least 0.9; 0.8; 0.7; 0.6; 0.5; 0.4; 0.3; 0.2; 0.1 fold change of AHSG in invasive fungal infection vs. fungal colonization and no fungal infection, in particular at least 0.7; 0.5; 0.4; 0.2 fold change of AHSG; at least 0.97; 0.9, 0.8, 0.7; 0.6; 0.5; 0.4; 0.3; 0.2; 0.1 fold change of CPN1 in invasive fungal infection vs. no fungal infection, in particular at least 0.97; 0.9; 0.7; 0.6; 0.5; 0.4; 0.3 fold change of CPN1;
- at least 0.98; 0.9; 0.8; 0.7; 0.6; 0.5; 0.4; 0.3; 0.2; 0.1 fold change of CPN1 In invasive fungal infection vs. fungal colonization and no invasive fungal infection, in particular at least 0.98; 0.9; 0.7; 0.6; 0.5; 0.4 fold change of CPN1; at least 1.007; 1.03; 1.1; 1.2; 1.3; 1.4; 1.5; 1.6; 1.96; 1.9; 2.0; 2.1; 3; 4; 5; 6; 7; 8; 9; 10; 20; 50; 100 fold change of FABP1 in invasive fungal infection vs. no fungal infection, in particular at least 1.007; 1.03; 1.4; 1.5; 1.96; 2.1 fold change of FABP1;
- at least 1.003; 1.1; 1.2; 1.3; 1.4; 1.8; 1.9; 2.0; 2.1; 2.2; 2.5; 3; 4; 5; 6; 7; 8; 9; 10; 20; 50; 100 fold change of FABP1 In invasive fungal infection vs. fungal colonization, in particular at least 1.003; 1.1, 1.4, 1.9 fold change of FABP1;
- at least 0.9; 0.8; 0.7; 0.6; 0.5; 0.4; 0.3, 0.2, 0.1 fold change of HRG in invasive fungal infection vs. fungal colonization, in particular at least 0.8; 0.7; 0.5; 0.4; 0.2; 0.1 fold change of HRG;
- at least 0.9; 0.8; 0.7; 0.6; 0.5; 0.4; 0.3; 0.2; 0.1 fold change of HRG in invasive fungal infection vs. fungal colonization, in particular at least 0.9; 0.8; 0.6; 0.5; 0.4; 0.3; 0.2; 0.1 fold change of HRG;
- at least 0.9; 0.8; 0.7; 0.6; 0.5; 0.4; 0.3; 0.2; 0.1 fold change of HRG in invasive fungal infection vs. fungal colonization and no fungal infection, in particular at least 0.7; 0.6; 0.5; 0.3; 0.1 fold change of HRG;
- at least 1.1; 1.2; 1.3; 1.4; 1.5, 1.6; 1.7; 1.8; 1.9; 2.0; 2.1; 2.2; 2.3; 2.4; 2.5; 2.6; 2.7; 2.8; 2.9; 3.0; 3.1; 3.2; 3.3; 3.4; 3.5; 3.6; 3.7; 3.8; 3.9; 4.0; 4.1; 4.2; 4.3; 4.4; 4.5; 4.6; 4.7; 4.8; 4.9; 4.9; 5.0; 5.1; 5.2; 5.3; 5.4; 5.5; 5.6; 5.7; 5.8; 5.9; 6; 7; 8; 9; 10; 20; 50; 100 fold change of PIGR in invasive fungal infection vs. no fungal infection, in particular at least 1.3; 1.9; 2.1; 2.2; 2.3; 2.4; 2.7; 2.8; 3.5; 3.6; 5.7 fold change of PIGR;
- at least 1.1; 1.2; 1.3; 1.4; 1.5; 1.6; 1.7; 1.8; 1.9; 2.0; 2.1; 2.2; 2.3; 2.4; 2.5; 2.6; 2.7; 2.8; 2.9; 3.0; 3.1; 3.2; 3.3; 3.4; 3.5; 3.6; 3.7; 3.8; 3.9; 4.0; 4, 5, 6; 7; 8; 9; 10; 20; 50; 100 fold change of PIGR in invasive fungal infection vs. fungal colonization, in particular at least 1.1; 1.4; 2.1; 3.4; 4.0 fold change of PIGR;
- at least 1.1; 1.2; 1.3; 1.4; 1.5; 1.6; 1.7; 1.8; 1.9; 2.0; 2.1; 2.2; 2.3; 2.4; 2.5; 2.6; 2.7; 2.8; 2.9; 3.0; 3.1; 3.2; 3.3; 3.4; 3.5; 3.6; 3.7; 3.8; 3.9; 4.0, 4.1; 4.2; 4.3; 4.4; 4.5; 4.6; 4.7; 4.8; 4.9; 5.0, 6; 7; 8; 9; 10; 20; 50; 100 fold change of PIGR in invasive fungal infection vs. fungal colonization and no fungal infection, in particular at least 1.1; 1.3; 1.4; 1.9; 2.0; 2.1; 2.5; 3.1; 3.2; 3.4; 4.7 fold change of PIGR;
- at least 1.1; 1.2; 1.3; 1.4; 1.5; 1.6; 1.7; 1.8; 1.9; 2.0; 2.1; 2.2; 2.3; 2.4; 2.5; 2.6; 2.7; 2.8; 2.9; 3.0; 3.1; 3.2; 3.3; 3.4; 3.5; 3.6; 3.7; 3.8; 3.9; 4.0; 4, 5, 6; 7; 8; 9; 10; 20; 50; 100 fold change of ET-1 in invasive fungal infection vs. no fungal infection, in particular at least 1.1; 1.7; 2.0; 3.0; 3.5 fold change of ET-1;
- at least 0.95; 0.9, 0.8, 0.7; 0.6; 0.5; 0.4; 0.3; 0.2; 0.1; 0.09; 0.08; 0.07; 0.06; 0.05; 0.04; 0.03; 0.02; 0.01 fold change of RAP1 (RAP1A/RAP1B/RAPBL) in invasive fungal infection vs. no fungal infection, in particular at least 0.95; 0.7; 0.5; 0.4; 0.2; 0.04 fold change of RAP1A/RAP1B/RAPBL; at least 0.9; 0.8; 0.7; 0.6; 0.5; 0.4; 0.3; 0.2; 0.1 fold change of RAP1 (RAP1A/RAP1B/RAPBL) In invasive fungal infection vs. fungal colonization, in particular at least 0.8; 0.6; 0.5; 0.4; 0.3; 0.2; 0.1 fold change of RAP1 (RAP1A/RAP1B/RAPBL);
- at least 0.9; 0.8; 0.7; 0.6; 0.5; 0.4; 0.3; 0.2; 0.1 fold change of RAP1 (RAP1A/RAP1B/RAPBL) in invasive fungal infection vs. fungal colonization and no fungal infection, in particular at least 0.7; 0.4; 0.3; 0.2; 0.1 fold change of RAP1A/RAP1B/RAPBL;

at least 0.98; 0.9, 0.8, 0.7, 0.6; 0.5; 0.4; 0.3; 0.2; 0.1; 0.04 fold change of THBS1 in invasive fungal infection vs. no fungal infection, in particular at least 0.98; 0.8; 0.5; 0.4; 0.2; 0.04 fold change of THBS1.

at least 0.95; 0.9, 0.8; 0.7; 0.6; 0.5; 0.4; 0.3; 0.2; 0.1 fold change of THBS1 in invasive fungal infection vs. fungal colonization, in particular at least 0.95; 0.9; 0.4; 0.3; 0.2; 0.1 fold change of THBS1;

at least 0.9; 0.8; 0.7; 0.6; 0.5; 0.4; 0.3; 0.2; 0.1 fold change of THBS1 in invasive fungal infection vs. fungal colonization and no fungal infection, in particular at least 0.8; 0.7; 0.4; 0.3; 0.2; 0.1 fold change of THBS1;

at least 0.98; 0.97; 0.9, 0.8, 0.7, 0.6; 0.5; 0.4; 0.3; 0.2; 0.1 fold change VCL in invasive fungal infection vs. fungal colonization, in particular at least 0.98; 0.97; 0.8; 0.6; 0.5; 0.4; 0.3; 0.2 fold change of VCL;

at least 0.995; 0.9; 0.8; 0.7; 0.6; 0.5; 0.4; 0.3; 0.2; 0.1 fold change of VCL in invasive fungal infection vs. fungal colonization and no fungal infection, in particular at least 0.995; 0.9; 0.8; 0.6; 0.4; 0.2; 0.1 fold change of VCL;

at least 1.1; 1.2; 1.3; 1.4; 1.5; 1.6; 1.7; 1.8; 1.9; 2.0; 2.1; 2.2; 2.3; 2.4; 2.5; 2.6; 2.7; 2.8; 2.9; 3.0; 3.1; 3.2; 3.3; 3.4; 3.5; 3.6; 3.7; 3.8; 3.9; 4.0; 4.1; 4.2; 4.3; 4.4; 4.5; 4.6, 4.7; 4.8; 4.9; 5.0; 5.1; 5.2; 5.3; 5.4; 5.5; 5.6; 5.7; 5.8; 5.9; 6; 7; 8; 8.1; 8.2; 8.3; 8.4; 8.5; 8.6; 8.7; 8, 8; 8.9; 9; 9.1; 9.2; 9.3; 9.4; 9.5; 9.5; 9.6; 9.7; 9.8; 9.9; 10; 10.1; 10.2; 10.3; 10.4; 10.5; 10.6; 10.7; 10.8; 10.9; 11, 11.1; 11.2; 11.3; 11.4; 11.5; 11.6; 11.7; 11.8; 11.9; 12, 13, 14, 15, 15.1; 15.2; 15.3; 15.4; 15.5; 15.6; 15.7; 15.8; 15.9; 16, 17; 18; 19; 20; 25; 30; 35; 36; 37; 38; 39; 40; 40.1; 40.2; 40.3; 40.4; 40.5; 40.6; 40.7; 40.8; 40.9; 41; 41.1; 41.2; 41.3; 41.4; 41.5; 41.6; 41.7; 41.8; 41.9; 42; 43; 44; 45; 50; 55; 60; 61; 62; 63; 64; 65; 66; 67; 68; 69; 70; 75; 80; 85; 90; 95; 100 fold change of PCT in invasive fungal infection vs. no fungal infection in patients with a septic condition, especially septic shock, in particular at least 1.2; 1.7; 2.5; 4.5; 5.4; 9.2; 10.0; 11.7; 15.6; 40.9; 69.0 fold change of PCT;

at least 1.1; 1.2; 1.3; 1.4; 1.5; 1.6; 1.7; 1.8; 1.9; 2.0; 2.1; 2.2; 2.3; 2.4; 2.5; 2.6; 2.7; 2.8; 2.9; 3.0; 3.1; 3.2; 3.3; 3.4; 3.5; 3.6; 3.7; 3.8; 3.9; 4.0; 4.4; 5.0; 6; 7; 7.1; 7.2; 7.3; 7.4; 7.5; 7.6; 7.7; 7.8; 7.9; 8; 8.1; 8.2; 8.3; 8.4; 8.5; 8.6; 8.7; 8.8; 8.9; 9; 10; 10, 9; 11, 12; 12; 13, 14, 15, 16, 17; 18; 19; 20; 21; 22; 23; 24; 24.8; 25; 26; 27; 28; 29; 29.4; 30; 35; 40; 45; 50; 50.1; 50.2; 50.3; 50.4; 50.5; 50.6; 50.7; 50.8; 50.9; 60; 65; 70; 75; 80; 85; 90; 95; 100 fold change of PCT in invasive fungal infection vs. colonization in patients with a septic condition, especially septic shock, in particular at least 1.5; 2.1; 2.2; 3.6; 4.4; 7.1; 8.0; 8.7; 10.9; 12.3; 24.0; 24.8; 29.4; 50.7 fold change of PCT;

at least 1.1; 1.2; 1.3; 1.4; 1.5; 1.6; 1.7; 1.8; 1.9; 2.0; 2.1; 2.2; 2.3; 2.4; 2.5; 2.6; 2.7; 2.8; 2.9; 3.0; 3.1; 3.2; 3.3; 3.4; 3.5; 3.6; 3.7; 3.8; 3.9; 4.0; 4.1; 4.2; 4.3; 4.4; 4.5; 4.6; 4.7; 4.8; 4.9; 5.0; 6.0; 6.1; 6.2; 6.3; 6.4; 6.5; 6.6; 6.7; 6.8; 6.9; 7.0; 7.1; 7.2; 7.3; 7.4; 7.5; 7.6; 7.7; 7.8; 7.9; 8.0; 8.1; 8.2; 8.3; 8.4; 8.5; 8.6; 8.7; 8.8; 8.9; 9.0; 9.1; 9.2; 9.3; 9.4; 9.5; 9.6; 9.7; 9.8; 9.9; 10.0; 10.1; 10.2; 10.3; 10.4; 10.5; 10.6; 10.7; 10.8; 10.9; 11.0; 12; 13; 14; 15; 16; 17; 18; 19; 20; 21; 22; 23; 24; 25; 26; 26.1; 26.2; 26.3; 26.4; 26.5; 26.6; 26.7; 26.8; 26.9; 27, 27.1; 27.2; 27.3; 27.4; 27.5; 27.6; 27.7; 27.8; 27.9; 28; 28.1; 28.2; 28.3; 28.4; 28.5; 28.6; 28.7; 28.8; 28.9; 29; 30; 31; 32; 33; 34; 35; 36; 37; 38; 39; 39.1; 39.2; 39.3; 39.4; 39.5; 39.6; 39.7; 39.8; 39.9; 40; 40.1; 40.2; 40.3; 40.4; 40.5; 40.6; 40.7; 40.8; 40.9; 41; 42; 43; 44; 45; 50; 55; 60; 65; 70; 75; 80; 85; 90; 95; 100 fold change of PCT in invasive fungal infection vs. fungal colonization and no fungal infection in patients with a septic condition, especially septic shock, in particular at least 0.1.3; 2.0; 2.8; 4.6; 7.1; 7.2; 8.9; 10.5; 26.6; 28.1; 40.5 fold change of PCT.

As used herein, the term "infection" in general means a pathological process caused by the invasion of normally sterile tissue or fluid by pathogenic or potentially pathogenic microorganisms or agents. Accordingly, an infection can be a fungal infection, bacterial infection, viral infection, and/or parasite infection. An infection in general can be a local or systemic infection, it can be chronic or acute. In the present invention an invasive fungal infection is to be diagnosed (i.e. an acute and systemic fungal infection). Chronic infections of any kind, however, can be risk factors for getting a serious, especially invasive fungal infection.

An "invasive Infection" as used herein relates in the broadest sense to an acute, serious infection and can be systemic (i.e. circulating and not one locally, limited infection) that may, however, have a local origin and/or may be multifocal. In other words, subjects having a local fungal infection or fungal colonization with a potentially dangerous fungus may have a higher risk of getting an IFI than subjects without such a local infection or colonization. An invasive infection is a serious form of infection that can lead to sepsis or other critical outcomes with increased risk of mortality and needs a quick and effective treatment and patient management. As used herein, the invasive fungal infection is an acute, serious fungal infection, in particular a systemic fungal infection, a fungemia or a multifocal infection. Most preferably herein, the IFI is a systemic fungal infection.

A "local Infection" means a pathogenic "invasion" (not to be confused with IFI) of a limited or specific part of the body e.g. the abdomen, the bronchial system, the lung, the musculoskeletal system, the kidney, the urogenital tract, the skin etc. This kind of infection is often manageable locally at the site of infection, but can also develop into serious invasive or septic conditions when un-treated or not treated effectively. As mentioned above, local fungal infections are risk factors of getting an invasive fungal infection.

In the context of the present invention, the term "multifocal Infection" refers to a local infection, wherein one or more fungi species are present in at least two separable loci. In contrast to a multifocal infection, a unifocal infection may be restricted to one focus which may be for example but not limited to the trachea, pharynx, or the stomach. In this context, samples of fungi can be isolated from one focus when the fungal infection is considered to be unifocal or can be simultaneously isolated from various separable foci when the fungal infection is considered to be multifocal. Such samples can be obtained for example, but not limited to, from tracheal aspirates, pharyngeal exudates, gastric aspirates, urine, peripheral blood, intravascular lines, feces, wound exudates, surgical drains, skin or other infectious foci.

A "community-acquired Infection" means that the invasion of the pathogenic infective agent came into the body of the patient, outside from medical sites like the primary care room, the hospital, the ambulance, the Intensive Care Unit, the Emergency Department or during medical procedures like operations, wound treatment, minimal-invasive or invasive device applications e.g. catheter, needles, stents, apheresis.

A "nosocomial or iatrogenic Infection" means that the invasion of the pathogenic infective agent came into the body of the patient, in the area of medical sites like the primary care room, the hospital, the ambulance, the Intensive Care Unit, the Emergency Department or during medical procedures like operations, wound treatment, minimal-invasive or invasive device applications e.g. catheter, needles, stents, apheresis.

Further, as mentioned herein above, the subject may suffer from more than one source(s) of infection simultaneously, also termed as "mixed Infection". The sources are related on different types of pathogenic agents and/or different pathogenic species and/or subgroups as well as the same pathogen with different mutations. For example, the subject can suffer from a bacterial infection and fungal infection; from a viral and fungal infection; from a bacterial, fungal and viral infection, from a viral and bacterial infection or from multiple infections of one pathogen group e.g. more than one bacterial infection, more than one viral infection or more than one fungal infection. In the latter case, the subject may have an increased risk of getting a fungal infection. In particular, the development of the mixed infection can be simultaneously, meaning the invasion of pathogenic agents at the same time point or consecutive for example starting with one infection (e.g. bacterial or fungal) and the subject subsequently gets at least one further infection with another pathogenic agent or particle, e.g. fungal or bacterial or viral. A mixed infection herein can also be an infection with two different fungi.

As mentioned herein above, the present invention is particularly useful for a subject who has an increased risk of getting or having an invasive fungal infection. Such a subject may for example be a subject that is in a critical disease state. Such a subject may also be a subject selected from the group consisting of (i) a patient having at least one chronic or acute viral or bacterial infection; in particular a local and/or systemic bacterial and/or viral infection;

(ii) a patient having a mixed bacterial and viral infection;

(iii) a patient having an immune suppression, impaired immune response or dysregulated immune system, neutropenia, in particular Systemic Inflammatory Response Syndrome (SIRS), sepsis, severe sepsis, infection with an organ dysfunction or septic shock, and/or fungal colonization of two or more sites of the body.

The subject to be diagnosed in the context of the present invention may, thus, for instance suffer from a respiratory disease, particularly an infection of the lower respiratory tract or the lung. Further, the subject may suffer from an abdominal infection. Further, the subject may suffer from an infection of the urogenital tract, or the kidneys or have a urinary catheter. Further, the subject may suffer from an infection after surgery inter alia postoperative and/or necrotic peritonitis, or after an initial operation of the kidney, liver, pancreas, gastrointestinal tract, heart, after vasectomy and other surgeries with a risk of getting a fungal or be related to a fungal infection.

Further, the subject may suffer from an infection after transplantation of a fluid or solid tissue, for example the liver, the kidney, the cardio-vascular system, blood, blood-fractions or blood-precursor, skin, musculoskeletal system. Further, the infection may be present in a subject having one of the conditions of diabetes mellitus, arterial hypertension, coronary heart disease, chronic obstructive lung disease (COPD), renal insufficiency, renal replacement therapy, mechanical ventilation, antibiosis, liver cirrhosis, oncological disorders, tracheotomy, anastomosis leakage and fascial dehiscence. Further, the subject can be admitted to any medical site, preferably the subject is admitted to a hospital, more preferably the subject is admitted to an intensive care unit (ICU). Further, the subject may suffer from an infection based on an impaired or dysregulated immune system or microbiome. Further the subject may show at least one other risk factor of getting or having a fungal infection.

As used herein "respiratory disease" comprises pathological conditions affecting the organs and tissues that make gas exchange possible in higher organisms, and also includes conditions of the upper respiratory tract, trachea, bronchi, bronchioles, alveoli, pleura and pleural cavity, and the nerves and muscles of breathing.

The infection may be nosocomial or iatrogenic e.g. by the application of medical devices like needle(s), catheter(s), tubes or devices in relation to dialysis, apheresis, mechanical ventilation, artificial nutrition or surgery, or after surgery, tracheotomy, splenectomy, anastomosis leakage, fascia dehiscence. The infection may also be independent of any hospital stay or medical setting.

The infection can be caused or exacerbated by a defect of the immune system or natural microbiome e.g. by suffering from a comorbidity, a primary infection or caused by therapies and/or drugs e.g. antibiotics, chemotherapeutics.

The term "fungal infection", relates to any inflammatory condition caused by a fungus and can comprise a natural colonization or a systemic, invasive infection. The fungus includes all types fungal pathogens, preferably aspergillosis (e.g. *A. fumigatus* or other A. ssp), blastomycosis, candidiasis (e.g. *C. albicans, C. glabrata, C. krusei, C. auris* and other C. spp.), coccidioidomycosis, mucormycosis, *pneumocystis* pneumonia infection, *Cryptococcus* infection or histoplasmosis.

In particular positive results in blood cultures, intraoperative swabs, and *Aspergillus* spp. in deep respiratory tract specimens with accompanying pulmonary infiltrates are classified as an invasive infection.

Herein, the terms "invasive fungal infection (IFI) or invasive fungal disease (IFD)" are understood as described by the European Organization for Research and Treatment of Cancer/Invasive fungal infections (IFI) Cooperative Group; National Institute of Allergy and Infectious Diseases Mycoses Study Group (EORTC/MSG) Consensus Group in 2002 and 2008. IFI/IFD is associated with the risk of an adverse event, like death and increased morbidity. The terms IFI/IFD defining opportunistic invasive fungal infections in immunocompromised patients e.g. with cancer and hematopoietic stem cell transplants: an international consensus (Ascioglu et al. Clin Infect Dis. 2002). IFI describes a severe, systemic infection with yeasts or molds.

The term "IFI/IFD is associated with sepsis and/or septic shock" particularly comprises the comorbidity of these indications, i.e. In addition to an existing underlying disease (index disease), namely IFI/IFD, an existing, diagnostically distinguishable disease profile, such as sepsis and/or septic shock, is determined, i.e. there is an associated disease profile. This approach allows to prevent the adverse outcome of the underlying disease such a sepsis and/or septic shock due to the IFI/IFD, if an anti-fungal agent (drug) is timely applied to the patient. Similarly a misuse of a drug e.g. antibiotics or antifungal drugs can be avoided depending on the result of the method of the present invention.

The term "bacterial Infection" refers to the invasion of the host mammal by pathogenic bacteria. This includes the excessive growth of bacteria which are normally present in or on the body of a mammal. More generally, a bacterial infection can be any situation in which the presence of a bacterial population(s) is damaging to a host mammal. Thus, a mammal is "suffering" from a bacterial infection when excessive numbers of a bacterial population are present in or on a mammal's body, or when the effects of the presence of a bacterial population(s) is damaging the cells or other tissue of a mammal.

The term "subject" as used herein refers to a vertebrate, in particular a human or non-human organism that is receiving medical care or that should receive medical care due to a disease. This includes persons with no defined illness who are being investigated for signs of pathology. Thus the methods and assays described herein are applicable to both, human and veterinary disease. In a preferred embodiment, the subject of the present invention is a mammal, preferably is a human.

As explained herein above the term "risk of having or getting an (Invasive) fungal infection", characterizes a subject having at least one risk factor/condition that increase the probability of getting or having an (invasive) fungal infection, and can be, but is not limited to: An immune-modulation or immunosuppression due to medicament(s) (e.g. steroids, cytostatics, therapeutic antibodies, calcineurin inhibitors, TOR (target of rapamycin) inhibitors, chemotherapy, antibiotics) or disease(s) or due to means of inducing, enhancing, or suppressing an immune response including immunocompromised patients; an impaired microbiome; a wound; at least one further infection (mixed infection e.g. with bacterial, virus or fungi); sepsis or septic shock; local infections (e.g. respiratory tract, urinary tract, abdominal, skin); a chronic or an acute infection; a fungal colonization of two or more sites of the body; e.g. severe neutropenia, an acute necrotizing pancreatitis, cancer, diabetes mellitus, arterial hypertension, coronary heart disease, chronic obstructive lung disease (COPD), renal insufficiency; transplantation of the liver, the kidney, the heart; liver cirrhosis, cancer patients, diarrhoea; A pregnancy with complications e.g. at risk of getting a preterm birth; a surgery or a trauma (polytrauma), e.g. liver surgery; minimal- or invasive medical procedures or devices, e.g. a (venous or urinal) catheter(s), needles, cannula, bandages, (mechanical) ventilation, cardiopulmonary bypass, an internal prosthetic devices, a parenteral nutrition, a haemodialysis, renal replacement therapy, apheresis, infusions, burns; an increased risk of mortality or bad outcome; an age related risk of having an impaired immune system e.g. elderly or neonates; critically ill disease (e.g. in-hospitalized patients, especially on intensive care unit (ICU) (Muskett et al. Critical Care 2011; Table 1).

A fungal species, in particular *Candida* spp. and/or *Aspergillus* spp., in the respiratory tract or in fluids from e.g. drainages, lavages or e.g. from abdominal tract or in secretes or fluids or from the skin were classified as "colonization". The colonization can be partial or multiple located (FIG. 1).

The colonization is possible by commensals, i.e., growth enabled by conditions prevailing on the skin or intestinal surface without degradation of tissue and therefore in healthy people classifies as not having a pathogenic infection (non-infection) and is seen as natural microbiome of a subject. In a response-damage framework, all fungi are potentially able to cause disease, as a balance between their natural predilection and the immune status of the host. The switch from colonization to a pathogenic disease state is e.g. possible in a subject with delayed or defect immune response or microbiome e.g. in subjects with an increased risk e.g. with comorbidities, medications like antibiotics or immuno-suppressors (de Hoog S. et al. (2017). Microbiol Spectr.; Hof. International Journal of Infectious Disease 14. 2010. E458-e459).

"Sepsis" in the context of the invention refers to a systemic response to infection. Alternatively, sepsis may be seen as the combination of SIRS with a confirmed infectious process or an infection. Sepsis may be characterized as clinical syndrome defined by the presence of both infection and a systemic inflammatory response (Levy M M et al. 2001 SCCM/ESICM/ACCP/ATS/SIS International Sepsis Definitions Conference. Crit Care Med. 2003 April; 31(4): 1250-6). The term "sepsis" used herein includes, but is not limited to, sepsis, severe sepsis or septic shock. Severe sepsis in this context means sepsis associated with organ dysfunction, hypoperfusion abnormality, or sepsis-induced hypotension. Hypoperfusion abnormalities include lactic acidosis, oliguria and acute alteration of mental status.

The term "sepsis" also includes severe sepsis or septic shock based on the SEPSIS-2 definition (Bone et al., 2009). The term "sepsis" also includes subjects falling within the SEPSIS-3 definition (Singer et al., 2016).

The term "sepsis" used herein relates to all possible stages in the development of sepsis.

The term "septic state or condition or a state of sepsis", relate to all phases of a septic condition and can be an asymptomatic sepsis (early stage; before the onset of sepsis), sepsis, severe sepsis, infection with organ dysfunction or septic shock.

"Septic shock" is defined as severe sepsis with sepsis-induced hypotension persisting despite adequate fluid resuscitation, along with the presence of hypoperfusion abnormalities or organ dysfunction (Bone et al., CHEST 101(6): 1644-55, 1992). Sepsis-induced hypotension is defined by the presence of a systolic blood pressure of less than about 90 mm Hg or its reduction by about 40 mm Hg or more from baseline in the absence of other causes for hypotension (e.g. cardiogenic shock).

The term "systemic inflammatory response (SIRS)" relates to infective and non-infective etiologies such as sepsis, severe sepsis and septic shock caused by microbial stimuli i.e. bacteria, viruses, fungi and/or parasites, traumatic injury and/or hemorrhage, ischemia reperfusion injury, burn injuries, acute pancreatitis as well as interventional procedures such as e.g. cardio-pulmonary bypass, chemotherapy and radiotherapy where an individual is at risk of developing, endothelial tissue damage, thromboembolism and acute disseminated intravascular coagulation (DIC) contributing to single or multiple organ dysfunction and failure (in particular acute kidney injury, acute lung injury and liver injury) during the course of the disease.

"SIRS" in the context of the invention is a systemic inflammatory response syndrome with no signs of infection. It includes, but is not limited to more than one of the following clinical manifestations: (1) a body temperature greater than 38° C. or less than 36° C.; (2) a heart rate greater than 90 beats per minute; (3) tachypnea, manifested by a respiratory rate greater than 20 breaths per minute, or hyperventilation, as indicated by a PaCO2 of less than 32 mm Hg; and (4) an alteration in the white blood cell count such as a count greater than 12,000/$mm^2$, a count less than 4,000/$mm^3$, or the presence of more than 10% immature neutrophils (Bone et al., CHEST 101(6): 1644-55, 1992).

The term "sample", refers to bodily fluids or tissue e.g. blood or fractions thereof, plasma, serum, drainage fluid, intraoperative swabs, respiratory tract specimens e.g. bronchoalveolar lavage (BAL), skin, sweat, mucosa, saliva, sputum, pleural effusions, tears, urine, bone marrow, cerebrospinal fluid, fascial tissue, nasal swab, breath gas, wound secretions, stool, amniotic fluid, pulmonary infiltrates or a mixture thereof, are taken from the patient to be examined, and the diagnosis takes place in vitro/ex vivo, i.e. outside of the human or animal body. In addition, one of skill in the art would realize that some test samples would be more readily analyzed following a fractionation or purification procedure, for example, separation of whole blood into serum or plasma components. Thus, in one embodiment of the invention the sample is blood or a fraction thereof, drainage fluid, an intraoperative swab, a respiratory tract specimen such as a bronchoalveolar lavage (BAL), skin, sweat, mucosa, saliva, sputum, pleural effusion, tears, urine, bone marrow, cerebrospinal fluid, fascial tissue, nasal swab, breath gas, wound secretion, stool, amniotic fluid, a pulmonary infiltrate or a mixture thereof, preferably the sample is whole blood, serum or plasma. In a preferred embodiment of the invention the sample is selected from the group consisting of a blood sample, a serum sample, a plasma sample, a cerebrospinal fluid sample, a saliva sample and a urine sample or an extract of any of the aforementioned samples. Preferably, the sample is a blood sample such as a whole blood sample, most preferably a serum sample or a plasma sample.

Samples can be measured within a single step or in parallel with other markers or clinical parameters. One or more samples can be measured. The samples can be collected at the first contact at a clinical site, preferably a hospital, most preferably in a specialized hospital location, most preferred in the an emergency department (ED), any hospital unit, the intensive care unit (ICU), intraoperative, before and/or after surgery, or therapy, or medication, at ambulance, at primary care site.

A sample can be collected at different time points e.g. at hospital administration, at the onset of clinical symptom(s) of an infection, at the time of risk of getting or having an invasive fungal infection, in particular a infection at the time of risk of getting or having an co-infection, in particular a fungal infection, at onset of sepsis or at onset of an infection, or before and/or after clinical decisions like beginning, change or stop of a therapy e.g. medication, in particular antibiotics, antifungal drugs, statins, immune-suppressants.

The collection of samples can be done at time 0, meaning at the onset of the before mentioned constellations, after or every 1 hour, 6 hours, 12 hours, 18 hours, 24 hours, 2 days, 3, days, 4 days, 5 days, 6 days, 7 days, 8 days, 9 days, 11 days, 11 days, 12 days, 13 days, 14 days, 21 days, 28 days and thereafter.

"Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood) for at least 15 minutes at 2000 to 3000 g.

Therefore, it is preferred that plasma samples employed in the context of the present invention have been subjected to centrifugation at more than 1500 g for 30 min, preferably at least at 2000 g for at least 30 min, more preferably at least at 3000 g for at least 20 min, most preferably at least at 3000 g for at least 30 min.

The term "marker" or "biomarker", refers to measurable and quantifiable biological parameters (e.g. specific enzyme concentration, specific hormone concentration, specific gene phenotype distribution in a population, presence of biological substances) which serve as indices for health- and physiology-related assessments, such as disease risk, psychiatric disorders, environmental exposure and its effects, disease diagnosis, metabolic processes, substance abuse, pregnancy, cell line development, epidemiologic studies, etc. Furthermore, a biomarker is defined as a characteristic that is objectively measured and evaluated as an indicator of normal biological processes, pathogenic processes, or pharmacologic responses to a therapeutic intervention. A biomarker may be measured on a biosample (such as the samples defined above including blood, urine, or tissue test), it may be a recording obtained from a person (blood pressure, oxygen, or BMI) or it may be an imaging test (echocardiogram or CT scan) (Vasan et al. 2006, Circulation 113: 2335-2362). Biomarkers can indicate a variety of health or disease characteristics, including the level or type of exposure to an environmental factor, genetic susceptibility, genetic responses to exposures, biomarkers of subclinical or clinical disease, or indicators of response to therapy. Thus, a simplistic way to think of biomarkers is as indicators of disease trait (risk factor or risk biomarker), disease state (preclinical or clinical), or disease rate (progression). Accordingly, biomarkers can be classified as antecedent biomarkers (identifying the risk of developing an illness), screening biomarkers (screening for subclinical disease), diagnostic biomarkers (recognizing overt disease), staging biomarkers (categorizing disease severity), or prognostic biomarkers (predicting future disease course, including recurrence and response to therapy, and monitoring efficacy of therapy). Biomarkers may also serve as surrogate end points. A surrogate end point is one that can be used as an outcome in clinical trials to evaluate safety and effectiveness of therapies in lieu of measurement of the true outcome of interest. The underlying principle is that alterations in the surrogate end point track closely with changes in the outcome of interest. Surrogate end points have the advantage that they may be gathered in a shorter time frame and with less expense than end points such as morbidity and mortality, which require large clinical trials for evaluation. Additional values of surrogate end points include the fact that they are closer to the exposure/intervention of interest and may be easier to relate causally than more distant clinical events. An important disadvantage of surrogate end points is that if clinical outcome of interest is influenced by numerous factors (in addition to the surrogate end point), residual confounding may reduce the validity of the surrogate end point. It has been suggested that the validity of a surrogate end point is greater if it can explain at least 50% of the effect of an exposure or intervention on the outcome of interest. For instance, a biomarker may be a protein, peptide or a nucleic acid molecule. The National Institute of Health (NIH) defines a biomarker as a biological marker that is objectively measured and evaluated as an indicator of a normal biological process, pathogenic process, or pharmacological responses to therapeutic interventions [Danesh et al. Clin Pharmacol Ther 2001. 169:416-468].

As used herein, a "parameter" is a characteristic, feature, or measurable factor that can help in defining a particular system. A parameter is an important element for health- and physiology related assessments, such as a disease/disorder/clinical condition risk, preferably an adverse event. Furthermore, a parameter is defined as a characteristic that is objectively measured and evaluated as an indicator of normal biological processes, pathogenic processes, or pharmacologic responses to a therapeutic intervention. An exemplary parameter can be selected from the group consisting of Acute Physiology and Chronic Health Evaluation score (APACHE scores I-IV), the simplified acute physiology score 25 (SAPS I-III score), sequential organ failure assessment score (SOFA score), quick Sepsis-related Organ Failure Assessment score (qSOFA score), simplified acute physiology score II (SAPSII score), mortality probability model (MPM I-III), multiple organ dysfunction score (MODS), therapeutic intervention scoring system (TISS), nine equivalents of nursing manpower use score (NEMS), World Federation of Neurosurgical Societies (WFNS) grading, and Glasgow Coma Scale (GCS), CURB-65 pneumonia severity score, Pneumonia Severity Index (PSI), Ostrosky-Zeichner prediction rule, *Candida* score, age, gender, family history, ethnicity, body weight, body mass index (BMI), cystoscopy report, white blood cell count, imaging methods as such as CT scan, PET imaging or X-ray, blood pressure, heart rate, antihypertensive treatment, liquid intake, wheezing, body temperature, results from fluid, pathogen count and/or solid tissue culture(s); medication including antibiotics, immunosuppressive agents, statins, steroids e.g. glucocorticoids, cytostatics, therapeutic antibodies, calcineurin inhibitors, TOR (target of rapamycin) inhibitors, in particular medication including antibacterial therapy, antifungal therapy, statin therapy, or immune-suppressant therapy.

Further markers and/or parameters, mentioning a combination of at least one marker can used to improve the diagnostic value.

"Upregulation" of biomarkers means a quantitative/concentration or qualitative/activity increase of biomarkers in response to a stimulus, in particular fold changes above 1.0.

"Downregulation" of biomarkers means a quantitative/concentration or qualitative/activity decrease of biomarkers in response to a stimulus, in particular fold changes below 1.0.

"Intercellular adhesion molecule 1" (ICAM1, also referred to herein as "ICAM-1") is a protein with a length of 532 (505 without signal peptide) amino acids, has the sequence according to SEQ ID No: 1 and is a member of the adhesion immunoglobulin super family that maps to chromosome 19 p13.2-p13.3. ICAM1 exists as membrane bound surface glycoprotein and soluble (sICAM1) glycoprotein. sICAM1 Is expressed on the wide variety of human cells such as vascular endothelial cells, saphenous vein endothelial cells, aortic smooth muscle cell, astrocytes, keratinocytes, cells of the immune system and carcinoma cells. ICAM1 has classically been assigned the function of intercellular adhesion (cell-cell adhesion), extravasation, pro-inflammatory pathways and viral entry molecule. It binds to integrins of type leukocyte function-associated antigen (LFA-1A), macrophage-1 antigen (MAC1) or fibrinogen and is also exploited by rhinovirus as a receptor. ICAM1 also became known for its affinity for *Plasmodium falciparum*-infected erythrocytes, providing more of a role for ICAM1 in infectious disease. It is released into circulation through the proteolytic cleavage of extracellular region of membrane bound ICAM1 by Matrix Metalloproteinases (MMP), human leukocyte elastase and TNF-α converting enzyme (TACE), and is highly increased after cytokine stimulation. The level may be detected in blood (e.g. serum or plasma) and other body fluids. ICAM1 is secreted by endothelium during vascular inflammation and is responsible for formation, growth a rupture of atheroma. Studies suggested that circulating serum sICAM1 concentration can be used to predict the risk of post-transplant ischemic events or cardiac graft failure and Coronary Artery Disease (CAD) or is associated with cardiovascular disease, type 2 diabetes, organ transplant dysfunction (e.g. acute renal graft rejection), oxidant stress, increased abdominal fat mass, hypertension, liver disease, anterior uveitis, allergic inflammation, certain malignancies, and cerebral malaria. (Anbarasan et al. Indian Heart Journal 67. 2015; Entrez Gene or Uniprot: intercellular adhesion molecule 1; Bochkov et al. Curr Allergy Asthma Rep. 2017; ICAM1 Soluble Human Instant ELISA kit (Thermofisher Scientific, product overview). ICAM1 is upregulated in fungal infections, especially IFI/IFD. The invention includes ICAM1 or fragments thereof.

"Alpha-2-HS-glycoprotein (AHSG)" has the sequence according to SEQ ID No: 2 and is secreted from cells and therefore can be found in blood. It is known to promote endocytosis, possesses opsonic properties and influences the mineral phase of bone (Uniprot; Wuren T et al. Jpn J Infect Dis 2014; Toyotome T et al. Int J Med Microbiol. 2012). AHSG is downregulated in fungal infections, especially IFI/IFD. The invention includes AHSG or fragments thereof.

"Carboxypeptidase N catalytic chain (CPN1)" has the sequence according to SEQ ID No: 3 and is secreted from cells. It is known to be a carboxypeptidase that protects the body from potent vasoactive and inflammatory peptides (Uniprot). CPN1 is downregulated in fungal infections, especially IFI/IFD. The invention includes CPN1 or fragments thereof.

"Fatty acid-binding protein (FABP1)" has the sequence according to SEQ ID No: 4 and is located to the cytoplasm. It is known to play a role in lipoprotein-mediated cholesterol uptake in hepatocytes, binds cholesterol and free fatty acids and may be involved in intracellular lipid transport. FABP1 is upregulated in fungal infections, especially IFI/IFD. The invention includes FA81 or fragments thereof.

"Histidine-rich glycoprotein (HRG)" has the sequence according to SEQ ID No: 5. It is revealed as plasma glycoprotein that binds a number of ligands, acts as an adapter protein and is involved in processes such as immune complex and pathogen clearance, cell chemotaxis, cell adhesion, angiogenesis, coagulation and fibrinolysis (Uniprot; Rydengard V et al. PLoS Pathog 2008). HRG is downregulated in fungal infections, especially IFI/IFD. The invention includes HRG or fragments thereof.

"Polymeric Immunoglobulin receptor (PIGR)" has the sequence according to SEQ ID No: 6. It is revealed as membrane receptor as well as secreted form, binds polymeric IgA and IgM at the basolateral surface of epithelial cells for transport across the cell (Uniprot). PIGR is upregulated in fungal infections, especially IFI/IFD. The invention includes PIGR or fragments thereof.

"Ras-related protein Rap-1" has several forms including RAP1A, /RAP1B, and RAP1B-like (RAP1A/B/B-like). RAP1A for example has the sequence according to SEQ ID No: 7. It is revealed to counteract the mitogenic function of Ras, plays a role in neurite outgrowth, regulation of embryonic blood vessel formation as well as establishment of basal endothelial barrier function (Uniprot). RAP1 is downregulated in fungal infections, especially IFI/IFD. The invention includes RAP1A, RAP1B, RAP1B-like or fragments thereof.

"Thrombospondin-1" (THBS1, also referred to herein as "THBS-1") has different isoforms. Isoform 1 for example has the sequence according to SEQ ID No: 10. It is known to be localized in the ER and is an adhesive glycoprotein that mediates cell-to-cell and cell-to-matrix interactions, binds heparin and also may play a role in dentinogenesesis and antiangiogenesis, ER stress response. (Uniprot Martin-Manso G et al. PLoS One 2012). THBS1 is downregulated in fungal infections, especially IFI/IFD. The invention includes THBS1 or fragments thereof.

"Vinculin (VCL)" has different isoforms. Isoform 1 for example has the sequence according to SEQ ID No: 12. It is known to be located in the plasma membrane and cytoskeleton and act as actin-filament binding protein involved in cell-matrix adhesion and cell-cell-adhesion, regulates cell-surface E-cadherin expression and may play important roles in cell morphology and locomotion (Uniprot). VCL is down-regulated in fungal infections, especially IFI/IFD. The invention includes VCL or fragments thereof.

"Procalcitonin (PCT)" (Seq. ID Nr. 20) has become a well-established biomarker for the diagnosis of bacterial infections as well as sepsis diagnosis: PCT reflects the severity of bacterial infection and is in particular used to monitor progression of infection into sepsis, severe sepsis, or septic shock. It is possible to use PCT to measure the activity of the systemic inflammatory response, to control success of therapy e.g. for antibiotic stewardship, and to estimate prognosis (Assicot M et al.: Lancet 1993, 341:515-8; Clec'h C et al.: Diagnostic and prognostic value of procalcitonin in patients with septic shock. Crit Care Med 2004; 32:1166-9; Lee Y J et al, Yonsei Med J 2004, 45, 29-37; Meisner M Curr Opin Crit Care 2005, 11, 473-480; Wunder C et al. Inflamm Res 2004, 53, 158-163). The increase of PCT levels in patients with sepsis correlates with mortality (Oberhoffer M et al. Clin Chem Lab Med 1999; 37:363-368). It is known in the state of the art, that patients with a bacterial infection or septic condition as well as patients under antibiosis have a higher risk of getting a pathogenic fungal infection and other way around. PCT can be used as a preferred further marker together with the biomarkers of the present invention, in particular as a further marker for the improved diagnosis of mixed infections, the monitoring of patients, and/or the therapeutic guidance of patients to prevent a misuse of antibiotics or a missing of the usage or change of helpful antibiotics e.g. start, discontinuing or dose adaption. PCT is upregulated in fungal infections, especially IFI/IFD in patients with sepsis, especially septic shock and can be used as further marker for the therapeutic guidance and monitoring of patients. The invention includes PCT or fragments thereof.

"Endothelin (ET)-1" is derived from a larger precursor molecule named pro-endothelin-1. Pro-endothelin-1 can be proteolytically processed into various fragments as described (EP 2 108 958 A1; Proteolytic processing pattern of the endothelin-1 precursor in vivo. Peptides. 2005 December; 26(12):2482-6.). These fragments are subject to proteolytic degradation in the blood circulation, which can happen quickly or slowly, depending on the type of fragment and the type and concentration/activity of proteases present in the circulation. Thus, according to the present invention the level of any of these fragments of at least 12 amino acids may be measured, preferably fragments of at least 20 amino acids, more preferably of at least 30 amino acids. Preferably, C-terminal pro-ET-1 (CT-proET-1) or a fragment thereof may be measured. The level of endothelin-1 is preferably measured in the plasma or serum of a subject.

ET-1 is a potent endothelium-derived endogenous vasoconstrictor (Yanagisawa M, Kurihara H, Kimura S, Goto K, Masaki T. J Hypertens Suppl 1988; 6:S188-91). ET-1 exerts its vascular effects by activation of ET(A) and ET(B) receptors on smooth muscle cells, which causes an increase in intracellular calcium (Yanagisawa et al, J Hypertens Suppl 1988; 6:S188-91). Mature ET-1 is derived from a larger precursor termed Pro-ET-1. Pro-ET-1 can be proteolytically processed into various fragments as described (Struck J, Morgenthaler N G, Bergmann Peptides. 2005 December; 26(12)-2482-6). These fragments are subject to proteolytic degradation in the blood circulation, which can happen quickly or slowly, depending on the type of fragment and the type and concentration/activity of proteases present in the circulation. One example of these fragments is C-terminal pro-Endothelin-1 (CT-proET-1), which can be measured by a sandwich immunoassay (Papassotiriou J, Morgenthaler N G, Struck J, Alonso C, Bergmann A. Clin Chem. 2006 June; 52(6):1144-51).

The sequence of the 212 amino acid precursor peptide of ET-1 (pre-pro-ET-1) is provided in SEQ ID NO:15. Fragments thereof like pro-ET-1 (SEQ ID NO: 16) relates to the amino acid residues 18 to 212 of the sequence of pre-pro-ET-1. Pro-ET-1 is cleaved into mature ET-1 (SEQ ID NO: 17), big-ET-1 (SEQ ID NO: 19) and C-terminal proET-1 (CT-proET-1) (SEQ ID NO 18). ET-1 relates to the amino acid residues 53 to 73 of pre-pro-ET-1. CT-proET-1 relates to amino acid residues 168 to 212 of pre-pro-ET-1. Big-ET-1 comprises the amino acid residues 53 to 90 of pre-pro-ET-1. The invention includes ET-1 or fragments thereof.

As mentioned herein, an "assay" or "diagnostic assay" can be of any type or format applied in the field of diagnostics. Such an assay may be based on the binding of an analyte to be detected to one or more capture probes (capture molecules) with a certain affinity. Concerning the interaction between capture molecules and target molecules or molecules of interest, the affinity constant is preferably greater than $10^8$ $M^{-1}$.

The methods of the invention for example can be used for patient management which refers to:

- the decision for admission to hospital or intensive care unit,
- the decision for relocation of the patient to a specialized hospital or a specialized hospital unit,
- the evaluation for an early discharge from the intensive care unit or hospital,
- the allocation of resources (e.g. physician and/or nursing staff, diagnostics, therapeutics).

For this reason, the invention relates to the diagnosis and/or risk stratification of IFI/IFD, for example caused by *Candida* spp. (e.g. *C. albicans, C. glabrata*), *Aspergillus* spp. (e.g. *Aspergillus fumigatus*), *Pneumocystis* spp. (e.g. *P. jirovecii*) etc., which are the most common pathogens responsible for IFI/IFD, in particular IFI/IFD associated with sepsis or septic shock.

Hence in some instances of the invention, said fungal infection is an infection with a fungus selected from the group consisting of *Candida* spp. (*C. albicans, C. glabrata, C. krusei*), *Aspergillus* ssp. (*A. fumigatus*), *Saccharomyces* spp. (*S. cerevisiae*), *Hansenula* spp. (*H. anomala*), *Diplodocus* spp. (*D. capitatus*), *Mucor* spp., *Rhizopus* spp. (*R. microspores*), *Scedosporium* spp., *Trichosporon* spp. (*T. asahii*), Zygomycosis, *Fusarium* spp., *Cryptococcus* spp, preferably *Candida* spp. (e.g. *C. albicans, C. glabrata*), *Aspergillus* spp. (e.g. *A. fumigatus*), *Pneumocystis* spp. (e.g. *P. jirovecii*). In particular, said fungal infection may be aspergillosis (e.g. *A. fumigatus* or other A. ssp.), blastomycosis, candidiasis (e.g. *C. albicans, C. glabrata, C. krusei, C. auris* and other C. spp.), coccidioidomycosis, mucormycosis, *pneumocystis* pneumonia infection, *Cryptococcus* infection or histoplasmosis.

In a very preferred aspect the invention relates to the diagnosis and/or risk stratification of IFI/IFD associated with sepsis and/or septic shock.

In another aspect the invention relates to the diagnosis and/or risk stratification of IFI/IFD associated with an organ transplantation such as liver transplantation.

In a certain aspect of the invention, additionally the level of one or more further biomarker(s) and/or clinical score(s) and/or clinical parameter(s) and/or infection parameter(s) is/are determined. For example, the determination of one or more further biomarker may comprise carbamoyl phosphate synthetase 1 (CPS 1), adrenomedullin (ADM), in particular mid-regional proadrenomedullin (MR-proADM) (see Decker et al., 2019, Langenbecks Arch Surg. 2019 May; 404(3):309-325). CPS 1 for use as a diagnostic biomarker has been described, e.g. for detecting inflammations and infections, including sepsis, and liver failure in the case of multi-organ failure or inflammatory liver diseases and other diseases (see WO 03/089933 A1 and WO 2007/128570 A2).

As mentioned herein above, the biomarker(s) can be part of a marker panel which includes one or more further biomarkers (such as PCT) or it is/they are determined together with one or more other biomarkers, clinical scores and/or clinical parameters.

Thus, in certain aspects (i) said one or more further biomarker(s) may be selected from the group consisting of C-reactive protein (CRP), cytokines, such as TNF-alpha, for example, interleukins, such as IL-10, IL-6, IL-22, IL17A and IL-17ß, interleukin-1ß, procalcitonin (PCT), TNF-related apoptosis-inducing ligand (TRAIL), Neutrophil gelatinase-associated lipocalin (NGAL), Interferon-induced GTP-binding protein Mx1 (MX1), pancreatic stone protein (PSP) and fragments thereof, atrial natriuretic peptide (ANP, pro ANP), arginin vasopressin (AVP, pro-AVP, copeptin), angiotensin II, glucans, interferon gamma (INF-gamma), specific fungal related peptides or fragments e.g. from the hyphes, the mycelium, the spores, the cell wall, such as β-D-glucan, mannan or galactomannan, and adhesion molecules, such as VCAM; and/or (ii) said one or more clinical score(s) of said subject selected from the group consisting of sequential organ failure assessment score (SOFA), simplified acute physiology score (SAPSII score), the Acute Physiology and Chronic Health Evaluation II (APACHE II) score, and the Pneumonia Severity Index (PSI) score; and/or (iii) said one or more clinical parameter(s) is selected from the group consisting of age, gender, family history, ethnicity, body weight, body mass index (BMI), systolic blood pressure, diastolic blood pressure, heart rate, temperature, duration of a medicinal intervention e.g. time of surgery or duration of mechanical ventilation, surgical procedures, medication, in particular antibacterial therapy, antifungal therapy, statin therapy, or immune-suppressant therapy; and/or (iv) said one or more infection parameter(s) selected from the group consisting of leukocyte count, neutrophil count, isolates or cultures from one or different location of the body from said subject.

In one aspect of the methods as used in the present invention, one or more further biomarker(s) and/or clinical score and/or clinical parameter and/or infection parameter(s) are correlated with the level of the at least one biomarker, whereby the combination of said level of the at least one biomarker with said level of one or more further biomarker(s) and/or clinical score(s) and/or clinical parameter(s) and/or infection parameter(s) increases the predictive value of the level of the at least one biomarker for indicating a fungal infection, preferably an invasive infection; and optionally for indicating whether a patient is in a need to receive and/or adjustment of an anti-fungal therapy, and/or the course and/or the severity of a fungal infection in sample of a patient, preferably an invasive infection.

In particular, detection of mannan, galactomannan, β-D-glucan or other pathogen specific targets in bodily fluid may be used to diagnose invasive fungal infections in humans.

In another embodiment of the invention, the method according to the invention can be carried out by means of parallel or simultaneous determinations of the markers (e.g. multi-titer plates with 96 cavities and more), where the determinations are carried out on at least one patient sample.

Furthermore the results of the measurements can be calculated by using mathematical algorithms. The invention also relates to a computer-implemented method and a kit for conducting the method of the invention. Wherein said comparing of two different conditions e.g. an invasive fungal infection or critical fungal infection with an uncritical fungal colonization or non-fungal infection, as well as the monitoring or treatment of the conditions is carried out in a computer processor using computer executable code.

In one aspect of the present invention, the level of the biomarker is determined by mass in a certain aspect of the invention, spectrometry or in an immunoassay.

In a certain aspect of the present invention, the level of the at least one biomarker is determined using a method selected from the group consisting of Luminescence immunoassay (LIA), radioimmunoassay (RIA), chemiluminescence- and fluorescence-immunoassay, enzyme immunoassay (EIA), Enzyme-linked immunoassay (ELISA), luminescence-based bead array, magnetic beads based array, protein microarray assay, rapid test formats, test strips, automated immune assay systems, a homogeneous or heterogeneous immune assay format and rare cryptate assay.

In this context, the method according to the invention and its determinations can be carried out using an automated analysis devices, such as a Kryptor (BRAHMS GmbH, Hennigsdorf, Germany).

In another aspect, the method according to the invention and its determinations are carried out by means of a rapid test (e.g. lateral flow test), whether using single-parameter or multi-parameter determinations.

Moreover, a marker can be determined by mass spectrometric based methods, such as methods determining the relative quantification or determining the absolute quantification of the protein or fragment thereof of interest.

Relative quantification "rSRM" may e.g. be achieved by:

1. Determining increased or decreased presence of the target protein by comparing the SRM (Selected reaction monitoring) signature peak area from a given target fragment peptide detected in the sample to the same SRM signature peak area of the target fragment peptide in at least a second, third, fourth or more biological samples.

2. Determining increased or decreased presence of target protein by comparing the SRM signature peak area from a given target peptide detected in the sample to SRM signature peak areas developed from fragment peptides from other proteins, in other samples derived from different and separate biological sources, where the SRM signature peak area comparison between the two samples for a peptide fragment are normalized for e.g. to amount of protein analyzed in each sample.

3. Determining increased or decreased presence of the target protein by comparing the SRM signature peak area for a given target peptide to the SRM signature peak areas from other fragment peptides derived from different proteins within the same biological sample in order to normalize changing levels of the biomarker to levels of other proteins that do not change their levels of expression under various cellular conditions.

4. These assays can be applied to both unmodified fragment peptides and to modified fragment peptides of the target proteins, where the modifications include, but are not limited to phosphorylation and/or glycosylation, acetylation, methylation (mono, di, tri), citrullination, ubiquitinylation and where the relative levels of modified peptides are determined in the same manner as determining relative amounts of unmodified peptides.

Absolute quantification of a given peptide may be achieved by:

1. Comparing the SRM/MRM signature peak area for a given fragment peptide from the target proteins in an individual biological sample to the SRM/MRM signature peak area of an internal fragment peptide standard spiked into the protein lysate from the biological sample. The internal standard may be a labeled synthetic version of the fragment peptide from the target protein that is being interrogated or the labeled recombinant protein. This standard is spiked into a sample in known amounts before (mandatory for the recombinant protein) or after digestion, and the SRM/MRM signature peak area can be determined for both the internal fragment peptide standard and the native fragment peptide in the biological sample separately, followed by comparison of both peak areas. This can be applied to unmodified fragment peptides and modified fragment peptides, where the modifications include but are not limited to phosphorylation and/or glycosylation, acetylation, methylation (e.g. mono-, di-, or tri-methylation), citrullination, ubiquitinylation, and where the absolute levels of modified peptides can be determined in the same manner as determining absolute levels of unmodified peptides.

2. Peptides can also be quantified using external calibration curves. The normal curve approach uses a constant amount of a heavy peptide as an internal standard and a varying amount of light synthetic peptide spiked into the sample. A representative matrix similar to that of the test samples needs to be used to construct standard curves to account for a matrix effect. Besides, reverse curve method circumvents the issue of endogenous analyte in the matrix, where a constant amount of light peptide is spiked on top of the endogenous analyte to create an internal standard and varying amounts of heavy peptide are spiked to create a set of concentration standards. Test samples to be compared with either the normal or reverse curves are spiked with the same amount of standard peptide as the internal standard spiked into the matrix used to create the calibration curve.

In the context of the present invention, "capture molecules" are molecules which may be used to bind target molecules or molecules of interest, i.e. analytes (i.e. in the context of the present invention the cardiovascular peptide(s)), from a sample. Capture molecules must thus be shaped adequately, both spatially and in terms of surface features, such as surface charge, hydrophobicity, hydrophilicity, presence or absence of Lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, capture molecules may for instance be selected from the group comprising a nucleic acid molecule, a carbohydrate molecule, a RNA molecule, a protein, an antibody, a peptide or a glycoprotein. Preferably, the capture molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

In a particular aspect the assay comprises at least one or two capture molecules, preferably antibodies which are both present as dispersions in a liquid reaction mixture, wherein a first labeling component is attached to the first capture molecule, wherein said first labeling component is part of a labeling system based on fluorescence- or chemiluminescence-quenching or amplification, and a second labeling component of said marking system is attached to the second capture molecule, so that upon binding of both capture molecules to the analyte a measurable signal is generated that allows for the detection of the formed sandwich complexes in the solution comprising the sample.

Even more particular, said "labeling system" comprises rare earth cryptates or rare earth chelates in combination with a fluorescence dye or chemiluminescence dye, more in particular a dye of the cyanine type. Capture molecules or molecular scaffolds include, for example aptamers, DARpins (Designed Ankyrin Repeat Proteins) or Affimers.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4',7,4,7-hexachlorofluorescein (HEX), TET, 6-Carboxy-4',5'-dichloro-2',7'-dimethoxyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in Kirk-Othmer, Encyclopedia of chemical technology, 4th ed., executive editor, J. I. Kroschwitz; editor, M. Howe-Grant, John Wiley & Sons, 1993, vol. 15, p. 518-562. Preferred chemiluminescent dyes are acridiniumesters.

The detection of a biomarker in the method of the present invention may, thus, in one instance be performed as an immunoassay comprising the steps of:

a) contacting the sample with
   (i) a first antibody or an antigen-binding fragment or derivative thereof specific for a first epitope of the biomarker, and
   (ii) a second antibody or an antigen-binding fragment or derivative thereof specific for a second epitope of the biomarker; and
b) detecting the binding of the first and second antibodies or antigen-binding fragments or derivates thereof to the biomarker.

In particular, the first antibody and the second antibody may be present dispersed in a liquid reaction mixture, and wherein a first labelling component which is part of a labelling system based on fluorescence or chemiluminescence extinction or amplification is bound to the first antibody, and a second labelling component of said labelling system is bound to the second antibody so that, after binding of both antibodies to at least one biomarker or fragment thereof, a measurable signal which permits detection of the resulting sandwich complexes in the measuring solution is generated.

The invention furthermore relates to a "kit" or the use of such a kit for in vitro diagnosis or risk stratification of IFI/IFD, in particular IFI/IFD associated with sepsis or septic shock, where a determination of at least one marker selected from the group of ICAM1, AHSG, CPN1, FABP1, HRG, PIGR, RAP1, THBS1, VCL and ET-1, is carried out in a subject to be investigated, particularly in a method according to the invention. The kit comprises detection reagents comprising capture molecules like antibodies, and optionally further reagents such as buffers and/or calibrators.

In a certain aspect of the present invention, the kit or the use of such a kit for the determination of at least one marker selected from the group of ICAM1, AHSG, CPN1, FABP1, HRG, PIGR, RAP1, THBS1, VCL and ET-1 (or combination thereof, i.e. a panel or cluster of biomarkers) for the determination of different infection markers as provided herein may be comprised of different diagnostic methods e.g. the combination of immunoassays with known detection methods like molecular diagnostics e.g. PCR (polymerase chain reaction) or NGS (Next Generation Sequencing), MS (Mass Spectrometry), Flow Cytometry, imaging techniques e.g. X-ray or tomographies, or microbiological detection methods that can be used for an improved diagnosis, therapy guidance or control, e.g. the biomarkers of the invention in combination with PCT as a marker for a bacterial infection and the combination with PCR for the detection of biomarkers or for the detection of pathogens or for the detection of drug resistant pathogens.

In one aspect of the present invention, specific peptide sequences of the biomarkers (or combination thereof, i.e. a panel or cluster of peptides of biomarkers) are used for the detection of the biomarkers of the present invention, e.g. as an epitope for antibodies in immunoassays or as peptides determined in MS analysis. Hence, the kit of the present invention uses specific peptide sequences of the biomarkers of the present invention in order to detect these biomarkers, e.g. in that a kit may contain antibodies against one or more of said epitopes. In particular, the peptides of the markers may contain the following amino acid sequences, which are defined by the positions of amino acids in the amino acid sequence of the respective biomarker of the present invention. In particular, the peptide of ICAM1 contains amino acids from position 57 to position 66 of SEQ ID NO: 1 (SEQ ID NO: 21); the peptide of AHSG contains amino acids from position 125 to position 131 of SEQ ID NO: 2 (SEQ ID NO: 22); the peptide of CPN1 contains amino acids from position 38 to position 47 of SEQ ID NO: 3 (SEQ ID NO: 23); the peptide of FABP1 contains amino acids from position 21 to position 31 of SEQ ID NO: 4 (SEQ ID NO: 24); the peptide of HRG contains amino acids from position 44 to position 52 of SEQ ID NO: 5 (SEQ ID NO: 25); the peptide of PIGR contains amino acids from position 110 to position 117 of SEQ ID NO: 6 (SEQ ID NO: 26); the peptide of RAP1 contains amino acids from position 129 to position 136 of SEQ ID NO: 7 (SEQ ID NO: 27); the peptide of THBS1 contains amino acids from position 217 to position 228 of SEQ ID NO: 10 (SEQ ID NO: 28) and the peptide of VCL contains amino acids from position 916 to position 924 of SEQ ID NO: 12 (SEQ ID NO: 29). Such peptides or the respective epitopes may be measured by the kit of the present invention, wherein the kit may be used in and adapted for different diagnostic methods e.g. the combination of immunoassays with known detection methods like molecular diagnostics e.g. PCR (polymerase chain reaction) or NGS (Next Generation Sequencing), MS (Mass Spectrometry), Flow Cytometry, imaging techniques e.g. X-ray or tomographies, or microbiological detection methods that can be used for an improved diagnosis, therapy guidance or control, e.g. the biomarkers of the invention in combination with PCT as a marker for a bacterial infection and the combination with PCR for the detection of biomarkers or for the detection of pathogens or for the detection of drug resistant pathogens. Preferably, the kit may be for use in immunoassays. Thereby, the immunoassay kit may comprise one or more antibodies that are directed against the portion of amino acids of the respective biomarkers as defined above with respect to the corresponding SEQ ID NO.

In one aspect of the method of the present invention, the method additionally comprises treating the subject according to the outcome of the method, either (A) for a fungal infectious disease, in particular an invasive fungal infection wherein said treating comprises administration of appropriate anti-infectious therapeutic agents, such as common anti-fungal therapeutic agents, or (B) for a mixed infection condition with different kind of pathogens e.g. bacterial and/or fungal pathogens, such as common anti-fungal and/or anti-bacterial agents, or (C) for a condition without an infection or with uncritical fungal colonization, without administering anti-infectious therapeutic agents.

In the context of the present invention, an "algorithm" or "mathematical algorithm" refers to the use of a mathematical or statistical method or model used to compare a certain measured value with values of a reference population in order to stratify said measured value. This may for instance be the median of the level of a certain entity in an ensemble of pre-determined samples, which means that the measured level of said entity is compared with the mathematical median of the level of said entity in a given number of samples. The number of samples used to determine the median is not particularly limited, but should be sufficient in order to ensure statistical significance of the median. The number of samples used to determine the median may even increase over the course of time, as the results of further measurement values from clinical samples are added in order to increase the statistical significance of the median. Preferably, the sample number is chosen such that statistical significance of the median is ensured. Thus, said median is used as a reference value, whereby the measured level of the aforementioned entity can be statistically correlated with a certain physiological state, e.g. the propensity of an fungal infection and/or invasive fungal infection or the differentiation of a fungal colonization with a fungal infection for a patient, depending on the relative level above or below the median and the extent of deviation of the measured value from said median, in particular the fold change value. In place of the median, other statistical methods, such as the determination of quantiles (e.g. quartiles or percentiles) or mathematical models, preferably Cox Regression may be used analogously to the above description in order to obtain the above-mentioned reference value and/or otherwise determine the significance of a measured value with respect to the physiological status of a given subject from which the sample has been obtained. Said mathematical or statistical methods or models are well known to the person skilled in the art and the use thereof in the context of medicinal applications is well established.

In certain instances of the invention, a software system can be employed, in which a machine learning algorithm is used, preferably to identify patients with an invasive fungal infection using data from electronic health records (EHRs). A machine learning approach can be trained on a random forest classifier using EHR data (such as labs, biomarker expression, vitals, scores, treatments and demographics) from patients. Machine learning is a type of artificial intelligence that provides computers with the ability to learn complex patterns in data without being explicitly programmed, unlike simpler rule-based systems. In the context of the present invention, the processing of at least one level of a biomarker of the present invention (and optionally the level of at least one further biomarker such as PCT) may be incorporated into appropriate software for comparison to existing data sets, for example ICAM1 levels may also be processed in machine learning software to assist in diagnosing fungal infection.

One aspect of the present invention is related to therapy guidance of a fungal infection or a differentiation of a fungal infection from a fungal colonization or mixed infection in a subject at risk of getting or having fungal infection, wherein the therapeutic guidance comprises the use of the methods of the present invention for determining whether the subject is in a need to receive and/or adjustment of an anti-fungal therapy, and/or the course and/or the severity of a fungal infection.

ITEMS OF THE PRESENT INVENTION

In particular aspects, the present invention relates to the following items:

1. A method for the diagnosis, prognosis, risk assessment and/or therapy monitoring of a fungal infection in a subject, comprising the step of
   determining the level of at least one biomarker selected from the group consisting of intercellular adhesion molecule 1 (ICAM1), alpha-2-HS-glycoprotein (AHSG), carboxypeptidase N catalytic chain 1 (CPN1), fatty-acid binding protein 1 (FABP1), histidine rich glycoprotein (HRG), polymeric immunoglobulin receptor (PIGR), ras-related protein 1 (RAP1), thrombospondin-1 (THBS1), vinculin (VCL) and endothelin 1 (ET-1) in a sample of said subject,
   wherein said level of the at least one biomarker is indicative for the presence, the risk of getting, the severity and/or the type of fungal infection in said subject.
2. The method of item 1, wherein the method is for the diagnosis of an invasive fungal infection in a subject, comprising the step of
   determining the level of at least one biomarker selected from the group consisting of ICAM1, AHSG, CPN1, FABP1, HRG, PIGR, RAP1, THBS1, VCL and ET-1 in a sample of said subject,
   wherein said level of the at least one biomarker is indicative for the presence of an invasive fungal infection in said subject.
3. The method of item 1, wherein the method is for assessing whether a subject is in a need and/or for the adjustment of an anti-fungal treatment, wherein the method comprises the step of
   determining the level of at least one biomarker selected from the group consisting of ICAM1, AHSG, CPN1, FABP1, HRG, PIGR, RAP1, THBS1, VCL and ET-1 or fragments thereof in a sample of said subject,
   wherein the level of the at least one biomarker is indicative of a need of said subject to receive anti-fungal treatment.
4. The method of any of the preceding items, wherein the invasive fungal infection is an acute, serious fungal infection, in particular a systemic fungal infection, a fungemia or a multifocal infection.
5. The method of any of the preceding items, wherein the level of said biomarker(s) is determined after the subject is diagnosed of having or getting a fungal infection or the subject is diagnosed to be in a critical disease state and/or after admission of the subject to a medical site, preferably into ICU or hospital.
6. The method of any one of items 1 to 5, wherein said level of the at least one biomarker is compared to a reference value of said at least one biomarker, wherein
   (i) when the biomarker is selected from the group consisting of ICAM1, FABP1, PIGR and ET-1, a level above said reference value in the sample is indicative for the presence of an invasive fungal infection in the subject; or
   (ii) when the biomarker is selected from the group consisting of AHSG, CPN1, HRG, RAP1, THBS1 and VCL, a level below said reference value in the sample of the subject is indicative for the presence of an invasive fungal infection in the subject.
7. The method of any one of items 1 to 6, wherein said reference value is derived from the level of the respective biomarker in (a) sample(s) of a reference subject or a population of reference subjects without said invasive fungal infection.
8. The method of item 7, wherein said reference value is derived from the level of the respective biomarker in (a) sample(s) of a reference subject or a population of reference subjects without a fungal colonization.
9. The method of item 7, wherein said reference value is derived from the level of the respective biomarker in (a) sample(s) of a reference subject or a population of reference subjects which has/have a fungal colonization.
10. The method of item 9, wherein said subject has been diagnosed as having a fungal colonization.
11. The method of any one of items 7 to 10, wherein said reference value is derived from the level of the respective biomarker in (a) sample(s) of a subject or a population of subjects without said invasive fungal infection, wherein
   (a) when the biomarker is ICAM1, a level of at least the 1.1 fold, preferably at least the 1.3 fold, more preferably at least the 1.6 fold, more preferably of at least the 1.7 fold, more preferably at least the 1.9 fold, more preferably at least the 2.3 fold, more preferably at least the 2.8 fold is indicative for the presence of an invasive fungal infection in the subject;
   (b) when the biomarker is FABP1, a level of at least the 1.03 fold, preferably at least the 1.4 fold, more preferably at least the 1.5 fold, more preferably at least the 1.9 fold, more preferably at least the 2.0 fold, more preferably 2.1 fold is indicative for the presence of an invasive fungal infection in the sample of the subject;
   (c) when the biomarker is PIGR, a level of at least the 1.3 fold, more preferably at least the 1.9 fold, more preferably of at least the 2.1 fold, more preferably at least the 2.8 fold, more preferably at least the 3.5 fold, more preferably at least the 3.6 fold, more preferably at least the 5.7 fold is indicative for the presence of an invasive fungal infection in the subject;
   (d) when the biomarker is ET-1, particularly CT-proET-1, a level of at least the 1.1 fold, more preferably at least the 1.7 fold, even more preferably at least the 2.0 fold, even more preferably at least the 3.0 fold; even more preferably at least the 3.5 fold is indicative of the presence of an invasive fungal infection in the subject.

(e) when the biomarker is AHSG, a level of at least the 0.7 fold, preferably at least the 0.6 fold, more preferably at least the 0.4 fold, more preferably at least the 0.3 fold, more preferably at least the 0.1 fold is indicative of the presence of an invasive fungal infection in the subject;

(f) when the biomarker is CPN1, a level of at least the 0.9 fold, preferably at least the 0.7 fold, more preferably at least the 0.6 fold, more preferably at least the 0.5 fold, more preferably at least the 0.4 fold, more preferably at least the 0.3 fold is indicative for the presence of an invasive fungal infection in the subject;

(g) when the biomarker is HRG, a level of at least the 0.8 fold, preferably at least the 0.7 fold, more preferably at least the 0.4 fold, preferably at least the 0.2 fold, preferably at least the 0.1 fold is indicative of the presence of an invasive fungal infection in the subject;

(h) when the biomarker is RAP1A, a level of at least the 0.9 fold, preferably at least the 0.7 fold, more preferably at least the 0.5 fold, even more preferably at least the 0.2 fold, preferably at least the 0.04 fold is indicative of the presence of an invasive fungal infection in the subject;

(i) when the biomarker is THBS1, a level of at least the 0.9 fold, preferably at least the 0.8 fold, more preferably at least the 0.4 fold, even more preferably at least the 0.2 fold, even more preferably at least the 0.04 fold is indicative of the presence of an invasive fungal infection in the subject.

12. The method of any one of items 1 to 11, wherein the level of said biomarker is determined between day 0 and day 14 after the subject is first diagnosed of having or getting a fungal infection and/or after the subject is first diagnosed to be in a critical disease state and/or risk of having or getting an invasive fungal infection and/or after admission of the subject to a medical site, preferably into an intensive care unit (ICU) or a hospital.

13. The method of any of the preceding items, wherein the subject is a subject having an increased risk of getting or having an invasive fungal infection.

14. The method of item 13, wherein said subject is in a critical disease state.

15. The method of item 13, wherein said subject is a subject selected from the group consisting of (i) a patient having at least one chronic or acute viral or bacterial infection; In particular a local and/or systemic bacterial and/or viral infection;

(ii) a patient having a mixed bacterial and viral infection;

(iii) a patient having an immune suppression, impaired immune response or dysregulated immune system, in particular Systemic Inflammatory Response Syndrome (SIRS), sepsis, severe sepsis, infection with an organ dysfunction or septic shock, and/or fungal colonization of two or more sites of the body.

16. The method of any of the preceding items wherein the subject is a mammal, preferably a human.

17. The method of any of the preceding items, wherein the sample is blood or a fraction thereof, drainage fluid, an intraoperative swab, a respiratory tract specimen such as a bronchoalveolar lavage (BAL), skin, sweat, mucosa, saliva, sputum, pleural effusion, tears, urine, bone marrow, cerebrospinal fluid, fascial tissue, nasal swab, breath gas, wound secretion, stool, amniotic fluid, a pulmonary infiltrate or a mixture thereof, preferably the sample is whole blood, serum or plasma.

18. The method of any of the preceding items, wherein additionally the level of one or more further biomarker(s) and/or clinical score(s) and/or clinical parameter(s) and/or infection parameter(s) is/are determined.

19. The method of item 18, wherein (i) said one or more further biomarker(s) is selected from the group consisting of C-reactive protein (CRP), cytokines, such as TNF-alpha, for example, interleukins, such as IL-10, IL-6, IL-22, IL17A and IL-17B, interleukin-10ß, procalcitonin (PCT), TRAIL, NGAL, MX1, PSP, atrial natriuretic peptide (ANP, pro ANP), arginin vasopressin (AVP, pro-AVP, copeptin), angiotensin II, glucans, interferon gamma (INF-gamma), specific fungal related peptides or fragments e.g. from the hyphes, the mycelium, the spores, the cell wall, such as beta-D-glucan, mannan or galactomannan, and adhesion molecules, such as VCAM; and/or (ii) said one or more clinical score(s) of said subject selected from the group consisting of sequential organ failure assessment score (SOFA), simplified acute physiology score (SAPSII score), the Acute Physiology and Chronic Health Evaluation II (APACHE II) score, and the Pneumonia Severity Index (PSI) score; and/or (iii) said one or more clinical parameter(s) is selected from the group consisting of age, gender, family history, ethnicity, body weight, body mass index (BMI), systolic blood pressure, diastolic blood pressure, heart rate, temperature, duration of a medicinal intervention e.g. time of surgery or duration of mechanical ventilation, surgical procedures, medication, in particular antibacterial therapy, antifungal therapy, statin therapy, or immune-suppressant therapy, and/or (iv) said one or more infection parameter(s) selected from the group consisting of leukocyte count, neutrophil count, isolates or cultures from one or different location of the body from said subject.

20. The method of any of the preceding items, wherein the level of the biomarker is determined by mass spectrometry or in an immunoassay.

21. The method of any one of item 20, wherein said level of the at least one biomarker is determined using a method selected from the group consisting of Luminescence immunoassay (LIA), radioimmunoassay (RIA), chemiluminescence- and fluorescence-immunoassay, enzyme immunoassay (EIA), Enzyme-linked immunoassay (ELISA), luminescence-based bead array, magnetic beads based array, protein microarray assay, rapid test formats, test strips, automated immune assay systems, a homogeneous or heterogeneous immune assay format and rare cryptate assay.

22. The method of item 20 or 21, wherein the method is an immunoassay comprising the steps of:

a) contacting the sample with (i) a first antibody or an antigen-binding fragment or derivative thereof specific for a first epitope of the at least one biomarker, and (ii) a second antibody or an antigen-binding fragment or derivative thereof specific for a second epitope of the at least one biomarker; and b) detecting the binding of the first and second antibodies or antigen-binding fragments or derivates thereof to the at least one biomarker.

23. The method of item 22, wherein the first antibody and the second antibody are present dispersed in a liquid reaction mixture, and wherein a first labelling component which is part of a labelling system based on fluorescence or chemiluminescence extinction or amplification is bound to the first antibody, and a second labelling component of said labelling system is bound to the second antibody so that, after binding of both antibodies to at least one biomarker or fragment thereof, a measurable signal which permits detection of the resulting sandwich complexes in the measuring solution is generated.

24. The method of any of the preceding items, further comprising the diagnosis and/or risk stratification for the course and/or the severity of a fungal infection, preferably invasive fungal infection, in the sample of the patient as an accompaniment to a therapy; wherein said therapy is adjusted comprising administration of appropriate anti-infectious therapeutic agents, such as common anti-fungal therapeutic agents.

25. The method of any of the preceding items, wherein said fungal infection is an infection with a fungus selected from the group consisting of *Candida* spp. (*C. albicans, C. glabrata, C. krusei*), *Aspergillus* ssp. (*A. fumigatus*), *Saccharomyces* spp. (*S. cerevisiae*), *Hansenula* spp. (*H. anomala*), *Diplodocus* spp. (*D. capitatus*), *Mucor* spp., *Rhizopus* spp. (*R. microspores*), *Scedosporium* spp., *Trichosporon* spp. (*T. asahii*), *Zygomycosis, Fusarium* spp., *Cryptococcus* spp, preferably *Candida* spp. (e.g. *C. albicans, C. glabrata*), *Aspergillus* spp. (e.g. *A. fumigatus*), *Pneumocystis* spp. (e.g. *P. jiroveci*).

26. The method of any one of items 1 to 25, wherein said fungal infection is aspergillosis (e.g. *A. fumigatus* or other A. ssp.), blastomycosis, candidiasis (e.g. *C. albicans, C. glabrata, C. krusei, C. auris* and other C. spp.), coccidioidomycosis, mucormycosis, *pneumocystis* pneumonia infection, *Cryptococcus* infection or histoplasmosis.

27. An antifungal agent for use in treating an invasive fungal infection in a subject, wherein said antifungal agent is administered to said subject if an invasive fungal infection has been diagnosed or predicted in said subject by a method according to any one of items 1 to 26.

All patent and not-patent references cited herein are hereby incorporated by reference in their entirety.

DESCRIPTION OF THE DRAWINGS

FIG. 1: Identification of fungal pathogens in patients with septic shock (n=50).

FIGS. 2.1A-2.1C: ICAM1 differentiates between invasive fungal infection and fungal colonization or no fungal infection.

A) Box-Blots for ICAM1 measured in patients suffering from septic shock with an invasive fungal infection (IFI, dark grey box), a fungal colonization (light grey box) or without any fungal findings (white box) for the time points: onset of septic shock (T0), and 1 day (T1), 2 days (T2), 7 days (T3), 14 days (T4), 21 days (T5) and 28 days (T6) afterwards (box plots as median, 25th percentile, 75th percentile with the 10th as well as 90th percentile at the end of the whiskers. Concerning symbolism and higher orders of significance: $p<0.05^*$, $p<0.01^{}$, $p<0.001^{*}$).

B) Receiver operating characteristic (ROC) analysis with ICAM1 in all participating patients at sepsis onset (T0), and 1 day (T1), 2 days (T2) as well as 7 days (T3) afterwards with regard to the prediction of an invasive fungal infection (IFI) up to day 28 (target group: patients with an invasive fungal infection (IFI), controls: patients with a fungal colonization or without any fungal isolates).

C) Plasma concentrations of ICAM1 measured in patients suffering from septic shock with an invasive fungal infection (dark grey box), a fungal colonization (light grey box) or without any fungal findings (white box). Plasma samples were calculated at 1 day (T1), 2 days (T2) and 7 days (T3) compared to the onset of septic shock (T0), i.e. change from T0 to T1, T0 to T2 and T0 to T3 (box plots as median, 25th percentile, 75th percentile with the 10th as well as 90th percentile at the end of the whiskers. Concerning symbolism and higher orders of significance: $p<0.05^*$, $p<0.01^{}$, $p<0.001^{*}$).

FIG. 2.2: Receiver operating characteristic (ROC) analysis of ICAM1 change from T0 to T1, T0 to T2 or T0 to T3, respectively (target group: patients with an invasive fungal infection (IFI), controls: patients with a fungal colonization or without any fungal isolates).

FIG. 2.3: Plasma concentrations of ICAM1 in patients suffering from septic shock with an invasive fungal infection (IFI, dark grey box), a fungal colonization (light grey box) or without any fungal findings (white box) In IFI patients as well as in those with a fungal colonization, plasma concentrations of ICAM1 at the time point of first fungal detection in microbiological samples are presented. In patients with no fungal findings, plasma concentrations of ICAM1 at sepsis onset are presented (box plots as median, 25th percentile, 75th percentile with the 10th as well as 90th percentile at the end of the whiskers. Concerning symbolism and higher orders of significance: $p<0.05^*$.

FIG. 2.4: Receiver operating characteristic (ROC) analysis with ICAM1 in patients with an invasive fungal infection (IFI) or fungal colonization at the time point of first fungal detection in microbiological samples with regard to the prediction of an invasive fungal infection (IFI) (target group: patients with an invasive fungal infection (IFI), controls: patients with a fungal colonization). Data of patients without any fungal findings were not included in this ROC analysis.

FIG. 2.5: Receiver operating characteristic (ROC) analysis with ICAM1 in patients with an invasive fungal infection (IFI), a fungal colonization or without any fungal findings with regard to the prediction of an invasive fungal infection. In IFI patients as well as in those with a fungal colonization, plasma concentrations of ICAM1 at the time point of first fungal detection in microbiological samples are presented. In patients with no fungal findings, plasma concentrations of ICAM1 at sepsis onset are presented (target group: patients with an invasive fungal infection (IFI), controls: patients with a fungal colonization or without any fungal isolates).

FIGS. 3A-3B: THBS1 differentiates between invasive fungal infection and fungal colonization or no fungal infection, respectively.

A) Plasma concentrations of THBS1 in septic shock with an invasive fungal infection (IFI, dark grey box), a fungal colonization (light grey box) or without any fungal findings (white box) for the time points: onset of septic shock (T0), and 1 day (T1), 2 days (T2), 7 days (T3), 14 days (T4), 21 days (T5) and 28 days (T6) afterwards (box plots as median, 25th percentile, 75th percentile with the 10th as well as 90th percentile at the end of the whiskers. Concerning symbolism and higher orders of significance: p<0.05*, p<0.001***.

B) ROC analysis with THBS1 in all participating patients at sepsis onset (T0), and 1 day (T1), 2 days (T2), (T3) as well as 14 days (T4) afterwards with regard to the prediction of an invasive fungal infection (IFI) up to day 28 (target group: patients with an invasive fungal infection (IFI), controls: patients with a fungal colonization or without any fungal isolates).

FIGS. 4.1A-4.1B: RAP1 differentiates between invasive fungal infection and fungal colonization.

A) Plasma concentrations of RAP1 were measured in patients suffering from septic shock with an invasive fungal infection (IFI, dark grey box), a fungal colonization (light grey box) or without any fungal findings (white box) for the time points: onset of septic shock (T0), and 1 day (T1), 2 days (T2), 7 days (T3), 14 days (T4), 21 days (T5) and 28 days (T6) afterwards (box plots as median, 25th percentile, 75th percentile with the 10th as well as 90th percentile at the end of the whiskers. Concerning symbolism and higher orders of significance: p<0.05*, p<0.01, p<0.001*.

B) ROC analysis with RAP1 in al participating patients at sepsis onset (T0), and 1 day (T1), 2 days (T2), 7 days (T3) as well as 14 days (T4) afterwards with regard to the prediction of an invasive fungal infection (IFI) up to day 28 (target group: patients with an invasive fungal infection (IFI), controls: patients with a fungal colonization or without any fungal isolates).

FIG. 4.2: Plasma concentrations of RAP1 in patients suffering from septic shock with an invasive fungal infection (IFI, dark grey box), a fungal colonization (light grey box) or without any fungal findings (white box). In IFI patients as well as in those with a fungal colonization, plasma concentrations of RAP1 at the time point of first fungal detection in microbiological samples are presented. In patients with no fungal findings, plasma concentrations of RAP1 at sepsis onset are presented (box plots as median, 25th percentile, 75th percentile with the 10th as well as 90th percentile at the end of the whiskers. Concerning symbolism and higher orders of significance: p<0.05*.

FIG. 4.3: Receiver operating characteristic (ROC) analysis with RAP1 in patients with an invasive fungal infection (IFI) or fungal colonization at the time point of first fungal detection in microbiological samples with regard to the prediction of an invasive fungal infection (IFI) (target group: patients with an invasive fungal infection (IFI), controls: patients with a fungal colonization). Data of patients without any fungal findings were not included in this ROC analysis.

FIG. 4.4: Receiver operating characteristic (ROC) analysis with RAP1 in patients with an invasive fungal infection (IFI), a fungal colonization or without any fungal infection (IFI). In IFI patients as well as in those with a fungal colonization, plasma concentrations of RAP1 at the time point of first fungal detection in microbiological samples are presented. In patients with no fungal findings, plasma concentrations of RAP1 at sepsis onset are presented (target group: patients with an invasive fungal infection (IFI), controls: patients with a fungal colonization or without any fungal isolates).

FIGS. 5.1A-5.1B: VCL differentiates between invasive fungal infection and fungal colonization.

A) Plasma concentrations of VCL in septic shock with an invasive fungal infection (IFI, dark grey box), a fungal colonization (light grey box) or without any fungal findings (white box) for the time points: onset of septic shock (T0), and 1 day (T1), 2 days (T2), 7 days (T3), 14 days (T4), 21 days (T5) and 28 days (T6) afterwards (box plots as median, 25th percentile, 75th percentile with the 10th as well as 90th percentile at the end of the whiskers. Concerning symbolism and higher orders of significance: p<0.05*, p<0.01, p<0.001*.

B) ROC analysis with VCL in sepsis onset (T0), and 1 day (T1), 2 days (T2), (T3) as well as days 14 (T4) afterwards with regard to the prediction of an invasive fungal infection (IFI) up to day 28 (target group: patients with an invasive fungal infection (IFI), controls: patients with a fungal colonization or without any fungal isolates).

FIG. 5.2: Plasma concentrations of VCL in patients suffering from septic shock with an invasive fungal infection (IFI, dark grey box), a fungal colonization (light grey box) or without any fungal findings (white box). In IFI patients as well as in those with a fungal colonization, plasma concentrations of VCL are presented for the time point of first fungal detection in microbiological samples. In patients with no fungal findings, plasma concentrations of VCL at sepsis onset are presented (box plots as median, 25th percentile, 75th percentile with the 10th as well as 90th percentile at the end of the whiskers. Concerning symbolism and higher orders of significance: p<0.05*.

FIG. 5.3: Receiver operating characteristic (ROC) analysis with VCL in patients with an invasive fungal infection (IFI) or fungal colonization at the time point of first fungal detection in microbiological samples with regard to the prediction of an invasive fungal infection (IFI) (target group: patients with an invasive fungal infection (IFI), controls: patients with a fungal colonization). Data of patients without any fungal findings were not included.

FIG. 5.4: Receiver operating characteristic (ROC) analysis with VCL in patients with an invasive fungal infection (IFI) a fungal colonization or without any fungal findings with regard to the prediction of an IFI. In IFI patients as well as in those with a fungal colonization, plasma concentrations of VCL at the time point of first fungal detection in microbiological samples are presented. In patients with no fungal findings, plasma concentrations of VCL at sepsis onset are presented (target group: patients with an invasive fungal infection (IFI), controls: patients with a fungal colonization or without any fungal isolates).

FIGS. 6A-6B: CT-proET-1 differentiates between invasive fungal infection and fungal colonization or no fungal infection, respectively.

A) Plasma concentrations of CT-proET-1 were measured in patients suffering from septic shock with an invasive fungal infection (IFI, dark grey box), a fungal colonization (light grey box) or without any fungal findings (white box). Plasma samples were collected at the onset of septic shock (T0), and 1 day (T1) afterwards. Data in box plots are given as median, 25th percentile, 75th percentile with the 10th as well as 90th percentile at the end of the whiskers. Concerning symbolism and higher orders of significance: p<0.05: *.

B) Receiver operating characteristic (ROC) analysis with CT-proET-1 in all participating patients at sepsis onset (T0) and 1 day (T1) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIGS. 7A-7K: ICAM1 kinetic in IFI/IFD, 8 examples (different patients) with different pathogens (white boxes), treatments (grey boxes), time points and outcome.

FIG. 7A: Time course of ICAM1 in patient S10 with IFI (fungal treatment: grey box; pathogen and sample/source of fungal isolation: white boxes). The patient survived until 20 d after sepsis onset.

FIG. 7B: Time course of ICAM1 in patient S12 with invasive fungal infection (fungal treatment: grey box; pathogen and sample/source of fungal isolation: white boxes). The patient survived until 46 d after sepsis onset.

FIG. 7C: Time course of ICAM1 in patient S16 with invasive fungal infection (fungal treatment: grey boxes; pathogen and sample/source of fungal isolation: white boxes). The patient survived until 31 d after sepsis onset.

FIG. 7D: Time course of ICAM1 in patient S23 with invasive fungal infection (fungal treatment: grey boxes; pathogen and sample/source of fungal isolation: white boxes). The patient survived until >90 d after sepsis onset.

FIG. 7E: Time course of ICAM1 in patient S25 with invasive fungal infection (pathogen and sample/source of fungal isolation: white boxes). The patient survived until >90 d after sepsis onset.

FIG. 7F: Time course of ICAM1 in patient S35 with invasive fungal infection (fungal treatment: grey boxes; pathogen and sample/source of fungal isolation: white boxes). The patient survived until >90 d after sepsis onset.

FIG. 7G: Time course of ICAM1 in patient S38 with invasive fungal infection (fungal treatment: grey boxes; pathogen and sample/source of fungal isolation: white boxes). The patient survived until 37 d after sepsis onset.

FIG. 7H: Time course of ICAM1 in patient S39 with invasive fungal infection (pathogen and sample/source of fungal isolation: white boxes). The patient survived until >90 d after sepsis onset.

FIG. 7I: Time course of ICAM1 in patient S44 with invasive fungal infection (fungal treatment: grey box; pathogen and sample/source of fungal isolation: white boxes). The patient survived until 78 d after sepsis onset.

FIG. 7J: Time course of ICAM1 in patient S46 with invasive fungal infection (fungal treatment: grey box; pathogen and sample/source of fungal isolation: white boxes). The patient survived until >90 d after sepsis onset.

FIG. 7K: Time course of ICAM1 in patient S53 with invasive fungal infection (fungal treatment: grey box; pathogen and sample/source of fungal isolation: white box). The patient survived until >90 d after sepsis onset.

FIGS. 8A-8E: VCL kinetic in IFI/IFD, especially for the diagnosis and/or prediction of positive fungal cultures. VCL regulation, i.e. falling below T0 cut-off 0.1533, for example in case of *C. albicans* and *C. krusei* in swab (FIG. 8A S12 T0, FIG. 8B S23 T0, FIG. 8C S38 T5-T6, FIG. 8D S39 T0, FIG. 8E S44 T0 and T3-T5).

FIG. 8A: Time course of VCL in patient S12 with invasive fungal infection (fungal treatment: grey box; pathogen and sample/source of fungal isolation: white boxes).

FIG. 8B: Time course of VCL in patient S23 with invasive fungal infection (fungal treatment: grey boxes; pathogen and sample/source of fungal isolation: white boxes).

FIG. 8C: Time course of VCL in patient S38 with invasive fungal infection (fungal treatment: grey boxes; pathogen and sample/source of fungal isolation: white boxes).

FIG. 8D: Time course of VCL in patient S39 with invasive fungal infection (pathogen and sample/source of fungal isolation: white boxes).

FIG. 8E: Time course of VCL in patient S44 with invasive fungal infection (fungal treatment: grey boxes; pathogen and sample/source of fungal isolation: white boxes).

FIGS. 9A-9B: VCL in therapeutic guidance, therapy control and monitoring: Examples for VCL and its association in anti-fungal therapy.

FIG. 9A: Time course of VCL in patient S16 with invasive fungal infection. Grey boxes indicate antifungal treatment. White boxes mark time points, pathogen and sample of fungal isolation.

FIG. 9B: Time course of VCL in patient S35 with invasive fungal infection. Grey boxes indicate antifungal treatment. White boxes mark time points, pathogen and sample of fungal isolation.

FIGS. 10.1A-10.1B: PIGR differentiates between invasive fungal infection, colonization and no fungal isolates (A) and prediction of an invasive fungal infection (B)

A) Plasma concentrations of PIGR in septic shock with an invasive fungal infection (IFI, dark grey box), a fungal colonization (light grey box) or without any fungal findings (white box) for the time points: onset of septic shock (T0), and 1 day (T1), 2 days (T2), 7 days (T3), 14 days (T4), 21 days (T5) and 28 days (T6) afterwards (box plots as median, 25th percentile, 75th percentile with the 10th as well as 90th percentile at the end of the whiskers. Concerning symbolism and higher orders of significance: $p<0.05$*, $p<0.01$**.

B) Receiver operating characteristic (ROC) analysis with PIGR 1 day (T1), 2 days (T2), 7 days (T3) as well as 14 days (T4) after sepsis onset with regard to the prediction of an invasive fungal infection (IFI) up to day 28 (target group: patients with an invasive fungal infection (IFI), controls: patients with a fungal colonization or without any fungal isolates).

FIG. 10.2: PIGR in septic shock with an invasive fungal infection (IFI, dark grey box), a fungal colonization (light grey box) or without any fungal findings (white box), for the time point of first fungal detection in microbiological samples. Plasma concentrations of PIGR in septic shock with an invasive fungal infection (IFI, dark grey box), a fungal colonization (light grey box) or without any fungal findings (white box), for the time point of first fungal detection in microbiological samples (box plots as median, $25^{th}$ percentile, $75^{th}$ percentile with the $10^{th}$ as well as 90 percentile at the end of the whiskers. Concerning symbolism and higher orders of significance: $p<0.05$*.

FIG. 10.3: Receiver operating characteristic (ROC) analysis with PIGR in patients with an IFI, a fungal colonization or without any fungal findings with regard to the prediction of an IFI, at the time point of first fungal detection in microbiological samples (target group: patients with an invasive fungal infection (IFI), control: patients with a fungal colonization or without any fungal findings). Area under the curve was 0.727 with sensitivity of 0.636, 1-specificity of 0.205 at the best cut-off 0.0451.

FIGS. 11.1A-11.1B: CPN1 differentiates between invasive fungal infection, colonization and no fungal isolates (A) and prediction of an invasive fungal infection (B)

A) Plasma concentrations of CPN1 in septic shock with an invasive fungal infection (IFI, dark grey box), a fungal colonization (light grey box) or without any fungal findings (white box) for the time points: onset of septic shock (T0), and 1 day (T1), 2 days (T2), 7 days (T3), 14 days (T4), 21 days (T5) and 28 days (T6)

afterwards (box plots as median, 25th percentile, 75th percentile with the 10th as well as 90th percentile at the end of the whiskers. Concerning symbolism and higher orders of significance: $p<0.05$*, $p<0.01$**.

B) Receiver operating characteristic (ROC) analysis with CPN1 in sepsis onset (T0), and 1 day (T1), 2 days (T2) as well as 7 days (T3) afterwards with regard to the prediction of an invasive fungal infection (IFI) up to day 28 (target group: patients with an invasive fungal infection (IFI), controls: patients with a fungal colonization or without any fungal isolates).

FIG. 11.2: CPN1 in septic shock with an invasive fungal infection (IFI, dark grey box), a fungal colonization (light grey box) or without any fungal findings (white box), for the time point of first fungal detection in microbiological samples. Plasma concentrations of CPN1 in septic shock with an invasive fungal infection (IFI, dark grey box), a fungal colonization (light grey box) or without any fungal findings (white box), for the time point of first fungal detection in microbiological samples (box plots as median, $25^{th}$ percentile, $75^{th}$ percentile with the $10^{th}$ as well as $90^{th}$ percentile at the end of the whiskers. Concerning symbolism and higher orders of significance: $p<0.05$*, $p<0.01$**.

FIG. 11.3: ROC analysis with CPN1 in patients with an IFI, or fungal colonization at the time point of first fungal detection in microbiological samples with regard to the prediction of an invasive fungal infection (IFI) (target group: Patients with IFI, control: with a fungal colonization). Data of patients without any fungal findings were not included. Area under the curve was 0.231 with sensitivity of 0.182, 1-specificity of 0.773 at the best cut-off 0.0373.

FIG. 11.4: ROC analysis with CPN1 in patients with an IFI, a fungal colonization or without any fungal findings with regard to the prediction of an IFI, at the time point of first fungal detection in microbiological samples (target group: with IFI, control: fungal colonization or without any fungal findings). Area under the curve was 0.200 with sensitivity of 0.182, 1-specificity of 0.821 at the best cut-off 0.0369.

FIGS. 12.1A-12.1B: HRG differentiates between invasive fungal infection, colonization and no fungal isolates (A) and prediction of an invasive fungal infection (B)

A) Plasma concentrations of HRG in septic shock with an invasive fungal infection (IFI, dark grey box), a fungal colonization (light grey box) or without any fungal findings (white box) for the time points: onset of septic shock (T0), and 1 day (T1), 2 days (T2), 7 days (T3), 14 days (T4), 21 days (T5) and 28 days (T6) afterwards (box plots as median, 25th percentile, 75th percentile with the 10th as well as 90th percentile at the end of the whiskers. Concerning symbolism and higher orders of significance: $p<0.05$*, $p<0.01$, $p<0.001$*).

B) Receiver operating characteristic (ROC) analysis with HRG 14 days (T4) after sepsis onset with regard to the prediction of an invasive fungal infection (IFI) up to day 28 (target group: patients with an invasive fungal infection (IFI), controls: patients with a fungal colonization or without any fungal isolates).

FIGS. 13A-13B: AHSG differentiates between invasive fungal infection, colonization and no fungal isolates (A) and prediction of an invasive fungal infection (B)

A) Plasma concentrations of AHSG in septic shock with an invasive fungal infection (IFI, dark grey box), a fungal colonization (light grey box) or without any fungal findings (white box) for the time points: onset of septic shock (T0), and 1 day (T1), 2 days (T2), 7 days (T3), 14 days (T4), 21 days (T5) and 28 days (T6) afterwards (box plots as median, 25th percentile, 75th percentile with the 10th as well as 90th percentile at the end of the whiskers. Concerning symbolism and higher orders of significance: $p<0.05$: *, $p<0.01$: , $p<0.001$*.

B) Receiver operating characteristic (ROC) analysis with AHSG 7 days (T3) and 14 days (T4) after sepsis onset with regard to the prediction of an invasive fungal infection (IFI) up to day 28 (target group: patients with an invasive fungal infection (IFI), controls: patients with a fungal colonization or without any fungal isolates).

FIGS. 14A-14B: FABP1 differentiates between invasive fungal infection, colonization and no fungal isolates (A) and prediction of an invasive fungal infection (B)

(A) Plasma concentrations of FABP1 in septic shock with an invasive fungal infection (IFI, dark grey box), a fungal colonization (light grey box) or without any fungal findings (white box) for the time points: onset of septic shock (T0), and 1 day (T1), 2 days (T2), 7 days (T3), 14 days (T4), 21 days (T5) and 28 days (T6) afterwards (box plots as median, 25th percentile, 75th percentile with the 10th as well as 90th percentile at the end of the whiskers. Concerning symbolism and higher orders of significance: $p<0.05$*, $p<0.01$**.

(B) Receiver operating characteristic (ROC) analysis with FABP1 1 day (T1) and 2 days (T2) after sepsis onset with regard to the prediction of an invasive fungal infection (IFI) up to day 28 (target group: patients with an invasive fungal infection (IFI), controls: patients with a fungal colonization or without any fungal isolates).

FIGS. 15A-158: Immunoassay-based measurements of plasmatic sICAM-1 concentrations for the detection of an IFI in patients with septic shock.

(A) Plasma concentrations of sICAM-1 in patients suffering from septic shock with an invasive fungal infection (IFI, dark grey box), a fungal colonization (light grey box) or without any fungal findings (white box) for the time points onset of septic shock (T0) and 1 day (T1) afterwards (box plots are given as median, 25th percentile, 75th percentile with the 10th as well as 90th percentile at the end of the whiskers. Concerning symbolism and higher orders of significance: $p<0.05$: *).

(B) Receiver operating characteristic (ROC) analysis with sICAM-1 in all participating patients at sepsis onset (T0) and 1 day (T1) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIG. 16: ROC-analysis for measurements of PCT for the detection of an IFI in patients with septic shock.

Receiver operating characteristic (ROC) analysis with PCT in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIG. 17: FIG. 17: ROC-analysis the combined measurement of PCT and ICAM-1 for the detection of an IFI in patients with septic shock.

Receiver operating characteristic (ROC) analysis with PCT and ICAM-1 in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIG. 18: ROC-analysis the combined measurement of PCT, ICAM-1 and ADM for the detection of an IFI in patients with septic shock.

Receiver operating characteristic (ROC) analysis with PCT, ICAM-1 and ADM in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIG. 19: FIG. 19: ROC-analysis the combined measurement of PCT, ICAM-1, ADM and IL17 for the detection of an IFI in patients with septic shock.

Receiver operating characteristic (ROC) analysis with PCT, ICAM-1, ADM and IL17 in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIG. 20: ROC-analysis the combined measurement of PCT and ADM for the detection of an IFI in patients with septic shock.

Receiver operating characteristic (ROC) analysis with PCT and ADM in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIG. 21: FIG. 21: ROC-analysis the combined measurement of ADM and ICAM-1 for the detection of an IFI in patients with septic shock.

Receiver operating characteristic (ROC) analysis with ADM and ICAM-1 in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIG. 22: FIG. 22: ROC-analysis the combined measurement of ADM, ICAM-1 and IL17 for the detection of an IFI in patients with septic shock.

Receiver operating characteristic (ROC) analysis with ADM, ICAM-1 and IL17 In all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIG. 23: ROC-analysis the measurement of ADM for the detection of an IFI in patients with septic shock.

Receiver operating characteristic (ROC) analysis with ADM in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIG. 24: FIG. 24: ROC-analysis the combined measurement of PCT and THBS1 for the detection of an IFI in patients with septic shock.

Receiver operating characteristic (ROC) analysis with PCT and THBS1 in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIG. 25: ROC-analysis the combined measurement of ADM and THBS1 for the detection of an IFI in patients with septic shock.

Receiver operating characteristic (ROC) analysis with ADM and THBS1 in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIG. 26: FIG. 26: ROC-analysis the combined measurement of PCT, ADM and THBS1 for the detection of an IFI in patients with septic shock.

Receiver operating characteristic (ROC) analysis with PCT, ADM and THBS1 in al participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIG. 27: ROC-analysis the combined measurement of PCT and VCL for the detection of an IFI in patients with septic shock.

Receiver operating characteristic (ROC) analysis with PCT and VCL in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIG. 28: ROC-analysis the combined measurement of ADM and VCL for the detection of an IFI in patients with septic shock.

Receiver operating characteristic (ROC) analysis with ADM and VCL in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIG. 29: ROC-analysis the combined measurement of ADM, VCL and PCT for the detection of an IFI in patients with septic shock.

Receiver operating characteristic (ROC) analysis with ADM, VCL and PCT in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIG. 30: ROC-analysis the combined measurement of ICAM1 and THBS1 for the detection of an IFI in patients with septic shock.

Receiver operating characteristic (ROC) analysis with ICAM1 and THBS1 in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIG. 31: ROC-analysis the combined measurement of ICAM1 and VCL for the detection of an IFI in patients with septic shock.

Receiver operating characteristic (ROC) analysis with ICAM1 and VCL in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIG. 32: ROC-analysis the combined measurement of ICAM1, THBS1 and VCL for the detection of an IFI in patients with septic shock.

Receiver operating characteristic (ROC) analysis with ICAM1, THBS1 and VCL in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIG. 33: ROC-analysis for combined measurements of sICAM-1, thrombospondin-1 and vinculin for the detection of an IFI in patients with septic shock.

Receiver operating characteristic (ROC) analysis with sICAM-1, thrombospondin-1 and vinculin in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIG. 34: ROC-analysis for combined measurements of MR-proADM and sICAM-1 for the detection of an IFI in patients with septic shock.

Receiver operating characteristic (ROC) analysis with MR-proADM and sICAM-1 in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIGS. 35.1A-35.1B: (A) Plasma concentrations of ICAM-1 were measured in patients following liver transplantation with an invasive fungal infection (IFI, dark grey box), a fungal colonization (light grey box) or without any fungal findings (white box). Plasma samples were collected on day of the transplantation (T0), and 1 day (T1), 2 days (T2), 7 days (T3), 14 days (T4), 21 days (T5) and 28 days (T6) afterwards. Data in box plots are given as median, $25^{th}$ percentile, $75^{th}$ percentile with the $10^{th}$ as well as $90^{th}$ percentile at the end of the whiskers. Concerning symbolism and higher orders of significance: p<0.05: , p<0.01: , p<0.001: ***.

(B) Receiver operating characteristic (ROC) analysis with ICAM-1 in all participating patients on the day of liver transplantation (T0), and 1 day (T1), 14 days (T4) as well as 21 days (T5) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIGS. 35.2A-35.28: (A) Plasma concentrations of ICAM-1 were measured in patients following liver transplantation with an invasive fungal infection (IFI, dark squared grey box) or a fungal colonization (light grey box). Plasma samples were adjusted to the time point of the first fungal detection in microbiological samples. Data in box plots are given as median, $25^{th}$, percentile, $75^{th}$ percentile with the $10^{th}$ as well as 90 percentile at the end of the whiskers. Concerning symbolism and higher orders of significance: p<0.05: *.

(B) Receiver operating characteristic (ROC) analysis with ICAM-1 in patients with an invasive fungal infection or fungal colonization at first time of the fungal detection in microbiological diagnostics with regard to the prediction of an invasive fungal infection (IFI). AUC, Area under the curve.

FIGS. 36A-368: (A) Plasma concentrations of MR-proADM were measured in patients following liver transplantation with an invasive fungal infection (IFI, dark squared grey box) or a fungal colonization (light grey box). Plasma samples were adjusted to the time point of the first fungal detection in microbiological samples. Data in box plots are given as median, $25^{th}$ percentile, $75^{th}$ percentile with the $10^{th}$ as well as $90^{th}$ percentile at the end of the whiskers. Concerning symbolism and higher orders of significance: $p<0.05$: *.

(B) Receiver operating characteristic (ROC) analysis with MR-proADM in patients with an invasive fungal infection or fungal colonization at first time of the fungal detection in microbiological diagnostics with regard to the prediction of an invasive fungal infection (IFI). AUC, Area under the curve.

FIG. 37: Receiver operating characteristic (ROC) analysis with ICAM-1 and MR-proADM in all participating patients on the day of liver transplantation (T0), and 1 day (T1), day 2 (T2), Day 7 (T3), day 14 (T4) as well as 21 days (T5) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis. Values calculated as predictive values.

Figure 38D:
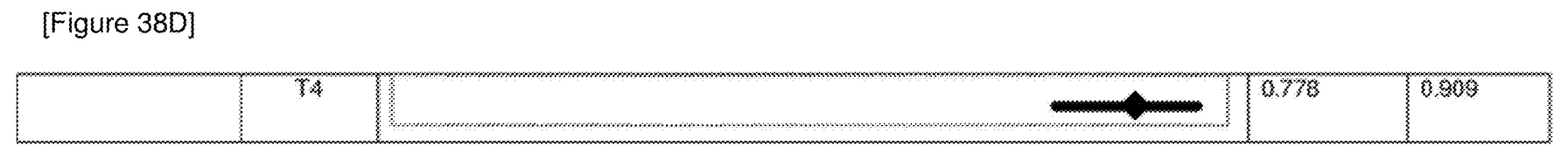

FIGS. 38A-38D: FIGS. 38A-D corresponds to Table 36. Receiver Operator Curve (ROC)-analyses for different biomarker combinations. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval. The diagnostic value of the combination of PCT, MR-proADM, sICAM-1 and/or IL-17A for the diagnosis, differentiation, monitoring and prognosis/risk stratification of an (invasive) fungal infection in different time points, in patients with risk of having or getting a (invasive) fungal infection, in particular sepsis, especially septic shock are presented. The results are transferrable to all kind of subjects, with and without special risk.

The following examples and figures serve for a more detailed explanation of the invention, but without restricting the invention to these examples and figures.

EXAMPLES

Example 1: IFI in the Context of Sepsis, Especially Patients with Septic Shock Study design: The observational clinical study was approved by the local ethics committee (Ethics Committee of the Medical Faculty of Heidelberg, Trial Code No. S-097/2013/German Clinical Trials Register: DRKS00005463) and was conducted in the surgical intensive care unit of Heidelberg University Hospital, Germany between November 2013 and January 2015. All study patients or their legal designees gave written informed consent. In total 50 patients suffering from septic shock according to the criteria of the Surviving Sepsis Campaign: International Guidelines for Management of Severe Sepsis and Septic Shock 2012 were enrolled in this study (Dellinger et al. Crit Care Med. 2012 41:580-637; Romani. Nat Rev Immunol. 2004 4:1-23); Schroeder M et al. Crit Care. 2016 20:139; Zedek D C et al. J Clin Microbiol. 2006 44:1601).

Blood sample were collected at sepsis onset (T0) and 1 day (T1), 2 days (T2), 7 days (T3) 14 days (T4), 21 days (T5) and 28 days (T6) afterwards. Relevant baseline data (demographic data, primary site of infection), clinical data (disease severity scores, such as Simplified Acute Physiology Score (SAPS II), Sequential Organ Failure Assessment Score (SOFA) and Acute Physiology Health Evaluation score (APACHE II), surgical procedures, antifungal therapy, outcome parameters) as well as routine infection parameters (e.g. leukocytes, C-reactive protein (CRP), procalcitonin (PCT), body temperature) were collected (Table 1).

Immunoassays. Plasma concentrations of β-D-glucan (BD) were measured using the Glucatell®-Kit (Pyroquant Diagnostik GmbH) according to the manufacturer's instructions. In al patients, concentrations of Galactomannan (GM) were measured using an enzyme-linked immunoassay (Platelia™ *Aspergillus* AG, Biorad, and Munich) in plasma samples at all time points. Concentrations of GM in bronchoalveolar lavage fluid (BALF) were measured using the same technique, however only in selected cases of suspected invasive aspergillosis (IA). The following GM concentrations were used as cut-off values: Plasma >0.5, BALF>1.0

The biomarkers ICAM1, AHSG, CPN1, FABP1, HRG, PIGR, RAP1, THBS1, VCL were measured in quantitative selected reaction monitoring (SRM) assays by LC-MS/MS technology (TSQ Quantiva mass spectrometer (MS); ThermoFisher Scientific). PCT and ET-1 were measured by the automated immunoassay platform Kryptor Brahms PCT.

SEQUENCE LISTING

The Sequence Listing is submitted as an ASCII text file [10278-105441-01_Sequence_Listing.txt, Nov. 23, 2020, 73.6 KB], which is incorporated by reference herein.

Clinical Microbiology.

Blood Culture:

Blood culture testing at Heidelberg University Hospital is routinely performed as described elsewhere (Gumbinger C et al. J Neurol Sci. 2013 325:46-50). Whole blood samples are obtained via direct venipuncture (e.g., antecubital vein) applying sterile techniques and 10 mL blood is inoculated to both an aerobic and an anaerobic liquid culture medium (BACTEC PLUS, BD Biosciences, Heidelberg, Germany). Cultures are incubated for 5 days (BACTEC, BD Biosciences, Heidelberg, Germany) and positive cultures are analyzed according to approved inhouse hospital standard techniques, including identification by VITEK2 (Biomerieux, Nuertingen, Germany) or MALDI TOF (Bruker, Madison, WI, USA) and automated antimicrobial susceptibility testing (VITEK 2).

Culture-Based Diagnostic Procedures in Tracheal Secretion, Wound Swabs and Drainage Fluids:

Briefly, tracheal aspirates and drainage fluids were streaked manually on Columbia (BD), chocolate (bM), MacConkey (bM), Schaedler and kanamycin-vancomycin (BD, Bi-plate) and chromogenic *Candida agar* (BD), while wound swabs were inoculated semi-automated by PREVI Isola™ instrument on the same *agar* types. All plates were incubated at 37° C. in 5% $CO_2$ for 24 to 48h, except the Schaedler-KV bi-plates, which were incubated at 37° C. in an anaerobic chamber (GasPak; Becton, Dickinson, Franklin Lakes, NJ) for 48h as described (Mischnik A et al. J Clin Microbiol. 2012 50:2732-2736). Bacterial and fungal colonies were identified by MALDI-ToF mass spectrometry and automated AST was performed on VITEK II instruments (bM).

Group Definitions

*Candida* spp. in the respiratory tract or in fluids from drainages were classified as colonization. Positive results in blood cultures, intraoperative swabs and *Aspergillus* spp. in deep respiratory tract specimens with accompanying pulmonary infiltrates were classified as infection.

Anti-*Candida*-antibody titer: *Candida albicans* specific IgM, IgA and IgG antibodies in serum were detected and quantified using Serion ELISA Classic™ *Candida albicans* IgA/IgG/IgM (ESR 117A/G/M, Virion Serion, Wuerzburg, Germany) as described in the manufacturer's instructions using a Behring ELISA Processor (BEP III, Siemens Healthcare Diagnostics, Marburg, Germany), (Zou M et al. PLoS One. 2012 7:e43347).

Statistical Analyses

The resulting data were entered into an electronic database (Excel 2010; Microsoft Corp, Redmond, USA) and evaluated using the SPSS software (Version 21.0; SPSS, Inc., Chicago, USA). Categorical data were summarized using absolute and relative frequencies. Quantitative data were summarized using median with quartiles. The Kolmogorov-Smirnov test was applied to check for normal distribution. Due to non-normally distributed data, non-parametric methods for evaluation were used (Chi-square test for categorical data, Mann-Whitney U test for continuous data). Appropriate cut-off values for the detection of a fungal infection were calculated using ROC analyses. A p-value <0.05 was considered statistically significant. Concerning symbolism and higher orders of significance: p<0.05: *, p<0.01: , p<0.001: *.

Multiple comparison analysis has been performed by one-way analysis of variance (ANOVA) followed by a Dunnett's post hoc test.

Results

Patient's characteristics. In total, 50 patients with septic shock were included in the presented investigation. Patients' characteristics are presented in Table 1. The underlying septic focus was the abdomen (n=43; 86%), followed by the lung (n=6; 12%), as well as the urogenital tract (n=1; 2%). The overall 28-day as well as 90-day mortality was 22% (n=11) and 34% (n=17), respectively. The median length of ICU as well as hospital stay was 20 days, and 44 days, respectively.

TABLE 1

Patient's characteristics (n = 50)

| | All patients (n = 50) | without fungal isolates (n = 17) | with fungal isolates (n = 33) | p for patients without fungal isolates vs. patients with fungal isolates |
|---|---|---|---|---|
| Gender male | 38 (76) | 11 (64.7) | 27 (81.8) | 0.160 |
| Age (years) | 66 (61-75) | 71 (64-80) | 66 (59-74) | 0.117 |
| BMI (kg/m$^2$) | 27.2 (24.4-30.9) | 27.2 (25.7-34.9) | 26.9 (23.1-30.9) | 0.401 |
| Postoperatively peritonitis | 31 | 9 (52.9) | 22 (66.7) | 0.206 |
| initial operation | | | | |
| Kidney | 2 (4) | 0 (0) | 2 (6.1) | 0.431 |
| Liver | 11 (22) | 1 (2.1) | 10 (30.3) | 0.047* |
| Pancreas | 2 (10) | 1 (5.9) | 1 (3.0) | 0.569 |
| GIT | 38 ((76) | 14 (82.4) | 24 (72.7) | 0.350 |
| VAS | 3 (6) | 2 (11.8) | 1 (3.0) | 0.264 |
| Others | 12 (24) | 3 (17.6) | 9 (27.3) | 0.350 |
| ≥48 h after hospital admission | 25 (50) | 7 (41.2) | 18 (54.5) | 0.276 |
| NYHA 0-I | 41 (82) | 13 (76.4) | 28 (84.8) | 0.358 |
| Diabetes mellitus | 17 (34) | 5 (29.4) | 12 (36.3) | 0.434 |
| Arterial hypertension | 34 (68) | 12 (70.6) | 22 (66.7) | 0.520 |
| Coronary heart disease | 8 (16) | 5 (29.4) | 3 (9.1) | 0.076 |
| Chronic obstructive lung disease | 10 (20) | 5 (29.4) | 5 (15.2) | 0.204 |
| Renal insufficiency | 7 (14) | 1 (5.9) | 6 (18.2) | 0.231 |
| Renal replacement therapy | 15 (30) | 2 (11.8) | 13 (39.4) | 0.041* |
| Liver cirrhosis | 13 (26) | 3 (17.6) | 10 (30.3) | 0.270 |
| Oncological disease | 33 (66) | 11 (64.7) | 22 (66.7) | 0.566 |
| APACHE II* | 30 (28-35) | 32 (28-36) | 30 (28-34) | 0.491 |
| SOFA* | 11 (10-14) | 11 (10-14) | 11 (10-14) | 0.959 |
| SAPS* | 65 (49-75) | 72 (48-75) | 65 (51-72) | 0.467 |
| *Candida* colonization | 22 (44) | 0 (0) | 22 (66.7) | — |
| *Candida* infection | 10 (20) | 0 (0) | 10 (30.3) | — |
| Candidemia | 3 (6) | 0 (0) | 3 (9.1) | — |
| *Aspergillus* spp. | 1 (3) | 0 (0) | 1 (3.0) | |
| Candida-Score | 4 (4-4) | 4 (4-4) | 4 (4-4) | 0.080 |
| Duration of (hours) mechanical ventilation | 145.5 (67.3-450) | 89 (46-145) | 181 (77-682) | 0.015* |
| ICU length of stay (days) | 19.5 (12-44) | 12 (3-17) | 24 (15-46) | 0.002** |
| Hospital length of stay (days) | 44 (23.3-68.5) | 24 (12-40) | 51 (39-78) | 0.007** |

TABLE 1-continued

| Patient's characteristics (n = 50) | | | | |
|---|---|---|---|---|
| | All patients (n = 50) | without fungal isolates (n = 17) | with fungal isolates (n = 33) | p for patients without fungal isolates vs. patients with fungal isolates |
| Tracheotomy | 14 (28) | 2 (11.8) | 12 (36.3) | 0.063 |
| Anastomosis leakage | 24 (48) | 7 (41.2) | 17 (51.5) | 0.347 |
| Fascia dehiscence | 12 (24) | 2 (11.8) | 10 (30.3) | 0.134 |
| 90 day mortality | 17 (34) | 8 (47.1) | 9 (27.3) | 0.175 |
| 28 day mortality | 11 (22) | 7 (41.2) | 4 (12.1) | 0.025* |

Data are presented as either number (with the corresponding percentage value) or median (with accompanying quartiles).

The results of the cultured samples (standard diagnostics) has been used as criteria for the classification of patients in no fungal infection (n=17), (invasive) fungal infection (n=11) and fungal colonization (n=22) and were subdivided in different pathogens and locations of the infection, being presented in FIG. 1.

Fungal Pathogens and Infection Sites.

Culture-based microbiological diagnostics: As assessed by culture-based microbiological diagnostics, fungal pathogens were present in 33 patients (66.0%), whereas 17 patients (34.0%) revealed negative fungal cultures. Fungal isolates were found in one or multiple locations in 25 (75.8%), or 8 (24.2%) patients respectively and were located at the following sites: respiratory tract (n=17; 51.5%), abdominal site (n=21; 63.6%) and blood culture (n=3; 9.1%). Characteristics of patients with or without fungal pathogens are presented in Table 1. Patients with fungal pathogens underwent more frequently liver surgery prior to study inclusion and the need for renal replacement therapy was shown to be significantly increased. Concerning further markers for morbidity, fungal-positive patients revealed a significant prolonged duration of mechanical ventilation and the need for tracheostomy tended to be increased. Moreover, length of ICU stay as well as hospital stay was significantly prolonged in patients with fungal pathogens. Surprisingly, 28-day mortality was significantly increased in patients without fungal pathogens, whereas 90-day mortality was shown to be comparable.

Based on the group definitions as described in the methods section, colonization and infection was found in 22 (44.0%), and 11 (22.0%) patients, respectively. In colonized patients, 8 (16.0%) participants exclusively revealed *Candida* spp. in respiratory secretions (5× *C. albicans,* 1× *C. albicans* and *glabrata,* 2× *C. albicans* and C. spp), whereas in 6 (12.0%) patients *Candida* spp. could only be cultured from drainage fluids (3× *C. albicans,* 2× *C. glabrata,* 1× *C. albicans* and *C. glabrata*). Contrariwise, 8 (16.0%) patients were colonized at both sides (4× *C. albicans,* 1× *C. albicans* and C. spp., 3× *C. albicans* and *C. glabrata*). In infected patients, fungemia was found in 3 (6.0%) patients (2× *C. albicans,* 1× *C. glabrata*) and positive abdominal wound swabs were found in 7 (14.0%) patients (4× *C. albicans,* 1× *C. glabrata,* 1× *C. krusei,* 1× *C. albicans* and *C. glabrata*). Moreover, in one (2.0%) patient *Aspergillus fumigatus* was isolated in respiratory tract secretions. Concerning risk factors, liver surgery prior to study inclusion as well as liver cirrhosis could be observed more frequently in patients with a fungal infection. Moreover, the duration of ICU stay as well as mechanical ventilation was significantly prolonged and the need for tracheotomy was significantly increased in patients suffering from a fungal infection. Although morbidity was shown to be increased, mortality at 28 and 90 days did not differ significantly between infected and uninfected patients.

Antifungal therapy. In total, 21 of 50 (42.0%) patients received an antifungal therapy during study participation. Of 17 patients without any fungal isolates, 2 (11.8%) patients received an empiric antifungal therapy. Of the remaining 33 patients with fungal isolates, 19 (57.6%) patients received an antifungal therapy, which was initiated in terms a specific therapy in 15 (78.9%) patients. Vice versa, treatment was initiated in terms of an empiric therapy in the remaining 4 (21.1%) cases, which was stopped later on in all of these patients. In 7 (33.3%) patients, the initial antifungal therapy was changed in the course of the disease.

(1,3)-ß-D-glucan (BG). Plasma concentrations of BG were comparable between the three subgroups throughout the entire study period and therefore failed to be of diagnostic value for the prediction of a fungal infection (data not shown). Even in patients suffering from candidemia, plasma concentrations of BG were not increased reliably.

Galactomannan (GM). Plasma concentrations of GM remained below the cut-off value of <0.5 in 46 of 50 patients (92.0%). Contrariwise, 4 patients (8.0%) presented with sporadically increased plasma concentrations of GM above the cut-off value without any other (clinical, radiological, cultural) signs or risk factors for an IA (data not shown). In these cases, increased plasma concentrations of GM were most probably attributable to the underlying antibiotic therapy (e.g. piperacillin-tazobactam), which is well known to be associated with increased GM concentrations.

One patient presented with the diagnosis of an IA as assessed by cultural detection of *Aspergillus fumigatus* in BALF, which was confirmed by high-resolution computed tomography. Moreover, GM concentrations in BALF were increased above the cut-off value, whereas plasma concentrations of GM remained below the cut-off value at all time points. Apart from septic shock as well as preexisting adipositas per *magna* and insulin-depending diabetes mellitus, the patient did not suffer from classical predisposing risk factors for IA (e.g. neutropenia, hemato-oncological diseases treated with cytotoxic agents, intake of corticosteroids, innate or acquired immunodeficiency). The patient was treated with liposomal amphotericin B for 6 weeks, which led to a decrease of GM in BALF below the cut-off value. Moreover, culture of BALF remained negative for *Aspergillus fumigatus* after the end the treatment period.

Anti-*Candida* antibody titer. In the subgroup of patients without any fungal findings (n=17), 4 patients (23.5%) presented with a "false" positive anti-*Candida* antibody titer (>1:320), whereas colonized patients (n=22) were shown to have positive test results in 81.8% (n=18). Patients suffering from a fungal infection (n=11) also revealed positive test results in 81.8% (n=9), but unfortunately two patients presenting with candidemia (at sepsis onset) failed to show a positive anti-*Candida* antibody titer.

TABLE 2

Biomarkers with significant values for the diagnosis and/or differentiation between invasive fungal infection and no invasive fungal infection. Fold change, 95% confidence interval (CI) and significant change, are indicated at different time points.

| Gene name | T0 | T1 | T2 | T3 | T4 | T5 | T6 |
|---|---|---|---|---|---|---|---|
| PIGR | | | 1.9 | 2.8 | 2.1 | | |
| (fold change/ | | | 1.0-3.5 | 1.3-5.7 | 1.3-3.6 | | |
| 95% CI/ | | | 0.046 | 0.004 | 0.003 | | |
| p-value) | | | | | | | |
| ICAM1 | 1.6 | 1.6 | 1.6 | 1.9 | 1.7 | | |
| (fold change/ | 1.1-2.3 | 1.1-2.3 | 1.1-2.3 | 1.3-2.8 | 1.1-2.8 | | |
| 95% CI/ | 0.013 | 0.023 | 0.009 | <0.001 | 0.025 | | |
| p-value) | | | | | | | |
| CPN1 | | 0.6 | 0.7 | | 0.4 | | |
| (fold change/ | | 0.5-0.9 | 0.5-0.97 | | 0.3-0.7 | | |
| 95% CI/ | | 0.005 | 0.03 | | 0.001 | | |
| p-value) | | | | | | | |
| HRG | | | | | 0.4 | | 0.2 |
| (fold change/ | | | | | 0.2-0.7 | | 0.1-0.8 |
| 95% CI/ | | | | | <0.001 | | 0.016 |
| p-value) | | | | | | | |
| THBS1 | | | | | 0.4 | | 0.2 |
| (fold change/ | | | | | 0.2-0.98 | | 0.04-0.8 |
| 95% CI/ | | | | | 0.045 | | 0.019 |
| p-value) | | | | | | | |
| RAP1A | | | | | 0.5 | | 0.2 |
| (fold change/ | | | | | 0.2-0.95 | | 0.04-0.7 |
| 95% CI/ | | | | | 0.035 | | 0.012 |
| p-value) | | | | | | | |
| AHSG | | | | | 0.4 | | 0.3 |
| (fold change/ | | | | | 0.3-0.6 | | 0.1-0.7 |
| 95% CI/ | | | | | <0.001 | | 0.004 |
| p-value) | | | | | | | |
| FABP1 | | | | 1.5 | 1.4 | | |
| (fold change/ | | | | 1.03-2.1 | 1.007-1.96 | | |
| 95% CI/ | | | | 0.03 | 0.044 | | |
| p-value) | | | | | | | |
| CT-proET-1 | 2.0 | | | | | | |
| (fold change/ | 1.1-3.5 | | | | | | |
| 95% CI/ | 0.015 | | | | | | |
| p-value) | | | | | | | |
| PCT | | | | 4.5 | 10.0 | | 9.2 |
| (fold change/ | | | | 1.7-11.7 | 2.5-40.9 | | 1.2-69.0 |
| 95% CI/ | | | | 0.001 | 0.001 | | 0.029 |
| p-value) | | | | | | | |

The Table 2 shows the results of the biomarkers PIGR, ICAM1, CPN1, HRG, THBS1, RAP1A AHSG, FABP1, ET-1 and PCT, tested at septic shock onset (T0), and 1 day (T1), 2 days (T2), 7 days (T3), 14 days (T4), 21 days (T5) and 28 days (T6) with a significance (p value <0.05) and mean-fold change (presented below the p-value), whereby the significant biomarker values diagnose and/or differentiate invasive fungal infection compared to no invasive fungal infection. Biomarkers with mean-fold-changes below 1.0 indicate a downregulation of the biomarker (CPN1, THBS1, RAP1) and above 1.0 an upregulation of the biomarker (ICAM1, PIGR, FABP1, ET-1, PCT). Therefore the biomarkers show the same functionality in diagnosing and differentiation of invasive fungal infections vs. no invasive fungal infection and can be used alone or In combination (Table 3-6).

TABLE 3

Area under the curve (AUC), sensitivity, 1-specificity and best cut-off from receiver operating characteristic (ROC) analysis with ICAM1 in all participating patients at sepsis onset (T0), and 1 day (T1), 2 days (T2) as well as 7 days (T3) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC analysis.

| Time point | AUC | Sensitivity | 1-Specificity | Best Cut off |
|---|---|---|---|---|
| T0 | 0.739 | 0.727 | 0.156 | 0.01996 |
| T1 | 0.790 | 0.727 | 0.156 | 0.02334 |
| T2 | 0.818 | 0.727 | 0.063 | 0.0264 |
| T3 | 0.841 | 0.727 | 0.094 | 0.0237 |

Table 3: Area under the curve (AUC), sensitivity, 1-specificity and best cut-off from receiver operating characteristic (ROC) analysis with ICAM1 in all participating patients at sepsis onset (T0), and 1 day (T1), 2 days (T2) as well as 7 days (T3) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC analysis.

TABLE 4

Area under the curve (AUC), sensitivity, 1-specificity and best cut-off from receiver operating characteristic (ROC) analysis with THBS1 in all participating patients at sepsis onset (T0), and 1 day (T1), 2 days (T2), 7 days (T3) as well as 14 days (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC analysis.

| Time point | AUC | Sensitivity | 1-Specificity | Best Cut off |
|---|---|---|---|---|
| T0 | 0.279 | 0.30 | 0.7 | 0.1693 |
| T1 | 0.350 | 0.3 | 0.708 | 0.1448 |
| T2 | 0.287 | 0.30 | 0.7 | 0.1205 |
| T3 | 0.387 | 0.1 | 0.333 | 0.3452 |
| T4 | 0.129 | 0.2 | 0.917 | 0.2314 |

Table 4 presents the diagnostic value of THBS for the diagnosis, differentiation, monitoring and prognosis/risk stratification of an (invasive) fungal infection in different time points, in patients with risk of having or getting a (invasive) fungal infection, in particular sepsis, especially septic shock. The results are transferrable to all kind of subjects, with and without special risk.

TABLE 5

Area under the curve (AUC), sensitivity, 1-specificity and best cut-off from receiver operating characteristic (ROC) analysis with RAP1 (RAP1A/RAP1B/ RP1BL) in all participating patients at sepsis onset (T0), and 1 day (T1), 2 days (T2), days (T3) as well as 14 days (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC analysis.

| Time point | AUC | Sensitivity | 1-Specificity | Best Cut off |
|---|---|---|---|---|
| T0 | 0.288 | 0.30 | 0.75 | 0.0479 |
| T1 | 0.292 | 0.2 | 0.708 | 0.0462 |
| T2 | 0.271 | 0.1 | 0.667 | 0.0476 |
| T3 | 0.393 | 0.0 | 0.292 | 0.1022 |
| T4 | 0.121 | 0.2 | 0.875 | 0.0618 |

Table 5 presents the diagnostic value of RAP1 for the diagnosis, differentiation, monitoring and prognosis/risk stratification of an (invasive) fungal infection in different time points, in patients with risk of having or getting a (invasive) fungal infection, in particular sepsis, especially septic shock. The results are transferrable to all kind of subjects, with and without special risk.

TABLE 6

Area under the curve (AUC), sensitivity, 1-specificity and best cut-off from receiver operating characteristic (ROC) analysis with VCL in all participating patients at sepsis onset (T0), and 1 day (T1), 2 days (T2), 7 days (T3) as well as 14 days (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC analysis.

| Time point | AUC | Sensitivity | 1-Specificity | Best Cut off |
|---|---|---|---|---|
| T0 | 0.338 | 0.5 | 0.833 | 0.1533 |
| T1 | 0.296 | 0.2 | 0.542 | 0.238 |
| T2 | 0.258 | 0.1 | 0.625 | 0.213 |
| T3 | 0.413 | 0.1 | 0.375 | 0.378 |
| T4 | 0.150 | 0.3 | 0.917 | 0.2337 |

Table 6 presents the diagnostic value of VCL for the diagnosis, differentiation, monitoring and prognosis/risk stratification of an (invasive) fungal infection in different time points, in patients with risk of having or getting a (invasive) fungal infection, in particular sepsis, especially septic shock. The results are transferrable to all kind of subjects, with and without special risk.

TABLE 7

Area under the curve (AUC), sensitivity, 1-specificity and best cut-off from receiver operating characteristic (ROC) analysis with C-terminal Proendothelin-1 (CT-proET-1) in all participating patients at sepsis onset (T0), and 1 day (T1) afterwards with regard to the prediction of an invasive fungal infection (IFl) up to day 28. Patients suffering from an invasive fungal infection (IFI) represented the target group, whereas both, patients with a fungal colonization as well as patients without any fungal isolates served as controls for this ROC analysis.

| Time point | AUC | Sensitivity | 1-Specificity | Best Cut off [pmol/l] |
|---|---|---|---|---|
| T0 | 0.710 | 0.7 | 0.29 | 188.493 |
| T1 | 0.716 | 0.8 | 0.323 | 155.492 |

Table 7 presents the diagnostic value of CT-proET-1 for the diagnosis, differentiation, monitoring and prognosis/risk stratification of an (invasive) fungal infection in different time points, in patients with risk of having or getting a (invasive) fungal infection, in particular sepsis, especially septic shock. The results are transferrable to all kind of subjects, with and without special risk.

TABLE 8

Biomarkers with significant values for the diagnosis and/or differentiation between (invasive) fungal infection and no invasive fungal infection or fungal colonization. Fold change, 95% confidence interval (CI) and significant change are indicated at different time points.

| Gene name | T0 | T1 | T2 | T3 | T4 | T5 | T6 |
|---|---|---|---|---|---|---|---|
| PIGR (fold change/ 95% CI/ p-value) | | 1.9<br>1.1-3.2<br>0.023 | 2.0<br>1.1-3.4<br>0.012 | 2.5<br>1.4-4.7<br>0.002 | 2.1<br>1.3-3.1<br>0.001 | | |
| ICAM1 (fold change/ 95% CI/ p-value) | 1.5<br>1.04-2.0<br>0.027 | 1.5<br>1.1-2.2<br>0.009 | 1.7<br>1.2-2.3<br>0.001 | 1.8<br>1.3-2.5<br><0.001 | 1.7<br>1.1-2.5<br>0.007 | | |
| CPN1 (fold change/ 95% CI/ p-value) | | 0.7<br>0.5-0.9<br>0.01 | 0.7<br>0.5-0.98<br>0.036 | | 0.6<br>0.4-0.9<br>0.013 | | |
| HRG (fold change/ 95% CI/ p-value) | | | | | 0.5<br>0.3-0.7<br>0.001 | | 0.3<br>0.1-0.6<br>0.001 |
| THBS1 (fold change/ 95% CI/ p-value) | | | | | 0.4<br>0.2-0.8<br>0.007 | | 0.3<br>0.1-0.7<br>0.008 |
| RAP1A (fold change/ 95% CI/ p-value) | | | | | 0.4<br>0.2-0.7<br>0.002 | | 0.3<br>0.1-0.7<br>0.003 |
| AHSG (fold change/ 95% CI/ p-value) | | | | | 0.5<br>0.4-0.7<br><0.001 | | 0.4<br>0.2-0.7<br>0.002 |
| VCL (fold change/ 95% CI/ p-value) | | | 0.6<br>0.4-0.995<br>0.047 | | 0.4<br>0.2-0.8<br>0.003 | | 0.4<br>0.1-0.9<br>0.019 |
| PCT (fold change/ 95% CI/ p-value) | | | | 4.6<br>2.0-10.5<br><0.001 | 8.9<br>2.8-28.1<br><0.001 | 7.1<br>1.3-40.5<br>0.024 | 7.2<br>2.0-26.6<br>0.002 |

Table 8 shows the results of the biomarkers PIGR, ICAM1, CPN1, HRG, THBS1, RAP1A, AHSG, VCL and PCT, tested at septic shock onset (T0), and 1 day (T1), 2 days (T2), 7 days (T3), 14 days (T4), 21 days (T5) and 28 days (T6) with a significance (p value <0.05) and mean-fold change (presented below the p-value), whereby the significant biomarker values diagnose and/or differentiate (invasive) fungal infection compared to no invasive fungal infection or fungal colonization. Biomarkers with Mean-fold-changes below 1.0 indicate a downregulation of the biomarker (PIGR, CPN1, HRG, THBS1, RAP1A (RAP1A/RAP1B/RAPBL), AHSG, VCL) and above 1.0 an upregulation of the biomarker (ICAM1, PCT). Therefore the biomarkers show the same functionality in diagnosing, and/or ruling out an invasive fungal infection and/or differentiation of an invasive fungal infection vs. no fungal infection or differentiation of an invasive fungal infection vs. no invasive fungal infection or fungal colonization and can be used alone or in combination.

TABLE 9

Area under the curve (AUC) for prediction of an invasive fungal infection (IFI) compared to patients with fungal colonization at the time point of first fungal detection in microbiological samples.

| Marker | AUC | Sensitivity | 1-Specificity | Best Cut off |
|---|---|---|---|---|
| ICAM1 | 0.707 | 0.727 | 0.273 | 0.02263 |
| THBS1 | 0.302 | 0.273 | 0.7773 | 0.1713 |
| RAP1 | 0.281 | 0.091 | 0.682 | 0.0544 |
| VCL | 0.264 | 0.091 | 0.773 | 0.2178 |

TABLE 10

Area under the curve (AUC) for prediction of an invasive fungal infection (IFI) compared to patients with fungal colonization and patients without any fungal findings at the time point of first fungal detection in microbiological samples. In patients with no fungal findings, plasma concentrations of markers at sepsis onset were used.

| Marker | AUC | Sensitivity | 1-Specificity | Best Cut off |
|---|---|---|---|---|
| ICAM1 | 0.767 | 0.727 | 0.154 | 0.02263 |
| THBS1 | 0.336 | 0.091 | 0.513 | 0.23684 |
| RAP1 | 0.322 | 0.091 | 0.615 | 0.05448 |
| VCL | 0.308 | 0.091 | 0.667 | 0.21783 |

Table 9 and 10 present the predictive and/or diagnostic value of an (invasive) fungal infection and/or the ruling out of an (invasive) fungal infection (Tables 9 and 10) and/or the differentiation value of (invasive) fungal infection vs. fungal colonization (Table 9) of ICAM1, THBS1, RAP1 (RAP1A/RAP1B/RAPBL) and VCL and show the correlation with the first detection in microbiological samples. Therefore the biomarkers are usable for detecting the first onset of an (invasive) fungal infection and can differentiate between uncritical fungal colonization and a (invasive) fungal infection (Table 9).

TABLE 11

Area under the curve (AUC), sensitivity, 1-specificity and best cut-off from receiver operating characteristic (ROC) analysis with ICAM1 in all participating patients change from 0 day (T0) to 1 day (T1), 0 day (T0) to 2 days (T2) or 0 day (T0) to 7 days (T3) after sepsis onset with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC analysis.

| Time point | AUC | Sensitivity | 1-Specificity | Best Cut off |
|---|---|---|---|---|
| T1 vs T0 | 0.681 | 0.636 | 0.256 | 0.003245 |
| T2 vs T0 | 0.741 | 0.727 | 0.205 | 0.00385 |
| T3 vs T0 | 0.695 | 0.545 | 0.077 | 0.007489 |

ROC analysis of ICAM1 change results in best diagnostic value of ICAM1 increase from T0 to T2 (target group: patients with an invasive fungal infection (IFI), controls: patients with a fungal colonization or without any fungal isolates).

TABLE 12

Area under the curve (AUC), sensitivity, 1-specificity and best cut-off from receiver operating characteristic (ROC) analysis with PIGR in all participating patients 1 day (T1), 2 days (T2), 7 days (T3) as well as 14 days (T4) after sepsis onset with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC analysis.

| Time point | AUC | Sensitivity | 1-Specificity | Best Cut off |
|---|---|---|---|---|
| T1 | 0.704 | 0.6 | 0.167 | 0.034 |
| T2 | 0.729 | 0.5 | 0.042 | 0.0588 |
| T3 | 0.846 | 0.9 | 0.292 | 0.0464 |
| T4 | 0.833 | 0.8 | 0.208 | 0.0625 |

TABLE 13

Area under the curve (AUC), sensitivity, 1-specificity and best cut-off from receiver operating characteristic (ROC) analysis with CPN1 in all participating patients at sepsis onset (T0), and 1 day (T1), 2 days (T2) as well as 7 days (T3) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC analysis.

| Time point | AUC | Sensitivity | 1-Specificity | Best Cut off |
|---|---|---|---|---|
| T0 | 0.295 | 0.273 | 0.656 | 0.0428 |
| T1 | 0.250 | 0.273 | 0.844 | 0.0379 |
| T2 | 0.241 | 0.273 | 0.781 | 0.0483 |
| T3 | 0.222 | 0.182 | 0.813 | 0.0358 |

TABLE 14

Area under the curve (AUC), sensitivity, 1-specificity and best cut-off from receiver operating characteristic (ROC) analysis with HRG in all participating patients 14 days (T4) after sepsis onset with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC analysis.

| Time point | AUC | Sensitivity | 1-Specificity | Best Cut off |
|---|---|---|---|---|
| T4 | 0.160 | 0.1 | 0.6 | 0.6408 |

TABLE 15

Area under the curve (AUC), sensitivity, 1-specificity and best cut-off from receiver operating characteristic (ROC) analysis with AHSG in all participating patients 7 days (T3) and 14 days (T4) after sepsis onset with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC analysis.

| Time point | AUC | Sensitivity | 1-Specificity | Best Cut off |
|---|---|---|---|---|
| T3 | 0.212 | 0.1 | 0.658 | 0.2664 |
| T4 | 0.120 | 0.0 | 0.64 | 0.4125 |

TABLE 16

Area under the curve (AUC), sensitivity, 1-specificity and best cut-off from receiver operating characteristic (ROC) analysis with FABP1 in all participating patients 1 day (T1) and 2 days (T2) after sepsis onset with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC analysis.

| Time point | AUC | Sensitivity | 1-Specificity | Best Cut off |
|---|---|---|---|---|
| T1 | 0.716 | 0.818 | 0.333 | 0.0058 |
| T2 | 0.837 | 1.0 | 0.303 | 0.0054 |

A new and surprising finding was ICAM1 as biomarker for the diagnosis and/or risk prediction and/or risk stratification and/or monitoring and/or ruling in or ruling out of an invasive fungal infection, an fungal colonization and no fungal infection in a subject, in particular a risk group of getting or having an (invasive) fungal infection, especially sepsis e.g. septic shock.

FIGS. 2.1 A-C represent the ICAM1 findings by ROC curves and Box plots, demonstrating the power to diagnose and/or differentiate between (invasive) fungal infection and fungal colonization or no fungal infection, respectively.

Plasma samples were collected at the onset of septic shock (T0), and 1 day (T1), 2 days (T2), 7 days (T3), 14 days (T4), 21 days (T5) and 28 days (T6) afterwards and ICAM1 was measured. FIG. 2.1A shows significant ICAM1 changes in invasive fungal infection (IFI, dark grey box), a fungal colonization (light grey box) or without any fungal findings (white box). Data in box plots are given as median, 25th percentile, 75th percentile with the 10th as well as 90th percentile at the end of the whiskers (FIG. 2.1 A). FIG. 2.1C presents also differences in plasma concentrations of ICAM1 measured in patients suffering from septic shock with an invasive fungal infection (dark grey box), a fungal colonization (light grey box) or without any fungal findings (white box). Plasma concentration of ICAM1 was calculated at 1 day (T1), 2 days (T2) and 7 days (T3) compared to the onset of septic shock (T0), i.e. change from T0 to T1, T0 to T2 and T0 to T3. Data in box plots are given as median, 25th percentile, 75th percentile with the 10th as well as 90th percentile at the end of the whiskers. (Concerning symbolism and higher orders of significance: $p<0.05$: *, $p<0.01$: , $p<0.001$:*).

FIG. 2.1B shows Receiver operating characteristic (ROC) analysis with ICAM1 in al participating patients at sepsis onset (T0), and 1 day (T1), 2 days (T2) as well as 7 days (T3) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC analysis. FIG. 2.2 and Table 11 presents a ROC analysis with changes of ICAM1 in all patients. Patients suffering from an invasive fungal infection represented the target group, whereas both, patients with a fungal colonization as well as patients without any fungal isolates served as controls for this ROC analysis.

FIG. 2.3 shows the diagnostic power of ICAM1 for the diagnosis, ruling out and differentiation of an invasive fungal infection (IFI, dark grey box), and/or fungal colonization (light grey box) and/or no fungal infection (white box). In IFI patients as well as in those with a fungal colonization, plasma concentrations of ICAM1 are presented for the time point of first fungal detection in microbiological samples. In patients with no fungal findings, plasma concentrations of ICAM1 at sepsis onset are presented. Data in box plots are given as median, $25^{th}$ percentile, $75^{th}$ percentile with the $10^{th}$ as well as $90^{th}$ percentile at the end of the whiskers.

FIG. 2.4 shows a ROC analysis with ICAM1 in patients with an invasive fungal infection (IFI) or fungal colonization at the time point of first fungal detection in microbiological samples with regard to the prediction of an invasive fungal infection (IFI). Patients suffering from an IFI represented the target group, whereas patients with a fungal colonization served as controls for this ROC analysis. Data of patients without any fungal findings were not included in this ROC analysis.

FIG. 2.5 presents the diagnostic and/or prognostic effect and/or the power to differentiate and/or ruling out or ruling in of ICAM1 with the shown ROC analysis, in patients with an invasive fungal infection (IFI), a fungal colonization or without any fungal findings with. In IFI patients as well as in those with a fungal colonization, plasma concentrations of ICAM1 at the time point of first fungal detection in microbiological samples were used for this ROC analysis. Contrariwise, in patients with no fungal findings, plasma concentrations of ICAM1 at sepsis onset were used. Patients suffering from an IFI represented the target group, whereas patients with a fungal colonization as well as those without any fungal findings served as controls for this ROC analysis.

The FIGS. 7A-K demonstrate the potency of ICAM1, especially for the diagnosis and/or prediction of positive fungal cultures for different source and fungal pathogens (white boxed), treatments (grey boxes), time points and outcome. The monitoring and therapeutic guidance of patients with a risk of getting or having an (invasive) fungal infection by determining ICAM1 is also shown. An increase of ICAM1 from T0 to T1 Is Indicative of invasive fungal infections (in 9 out of all 11 patients; FIG. 7A-K). However, ICAM1 increased from T0 to T1 with fungal colonization as well (in 5 out of 7 patients; FIG. 7A-K).

ICAM1 increases on last time point compared to previous time point if patient died before 90 d, (FIGS. 7A, 7B, 7C and 7G) and remains low if patient survived until 90 d (FIGS. 7D, 7E, 7F, 7H, 7J and 7K) and can therefore also be used for the risk prediction of a patient, especially the mortality risk. The knowledge of an increased risk or decreased risk of getting adverse events or mortality or the knowledge of an (invasive) fungal infection, fungal colonization or no-fungal infection have direct consequences for the management and/or treatment of a patient e.g. therapeutic changes in medication and/or monitoring. A decrease indicates the efficacy of the therapeutic management. A remaining ICAM1 value or an increase indicated a therapeutic mismanagement (e.g. wrong anti-fungal therapeutic, an underdosing of the anti-fungal medication e.g. by low concentrations or to short duration of the treatment; missed anti-fungal therapeutic) whereby it can be solved by the adaption of the concentration and/or duration of treatment and/or change, starting, addition of another antifungal therapy.

A new and surprising finding was THBS1 as biomarker for the diagnosis and/or risk prediction and/or risk stratification and/or monitoring and/or ruling in or ruling out of an invasive fungal infection, an fungal colonization and no fungal infection in a subject, in particular a risk group of getting or having an (invasive) fungal infection, especially sepsis e.g. septic shock.

FIGS. 3 A-B represent the THBS findings by ROC curves and Box plots, demonstrating the power to diagnose and/or differentiate between (invasive) fungal infection and fungal colonization or no fungal infection, respectively.

Plasma samples were collected at the onset of septic shock (T0), and 1 day (T1), 2 days (T2), 7 days (T3), 14 days (T4), 21 days (T5) and 28 days (T6) afterwards and THBS1 was measured. FIG. 3A shows significant THBS1 changes in invasive fungal infection (IFI, dark grey box), a fungal colonization (light grey box) or without any fungal findings (white box). Data in box plots are given as median, 25th percentile, 75th percentile with the 10th as well as 90th percentile at the end of the whiskers.

FIG. 3B shows Receiver operating characteristic (ROC) analysis with THBS1 in all participating patients at sepsis onset (T0), and 1 day (T1), 2 days (T2) as well as 7 days (T3) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC analysis.

A new and surprising finding was RAP1 (RAP1A/RAP1B/RP1BL) as biomarker for the diagnosis and/or risk prediction and/or risk stratification and/or monitoring and/or ruling in or ruling out of an invasive fungal infection, an fungal colonization and no fungal infection in a subject, in particular a risk group of getting or having an (invasive) fungal infection, especially sepsis e.g. septic shock.

FIGS. 4.1 A-B represent the RAP1 (RAP1A/RAP1B/RP1BL) findings by ROC curves and Box plots, demonstrating the power to diagnose and/or differentiate between (invasive) fungal infection and fungal colonization or no fungal infection, respectively.

Plasma samples were collected at the onset of septic shock (T0), and 1 day (T1), 2 days (T2), 7 days (T3), 14 days (T4), 21 days (T5) and 28 days (T6) afterwards and RAP1 (RAP1A/RAP1B/RP1BL) was measured. FIG. 4.1A shows significant RAP1 (RAP1A/RAP1B/RP1BL) changes in invasive fungal infection (IFI, dark grey box), a fungal colonization (light grey box) or without any fungal findings (white box). Data in box plots are given as median, 25th percentile, 75th percentile with the 10th as well as 90th percentile at the end of the whiskers.

FIG. 4.1B shows a ROC analysis with RAP1 (RAP1A/RAP1B/RP1BL) in all participating patients at sepsis onset (T0), and 1 day (T1), 2 days (T2) as well as 7 days (T3) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC analysis.

FIG. 4.2 shows the diagnostic power of RAP1 (RAP1A/RAP1B/RP1BL) for the diagnosis, ruling out and differentiation of an invasive fungal infection (IFI, dark grey box), and/or fungal colonization (light grey box) and/or no fungal infection (white box). In IF patients as well as in those with a fungal colonization, plasma concentrations of RAP1 (RAP1A/RAP1B/RP1BL) are presented for the time point of first fungal detection in microbiological samples. In patients with no fungal findings, plasma concentrations of RAP1 (RAP1A/RAP1B/RP1BL) at sepsis onset are presented. Data in box plots are given as median, $25^{th}$ percentile, $75^{th}$ percentile with the $10^{th}$ as well as $90^{th}$ percentile at the end of the whiskers. Concerning symbolism and higher orders of significance: $p<0.05$: *.

TABLE 17

Biomarkers with significant values for the diagnosis and/or differentiation between (invasive) fungal infection and fungal colonization. Fold change, 95% confidence interval (CI) and significant change are indicated at different time points.

| Gene name | T0 | T1 | T2 | T3 | T4 | T5 | T6 |
|---|---|---|---|---|---|---|---|
| PIGR (fold change/ 95% CI/ p-value) | | | | 2.1<br>1.1-4.0<br>0.021 | 2.1<br>1.4-3.4<br>0.001 | | |
| ICAM1 (fold change/ 95% CI/ p-value) | 1.5<br>1.02-2.1<br>0.037 | 1.5<br>1.03-2.1<br>0.029 | 1.6<br>1.1-2.3<br>0.006 | 1.6<br>1.1-2.2<br>0.005 | 1.6<br>1.1-2.5<br>0.015 | | |
| HRG (fold change/ 95% CI/ p-value) | | | | | 0.5<br>0.3-0.8<br>0.004 | 0.4<br>0.2-0.9<br>0.03 | 0.3<br>0.1-0.6<br>0.001 |
| THBS1 (fold change/ 95% CI/ p-value) | | | | | 0.4<br>0.2-0.9<br>0.022 | | 0.4<br>0.1-0.95<br>0.038 |
| RAP1A (fold change/ 95% CI/ p-value) | | | | | 0.4<br>0.2-0.8<br>0.004 | | 0.3<br>0.1-0.8<br>0.015 |
| AHSG (fold change/ 95% CI/ p-value) | | | | | 0.6<br>0.4-0.8<br>0.002 | 0.5<br>0.3-0.9<br>0.019 | 0.4<br>0.2-0.8<br>0.003 |
| VCL (fold change/ 95% CI/ p-value) | | 0.6<br>0.3-0.98<br>0.041 | 0.6<br>0.3-0.97<br>0.035 | | 0.4<br>0.2-0.8<br>0.007 | | |
| FABP1 (fold change/ 95% CI/ p-value) | | | | 1.4<br>1.003-1.9<br>0.047 | 1.4<br>1.1-1.9<br>0.009 | | |
| PCT (fold change/ 95% CI/ p-value) | | | | 3.6<br>1.5-8.7<br>0.002 | 7.1<br>2.1-24.0<br>0.001 | 8.7<br>1.5-50.7<br>0.014 | 8.0<br>2.2-29.4<br>0.002 |

Table 17 shows the results of the biomarkers PIGR, ICAM1, HRG, THBS1, RAP1A AHSG, VCL FABP1 and PCT, tested at septic shock onset (T0), and 1 day (T1), 2 days (T2), 7 days (T3), 14 days (T4), 21 days (T5) and 28 days (T6) with a significance (p value <0.05) and mean-fold change (presented below the p-value), whereby the significant biomarker values diagnose and/or differentiate (invasive) fungal infection compared to fungal colonization. Biomarkers with fold-changes below 1.0 indicate a down-regulation of the biomarker (HRG, THBS1, RAP1A (RAP1A/RAP1B/RAPBL), AHSG, VCL) and above 1.0 an upregulation of the biomarker (ICAM1, FABP1, PCT). Therefore the biomarkers show the same functionality in diagnosing, and/or ruling out an invasive fungal infection and/or differentiation of an invasive fungal infection vs. no invasive fungal infection and/or differentiation of an invasive fungal infection vs. no invasive fungal infection and/or fungal colonization and differentiation of an invasive fungal infection vs. fungal colonization and can be used alone or in combination.

FIG. 4.3 presents a ROC analysis with RAP1 (RAP1A/RAP1B/RP1BL) in patients with an invasive fungal infection (IFI) or fungal colonization at the time point of first fungal detection in microbiological samples with regard to the prediction of an invasive fungal infection (IFI). Patients suffering from an IFI represented the target group, whereas patients with a fungal colonization served as controls for this ROC analysis. Data of patients without any fungal findings were not included in this ROC analysis.

FIG. 4.4 shows a ROC analysis with RAP1 (RAP1A/RAP1B/RP1BL) in patients with an invasive fungal infection (IFI), a fungal colonization or without any fungal findings with regard to the prediction of an invasive fungal infection (IFI). In IFI patients as well as in those with a fungal colonization, plasma concentrations of RAP1A at the time point of first fungal detection in microbiological samples were used for this ROC analysis. Contrariwise, in patients with no fungal findings, plasma concentrations of RAP1A at sepsis onset were used. Patients suffering from an IFI represented the target group, whereas patients with a fungal colonization as well as those without any fungal findings served as controls for this ROC analysis.

A new and surprising finding was VCL as biomarker for the diagnosis and/or risk prediction and/or risk stratification and/or monitoring and/or ruling in or ruling out of an invasive fungal infection, an fungal colonization and no fungal infection in a subject, in particular a risk group of getting or having an (invasive) fungal infection, especially sepsis e.g. septic shock.

FIG. 5.1A-B represent the VCL findings by ROC curves and Box plots, demonstrating the power to diagnose and/or differentiate between (invasive) fungal infection and fungal colonization or no fungal infection, respectively.

Plasma samples were collected at the onset of septic shock (T0), and 1 day (T1), 2 days (T2), 7 days (T3), 14 days (T4), 21 days (T5) and 28 days (T6) afterwards and VCL was measured. FIG. 5.1A shows significant VCL changes in invasive fungal infection (IFI, dark grey box), a fungal colonization (light grey box) or without any fungal findings (white box). Data in box plots are given as median, 25th percentile, 75th percentile with the 10th as well as 90th percentile at the end of the whiskers.

FIG. 5.1B shows a ROC analysis with VCL in all participating patients at sepsis onset (T0), and 1 day (T1), 2 days (T2) as well as 7 days (T3) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC analysis.

FIG. 5.2 shows the diagnostic power of VCL for the diagnosis, ruing out and differentiation of an invasive fungal infection (IFI, dark grey box), and/or fungal colonization (light grey box) and/or no fungal infection (white box). In IFI patients as well as in those with a fungal colonization, plasma concentrations of VCL are presented for the time point of first fungal detection in microbiological samples. In patients with no fungal findings, plasma concentrations of VCL at sepsis onset are presented. Data in box plots are given as median, $25^{th}$ percentile, $75^{th}$ percentile with the $10^{th}$ as well as $90^{th}$ percentile at the end of the whiskers. Concerning symbolism and higher orders of significance: $p<0.05$: *.

FIG. 5.3 presents a ROC analysis with VCL in patients with an invasive fungal infection (IFI) or fungal colonization at the time point of first fungal detection in microbiological samples with regard to the prediction of an invasive fungal infection (IFI). Patients suffering from an IFI represented the target group, whereas patients with a fungal colonization served as controls for this ROC analysis. Data of patients without any fungal findings were not included in this ROC analysis.

FIG. 5.4 shows a ROC analysis with VCL in patients with an invasive fungal infection (IFI), a fungal colonization or without any fungal findings with regard to the prediction of an invasive fungal infection (IFI). In IFI patients as well as in those with a fungal colonization, plasma concentrations of VCL at the time point of first fungal detection in microbiological samples were used for this ROC analysis. Contrariwise, in patients with no fungal findings, plasma concentrations of VCL at sepsis onset were used. Patients suffering from an IFI represented the target group, whereas patients with a fungal colonization as well as those without any fungal findings served as controls for this ROC analysis.

A new and surprising finding was CT-proET-1 as biomarker for the diagnosis and/or risk prediction and/or risk stratification and/or monitoring and/or ruling in or ruling out of an invasive fungal infection, an fungal colonization and no fungal infection in a subject, in particular a risk group of getting or having an (invasive) fungal infection, especially sepsis e.g. septic shock.

FIGS. 6 A-B represents the CT-proET-1 findings by ROC curves and Box plots, demonstrating the power to diagnose and/or differentiate between (invasive) fungal infection and fungal colonization or no fungal infection, respectively.

Plasma samples were collected at the onset of septic shock (T0), and 1 day (T1) afterwards and CT-proET-1 was measured. FIG. 6A shows CT-proET-1 changes in invasive fungal infection (IFI, dark grey box), a fungal colonization (light grey box) or without any fungal findings (white box). Data in box plots are given as median, 25th percentile, 75th percentile with the 10th as well as 90th percentile at the end of the whiskers.

FIG. 6B shows Receiver operating characteristic (ROC) analysis with CT-proET-1 in all participating patients at sepsis onset (T0), and 1 day (T1) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC analysis.

At the time point of a first fungal detection, ICAM1, THBS1, RAP1A; VCL and CT-proET-1 are able to differentiate invasive fungal infection from fungal colonization and patients without fungal findings (FIGS. 2.3, 2.4, 2.5, 4.2, 4.3, 4.4, 5.2, 5.3, 5.4, 6; Tables 7, 9 and 10).

FIGS. 8A-E and FIGS. 9 A-B demonstrate the potency of VCL, especially for the diagnosis and/or prediction of positive fungal cultures for different sources and fungal pathogens (white boxes), treatments (grey boxes, especially antifungal-treatment), time points (onset of septic shock (T0), day 1 (T1), day 2 (T2), day 7 (T3), day 14 (T4), day 21 (T5), day 28 (T6) afterwards) and outcome (especially mortality). The monitoring and therapeutic guidance of patients with a risk of getting or having an (invasive) fungal infection by determining VCL is also shown. A downregulation of VCL below a cut-off is indicative of invasive fungal infections (for example in case of C. spp in swab (intraoperative, wound), BAL, blood (BC), sputum or drainage fluid (FIG. 8A S12 T0, FIG. 8B S23 T0, FIG. 8C S38 T5-T6, FIG. 8D S39 T0, FIG. 8E S44 T0 and T3-T5, FIG. 9A S16 T3-T6, FIG. 9B S35 T2-T4). In patient S23, VCL is low at the beginning, rises with treatment and is decreasing again which might reflect missing treatment response and switch in antifungals (FIG. 8B). Patients S35 (FIG. 9B), S38 (FIG. 8C) and S44 (FIG. 8E) have further late fungal isolates and change in antifungals. Of note, in patient S44 *C. krusei* has been isolated which is known to be not responsive to fluconazole treatment but sensitive to caspofungin resulting in immediately rising VCL levels after switch of treatment (FIG. 8B) and showing the correlation of VCL and treatment efficacy. The knowledge of an increased risk or decreased risk of getting or having an (invasive) fungal infection, or having a fungal colonization or no-fungal infection have direct consequences for the management and/or treatment of a patient e.g. therapeutic changes in medication and/or monitoring.

In addition, plasma levels of sICAM-1 were assessed by Human sICAM-1 Platinum ELISA (eBioscience, Thermo Fisher Scientific), an immunoassay-based procedure, for the time points T0 as well as T1.

TABLE 18

Area under the curve (AUC), sensitivity with 95%-confidence intervals (CI), sensitivity, 1-specificity and best cut-off from receiver operating characteristic (ROC) analysis with sICAM-1 in all participating patients at sepsis onset (T0) and 1 day (T1) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

| Time point | AUC (with 95%-CI) | Sensitivity | 1-Specificity | Best Cut off (ng/L) |
|---|---|---|---|---|
| T0 | 0.656 (438-0.874) | 0.545 | 0.121 | 1705 |
| T1 | 0.716 (0.502-0.931) | 0.727 | 0.182 | 1591 |

FIG. 15 A-B: Immunoassay-based measurements of plasmatic sICAM-1 concentrations for the detection of an IFI in patients with septic shock.

(A) Plasma concentrations of sICAM-1 were measured in patients suffering from septic shock with an invasive fungal infection (IFI, dark grey box), a fungal colonization (light grey box) or without any fungal findings (white box). Plasma samples were collected at the onset of septic shock (T0) and 1 day (T1) afterwards. Data in box plots are given as median, 25th percentile, 75th percentile with the 10th as well as 90th percentile at the end of the whiskers. Concerning symbolism and higher orders of significance: $p<0.05$: *.

(B) Receiver operating characteristic (ROC) analysis with sICAM-1 in all participating patients at sepsis onset (T0) and 1 day (T1) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

TABLE 19

Receiver Operator Curve (ROC)-analyses for the measurement of PCT. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| | | | | Asymptotic 95% Confidence Interval | |
|---|---|---|---|---|---|
| Test Result Variable(s) | Area | Std. Error[a] | Asymptotic Sig.[b] | Lower Bound | Upper Bound |
| PCT T0 | .525 | .105 | .821 | .319 | .731 |
| PCT T1 | .533 | .112 | .762 | .314 | .753 |
| PCT T2 | .583 | .109 | .450 | .370 | .796 |
| PCT T3 | .879 | .067 | .001 | .759 | .999 |
| PCT T4 | .896 | .055 | .000 | .789 | 1.000 |

[a]Under the nonparametric assumption
[b]Null hypothesis: true area = .05

FIG. 16: ROC-analysis for measurements of PCT for the detection of an IFI in patients with septic shock.

Receiver operating characteristic (ROC) analysis with PCT in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

TABLE 20

Receiver Operator Curve (ROC)-analyses for the combined measurement of PCT and ICAM-1. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| | | | | Asymptotic 95% Confidence Interval | |
|---|---|---|---|---|---|
| Test Result Variable(s) | Area | Std. Error[a] | Asymptotic Sig.[b] | Lower Bound | Upper Bound |
| Predicted probability | .729 | .109 | .038 | .516 | .942 |
| Predicted probability | .779 | .110 | .011 | .564 | .995 |
| Predicted probability | .813 | .107 | .005 | .602 | 1.000 |
| Predicted probability | .900 | .080 | .000 | .743 | 1.000 |
| Predicted probability | .837 | .070 | .002 | .700 | .975 |

FIG. 17: ROC-analysis the combined measurement of PCT and ICAM for the detection of an IFI in patients with septic shock.

Receiver operating characteristic (ROC) analysis with PCT and ICAM in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

TABLE 21

Receiver Operator Curve (ROC)-analyses for the combined measurement of PCT, ICAM-1 and ADM. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| | | | | Asymptotic 95% Confidence Interval | |
|---|---|---|---|---|---|
| Test Result Variable(s) | Area | Std. Error[a] | Asymptotic Sig.[b] | Lower Bound | Upper Bound |
| Predicted probability | .796 | .096 | .008 | .607 | .984 |
| Predicted probability | .813 | .096 | .005 | .625 | 1.000 |

TABLE 21-continued

Receiver Operator Curve (ROC)-analyses for the combined measurement of PCT, ICAM-1 and ADM. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| | | | | Asymptotic 95% Confidence Interval | |
|---|---|---|---|---|---|
| Test Result Variable(s) | Area | Std. Error[a] | Asymptotic Sig.[b] | Lower Bound | Upper Bound |
| Predicted probability | .830 | .103 | .003 | .628 | 1.000 |
| Predicted probability | .909 | .072 | .000 | .768 | 1.000 |
| Predicted probability | .896 | .056 | .000 | .785 | 1.000 |

FIG. 18: ROC-analysis the combined measurement of PCT, ICAM-1 and ADM for the detection of an IFI in patients with septic shock.

Receiver operating characteristic (ROC) analysis with PCT, ICAM and ADM in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

TABLE 22

Receiver Operator Curve (ROC)-analyses for the combined measurement of PCT, ICAM-1, ADM and IL17. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| | | | | Asymptotic 95% Confidence Interval | |
|---|---|---|---|---|---|
| Test Result Variable(s) | Area | Std. Error[a] | Asymptotic Sig.[b] | Lower Bound | Upper Bound |
| Predicted probability | .803 | .104 | .009 | .600 | 1.000 |
| Predicted probability | .838 | .098 | .004 | .645 | 1.000 |
| Predicted probability | .803 | .118 | .009 | .573 | 1.000 |
| Predicted probability | .909 | .074 | .000 | .764 | 1.000 |
| Predicted probability | .919 | .053 | .000 | .813 | 1.000 |

FIG. 19: ROC-analysis the combined measurement of PCT, ICAM-1, ADM and IL17 for the detection of an IF in patients with septic shock.

Receiver operating characteristic (ROC) analysis with PCT, ICAM-1, ADM and IL17 in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

TABLE 23

Receiver Operator Curve (ROC)-analyses for the combined measurement of PCT and ADM. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| | | | | Asymptotic 95% Confidence Interval | |
|---|---|---|---|---|---|
| Test Result Variable(s) | Area | Std. Error[a] | Asymptotic Sig.[b] | Lower Bound | Upper Bound |
| Predicted probability | .674 | .107 | .117 | .464 | .884 |
| Predicted probability | .661 | .101 | .147 | .463 | .858 |
| Predicted probability | .683 | .106 | .100 | .475 | .890 |
| Predicted probability | .883 | .064 | .001 | .756 | 1.000 |
| Predicted probability | .887 | .059 | .000 | .772 | 1.000 |

FIG. 20: ROC-analysis the combined measurement of PCT and ADM for the detection of an IFI in patients with septic shock.

Receiver operating characteristic (ROC) analysis with PCT and ADM in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

TABLE 24

Receiver Operator Curve (ROC)-analyses for the combined measurement of ADM and ICAM-1. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| | | | | Asymptotic 95% Confidence Interval | |
|---|---|---|---|---|---|
| Test Result Variable(s) | Area | Std. Error[a] | Asymptotic Sig.[b] | Lower Bound | Upper Bound |
| Predicted probability | .787 | .087 | .010 | .617 | .957 |
| Predicted probability | .835 | .080 | .003 | .677 | .992 |
| Predicted probability | .852 | .091 | .002 | .673 | 1.000 |
| Predicted probability | .887 | .071 | .000 | .748 | 1.000 |
| Predicted probability | .909 | .052 | .000 | .808 | 1.000 |

FIG. 21: ROC-analysis the combined measurement of ADM and ICAM-1 for the detection of an IFI in patients with septic shock.

Receiver operating characteristic (ROC) analysis with ADM and ICAM-1 in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

TABLE 25

Receiver Operator Curve (ROC)-analyses for the combined measurement of ADM, ICAM-1 and IL17. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| | | | | Asymptotic 95% Confidence Interval | |
|---|---|---|---|---|---|
| Test Result Variable(s) | Area | Std. Error[a] | Asymptotic Sig.[b] | Lower Bound | Upper Bound |
| Predicted probability | .788 | .100 | .013 | .593 | .983 |
| Predicted probability | .848 | .086 | .003 | .679 | 1.000 |
| Predicted probability | .828 | .102 | .005 | .628 | 1.000 |
| Predicted probability | .879 | .077 | .001 | .727 | 1.000 |
| Predicted probability | .899 | .067 | .001 | .767 | 1.000 |

[b]Null hypothese: true area = 0.5

FIG. 22: ROC-analysis the combined measurement of ADM, ICAM-1 and IL17 for the detection of an IFI in patients with septic shock.

Receiver operating characteristic (ROC) analysis with ADM, ICAM and IL17 in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

TABLE 26

Receiver Operator Curve (ROC)-analyses for the measurement of ADM. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| | | | | Asymptotic 95% Confidence Interval | |
|---|---|---|---|---|---|
| Test Result Variable(s) | Area | Std. Error[a] | Asymptotic Sig.[b] | Lower Bound | Upper Bound |
| T0 | .700 | .097 | .070 | .509 | .891 |
| T1 | .663 | .101 | .140 | .464 | .861 |
| T2 | .725 | .100 | .041 | .529 | .921 |
| T3 | .783 | .093 | .010 | .600 | .966 |
| T4 | .908 | .051 | .000 | .808 | 1.000 |

[a]Under the nonparametric assumption
[b]Null hypothesis: true area = .05

FIG. 23: ROC-analysis the measurement of ADM for the detection of an IFI in patients with septic shock.

Receiver operating characteristic (ROC) analysis with ADM in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

TABLE 27

Receiver Operator Curve (ROC)-analyses for the combined measurement of PCT and THBS-1. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| | | | | Asymptotic 95% Confidence Interval | |
|---|---|---|---|---|---|
| Test Result Variable(s) | Area | Std. Error[a] | Asymptotic Sig.[b] | Lower Bound | Upper Bound |
| Predicted probability | .687 | .099 | .089 | .493 | .882 |
| Predicted probability | .629 | .116 | .241 | .402 | .857 |
| Predicted probability | .708 | .102 | .059 | .509 | .908 |
| Predicted probability | .879 | .061 | .001 | .759 | .999 |
| Predicted probability | .879 | .067 | .001 | .747 | 1.000 |

FIG. 24: ROC-analysis the combined measurement of PCT and THBS-1 for the detection of an IFI in patients with septic shock.

Receiver operating characteristic (ROC) analysis with PCT and THBS-1 in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

TABLE 28

Receiver Operator Curve (ROC)-analyses for the combined measurement of ADM and THBS-1. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| | | | | Asymptotic 95% Confidence Interval | |
|---|---|---|---|---|---|
| Test Result Variable(s) | Area | Std. Error[a] | Asymptotic Sig.[b] | Lower Bound | Upper Bound |
| Predicted probability | .730 | .102 | .038 | .531 | .930 |
| Predicted probability | .704 | .112 | .066 | .485 | .923 |

TABLE 28-continued

Receiver Operator Curve (ROC)-analyses for the combined measurement of ADM and THBS-1. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| | | | | Asymptotic 95% Confidence Interval | |
|---|---|---|---|---|---|
| Test Result Variable(s) | Area | Std. Error[a] | Asymptotic Sig.[b] | Lower Bound | Upper Bound |
| Predicted probability | .735 | .102 | .034 | .534 | .965 |
| Predicted probability | .804 | .079 | .006 | .649 | .960 |
| Predicted probability | .909 | .052 | .000 | .807 | 1.000 |

FIG. 25: ROC-analysis the combined measurement of ADM and THBS-1 for the detection of an IFI in patients with septic shock.

Receiver operating characteristic (ROC) analysis with ADM and THBS-1 in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

TABLE 29

Receiver Operator Curve (ROC)-analyses for the combined measurement of PCT, ADM and THBS-1. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| | | | | Asymptotic 95% Confidence Interval | |
|---|---|---|---|---|---|
| Test Result Variable(s) | Area | Std. Error[a] | Asymptotic Sig.[b] | Lower Bound | Upper Bound |
| Predicted probability | .709 | .106 | .060 | .501 | .917 |
| Predicted probability | .657 | .111 | .158 | .440 | .874 |
| Predicted probability | .726 | .104 | .042 | .522 | .930 |
| Predicted probability | .870 | .067 | .001 | .739 | 1.000 |
| Predicted probability | .922 | .047 | .000 | .830 | 1.000 |

FIG. 26: ROC-analysis the combined measurement of PCT, ADM and THBS-1 for the detection of an IFI in patients with septic shock.

Receiver operating characteristic (ROC) analysis with PCT, ADM and THBS-1 in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

TABLE 30

Receiver Operator Curve (ROC)-analyses for the combined measurement of PCT and VCL. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| | | | | Asymptotic 95% Confidence Interval | |
|---|---|---|---|---|---|
| Test Result Variable(s) | Area | Std. Error[a] | Asymptotic Sig.[b] | Lower Bound | Upper Bound |
| Predicted probability | .638 | .103 | .212 | .436 | .839 |
| Predicted probability | .700 | .104 | .070 | .496 | .904 |
| Predicted probability | .742 | .094 | .028 | .557 | .927 |
| Predicted probability | .875 | .063 | .001 | .752 | .998 |
| Predicted probability | .862 | .064 | .001 | .736 | .989 |

FIG. 27: ROC-analysis the combined measurement of PCT and VCL for the detection of an IFI in patients with septic shock.

Receiver operating characteristic (ROC) analysis with PCT and VCL in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

TABLE 31

Receiver Operator Curve (ROC)-analyses for the combined measurement of ADM and VCL. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| | | | | Asymptotic 95% Confidence Interval | |
|---|---|---|---|---|---|
| Test Result Variable(s) | Area | Std. Error[a] | Asymptotic Sig.[b] | Lower Bound | Upper Bound |
| Predicted probability | .709 | .106 | .060 | .500 | .917 |
| Predicted probability | .757 | .103 | .021 | .554 | .959 |
| Predicted probability | .730 | .098 | .038 | .539 | .922 |
| Predicted probability | .765 | .091 | .017 | .587 | .943 |
| Predicted probability | .917 | .047 | .000 | .826 | 1.000 |

FIG. 28: ROC-analysis the combined measurement of ADM and VCL for the detection of an IFI in patients with septic shock.

Receiver operating characteristic (ROC) analysis with ADM and VCL in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

TABLE 32

Receiver Operator Curve (ROC)-analyses for the combined measurement of ADM, VCL and PCT. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| Test Result Variable(s) | Area | Std. Error[a] | Asymptotic Sig.[b] | Asymptotic 95% Confidence Interval Lower Bound | Upper Bound |
|---|---|---|---|---|---|
| Predicted probability | .696 | .106 | .078 | .488 | .903 |
| Predicted probability | .739 | .100 | .031 | .543 | .935 |
| Predicted probability | .748 | .097 | .026 | .558 | .937 |
| Predicted probability | .878 | .066 | .001 | .748 | 1.000 |
| Predicted probability | .922 | .046 | .000 | .831 | 1.000 |

FIG. 29: ROC-analysis the combined measurement of ADM, VCL and PCT for the detection of an IFI in patients with septic shock.

Receiver operating characteristic (ROC) analysis with ADM, VCL and PCT in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

TABLE 33

Receiver Operator Curve (ROC)-analyses for the combined measurement of ICAM1 and THBS-1. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| Test Result Variable(s) | Area | Std. Error[a] | Asymptotic Sig.[b] | Asymptotic 95% Confidence Interval Lower Bound | Upper Bound |
|---|---|---|---|---|---|
| Predicted probability | .787 | .091 | .009 | .609 | .966 |
| Predicted probability | .808 | .094 | .005 | .625 | .992 |

TABLE 33-continued

Receiver Operator Curve (ROC)-analyses for the combined measurement of ICAM1 and THBS-1. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| Test Result Variable(s) | Area | Std. Error[a] | Asymptotic Sig.[b] | Asymptotic 95% Confidence Interval Lower Bound | Upper Bound |
|---|---|---|---|---|---|
| Predicted probability | .833 | .090 | .002 | .656 | 1.000 |
| Predicted probability | .887 | .081 | .000 | .730 | 1.000 |
| Predicted probability | .887 | .058 | .000 | .775 | 1.000 |

FIG. 30: ROC-analysis the combined measurement of ICAM1 and THBS-1 for the detection of an IFI in patients with septic shock.

Receiver operating characteristic (ROC) analysis with ICAM1 and THBS-1 in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

TABLE 34

Receiver Operator Curve (ROC)-analyses for the combined measurement of ICAM1 and VCL. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| Test Result Variable(s) | Area | Std. Error[a] | Asymptotic Sig.[b] | Asymptotic 95% Confidence Interval Lower Bound | Upper Bound |
|---|---|---|---|---|---|
| Predicted probability | .771 | .098 | .014 | .579 | .962 |
| Predicted probability | .837 | .078 | .002 | .684 | .991 |
| Predicted probability | .883 | .075 | .001 | .736 | 1.000 |
| Predicted probability | .854 | .086 | .001 | .686 | 1.000 |
| Predicted probability | .883 | .061 | .001 | .763 | 1.000 |

FIG. 31: ROC-analyses the combined measurement of ICAM1 and VCL for the detection of an IFI in patients with septic shock.

Receiver operating characteristic (ROC) analysis with ICAM1 and VCL in all participating patients at sepsis onset (T0), day 1 (T1), day 2 (T2), day 7 (T3) and 14 day (T4)

afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

TABLE 35

Receiver Operator Curve (ROC)-analyses for the combined measurement of ICAM1, THBS-1 and VCL. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval.
Area Under the Curve

| Test Result Variable(s) | Area | Std. Error[a] | Asymptotic Sig.[b] | Asymptotic 95% Confidence Interval Lower Bound | Asymptotic 95% Confidence Interval Upper Bound |
|---|---|---|---|---|---|
| Predicted probability | .800 | .087 | .007 | .629 | .971 |
| Predicted probability | .846 | .076 | .002 | .696 | .996 |
| Predicted probability | .896 | .068 | .000 | .763 | 1.000 |
| Predicted probability | .921 | .046 | .000 | .831 | 1.000 |
| Predicted probability | .896 | .057 | .000 | .785 | 1.000 |

FIG. 32: ROC-analysis the combined measurement of ICAM1, THBS-1 and VCL for the detection of an IFI in patients with septic shock.

Receiver operating characteristic (ROC) analysis with ICAM1, THBS-1 and VCL in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

FIGS. 38A-D corresponds to Table 36: Receiver Operator Curve (ROC)-analyses for different biomarker combinations. ROC-analyses for fungally infected vs. fungally colonized or patients without any fungal findings. Data are given as AUCs with 95%-confidence intervals (CI) or absolute values for sensitivity and specificity. Abbreviations: AUC, area under the curve; CI, confidence interval FIGS. 38A-D presents the diagnostic value of the combination of PCT, MR-proADM, sICAM-1 and/or IL-17A for the diagnosis, differentiation, monitoring and prognosis/risk stratification of an (invasive) fungal infection in different time points, in patients with risk of having or getting a (invasive) fungal infection, in particular sepsis, especially septic shock. The results are transferrable to all kind of subjects, with and without special risk.

TABLE 37

Area under the curve (AUC), sensitivity with 95%-confidence intervals (CI), sensitivity and 1-specificity from receiver operating characteristic (ROC) analysis with sICAM-1, thrombospondin-1 and vinculin in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

| Time point | AUC (with 95%-CI) | Sensitivity | 1-Specificity |
|---|---|---|---|
| T0 | 0.800 (0.629-0.917) | 0.700 | 0.174 |
| T1 | 0.846 (696-0.996) | 0.800 | 0.174 |
| T2 | 0.896 (0.763-1.00) | 0.700 | 0.00 |
| T3 | 0.921 (0.831-1.0) | 0.900 | 0.174 |
| T4 | 0.896 (0.785-1.00) | 0.800 | 0.130 |

FIG. 33: ROC-analysis for combined measurements of sICAM-1, thrombospondin-1 and vinculin for the detection of an IFI in patients with septic shock.

Receiver operating characteristic (ROC) analysis with sICAM-1, thrombospondin-1 and vinculin in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

TABLE 38

Area under the curve (AUC), sensitivity with 95%-confidence intervals (CI), sensitivity and 1-specificity from receiver operating characteristic (ROC) analysis with MR-proADM and sICAM-1 in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

| Time point | AUC (with 95%-CI) | Sensitivity | 1-Specificity |
|---|---|---|---|
| T0 | 0.787 (0.617-0.957) | 0.700 | 0.083 |
| T1 | 0.835 (0.677-0.992) | 0.800 | 0.250 |
| T2 | 0.852 (0.673-1.000) | 0.900 | 0.208 |
| T3 | 0.887 (0.748-1.000) | 1.000 | 0.292 |
| T4 | 0.909 (0.808-1.000) | 0.900 | 0.208 |

FIG. 34: ROC-analysis for combined measurements of MR-proADM and sICAM-1 for the detection of an IFI in patients with septic shock.

Receiver operating characteristic (ROC) analysis with MR-proADM and sICAM-1 in all participating patients at sepsis onset (T0), day 1 (T1), day 2 (T2), day 7 (T3) and 14 day (T4) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

Example 2: IFI in the Context of Liver Transplantation, Especially Patients Following Liver Transplantation The following experiments were performed as described in Example 1. In brief, plasma concentrations of ICAM1, MR-proADM or ICAM1 and MR-proADM were measured in patients following liver transplantation (LTX) with an invasive fungal infection, a fungal colonization or without any fungal findings. In total, 93 patients following LTX were screened for the emergence of IFIs by the use of culture-based as well as image-producing procedures. In parallel, plasma samples were collected on day of liver transplantation (T0), and 1 day (T1), 2 days (T2), 7 days (T3), 14 days (T4), 21 days (T5) and 28 days (T6) afterwards.

2.1 ICAM1 for the Detection of an Invasive Fungal Infection Following Liver Transplantation

TABLE 39

Area under the curve (AUC), sensitivity, 1-specificity and best cut-off from receiver operating characteristic (ROC) analysis with ICAM1 in all participating patients on day of liver transplantation (T0), and 1 day (T1), 14 days (T4) as well as 21 days (T5) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC analysis.

| Time point | AUC (with 95%-CI) | Sensitivity | 1-Specificity | Best Cut off |
|---|---|---|---|---|
| T0 | 0.574 | 0.5 | 0.238 | 0.022375364 |
| T1 | 0.533 | 0.625 | 0.476 | 0.023814595 |
| T4 | 0.714 (0.546-0.882) | 0.875 | 0.429 | 0.025729737 |
| T5 | 0.783 (0.645-0.920) | 0.875 | 0.357 | 0.024646877 |

FIG. 35.1 A shows differences in plasma concentrations of ICAM1 measured in patients following liver transplantation with an invasive fungal infection (IFI, dark grey box), a fungal colonization (light grey box) or without any fungal findings (white box). Plasma concentration of ICAM1 were collected on the day of liver transplantation (T0), 1 day (T1), 2 days (T2), 7 days (T3), 14 days (T4), 21 days (T5) and 28 days (T6) afterwards. Data in box plots are given as median, $25^{th}$ percentile, $75^{th}$ percentile with the $10^{th}$ as well as $90^{th}$ percentile at the end of the whiskers (Concerning symbolism and higher orders of significance: p<0.05: *, p<0.01: **).

FIG. 35.1 B shows Receiver operating characteristic (ROC) analysis with ICAM1 in all participating patients on the day of liver transplantation (T0), and 1 day (T1), 14 days (T4) as well as 21 days (T5) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis.

2.2 ICAM1 for the Detection of Fungal Pathogens in IFI Vs. Fungal Colonization Following Liver Transplantation

TABLE 40

Area under the curve (AUC), sensitivity, 1-specificity and best cut-off from receiver operating characteristic (ROC) analysis with ICAM1 in patients with an invasive fungal infection (IFI) or fungal colonization on day of liver transplantation (T0), 1 day (T1) and 2 days (T2) afterwards with regard to the prediction of an invasive fungal infection (IFI) up to day 28. Patients suffering from an IFI represented the target group, whereas patients with a fungal colonization served as controls for this ROC analysis. Data of patients without any fungal findings were not included in this ROC analysis.

| Time point | AUC | Sensitivity | 1-Specificity | Best Cut off |
|---|---|---|---|---|
| T0 | 0.708 | 0.5 | 0.0 | 0.025947727 |
| T1 | 0.833 | 0.75 | 0.0 | 0.022376599 |
| T2 | 0.917 | 0.75 | 0.0 | 0.019209418 |

FIG. 35.2 A presents differences in plasma concentrations of ICAM1 measured in patients following liver transplantation with an invasive fungal infection (dark grey box) or a fungal colonization (light grey box). Plasma concentration of ICAM1 were collected on the day of liver transplantation (T0), at 1 day (T1) and 2 days (T2) Data in box plots are given as median, $25^{th}$ percentile, $75^{th}$ percentile with the $10^{th}$ as well as $90^{th}$ percentile at the end of the whiskers. (Concerning symbolism and higher orders of significance: p<0.05: *).

FIG. 35.2 B shows a ROC analysis with ICAM1 in patients with an invasive fungal infection (IFI) or fungal colonization at the time point of first fungal detection in microbiological samples with regard to the prediction of an invasive fungal infection (IFI). Patients suffering from an IFI represented the target group, whereas patients with a fungal colonization served as controls for this ROC analysis. Data of patients without any fungal findings were not included in this ROC analysis.

2.2 MR-proADM for the Detection of Fungal Pathogens in IFI Vs. Fungal Colonization Following Liver Transplantation

TABLE 41

Area under the curve (AUC), sensitivity, 1-specificity and best cut-off from receiver operating characteristic (ROC) analysis with MR-proADM in patients with an invasive fungal infection (IFI) or fungal colonization on day of liver transplantation (T0), 1 day (T1) and 2 days (T2) afterwards with regard to the prediction of an invasive fungal infection (IFI) up to day 28. Patients suffering from an IFI represented the target group, whereas patients with a fungal colonization served as controls for this ROC analysis. Data of patients without any fungal findings were not included in this ROC analysis.

| Time point | AUC | Sensitivity | 1-Specificity | Best Cut off |
|---|---|---|---|---|
| T0 | 0.679 | 1.0 | 0.5 | 3.06 |
| T1 | 0.750 | 1.0 | 0.5 | 4.69 |
| T2 | 0.857 | 0.857 | 0.25 | 5.80 |

FIG. 36.1 A presents differences in plasma concentrations of MR-proADM measured in patients following liver transplantation with an invasive fungal infection (dark grey box) or a fungal colonization (light grey box). Plasma concentration of MR-proADM were collected on the day of liver transplantation (T0), at 1 day (T1) and 2 days (T2) Data in box plots are given as median, 25$^{th}$ percentile, 75$^{th}$ percentile with the 10$^{th}$ as well as 90$^{th}$ percentile at the end of the whiskers. (Concerning symbolism and higher orders of significance: $p<0.05$: *).

FIG. 36.1 B shows a ROC analysis with MR-proADM in patients with an invasive fungal infection (IFI) or fungal colonization at the time point of first fungal detection in microbiological samples with regard to the prediction of an invasive fungal infection (IFI). Patients suffering from an IFI represented the target group, whereas patients with a fungal colonization served as controls for this ROC analysis. Data of patients without any fungal findings were not included in this ROC analysis.

2.3 ICAM-1 and MR-proADM for the Detection of an Invasive Fungal Infection Following Liver Transplantation

TABLE 42

Area under the curve (AUC), sensitivity and 1-specificity from receiver operating characteristic (ROC) analysis with ICAM1 and MR-proADM in all participating patients on day of liver transplantation (T0), and 1 day (T1), 2 days (T2), 7 days (T3), 14 days (T4) as well as 21 days (T5) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC analysis.

| Time point | AUC (with 95%-CI) | Sensitivity | 1-Specificity |
|---|---|---|---|
| T0 | 0.741<br>(0.465-1.00) | 0.571 | 0.0 |
| T1 | 0.511 | 0.286 | 0.0 |
| T2 | 0.575 | 0.429 | 0.105 |
| T3 | 0.865<br>(0.706-1.00) | 0.857 | 0.105 |
| T4 | 0.898<br>(0.758-1.00) | 0.857 | 0.053 |
| T5 | 0.902 | 0.857 | 0.079 |

FIG. 37 shows Receiver operating characteristic (ROC) analysis with ICAM1 and MR-proADM in all participating patients on the day of liver transplantation (T0), and 1 day (T1), 2 days (T2), 7 days (T3), 14 days (T4) as well as 21 days (T5) afterwards with regard to the prediction of an invasive fungal infection (IFI) up to day 28. Patients suffering from an invasive fungal infection (IFI) represented the target group, whereas both, patients with a fungal colonization as well as patients without any fungal isolates served as controls for this ROC-analysis. Values calculated as predicted values.

AMINO ACID SEQUENCES

| Marker | Amino acid sequence (SEQ ID NO) |
|---|---|
| Intercellular adhesion molecule 1 (ICAM1)<br>Uniprot No.: P05362<br>Length: 532 aa | MAPSSPRPALPALLVLLGALFPGPGNAQTS<br>VSPSKVILPRGGSVLVTCSTSCDQPK**LLGI**<br>**ETPLPK**KELLLPGNNRKVYELSNVQEDSQP<br>MCYSNCPDGQSTAKTFLTVYWTPERVELAP<br>LPSWQPVGKNLTLRCQVEGGAPRANLTVVL<br>LRGEKELKREPAVGEPAEVTTTVLVRRDHH<br>GANFSCRTELDLRPQGLELFENTSAPYQLQ<br>TFVLPATPPQLVSPRVLEVDTQGTVVCSLD<br>GLFPVSEAQVHLALGDQRLNPTVTYGNDSF<br>SAKASVSVTAEDEGTQRLTCAVILGNQSQE<br>TLQTVTIYSFPAPNVILTKPEVSEGTEVTV<br>KCEAHPRAKVTLNGVPAQPLGPRAQLLLKA<br>TPEDNGRSFSCSATLEVAGQLIHKNQTREL<br>RVLYGPRLDERDCPGNWTWPENSQQTPMCQ<br>AWGNPLPELKCLKDGTFPLPIGESVTVTRD<br>LEGTYLCRARSTQGEVTRKVTVNVLSPRYE<br>IVIITVVAAAVIMGTAGLSTYLYNRQRKIK<br>KYRLQQAQKGTPMKPNTQATPP<br>(SEQ ID NO 1) |
| Alpha-2-HS-glycoprotein (AHSG)<br>Uniprot No.: P02765<br>Length: 367 aa | MKSLVLLLCLAQLWGCHSAPHGPGLIYRQP<br>NCDDPETEEAALVAIDYINQNLPWGYKHTL<br>NQIDEVKVWPQQPSGELFEIEIDTLETTCH<br>VLDPTPVARCSVRQLKEHAVEGDCDFQLLK<br>LDGK**FSVVYAK**CDSSPDSAEDVRKVCQDCP<br>LLAPLNDTRVVHAAKAALAAFNAQNNGSNF<br>QLEEISRAQLVPLPPSTYVEFTVSGTDCVA<br>KEATEAAKCNLLAEKQYGFCKATLSEKLGG<br>AEVAVTCTVFQTQPVTSQPQPEGANEAVPT<br>PVVDPDAPPSPPLGAPGLPPAGSPPDSHVL<br>LAAPPGHQLHRAHYDLRHTFMGVVSLGSPS<br>GEVSHPRKTRTVVQPSVGAAAGPVVPPCPG<br>RIRHFKV<br>(SEQ ID NO 2) |
| Carboxypeptidase N catalytic chain (CPN1)<br>Uniprot No.: P15169<br>Length: 458 aa | MSDLLSVFLHLLLLFKLVAPVTFRHHRYDD<br>LVRTLYK**VQNECPGITR**VYSIGRSVEGRHL<br>YVLEFSDHPGIHEPLEPEVKYVGNMHGNEA<br>LGRELMLQLSEFLCEEFRNRNQRIVQLIQD<br>TRIHILPSMNPDGYEVAAAQGPNKPGYLVG<br>RNNANGVDLNRNFPDLNTYIYYNEKYGGPN<br>HHLPLPDNWKSQVEPETRAVIRWMHSFNFV<br>LSANLHGGAVVANYPYDKSFEHRVRGVRRT<br>ASTPTPDDKLFQKLAKVYSYAHGWMFQGWN<br>CGDYFPDGITNGASWYSLSKGMQDFNYLHT<br>NCFEITLELSCDKFPPEEELQREWLGNREA<br>LIQFLEQVHQGIKGMVLDENYNNLANAVIS<br>VSGINHDVTSGDHGDYFRLLLPGIYTVSAT<br>APGYDPETVTVTVGPAEPTLVNFHLKRSIP<br>QVSPVRRAPSRRHGVRAKVQPQARKKEMEM<br>RQLQRGPA<br>(SEQ ID NO 3) |
| Fatty acid-binding protein (FABP1)<br>Uniprot No.: P07148<br>Length: 127 aa | MSFSGKYQLQSQENFEAFMK**AIGLPEELIQ**<br>**K**CKDIKGVSEIVQNGKHFKFTITAGSKVIQ<br>NEFTVGEECELETMTGEKVKTVVQLEGDNK<br>LVTTFKNIKSVTELNGDIITNTMTLGDIVF<br>KRISKRI<br>(SEQ ID NO 4) |
| Histidine-rich glycoprotein (HRG)<br>Uniprot No.: P04196<br>Length: 525 aa | MKALIAALLLITLQYSCAVSPTDCSAVEPE<br>AEKALDLINKRRR**DGYLFQLLR**IADAHLDR<br>VENTTVYYLVLDVQESDCSVLSRKYWNDCE<br>PPDSRRPSEIVIGQCKVIATRHSHESQDLR<br>VIDFNCTTSSVSSALANTKDSPVLIDFFED<br>TERYRKQANKALEKYKEENDDFASFRVDRI<br>ERVARVRGGEGTGYFVDFSVRNCPRHHFPR<br>HPNVFGFCRADLFYDVEALDLESPKNLVIN<br>CEVFDPQEHENINGVPPHLGHPFHWGGHER<br>SSTTKPPFKPHGSRDHHHPHKPHEHGPPPP<br>PDERDHSHGPPLPQGPPPLLPMSCSSCQHA<br>TFGTNGAQRHSHNNNSSDLHPHKHHSHEQH<br>PHGHHPHAHHPHEHDTHRQHPHGHHPHGHH<br>PHGHHPHGHHPHGHHPHCHDFQDYGPCDPP<br>PHNQGHCCHGHGPPPGHLRRRGPGKGPRPF |

AMINO ACID SEQUENCES

| Marker | Amino acid sequence (SEQ ID NO) |
|---|---|
| | HCRQIGSVYRLPPLRKGEVLPLPEANFPSF<br>PLPHHKHPLKPDNQPFPQSVSESCPGKFKS<br>GFPQVSMFFTHTFPK<br>(SEQ ID NO 5) |
| Polymeric immunoglobulin receptor (PIGR)<br>Uniprot No.: P01833<br>Length: 764 aa | MLLFVLTCLLAVFPAISTKSPIFGPEEVNS<br>VEGNSVSITCYYPPTSVNRHTRKYWCRQGA<br>RGGCITLISSEGYVSSKYAGRANLTNFPEN<br>GTFVVNIAQLSQDDSGRYK**CGLGINSR**GLS<br>FDVSLEVSQGPGLLNDTKVYTVDLGRTVTI<br>NCPFKTENAQKRKSLYKQIGLYPVLVIDSS<br>GYVNPNYTGRIRLDIQGTGQLLFSVVINQL<br>RLSDAGQYLCQAGDDSNSNKKNADLQVLKP<br>EPELVYEDLRGSVTFHCALGPEVANVAKFL<br>CRQSSGENCDVVVNTLGKRAPAFEGRILLN<br>PQDKDGSFSVVITGLRKEDAGRYLCGAHSD<br>GQLQEGSPIQAWQLFVNEESTIPRSPTVVK<br>GVAGGSVAVLCPYNRKESKSIKYWCLWEGA<br>QNGRCPLLVDSEGWVKAQYEGRLSLLEEPG<br>NGTFTVILNQLTSRDAGFYWCLTNGDTLWR<br>TTVEIKIIEGEPNLKVPGNVTAVLGETLKV<br>PCHFPCKFSSYEKYWCKWNNTGCQALPSQD<br>EGPSKAFVNCDENSRLVSLTLNLVTRADEG<br>WYWCGVKQGHFYGETAAVYVAVEERKAAGS<br>RDVSLAKADAAPDEKVLDSGFREIENKAIQ<br>DPRLFAEEKAVADTRDQADGSRASVDSGSS<br>EEQGGSSRALVSTLVPLGLVLAVGAVAVGV<br>ARARHRKNVDRVSIRSYRTDISMSDFENSR<br>EFGANDNMGASSITQETSLGGKEEFVATTE<br>STTETKEPKKAKRSSKEEAEMAYKDFLLQS<br>STVAAEAQDGPQEA<br>(SEQ ID NO 6) |
| Ras-related protein Rap-1A (RAP1A)<br>Uniprot No.: P62834<br>Length: 184 aa | MREYKLVVLGSGGVGKSALTVQFVQGIFVE<br>KYDPTIEDSYRKQVEVDCQQCMLEILDTAG<br>TEQFTAMRDLYMKNGQGFALVYSITAQSTF<br>NDLQDLREQILRVKDTEDVPMILVGNKCDL<br>EDERVVGK**EQGQNLAR**QWCNCAFLESSAKS<br>KINVNEIFYDLVRQINRKTPVEKKKPKKKS<br>CLLL<br>(SEQ ID NO 7) |
| Ras-related protein Rap-1b (RAP1B)<br>Uniprot No.: P61224 isoform 1<br>Length: 184 aa | MREYKLVVLGSGGVGKSALTVQFVQGIFVE<br>KYDPTIEDSYRKQVEVDAQQCMLEILDTAG<br>TEQFTAMRDLYMKNGQGFALVYSITAQSTF<br>NDLQDLREQILRVKDTDDVPMILVGNKCDL<br>EDERVVGK**EQGQNLAR**QWNNCAFLESSAKS<br>KINVNEIFYDLVRQINRKTPVPGKARKKSS<br>CQLL(SEQ ID NO 8) |
| Ras-related protein Rap-1b-like protein (RP1BL)<br>Uniprot No.: A6NIZ1<br>Length: 184 aa | MREYKLVVLGSRGVGKSALTVQFVQGIFVE<br>KYDPTIEDSYREQVEVDAQQCMLEILDTAG<br>TEQFTAMRDLYMKNGQGFALVYSITAQSTF<br>NDLQDLREQILRVKDTDDVPMILVGNKCDL<br>EDERVVGK**EQGQNLAR**QWNNCAFLESSAKS<br>KINVNEIFYDLVRQINRKTPVPGKARKKSS<br>CQLL<br>(SEQ ID NO 9) |
| Thrombospondin-1 (THBS1)<br>Uniprot No.: P07996<br>Length:<br>a) isoform 1: 1,170 aa<br>b) isoform 2: 1,085 aa | a) Isoform 1:<br>MGLAWGLGVLFLMHVCGTNRIPESGGDNSV<br>FDIFELTGAARKGSGRRLVKGPDPSSPAFR<br>IEDANLIPPVPDDKFQDLVDAVRAEKGFLL<br>LASLRQMKKTRGTLLALERKDHSGQVFSVV<br>SNGKAGTLDLSLTVQGKQHVVSVEEALLAT<br>GQWKSITLFVQEDRAQLYIDCEKMENAELD<br>VPIQSVFTRDLASIARLRIAKGGVNDNFQG<br>VLQNVR**FVFGTTPEDILR**NKGCSSSTSVLL<br>TLDNNVVNGSSPAIRTNYIGHKTKDLQAIC<br>GISCDELSSMVLELRGLRTIVTTLQDSIRK<br>VTEENKELANELRRPPLCYHNGVQYRNNEE<br>WTVDSCTECHCQNSVTICKKVSCPIMPCSN |

AMINO ACID SEQUENCES

| Marker | Amino acid sequence (SEQ ID NO) |
|---|---|
| | ATVPDGECCPRCWPSDSADDGWSPWSEWTS<br>CSTSCGNGIQQRGRSCDSLNNRCEGSSVQT<br>RTCHIQECDKRFKQDGGWSHWSPWSSCSVT<br>CGDGVITRIRLCNSPSPQMNGKPCEGEARE<br>TKACKKDACPINGGWGPWSPWDICSVTCGG<br>GVQKRSRLCNNPTPQFGGKDCVGDVTENQI<br>CNKQDCPIDGCLSNPCFAGVKCTSYPDGSW<br>KCGACPPGYSGNGIQCTDVDECKEVPDACF<br>NHNGEHRCENTDPGYNCLPCPPRFTGSQPF<br>GQGVEHATANKQVCKPRNPCTDGTHDCNKN<br>AKCNYLGHYSDPMYRCECKPGYAGNGIICG<br>EDTDLDGWPNENLVCVANATYHCKKDNCPN<br>LPNSGQEDYDKDGIGDACDDDDDNDKIPDD<br>RDNCPFHYNPAQYDYDRDDVGDRCDNCPYN<br>HNPDQADTDNNGEGDACAADIDGDGILNER<br>DNCQYVYNVDQRDTDMDGVGDQCDNCPLEH<br>NPDQLDSDSDRIGDTCDNNQDIDEDGHQNN<br>LDNCPYVPNANQADHDKDGKGDACDHDDDN<br>DGIPDDKDNCRLVPNPDQKDSDGDGRGDAC<br>KDDFDHDSVPDIDDICPENVDISETDFRRF<br>QMIPLDPKGTSQNDPNWVVRHQGKELVQTV<br>NCDPGLAVGYDEFNAVDFSGTFFINTERDD<br>DYAGFVFGYQSSSRFYVVMWKQVTQSYWDT<br>NPTRAQGYSGLSVKVVNSTTGPGEHLRNAL<br>WHTGNTPGQVRTLWHDPRHIGWKDFTAYRW<br>RLSHRPKTGFIRVVMYEGKKIMADSGPIYD<br>KTYAGGRLGLFVFSQEMVFFSDLKYECRDP<br>(SEQ ID NO 10)<br>b) Isoform 2:<br>MGLAWGLGVLFLMHVCGTLLALERKDHSGQ<br>VFSVVSNGKAGTLDLSLTVQGKQHVVSVEE<br>ALLATGQWKSITLFVQEDRAQLYIDCEKME<br>NAELDVPIQSVFTRDLASIARLRIAKGGVN<br>DNFQGVLQNVR**FVFGTTPEDILR**NKGCSSS<br>TSVLLTLDNNVVNGSSPAIRTNYIGHKTKD<br>LQAICGISCDELSSMVLELRGLRTIVTTLQ<br>DSIRKVTEENKELANELRRPPLCYHNGVQY<br>RNNEEWTVDSCTECHCQNSVTICKKVSCPI<br>MPCSNATVPDGECCPRCWPSDSADDGWSPW<br>SEWTSCSTSCGNGIQQRGRSCDSLNNRCEG<br>SSVQTRTCHIQECDKRFKQDGGWSHWSPWS<br>SCSVTCGDGVITRIRLCNSPSPQMNGKPCE<br>GEARETKACKKDACPINGGWGPWSPWDICS<br>VTCGGGVQKRSRLCNNPTPQFGGKDCVGDV<br>TENQICNKQDCPIDGCLSNPCFAGVKCTSY<br>PDGSWKCGACPPGYSGNGIQCTDVDECKEV<br>PDACFNHNGEHRCENTDPGYNCLPCPPRFT<br>GSQPFGQGVEHATANKQVCKPRNPCTDGTH<br>DCNKNAKCNYLGHYSDPMYRCECKPGYAGN<br>GIICGEDTDLDGWPNENLVCVANATYHCKK<br>DNCPNLPNSGQEDYDKDGIGDACDDDDDND<br>KIPDDRDNCPFHYNPAQYDYDRDDVGDRCD<br>NCPYNHNPDQADTDNNGEGDACAADIDGDG<br>ILNERDNCQYVYNVDQRDTDMDGVGDQCDN<br>CPLEHNPDQLDSDSDRIGDTCDNNQDIDED<br>GHQNNLDNCPYVPNANQADHDKDGKGDACD<br>HDDDNDGIPDDKDNCRLVPNPDQKDSDGDG<br>RGDACKDDFDHDSVPDIDDICPENVDISET<br>DFRRFQMIPLDPKGTSQNDPNWVVRHQGKE<br>LVQTVNCDPGLAVGYDEFNAVDFSGTFFIN<br>TERDDDYAGFVFGYQSSSRFYVVMWKQVTQ<br>SYWDTNPTRAQGYSGLSVKVVNSTTGPGEH<br>LRNALWHTGNTPGQVRTLWHDPRHIGWKDF<br>TAYRWRLSHRPKTGFIRVVMYEGKKIMADS<br>GPIYDKTYAGGRLGLFVFSQEMVFFSDLKY<br>ECRDP<br>(SEQ ID NO 11) |
| Vinculin (VCL)<br>Uniprot No.: P18206<br>Length:<br>a) isoform 1: 1,066 aa | a) Isoform 1:<br>MPVFHTRTIESILEPVAQQISHLVIMHEEG<br>EVDGKAIPDLTAPVAAVQAAVSNLVRVGKE<br>TVQTTEDQILKRDMPPAFIKVENACTKLVQ<br>AAQMLQSDPYSVPARDYLIDGSRGILSGTS<br>DLLLTFDEAEVRKIIRVCKGILEYLTVAEV<br>VETMEDLVTYTKNLGPGMTKMAKMIDERQQ |

-continued

AMINO ACID SEQUENCES

| Marker | Amino acid sequence (SEQ ID NO) |
|---|---|
| b) isoform 2:<br>1,134 aa<br>c) isoform 3:<br>222 aa | ELTHQEHRVMLVNSMNTVKELLPVLISAMK<br>IFVTTKNSKNQGIEEALKNRNFTVEKMSAE<br>INEIIRVLQLTSWDEDAWASKDTEAMKRAL<br>ASIDSKLNQAKGWLRDPSASPGDAGEQAIR<br>QILDEAGKVGELCAGKERREILGTCKMLGQ<br>MTDQVADLRARGQGSSPVAMQKAQQVSQGL<br>DVLTAKVENAARKLEAMTNSKQSIAKKIDA<br>AQNWLADPNGGPEGEEQIRGALAEARKIAE<br>LCDDPKERDDILRSLGEISALTSKLADLRR<br>QGKGDSPEARALAKQVATALQNLQTKTNRA<br>VANSRPAKAAVHLEGKIEQAQRWIDNPTVD<br>DRGVGQAAIRGLVAEGHRLANVMMGPYRQD<br>LLAKCDRVDQLTAQLADLAARGEGESPQAR<br>ALASQLQDSLKDLKARMQEAMTQEVSDVFS<br>DTTTPIKLLAVAATAPPDAPNREEVFDERA<br>ANFENHSGKLGATAEKAAAVGTANKSTVEG<br>IQASVKTARELTPQVVSAARILLRNPGNQA<br>AYEHFETMKNQWIDNVEKMTGLVDEAIDTK<br>SLLDASEEAIKKDLDKCKVAMANIQPQMLV<br>AGATSIARRANRILLVAKREVENSEDPKFR<br>EAVKAASDELSKTISPMVMDAKAVAGNISD<br>PGLQKSFLDSGYRILGAVAKVREAFQPQEP<br>DFPPPPPDLEQLRLTDELAPPKPPLPEGEV<br>PPPRPPPPEEKDEEFPEQKAGEVINQPMMM<br>AARQLHDEARKWSSK**GNDIIAAAK**RMALLM<br>AEMSRLVRGGSGTKRALIQCAKDIAKASDE<br>VTRLAKEVAKQCTDKRIRTNLLQVCERIPT<br>ISTQLKILSTVKATMLGRTNISDEESEQAT<br>EMLVHNAQNLMQSVKETVREAEAASIKIRT<br>DAGFTLRWVRKTPWYQ<br>(SEQ ID NO 12)<br>b) Isoform 2:<br>MPVFHTRTIESILEPVAQQISHLVIMHEEG<br>EVDGKAIPDLTAPVAAVQAAVSNLVRVGKE<br>TVQTTEDQILKRDMPPAFIKVENACTKLVQ<br>AAQMLQSDPYSVPARDYLIDGSRGILSGTS<br>DLLLTFDEAEVRKIIRVCKGILEYLTVAEV<br>VETMEDLVTYTKNLGPGMTKMAKMIDERQQ<br>ELTHQEHRVMLVNSMNTVKELLPVLISAMK<br>IFVTTKNSKNQGIEEALKNRNFTVEKMSAE<br>INEIIRVLQLTSWDEDAWASKDTEAMKRAL<br>ASIDSKLNQAKGWLRDPSASPGDAGEQAIR<br>QILDEAGKVGELCAGKERREILGTCKMLGQ<br>MTDQVADLRARGQGSSPVAMQKAQQVSQGL<br>DVLTAKVENAARKLEAMTNSKQSIAKKIDA<br>AQNWLADPNGGPEGEEQIRGALAEARKIAE<br>LCDDPKERDDILRSLGEISALTSKLADLRR<br>QGKGDSPEARALAKQVATALQNLQTKTNRA<br>VANSRPAKAAVHLEGKIEQAQRWIDNPTVD<br>DRGVGQAAIRGLVAEGHRLANVMMGPYRQD<br>LLAKCDRVDQLTAQLADLAARGEGESPQAR<br>ALASQLQDSLKDLKARMQEAMTQEVSDVFS<br>DTTTPIKLLAVAATAPPDAPNREEVFDERA<br>ANFENHSGKLGATAEKAAAVGTANKSTVEG<br>IQASVKTARELTPQVVSAARILLRNPGNQA<br>AYEHFETMKNQWIDNVEKMTGLVDEAIDTK<br>SLLDASEEAIKKDLDKCKVAMANIQPQMLV<br>AGATSIARRANRILLVAKREVENSEDPKFR<br>EAVKAASDELSKTISPMVMDAKAVAGNISD<br>PGLQKSFLDSGYRILGAVAKVREAFQPQEP<br>DFPPPPPDLEQLRLTDELAPPKPPLPEGEV<br>PPPRPPPPEEKDEEFPEQKAGEVINQPMMM<br>AARQLHDEARKWSSKPGIPAAEVGIGVVAE<br>ADAADAAGFPVPPDMEDDYEPELLLMPSNQ<br>PVNQPILAAAQSLHREATKWSSK**GNDIIAA**<br>**AK**RMALLMAEMSRLVRGGSGTKRALIQCAK<br>DIAKASDEVTRLAKEVAKQCTDKRIRTNLL<br>QVCERIPTISTQLKILSTVKATMLGRTNIS<br>DEESEQATEMLVHNAQNLMQSVKETVREAE<br>AASIKIRTDAGFTLRWVRKTPWYQ<br>(SEQ ID NO 13)<br>c) Isoform 3:<br>MPPAFIKVENACTKLVQAAQMLQSDPYSVP<br>ARDYLIDGSRGILSGTSDLLLTFDEAEVRK<br>IIRVCKGILEYLTVAEVVETMEDLVTYTKN |

-continued

AMINO ACID SEQUENCES

| Marker | Amino acid sequence (SEQ ID NO) |
|---|---|
| | LGPGMTKMAKMIDERQQELTHQEHRVMLVN<br>SMNTVKELLPVLISAMKIFVTTKNSKNQGI<br>EEALKNRNFTVEKMSAEINEIIRVLQLTSW<br>DEDAWASKVRVLSGEISKIPNSPWLGVLIG<br>TCLILYLVIFVA<br>(SEQ ID NO 14) |
| Pre-pro<br>Endothelin 1<br>(ET-1)<br>Uniprot No.:<br>P05305<br>Length:<br>212 aa<br>Length of<br>fragments<br>of pre-pro<br>Endothelin:<br>a) 202 aa<br>b) 21 aa<br>c) 45 aa<br>d) 38 aa | MDYLLMIFSLLFVACQGAPETAVLGAELSA<br>VGENGGEKPTPSPPWRLRRSKRCSCSSLMD<br>KECVYFCHLDIIWVNTPEHVVPYGLGSPRS<br>KRALENLLPTKATDRENRCQCASQKDKKCW<br>NFCQAGKELRAEDIMEKDWNNHKKGKDCSK<br>LGKKCIYQQLVRGRKIRRSSEEHLRQTRSE<br>TMRNSVKSSFHDPKLKGKPSRERYVTHNRA<br>HW<br>(SEQ ID NO 15)<br>a) amino acid sequence of<br>pro-ET-1:<br>APETAVLGAELSAVGENGGEKPTPSPPWRL<br>RRSKRCSCSSLMDKECVYFC<br>HLDIIWVNTPEHWPYGLGSPRSKRALENLL<br>PTKATDRENRCQCASQKDKKCWNFCQAGKE<br>LRAEDIMEKDWNNHKKGKDCSKLGKKCIYQ<br>QLVRGRKIRRSSEEHLRQTRSETMRNSVKS<br>SFHDPKLKGKPSRERYVTHNRAHW<br>(SEQ ID NO 16)<br>b) amino acid sequence of ET-1:<br>CSCSSLMDKECVYFCHLDIIW<br>(SEQ ID NO 17)<br>c) amino acid sequence of<br>CT-ET-1:<br>RSSEEHLRQTRSETMRNSVKSSFHDPKLKG<br>KPSRERYVTHNRAHW<br>(SEQ ID NO 18)<br>d) amino acid sequence of<br>Big-ET-1:<br>CSCSSLMDKECVYFCHLDIIWVNTPEHWPY<br>GLGSPRS<br>(SEQ ID NO 19) |
| Procalcitonin<br>(PCT)<br>length 116 aa | APFRSALESSPADPATLSEDEARLLLAALV<br>QDYVQMKASELEQEQEREGSSLDSPRSKRC<br>GNLSTCMLGTYTQDFNKFHTFPQTAIGVGA<br>PGKKRDMSSDLERDHRPHVSMPQNAN<br>(SEQ ID NO 20) |
| SRM peptide<br>of ICAM1<br>Length:<br>10 aa | LLGIETPLPK<br>(SEQ ID NO 21) |
| SRM peptide<br>of AHSG<br>Length:<br>7 aa | FSVVYAK<br>(SEQ ID NO 22) |
| SRM peptide<br>of CPN1<br>Length:<br>10 aa | VQNECPGITR<br>(SEQ ID NO 23) |
| SRM peptide<br>of FABP1<br>Length:<br>11 aa | AIGLPEELIQK<br>(SEQ ID NO 24) |
| SRM peptide<br>of HRG<br>Length:<br>9 aa | DGYLFQLLR<br>(SEQ ID NO 25) |
| SRM peptide<br>of PIGR<br>Length:<br>8 aa | **CGLGINSR**<br>(SEQ ID NO 26) |

-continued

| AMINO ACID SEQUENCES | |
|---|---|
| Marker | Amino acid sequence (SEQ ID NO) |
| SRM peptide of RAP1A/ RAP1B/RA PBL Length: 8 aa | EQGQNLAR (SEQ ID NO 27) |
| SRM peptide of THBS1 Length: 12 aa | FVFGTTPEDILR (SEQ ID NO 28) |
| SRM peptide of VCL Length: 9 aa | GNDIIAAAK (SEQ ID NO 29) |

The invention claimed is:

1. A method for treating an acute invasive fungal infection in a subject, comprising the step of measuring a level of intercellular adhesion molecule 1 (ICAM1) in a sample from the subject, and administering an effective amount of an antifungal agent to the subject, wherein the level of ICAM1 is increased 1.5 fold as compared to the level of ICAM1 in a control and indicates the presence of the acute invasive fungal infection in the subject, thereby treating the acute fungal infection in the subject, wherein the subject has immune suppression, an impaired immune response or a dysregulated immune response.

2. The method of claim 1, wherein the method further comprises measuring a level of alpha-2-HS-glycoprotein (AHSG), carboxypeptidase N catalytic chain 1 (CPN1), fatty-acid binding protein 1 (FABP1), histidine rich glycoprotein (HRG), polymeric immunoglobulin receptor (PIGR), ras-related protein 1 (RAP1), thrombospondin-1 (THBS1), vinculin (VCL), endothelin 1 (ET-1), or any combination thereof in a sample from the subject.

3. The method of claim 1, wherein the method further comprises measuring a level of a) THBS1;

b) VCL; or c) THBS1 and VCL in a sample from the subject.

4. The method of claim 1, wherein the acute invasive fungal infection is a systemic fungal infection, a fungemia or a multifocal infection.

5. The method of claim 1, wherein the level of ICAM1 is determined after the subject is diagnosed of having a fungal infection, after the subject is diagnosed to be at risk for mortality from a fungal infection, and/or after admission of the subject to a medical site.

6. The method of claim 1 wherein the level of ICAM1 is compared to a reference value, and wherein a level of ICAM1 in the sample, above the reference value, indicates the presence of the acute invasive fungal infection in the subject.

7. The method of claim 6, wherein the reference value is a level of ICAM1 in one or more samples of a reference subject or a population of reference subjects without the acute invasive fungal infection and without a fungal colonization.

8. The method of claim 6, wherein the reference value is a level of ICAM1 in one or more samples of a reference subject or a population of reference subjects without the acute invasive fungal infection and having a fungal colonization.

9. The method of claim 1, wherein the subject is at risk for mortality from a fungal infection.

10. The method of claim 1, wherein the subject is a subject after organ transplantation.

11. The method of claim 9, wherein the subject is (i) a patient having at least one chronic or acute viral or bacterial infection;

(ii) a patient having a mixed bacterial and viral infection; or (iii) a patient having an immune suppression, impaired immune response or dysregulated immune system.

12. The method of claim 1, wherein the method further comprises measuring a level of C-reactive protein (CRP), cytokines, procalcitonin (PCT), tumor necrosis factor (TNF)-related apoptosis-inducing ligand (TRAIL), neutrophil gelatinase-associated lipocalin (NGAL), interferon-induced GTP-binding protein Mx1 (MX1), pancreatic stone protein (PSP), atrial natriuretic peptide, arginine vasopressin, angiotensin II, glucans, interferon gamma, or any combination thereof, in a sample from the subject.

13. The method of claim 12, wherein the method further comprises measuring a level of procalcitonin (PCT) in a sample from the subject.

14. The method of claim 1, wherein the level of ICAM1 is measured by mass spectrometry or in an immunoassay.

15. The method of claim 1, wherein the subject is a liver transplant recipient.

16. The method of claim 1, wherein the method further comprises measuring a level of one or more clinical scores, wherein:

the one or more clinical scores comprise sequential organ failure assessment score (SOFA), simplified acute physiology score (SAPSII score), the Acute Physiology and Chronic Health Evaluation II (APACHE II) score, the Pneumonia Severity Index (PSI) score, or any combination thereof.

17. The method of claim 1, wherein the method further comprises measuring a level of one or more clinical parameters, wherein:

the one or more clinical parameters comprise age, gender, family history, ethnicity, body weight, body mass index (BMI), systolic blood pressure, diastolic blood pressure, heart rate, temperature, duration of a medicinal intervention, surgical procedures, medication, or any combination thereof.

18. The method of claim 1, wherein the method further comprises measuring a level of one or more infection parameters, wherein:

the one or more infection parameters comprise leukocyte count, neutrophil count, or a combination thereof.

19. The method of claim 1, wherein the acute invasive fungal infection is caused by a *Candida* spp., an *Aspergillus* spp., or a combination thereof.

20. The method of claim 1, wherein the subject has Systemic Inflammatory Response Syndrome (SIRS) or sepsis.

21. The method of claim 1, wherein the antifungal agent comprises a polyene antifungal drug, an echinocandin, an azole antifungal drug, an allylamine antifungal drug, a morpholine antifungal drug, or an anti-metabolite antifungal drug.

22. A method for treating an acute invasive fungal infection in a subject, comprising the step of measuring a level of intercellular adhesion molecule 1 (ICAM1) in a sample from the subject, and administering an effective amount of an antifungal agent to the subject, wherein the level of ICAM1 is increased 1.5 fold as compared to the level of ICAM1 in a control and indicates the presence of the acute invasive fungal infection in the subject, thereby treating the subject, and wherein:

a) the fungal infection is caused by a *Candida* spp., an *Aspergillus* spp., or a combination thereof, b) the subject has Systemic Inflammatory Response Syndrome (SIRS) or sepsis;

c) the antifungal agent comprises a polyene antifungal drug, an echinocandin, an azole antifungal drug, an allylamine antifungal drug, a morpholine antifungal drug, or an anti-metabolite antifungal drug; and d) the control is the amount of ICAM1 in a sample from a subject with fungal colonization or the amount of ICAM1 is a sample from a subject without a fungal infection.

23. The method of claim 21, wherein the subject has a liver transplant or has septic shock.

* * * * *

SEQUENCE LISTING

<160> NUMBER OF SEQ ID NOS: 29

<210> SEQ ID NO 1
<211> LENGTH: 532
<212> TYPE: PRT
<213> ORGANISM: Homo sapiens
<220> FEATURE:
<223> OTHER INFORMATION: Intercellular adhesion molecule 1 (ICAM1)

<400> SEQUENCE: 1

Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala Gln Thr Ser Val Ser
            20                  25                  30

Pro Ser Lys Val Ile Leu Pro Arg Gly Gly Ser Val Leu Val Thr Cys
        35                  40                  45

Ser Thr Ser Cys Asp Gln Pro Lys Leu Leu Gly Ile Glu Thr Pro Leu
    50                  55                  60

Pro Lys Lys Glu Leu Leu Leu Pro Gly Asn Asn Arg Lys Val Tyr Glu
65                  70                  75                  80

Leu Ser Asn Val Gln Glu Asp Ser Gln Pro Met Cys Tyr Ser Asn Cys
                85                  90                  95

Pro Asp Gly Gln Ser Thr Ala Lys Thr Phe Leu Thr Val Tyr Trp Thr
            100                 105                 110

Pro Glu Arg Val Glu Leu Ala Pro Leu Pro Ser Trp Gln Pro Val Gly
        115                 120                 125

Lys Asn Leu Thr Leu Arg Cys Gln Val Glu Gly Gly Ala Pro Arg Ala
    130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
                165                 170                 175

Arg Asp His His Gly Ala Asn Phe Ser Cys Arg Thr Glu Leu Asp Leu
            180                 185                 190

Arg Pro Gln Gly Leu Glu Leu Phe Glu Asn Thr Ser Ala Pro Tyr Gln
        195                 200                 205

Leu Gln Thr Phe Val Leu Pro Ala Thr Pro Pro Gln Leu Val Ser Pro
    210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
                245                 250                 255

Gln Arg Leu Asn Pro Thr Val Thr Tyr Gly Asn Asp Ser Phe Ser Ala

```
            260                 265                 270

Lys Ala Ser Val Ser Val Thr Ala Glu Asp Glu Gly Thr Gln Arg Leu
        275                 280                 285

Thr Cys Ala Val Ile Leu Gly Asn Gln Ser Gln Glu Thr Leu Gln Thr
    290                 295                 300

Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
                325                 330                 335

Arg Ala Lys Val Thr Leu Asn Gly Val Pro Ala Gln Pro Leu Gly Pro
            340                 345                 350

Arg Ala Gln Leu Leu Leu Lys Ala Thr Pro Glu Asp Asn Gly Arg Ser
        355                 360                 365

Phe Ser Cys Ser Ala Thr Leu Glu Val Ala Gly Gln Leu Ile His Lys
    370                 375                 380

Asn Gln Thr Arg Glu Leu Arg Val Leu Tyr Gly Pro Arg Leu Asp Glu
385                 390                 395                 400

Arg Asp Cys Pro Gly Asn Trp Thr Trp Pro Glu Asn Ser Gln Gln Thr
                405                 410                 415

Pro Met Cys Gln Ala Trp Gly Asn Pro Leu Pro Glu Leu Lys Cys Leu
            420                 425                 430

Lys Asp Gly Thr Phe Pro Leu Pro Ile Gly Glu Ser Val Thr Val Thr
        435                 440                 445

Arg Asp Leu Glu Gly Thr Tyr Leu Cys Arg Ala Arg Ser Thr Gln Gly
    450                 455                 460

Glu Val Thr Arg Lys Val Thr Val Asn Val Leu Ser Pro Arg Tyr Glu
465                 470                 475                 480

Ile Val Ile Ile Thr Val Val Ala Ala Ala Val Ile Met Gly Thr Ala
                485                 490                 495

Gly Leu Ser Thr Tyr Leu Tyr Asn Arg Gln Arg Lys Ile Lys Lys Tyr
            500                 505                 510

Arg Leu Gln Gln Ala Gln Lys Gly Thr Pro Met Lys Pro Asn Thr Gln
        515                 520                 525

Ala Thr Pro Pro
    530


<210> SEQ ID NO 2
<211> LENGTH: 367
<212> TYPE: PRT
<213> ORGANISM: Homo sapiens
<220> FEATURE:
<223> OTHER INFORMATION: Alpha-2-HS-glycoprotein (AHSG)

<400> SEQUENCE: 2

Met Lys Ser Leu Val Leu Leu Leu Cys Leu Ala Gln Leu Trp Gly Cys
1               5                   10                  15

His Ser Ala Pro His Gly Pro Gly Leu Ile Tyr Arg Gln Pro Asn Cys
            20                  25                  30

Asp Asp Pro Glu Thr Glu Glu Ala Ala Leu Val Ala Ile Asp Tyr Ile
        35                  40                  45

Asn Gln Asn Leu Pro Trp Gly Tyr Lys His Thr Leu Asn Gln Ile Asp
    50                  55                  60

Glu Val Lys Val Trp Pro Gln Gln Pro Ser Gly Glu Leu Phe Glu Ile
65                  70                  75                  80

Glu Ile Asp Thr Leu Glu Thr Thr Cys His Val Leu Asp Pro Thr Pro
```

```
                85                  90                  95

Val Ala Arg Cys Ser Val Arg Gln Leu Lys Glu His Ala Val Glu Gly
            100                 105                 110

Asp Cys Asp Phe Gln Leu Leu Lys Leu Asp Gly Lys Phe Ser Val Val
        115                 120                 125

Tyr Ala Lys Cys Asp Ser Ser Pro Asp Ser Ala Glu Asp Val Arg Lys
    130                 135                 140

Val Cys Gln Asp Cys Pro Leu Leu Ala Pro Leu Asn Asp Thr Arg Val
145                 150                 155                 160

Val His Ala Ala Lys Ala Ala Leu Ala Ala Phe Asn Ala Gln Asn Asn
                165                 170                 175

Gly Ser Asn Phe Gln Leu Glu Glu Ile Ser Arg Ala Gln Leu Val Pro
            180                 185                 190

Leu Pro Pro Ser Thr Tyr Val Glu Phe Thr Val Ser Gly Thr Asp Cys
        195                 200                 205

Val Ala Lys Glu Ala Thr Glu Ala Ala Lys Cys Asn Leu Leu Ala Glu
    210                 215                 220

Lys Gln Tyr Gly Phe Cys Lys Ala Thr Leu Ser Glu Lys Leu Gly Gly
225                 230                 235                 240

Ala Glu Val Ala Val Thr Cys Thr Val Phe Gln Thr Gln Pro Val Thr
                245                 250                 255

Ser Gln Pro Gln Pro Glu Gly Ala Asn Glu Ala Val Pro Thr Pro Val
            260                 265                 270

Val Asp Pro Asp Ala Pro Pro Ser Pro Pro Leu Gly Ala Pro Gly Leu
        275                 280                 285

Pro Pro Ala Gly Ser Pro Pro Asp Ser His Val Leu Leu Ala Ala Pro
    290                 295                 300

Pro Gly His Gln Leu His Arg Ala His Tyr Asp Leu Arg His Thr Phe
305                 310                 315                 320

Met Gly Val Val Ser Leu Gly Ser Pro Ser Gly Glu Val Ser His Pro
                325                 330                 335

Arg Lys Thr Arg Thr Val Val Gln Pro Ser Val Gly Ala Ala Ala Gly
            340                 345                 350

Pro Val Val Pro Pro Cys Pro Gly Arg Ile Arg His Phe Lys Val
        355                 360                 365


<210> SEQ ID NO 3
<211> LENGTH: 458
<212> TYPE: PRT
<213> ORGANISM: Homo sapiens
<220> FEATURE:
<223> OTHER INFORMATION: Carboxypeptidase N catalytic chain (CPN1)

<400> SEQUENCE: 3

Met Ser Asp Leu Leu Ser Val Phe Leu His Leu Leu Leu Leu Phe Lys
1               5                   10                  15

Leu Val Ala Pro Val Thr Phe Arg His His Arg Tyr Asp Asp Leu Val
            20                  25                  30

Arg Thr Leu Tyr Lys Val Gln Asn Glu Cys Pro Gly Ile Thr Arg Val
        35                  40                  45

Tyr Ser Ile Gly Arg Ser Val Glu Gly Arg His Leu Tyr Val Leu Glu
    50                  55                  60

Phe Ser Asp His Pro Gly Ile His Glu Pro Leu Glu Pro Glu Val Lys
65                  70                  75                  80

Tyr Val Gly Asn Met His Gly Asn Glu Ala Leu Gly Arg Glu Leu Met
```

```
                85                  90                  95

Leu Gln Leu Ser Glu Phe Leu Cys Glu Glu Phe Arg Asn Arg Asn Gln
            100                 105                 110

Arg Ile Val Gln Leu Ile Gln Asp Thr Arg Ile His Ile Leu Pro Ser
        115                 120                 125

Met Asn Pro Asp Gly Tyr Glu Val Ala Ala Ala Gln Gly Pro Asn Lys
    130                 135                 140

Pro Gly Tyr Leu Val Gly Arg Asn Asn Ala Asn Gly Val Asp Leu Asn
145                 150                 155                 160

Arg Asn Phe Pro Asp Leu Asn Thr Tyr Ile Tyr Tyr Asn Glu Lys Tyr
                165                 170                 175

Gly Gly Pro Asn His His Leu Pro Leu Pro Asp Asn Trp Lys Ser Gln
            180                 185                 190

Val Glu Pro Glu Thr Arg Ala Val Ile Arg Trp Met His Ser Phe Asn
        195                 200                 205

Phe Val Leu Ser Ala Asn Leu His Gly Gly Ala Val Val Ala Asn Tyr
    210                 215                 220

Pro Tyr Asp Lys Ser Phe Glu His Arg Val Arg Gly Val Arg Arg Thr
225                 230                 235                 240

Ala Ser Thr Pro Thr Pro Asp Asp Lys Leu Phe Gln Lys Leu Ala Lys
                245                 250                 255

Val Tyr Ser Tyr Ala His Gly Trp Met Phe Gln Gly Trp Asn Cys Gly
            260                 265                 270

Asp Tyr Phe Pro Asp Gly Ile Thr Asn Gly Ala Ser Trp Tyr Ser Leu
        275                 280                 285

Ser Lys Gly Met Gln Asp Phe Asn Tyr Leu His Thr Asn Cys Phe Glu
    290                 295                 300

Ile Thr Leu Glu Leu Ser Cys Asp Lys Phe Pro Pro Glu Glu Glu Leu
305                 310                 315                 320

Gln Arg Glu Trp Leu Gly Asn Arg Glu Ala Leu Ile Gln Phe Leu Glu
                325                 330                 335

Gln Val His Gln Gly Ile Lys Gly Met Val Leu Asp Glu Asn Tyr Asn
            340                 345                 350

Asn Leu Ala Asn Ala Val Ile Ser Val Ser Gly Ile Asn His Asp Val
        355                 360                 365

Thr Ser Gly Asp His Gly Asp Tyr Phe Arg Leu Leu Leu Pro Gly Ile
    370                 375                 380

Tyr Thr Val Ser Ala Thr Ala Pro Gly Tyr Asp Pro Glu Thr Val Thr
385                 390                 395                 400

Val Thr Val Gly Pro Ala Glu Pro Thr Leu Val Asn Phe His Leu Lys
                405                 410                 415

Arg Ser Ile Pro Gln Val Ser Pro Val Arg Arg Ala Pro Ser Arg Arg
            420                 425                 430

His Gly Val Arg Ala Lys Val Gln Pro Gln Ala Arg Lys Lys Glu Met
        435                 440                 445

Glu Met Arg Gln Leu Gln Arg Gly Pro Ala
    450                 455
```

<210> SEQ ID NO 4
<211> LENGTH: 127
<212> TYPE: PRT
<213> ORGANISM: Homo sapiens
<220> FEATURE:
<223> OTHER INFORMATION: Fatty acid-binding protein (FABP1)

<400> SEQUENCE: 4

```
Met Ser Phe Ser Gly Lys Tyr Gln Leu Gln Ser Gln Glu Asn Phe Glu
1               5                   10                  15

Ala Phe Met Lys Ala Ile Gly Leu Pro Glu Glu Leu Ile Gln Lys Gly
            20                  25                  30

Lys Asp Ile Lys Gly Val Ser Glu Ile Val Gln Asn Gly Lys His Phe
        35                  40                  45

Lys Phe Thr Ile Thr Ala Gly Ser Lys Val Ile Gln Asn Glu Phe Thr
    50                  55                  60

Val Gly Glu Glu Cys Glu Leu Glu Thr Met Thr Gly Glu Lys Val Lys
65                  70                  75                  80

Thr Val Val Gln Leu Glu Gly Asp Asn Lys Leu Val Thr Thr Phe Lys
                85                  90                  95

Asn Ile Lys Ser Val Thr Glu Leu Asn Gly Asp Ile Ile Thr Asn Thr
            100                 105                 110

Met Thr Leu Gly Asp Ile Val Phe Lys Arg Ile Ser Lys Arg Ile
        115                 120                 125
```

<210> SEQ ID NO 5
<211> LENGTH: 525
<212> TYPE: PRT
<213> ORGANISM: Homo sapiens
<220> FEATURE:
<223> OTHER INFORMATION: Histidine-rich glycoprotein (HRG)

<400> SEQUENCE: 5

```
Met Lys Ala Leu Ile Ala Ala Leu Leu Leu Ile Thr Leu Gln Tyr Ser
1               5                   10                  15

Cys Ala Val Ser Pro Thr Asp Cys Ser Ala Val Glu Pro Glu Ala Glu
            20                  25                  30

Lys Ala Leu Asp Leu Ile Asn Lys Arg Arg Arg Asp Gly Tyr Leu Phe
        35                  40                  45

Gln Leu Leu Arg Ile Ala Asp Ala His Leu Asp Arg Val Glu Asn Thr
    50                  55                  60

Thr Val Tyr Tyr Leu Val Leu Asp Val Gln Glu Ser Asp Cys Ser Val
65                  70                  75                  80

Leu Ser Arg Lys Tyr Trp Asn Asp Cys Glu Pro Pro Asp Ser Arg Arg
                85                  90                  95

Pro Ser Glu Ile Val Ile Gly Gln Cys Lys Val Ile Ala Thr Arg His
            100                 105                 110

Ser His Glu Ser Gln Asp Leu Arg Val Ile Asp Phe Asn Cys Thr Thr
        115                 120                 125

Ser Ser Val Ser Ser Ala Leu Ala Asn Thr Lys Asp Ser Pro Val Leu
    130                 135                 140

Ile Asp Phe Phe Glu Asp Thr Glu Arg Tyr Arg Lys Gln Ala Asn Lys
145                 150                 155                 160

Ala Leu Glu Lys Tyr Lys Glu Glu Asn Asp Asp Phe Ala Ser Phe Arg
                165                 170                 175

Val Asp Arg Ile Glu Arg Val Ala Arg Val Arg Gly Gly Glu Gly Thr
            180                 185                 190

Gly Tyr Phe Val Asp Phe Ser Val Arg Asn Cys Pro Arg His His Phe
        195                 200                 205

Pro Arg His Pro Asn Val Phe Gly Phe Cys Arg Ala Asp Leu Phe Tyr
    210                 215                 220

Asp Val Glu Ala Leu Asp Leu Glu Ser Pro Lys Asn Leu Val Ile Asn
```

```
225                 230                 235                 240

Cys Glu Val Phe Asp Pro Gln Glu His Glu Asn Ile Asn Gly Val Pro
                245                 250                 255

Pro His Leu Gly His Pro Phe His Trp Gly Gly His Glu Arg Ser Ser
            260                 265                 270

Thr Thr Lys Pro Pro Phe Lys Pro His Gly Ser Arg Asp His His His
        275                 280                 285

Pro His Lys Pro His Glu His Gly Pro Pro Pro Pro Pro Asp Glu Arg
    290                 295                 300

Asp His Ser His Gly Pro Pro Leu Pro Gln Gly Pro Pro Pro Leu Leu
305                 310                 315                 320

Pro Met Ser Cys Ser Ser Cys Gln His Ala Thr Phe Gly Thr Asn Gly
                325                 330                 335

Ala Gln Arg His Ser His Asn Asn Asn Ser Ser Asp Leu His Pro His
            340                 345                 350

Lys His His Ser His Glu Gln His Pro His Gly His His Pro His Ala
        355                 360                 365

His His Pro His Glu His Asp Thr His Arg Gln His Pro His Gly His
    370                 375                 380

His Pro His Gly His His Pro His Gly His His Pro His Gly His His
385                 390                 395                 400

Pro His Gly His His Pro His Cys His Asp Phe Gln Asp Tyr Gly Pro
                405                 410                 415

Cys Asp Pro Pro Pro His Asn Gln Gly His Cys Cys His Gly His Gly
            420                 425                 430

Pro Pro Pro Gly His Leu Arg Arg Arg Gly Pro Gly Lys Gly Pro Arg
        435                 440                 445

Pro Phe His Cys Arg Gln Ile Gly Ser Val Tyr Arg Leu Pro Pro Leu
    450                 455                 460

Arg Lys Gly Glu Val Leu Pro Leu Pro Glu Ala Asn Phe Pro Ser Phe
465                 470                 475                 480

Pro Leu Pro His His Lys His Pro Leu Lys Pro Asp Asn Gln Pro Phe
                485                 490                 495

Pro Gln Ser Val Ser Glu Ser Cys Pro Gly Lys Phe Lys Ser Gly Phe
            500                 505                 510

Pro Gln Val Ser Met Phe Phe Thr His Thr Phe Pro Lys
        515                 520                 525


<210> SEQ ID NO 6
<211> LENGTH: 764
<212> TYPE: PRT
<213> ORGANISM: Homo sapiens
<220> FEATURE:
<223> OTHER INFORMATION: Polymeric immunoglobulin receptor (PIGR)

<400> SEQUENCE: 6

Met Leu Leu Phe Val Leu Thr Cys Leu Leu Ala Val Phe Pro Ala Ile
1               5                   10                  15

Ser Thr Lys Ser Pro Ile Phe Gly Pro Glu Glu Val Asn Ser Val Glu
            20                  25                  30

Gly Asn Ser Val Ser Ile Thr Cys Tyr Tyr Pro Pro Thr Ser Val Asn
        35                  40                  45

Arg His Thr Arg Lys Tyr Trp Cys Arg Gln Gly Ala Arg Gly Gly Cys
    50                  55                  60

Ile Thr Leu Ile Ser Ser Glu Gly Tyr Val Ser Ser Lys Tyr Ala Gly
```

```
65                  70                  75                  80

Arg Ala Asn Leu Thr Asn Phe Pro Glu Asn Gly Thr Phe Val Val Asn
                85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
        115                 120                 125

Gln Gly Pro Gly Leu Leu Asn Asp Thr Lys Val Tyr Thr Val Asp Leu
    130                 135                 140

Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175

Ile Asp Ser Ser Gly Tyr Val Asn Pro Asn Tyr Thr Gly Arg Ile Arg
            180                 185                 190

Leu Asp Ile Gln Gly Thr Gly Gln Leu Leu Phe Ser Val Val Ile Asn
        195                 200                 205

Gln Leu Arg Leu Ser Asp Ala Gly Gln Tyr Leu Cys Gln Ala Gly Asp
    210                 215                 220

Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
                245                 250                 255

Cys Ala Leu Gly Pro Glu Val Ala Asn Val Ala Lys Phe Leu Cys Arg
            260                 265                 270

Gln Ser Ser Gly Glu Asn Cys Asp Val Val Val Asn Thr Leu Gly Lys
        275                 280                 285

Arg Ala Pro Ala Phe Glu Gly Arg Ile Leu Leu Asn Pro Gln Asp Lys
    290                 295                 300

Asp Gly Ser Phe Ser Val Val Ile Thr Gly Leu Arg Lys Glu Asp Ala
305                 310                 315                 320

Gly Arg Tyr Leu Cys Gly Ala His Ser Asp Gly Gln Leu Gln Glu Gly
                325                 330                 335

Ser Pro Ile Gln Ala Trp Gln Leu Phe Val Asn Glu Glu Ser Thr Ile
            340                 345                 350

Pro Arg Ser Pro Thr Val Val Lys Gly Val Ala Gly Gly Ser Val Ala
        355                 360                 365

Val Leu Cys Pro Tyr Asn Arg Lys Glu Ser Lys Ser Ile Lys Tyr Trp
    370                 375                 380

Cys Leu Trp Glu Gly Ala Gln Asn Gly Arg Cys Pro Leu Leu Val Asp
385                 390                 395                 400

Ser Glu Gly Trp Val Lys Ala Gln Tyr Glu Gly Arg Leu Ser Leu Leu
                405                 410                 415

Glu Glu Pro Gly Asn Gly Thr Phe Thr Val Ile Leu Asn Gln Leu Thr
            420                 425                 430

Ser Arg Asp Ala Gly Phe Tyr Trp Cys Leu Thr Asn Gly Asp Thr Leu
        435                 440                 445

Trp Arg Thr Thr Val Glu Ile Lys Ile Ile Glu Gly Glu Pro Asn Leu
    450                 455                 460

Lys Val Pro Gly Asn Val Thr Ala Val Leu Gly Glu Thr Leu Lys Val
465                 470                 475                 480

Pro Cys His Phe Pro Cys Lys Phe Ser Ser Tyr Glu Lys Tyr Trp Cys
                485                 490                 495
```

```
Lys Trp Asn Asn Thr Gly Cys Gln Ala Leu Pro Ser Gln Asp Glu Gly
            500                 505                 510

Pro Ser Lys Ala Phe Val Asn Cys Asp Glu Asn Ser Arg Leu Val Ser
        515                 520                 525

Leu Thr Leu Asn Leu Val Thr Arg Ala Asp Glu Gly Trp Tyr Trp Cys
    530                 535                 540

Gly Val Lys Gln Gly His Phe Tyr Gly Glu Thr Ala Ala Val Tyr Val
545                 550                 555                 560

Ala Val Glu Glu Arg Lys Ala Ala Gly Ser Arg Asp Val Ser Leu Ala
                565                 570                 575

Lys Ala Asp Ala Ala Pro Asp Glu Lys Val Leu Asp Ser Gly Phe Arg
            580                 585                 590

Glu Ile Glu Asn Lys Ala Ile Gln Asp Pro Arg Leu Phe Ala Glu Glu
        595                 600                 605

Lys Ala Val Ala Asp Thr Arg Asp Gln Ala Asp Gly Ser Arg Ala Ser
    610                 615                 620

Val Asp Ser Gly Ser Ser Glu Glu Gln Gly Gly Ser Ser Arg Ala Leu
625                 630                 635                 640

Val Ser Thr Leu Val Pro Leu Gly Leu Val Leu Ala Val Gly Ala Val
                645                 650                 655

Ala Val Gly Val Ala Arg Ala Arg His Arg Lys Asn Val Asp Arg Val
            660                 665                 670

Ser Ile Arg Ser Tyr Arg Thr Asp Ile Ser Met Ser Asp Phe Glu Asn
        675                 680                 685

Ser Arg Glu Phe Gly Ala Asn Asp Asn Met Gly Ala Ser Ser Ile Thr
    690                 695                 700

Gln Glu Thr Ser Leu Gly Gly Lys Glu Glu Phe Val Ala Thr Thr Glu
705                 710                 715                 720

Ser Thr Thr Glu Thr Lys Glu Pro Lys Lys Ala Lys Arg Ser Ser Lys
                725                 730                 735

Glu Glu Ala Glu Met Ala Tyr Lys Asp Phe Leu Leu Gln Ser Ser Thr
            740                 745                 750

Val Ala Ala Glu Ala Gln Asp Gly Pro Gln Glu Ala
        755                 760


<210> SEQ ID NO 7
<211> LENGTH: 184
<212> TYPE: PRT
<213> ORGANISM: Homo sapiens
<220> FEATURE:
<223> OTHER INFORMATION: Ras-related protein Rap-1A

<400> SEQUENCE: 7

Met Arg Glu Tyr Lys Leu Val Val Leu Gly Ser Gly Gly Val Gly Lys
1               5                   10                  15

Ser Ala Leu Thr Val Gln Phe Val Gln Gly Ile Phe Val Glu Lys Tyr
            20                  25                  30

Asp Pro Thr Ile Glu Asp Ser Tyr Arg Lys Gln Val Glu Val Asp Cys
        35                  40                  45

Gln Gln Cys Met Leu Glu Ile Leu Asp Thr Ala Gly Thr Glu Gln Phe
    50                  55                  60

Thr Ala Met Arg Asp Leu Tyr Met Lys Asn Gly Gln Gly Phe Ala Leu
65                  70                  75                  80

Val Tyr Ser Ile Thr Ala Gln Ser Thr Phe Asn Asp Leu Gln Asp Leu
                85                  90                  95
```

```
Arg Glu Gln Ile Leu Arg Val Lys Asp Thr Glu Asp Val Pro Met Ile
            100                 105                 110

Leu Val Gly Asn Lys Cys Asp Leu Glu Asp Glu Arg Val Val Gly Lys
        115                 120                 125

Glu Gln Gly Gln Asn Leu Ala Arg Gln Trp Cys Asn Cys Ala Phe Leu
    130                 135                 140

Glu Ser Ser Ala Lys Ser Lys Ile Asn Val Asn Glu Ile Phe Tyr Asp
145                 150                 155                 160

Leu Val Arg Gln Ile Asn Arg Lys Thr Pro Val Glu Lys Lys Lys Pro
                165                 170                 175

Lys Lys Lys Ser Cys Leu Leu Leu
            180


<210> SEQ ID NO 8
<211> LENGTH: 184
<212> TYPE: PRT
<213> ORGANISM: Homo sapiens
<220> FEATURE:
<223> OTHER INFORMATION: Ras-related protein Rap-1b (RAP1B)

<400> SEQUENCE: 8

Met Arg Glu Tyr Lys Leu Val Val Leu Gly Ser Gly Gly Val Gly Lys
1               5                   10                  15

Ser Ala Leu Thr Val Gln Phe Val Gln Gly Ile Phe Val Glu Lys Tyr
            20                  25                  30

Asp Pro Thr Ile Glu Asp Ser Tyr Arg Lys Gln Val Glu Val Asp Ala
        35                  40                  45

Gln Gln Cys Met Leu Glu Ile Leu Asp Thr Ala Gly Thr Glu Gln Phe
    50                  55                  60

Thr Ala Met Arg Asp Leu Tyr Met Lys Asn Gly Gln Gly Phe Ala Leu
65                  70                  75                  80

Val Tyr Ser Ile Thr Ala Gln Ser Thr Phe Asn Asp Leu Gln Asp Leu
                85                  90                  95

Arg Glu Gln Ile Leu Arg Val Lys Asp Thr Asp Asp Val Pro Met Ile
            100                 105                 110

Leu Val Gly Asn Lys Cys Asp Leu Glu Asp Glu Arg Val Val Gly Lys
        115                 120                 125

Glu Gln Gly Gln Asn Leu Ala Arg Gln Trp Asn Asn Cys Ala Phe Leu
    130                 135                 140

Glu Ser Ser Ala Lys Ser Lys Ile Asn Val Asn Glu Ile Phe Tyr Asp
145                 150                 155                 160

Leu Val Arg Gln Ile Asn Arg Lys Thr Pro Val Pro Gly Lys Ala Arg
                165                 170                 175

Lys Lys Ser Ser Cys Gln Leu Leu
            180


<210> SEQ ID NO 9
<211> LENGTH: 184
<212> TYPE: PRT
<213> ORGANISM: Homo sapiens
<220> FEATURE:
<223> OTHER INFORMATION: Ras-related protein Rap-1b-like protein (RP1BL)

<400> SEQUENCE: 9

Met Arg Glu Tyr Lys Leu Val Val Leu Gly Ser Arg Gly Val Gly Lys
1               5                   10                  15

Ser Ala Leu Thr Val Gln Phe Val Gln Gly Ile Phe Val Glu Lys Tyr
```

```
            20                  25                  30

Asp Pro Thr Ile Glu Asp Ser Tyr Arg Glu Gln Val Glu Val Asp Ala
        35                  40                  45

Gln Gln Cys Met Leu Glu Ile Leu Asp Thr Ala Gly Thr Glu Gln Phe
    50                  55                  60

Thr Ala Met Arg Asp Leu Tyr Met Lys Asn Gly Gln Gly Phe Ala Leu
65                  70                  75                  80

Val Tyr Ser Ile Thr Ala Gln Ser Thr Phe Asn Asp Leu Gln Asp Leu
                85                  90                  95

Arg Glu Gln Ile Leu Arg Val Lys Asp Thr Asp Asp Val Pro Met Ile
            100                 105                 110

Leu Val Gly Asn Lys Cys Asp Leu Glu Asp Glu Arg Val Val Gly Lys
        115                 120                 125

Glu Gln Gly Gln Asn Leu Ala Arg Gln Trp Asn Asn Cys Ala Phe Leu
    130                 135                 140

Glu Ser Ser Ala Lys Ser Lys Ile Asn Val Asn Glu Ile Phe Tyr Asp
145                 150                 155                 160

Leu Val Arg Gln Ile Asn Arg Lys Thr Pro Val Pro Gly Lys Ala Arg
                165                 170                 175

Lys Lys Ser Ser Cys Gln Leu Leu
            180


<210> SEQ ID NO 10
<211> LENGTH: 1170
<212> TYPE: PRT
<213> ORGANISM: Homo sapiens
<220> FEATURE:
<223> OTHER INFORMATION: Thrombospondin-1 (THBS1)

<400> SEQUENCE: 10

Met Gly Leu Ala Trp Gly Leu Gly Val Leu Phe Leu Met His Val Cys
1               5                   10                  15

Gly Thr Asn Arg Ile Pro Glu Ser Gly Gly Asp Asn Ser Val Phe Asp
            20                  25                  30

Ile Phe Glu Leu Thr Gly Ala Ala Arg Lys Gly Ser Gly Arg Arg Leu
        35                  40                  45

Val Lys Gly Pro Asp Pro Ser Ser Pro Ala Phe Arg Ile Glu Asp Ala
    50                  55                  60

Asn Leu Ile Pro Pro Val Pro Asp Asp Lys Phe Gln Asp Leu Val Asp
65                  70                  75                  80

Ala Val Arg Ala Glu Lys Gly Phe Leu Leu Leu Ala Ser Leu Arg Gln
                85                  90                  95

Met Lys Lys Thr Arg Gly Thr Leu Leu Ala Leu Glu Arg Lys Asp His
            100                 105                 110

Ser Gly Gln Val Phe Ser Val Val Ser Asn Gly Lys Ala Gly Thr Leu
        115                 120                 125

Asp Leu Ser Leu Thr Val Gln Gly Lys Gln His Val Val Ser Val Glu
    130                 135                 140

Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Glu Lys Met Glu Asn
                165                 170                 175

Ala Glu Leu Asp Val Pro Ile Gln Ser Val Phe Thr Arg Asp Leu Ala
            180                 185                 190

Ser Ile Ala Arg Leu Arg Ile Ala Lys Gly Gly Val Asn Asp Asn Phe
```

```
        195                 200                 205

Gln Gly Val Leu Gln Asn Val Arg Phe Val Phe Gly Thr Thr Pro Glu
    210                 215                 220

Asp Ile Leu Arg Asn Lys Gly Cys Ser Ser Ser Thr Ser Val Leu Leu
225                 230                 235                 240

Thr Leu Asp Asn Asn Val Val Asn Gly Ser Ser Pro Ala Ile Arg Thr
                245                 250                 255

Asn Tyr Ile Gly His Lys Thr Lys Asp Leu Gln Ala Ile Cys Gly Ile
            260                 265                 270

Ser Cys Asp Glu Leu Ser Ser Met Val Leu Glu Leu Arg Gly Leu Arg
        275                 280                 285

Thr Ile Val Thr Thr Leu Gln Asp Ser Ile Arg Lys Val Thr Glu Glu
    290                 295                 300

Asn Lys Glu Leu Ala Asn Glu Leu Arg Arg Pro Pro Leu Cys Tyr His
305                 310                 315                 320

Asn Gly Val Gln Tyr Arg Asn Asn Glu Glu Trp Thr Val Asp Ser Cys
                325                 330                 335

Thr Glu Cys His Cys Gln Asn Ser Val Thr Ile Cys Lys Lys Val Ser
            340                 345                 350

Cys Pro Ile Met Pro Cys Ser Asn Ala Thr Val Pro Asp Gly Glu Cys
        355                 360                 365

Cys Pro Arg Cys Trp Pro Ser Asp Ser Ala Asp Asp Gly Trp Ser Pro
    370                 375                 380

Trp Ser Glu Trp Thr Ser Cys Ser Thr Ser Cys Gly Asn Gly Ile Gln
385                 390                 395                 400

Gln Arg Gly Arg Ser Cys Asp Ser Leu Asn Asn Arg Cys Glu Gly Ser
                405                 410                 415

Ser Val Gln Thr Arg Thr Cys His Ile Gln Glu Cys Asp Lys Arg Phe
            420                 425                 430

Lys Gln Asp Gly Gly Trp Ser His Trp Ser Pro Trp Ser Ser Cys Ser
        435                 440                 445

Val Thr Cys Gly Asp Gly Val Ile Thr Arg Ile Arg Leu Cys Asn Ser
    450                 455                 460

Pro Ser Pro Gln Met Asn Gly Lys Pro Cys Glu Gly Glu Ala Arg Glu
465                 470                 475                 480

Thr Lys Ala Cys Lys Lys Asp Ala Cys Pro Ile Asn Gly Gly Trp Gly
                485                 490                 495

Pro Trp Ser Pro Trp Asp Ile Cys Ser Val Thr Cys Gly Gly Gly Val
            500                 505                 510

Gln Lys Arg Ser Arg Leu Cys Asn Asn Pro Thr Pro Gln Phe Gly Gly
        515                 520                 525

Lys Asp Cys Val Gly Asp Val Thr Glu Asn Gln Ile Cys Asn Lys Gln
    530                 535                 540

Asp Cys Pro Ile Asp Gly Cys Leu Ser Asn Pro Cys Phe Ala Gly Val
545                 550                 555                 560

Lys Cys Thr Ser Tyr Pro Asp Gly Ser Trp Lys Cys Gly Ala Cys Pro
                565                 570                 575

Pro Gly Tyr Ser Gly Asn Gly Ile Gln Cys Thr Asp Val Asp Glu Cys
            580                 585                 590

Lys Glu Val Pro Asp Ala Cys Phe Asn His Asn Gly Glu His Arg Cys
        595                 600                 605

Glu Asn Thr Asp Pro Gly Tyr Asn Cys Leu Pro Cys Pro Pro Arg Phe
    610                 615                 620
```

```
Thr Gly Ser Gln Pro Phe Gly Gln Gly Val Glu His Ala Thr Ala Asn
625                 630                 635                 640

Lys Gln Val Cys Lys Pro Arg Asn Pro Cys Thr Asp Gly Thr His Asp
                645                 650                 655

Cys Asn Lys Asn Ala Lys Cys Asn Tyr Leu Gly His Tyr Ser Asp Pro
            660                 665                 670

Met Tyr Arg Cys Glu Cys Lys Pro Gly Tyr Ala Gly Asn Gly Ile Ile
        675                 680                 685

Cys Gly Glu Asp Thr Asp Leu Asp Gly Trp Pro Asn Glu Asn Leu Val
    690                 695                 700

Cys Val Ala Asn Ala Thr Tyr His Cys Lys Lys Asp Asn Cys Pro Asn
705                 710                 715                 720

Leu Pro Asn Ser Gly Gln Glu Asp Tyr Asp Lys Asp Gly Ile Gly Asp
                725                 730                 735

Ala Cys Asp Asp Asp Asp Asp Asn Asp Lys Ile Pro Asp Asp Arg Asp
            740                 745                 750

Asn Cys Pro Phe His Tyr Asn Pro Ala Gln Tyr Asp Tyr Asp Arg Asp
        755                 760                 765

Asp Val Gly Asp Arg Cys Asp Asn Cys Pro Tyr Asn His Asn Pro Asp
    770                 775                 780

Gln Ala Asp Thr Asp Asn Asn Gly Glu Gly Asp Ala Cys Ala Ala Asp
785                 790                 795                 800

Ile Asp Gly Asp Gly Ile Leu Asn Glu Arg Asp Asn Cys Gln Tyr Val
                805                 810                 815

Tyr Asn Val Asp Gln Arg Asp Thr Asp Met Asp Gly Val Gly Asp Gln
            820                 825                 830

Cys Asp Asn Cys Pro Leu Glu His Asn Pro Asp Gln Leu Asp Ser Asp
        835                 840                 845

Ser Asp Arg Ile Gly Asp Thr Cys Asp Asn Asn Gln Asp Ile Asp Glu
    850                 855                 860

Asp Gly His Gln Asn Asn Leu Asp Asn Cys Pro Tyr Val Pro Asn Ala
865                 870                 875                 880

Asn Gln Ala Asp His Asp Lys Asp Gly Lys Gly Asp Ala Cys Asp His
                885                 890                 895

Asp Asp Asp Asn Asp Gly Ile Pro Asp Asp Lys Asp Asn Cys Arg Leu
            900                 905                 910

Val Pro Asn Pro Asp Gln Lys Asp Ser Asp Gly Asp Gly Arg Gly Asp
        915                 920                 925

Ala Cys Lys Asp Asp Phe Asp His Asp Ser Val Pro Asp Ile Asp Asp
    930                 935                 940

Ile Cys Pro Glu Asn Val Asp Ile Ser Glu Thr Asp Phe Arg Arg Phe
945                 950                 955                 960

Gln Met Ile Pro Leu Asp Pro Lys Gly Thr Ser Gln Asn Asp Pro Asn
                965                 970                 975

Trp Val Val Arg His Gln Gly Lys Glu Leu Val Gln Thr Val Asn Cys
            980                 985                 990

Asp Pro Gly Leu Ala Val Gly Tyr Asp Glu Phe Asn Ala Val Asp Phe
        995                 1000                1005

Ser Gly Thr Phe Phe Ile Asn Thr Glu Arg Asp Asp Asp Tyr Ala Gly
    1010                1015                1020

Phe Val Phe Gly Tyr Gln Ser Ser Ser Arg Phe Tyr Val Val Met Trp
1025                1030                1035                1040
```

```
Lys Gln Val Thr Gln Ser Tyr Trp Asp Thr Asn Pro Thr Arg Ala Gln
                1045                1050                1055

Gly Tyr Ser Gly Leu Ser Val Lys Val Val Asn Ser Thr Thr Gly Pro
            1060                1065                1070

Gly Glu His Leu Arg Asn Ala Leu Trp His Thr Gly Asn Thr Pro Gly
        1075                1080                1085

Gln Val Arg Thr Leu Trp His Asp Pro Arg His Ile Gly Trp Lys Asp
    1090                1095                1100

Phe Thr Ala Tyr Arg Trp Arg Leu Ser His Arg Pro Lys Thr Gly Phe
1105                1110                1115                1120

Ile Arg Val Val Met Tyr Glu Gly Lys Lys Ile Met Ala Asp Ser Gly
                1125                1130                1135

Pro Ile Tyr Asp Lys Thr Tyr Ala Gly Gly Arg Leu Gly Leu Phe Val
            1140                1145                1150

Phe Ser Gln Glu Met Val Phe Phe Ser Asp Leu Lys Tyr Glu Cys Arg
        1155                1160                1165

Asp Pro
    1170


<210> SEQ ID NO 11
<211> LENGTH: 1085
<212> TYPE: PRT
<213> ORGANISM: Homo sapiens
<220> FEATURE:
<223> OTHER INFORMATION: Thrombospondin-1(THBS1)

<400> SEQUENCE: 11

Met Gly Leu Ala Trp Gly Leu Gly Val Leu Phe Leu Met His Val Cys
1               5                   10                  15

Gly Thr Leu Leu Ala Leu Glu Arg Lys Asp His Ser Gly Gln Val Phe
            20                  25                  30

Ser Val Val Ser Asn Gly Lys Ala Gly Thr Leu Asp Leu Ser Leu Thr
        35                  40                  45

Val Gln Gly Lys Gln His Val Val Ser Val Glu Glu Ala Leu Leu Ala
    50                  55                  60

Thr Gly Gln Trp Lys Ser Ile Thr Leu Phe Val Gln Glu Asp Arg Ala
65                  70                  75                  80

Gln Leu Tyr Ile Asp Cys Glu Lys Met Glu Asn Ala Glu Leu Asp Val
                85                  90                  95

Pro Ile Gln Ser Val Phe Thr Arg Asp Leu Ala Ser Ile Ala Arg Leu
            100                 105                 110

Arg Ile Ala Lys Gly Gly Val Asn Asp Asn Phe Gln Gly Val Leu Gln
        115                 120                 125

Asn Val Arg Phe Val Phe Gly Thr Thr Pro Glu Asp Ile Leu Arg Asn
    130                 135                 140

Lys Gly Cys Ser Ser Ser Thr Ser Val Leu Leu Thr Leu Asp Asn Asn
145                 150                 155                 160

Val Val Asn Gly Ser Ser Pro Ala Ile Arg Thr Asn Tyr Ile Gly His
                165                 170                 175

Lys Thr Lys Asp Leu Gln Ala Ile Cys Gly Ile Ser Cys Asp Glu Leu
            180                 185                 190

Ser Ser Met Val Leu Glu Leu Arg Gly Leu Arg Thr Ile Val Thr Thr
        195                 200                 205

Leu Gln Asp Ser Ile Arg Lys Val Thr Glu Glu Asn Lys Glu Leu Ala
    210                 215                 220
```

```
Asn Glu Leu Arg Arg Pro Pro Leu Cys Tyr His Asn Gly Val Gln Tyr
225                 230                 235                 240

Arg Asn Asn Glu Glu Trp Thr Val Asp Ser Cys Thr Glu Cys His Cys
                245                 250                 255

Gln Asn Ser Val Thr Ile Cys Lys Lys Val Ser Cys Pro Ile Met Pro
            260                 265                 270

Cys Ser Asn Ala Thr Val Pro Asp Gly Glu Cys Cys Pro Arg Cys Trp
        275                 280                 285

Pro Ser Asp Ser Ala Asp Asp Gly Trp Ser Pro Trp Ser Glu Trp Thr
    290                 295                 300

Ser Cys Ser Thr Ser Cys Gly Asn Gly Ile Gln Gln Arg Gly Arg Ser
305                 310                 315                 320

Cys Asp Ser Leu Asn Asn Arg Cys Glu Gly Ser Ser Val Gln Thr Arg
                325                 330                 335

Thr Cys His Ile Gln Glu Cys Asp Lys Arg Phe Lys Gln Asp Gly Gly
            340                 345                 350

Trp Ser His Trp Ser Pro Trp Ser Ser Cys Ser Val Thr Cys Gly Asp
        355                 360                 365

Gly Val Ile Thr Arg Ile Arg Leu Cys Asn Ser Pro Ser Pro Gln Met
    370                 375                 380

Asn Gly Lys Pro Cys Glu Gly Glu Ala Arg Glu Thr Lys Ala Cys Lys
385                 390                 395                 400

Lys Asp Ala Cys Pro Ile Asn Gly Gly Trp Gly Pro Trp Ser Pro Trp
                405                 410                 415

Asp Ile Cys Ser Val Thr Cys Gly Gly Gly Val Gln Lys Arg Ser Arg
            420                 425                 430

Leu Cys Asn Asn Pro Thr Pro Gln Phe Gly Gly Lys Asp Cys Val Gly
        435                 440                 445

Asp Val Thr Glu Asn Gln Ile Cys Asn Lys Gln Asp Cys Pro Ile Asp
    450                 455                 460

Gly Cys Leu Ser Asn Pro Cys Phe Ala Gly Val Lys Cys Thr Ser Tyr
465                 470                 475                 480

Pro Asp Gly Ser Trp Lys Cys Gly Ala Cys Pro Pro Gly Tyr Ser Gly
                485                 490                 495

Asn Gly Ile Gln Cys Thr Asp Val Asp Glu Cys Lys Glu Val Pro Asp
            500                 505                 510

Ala Cys Phe Asn His Asn Gly Glu His Arg Cys Glu Asn Thr Asp Pro
        515                 520                 525

Gly Tyr Asn Cys Leu Pro Cys Pro Pro Arg Phe Thr Gly Ser Gln Pro
    530                 535                 540

Phe Gly Gln Gly Val Glu His Ala Thr Ala Asn Lys Gln Val Cys Lys
545                 550                 555                 560

Pro Arg Asn Pro Cys Thr Asp Gly Thr His Asp Cys Asn Lys Asn Ala
                565                 570                 575

Lys Cys Asn Tyr Leu Gly His Tyr Ser Asp Pro Met Tyr Arg Cys Glu
            580                 585                 590

Cys Lys Pro Gly Tyr Ala Gly Asn Gly Ile Ile Cys Gly Glu Asp Thr
        595                 600                 605

Asp Leu Asp Gly Trp Pro Asn Glu Asn Leu Val Cys Val Ala Asn Ala
    610                 615                 620

Thr Tyr His Cys Lys Lys Asp Asn Cys Pro Asn Leu Pro Asn Ser Gly
625                 630                 635                 640

Gln Glu Asp Tyr Asp Lys Asp Gly Ile Gly Asp Ala Cys Asp Asp Asp
```

```
                645                 650                 655

Asp Asp Asn Asp Lys Ile Pro Asp Asp Arg Asp Asn Cys Pro Phe His
            660                 665                 670

Tyr Asn Pro Ala Gln Tyr Asp Tyr Asp Arg Asp Asp Val Gly Asp Arg
        675                 680                 685

Cys Asp Asn Cys Pro Tyr Asn His Asn Pro Asp Gln Ala Asp Thr Asp
    690                 695                 700

Asn Asn Gly Glu Gly Asp Ala Cys Ala Ala Asp Ile Asp Gly Asp Gly
705                 710                 715                 720

Ile Leu Asn Glu Arg Asp Asn Cys Gln Tyr Val Tyr Asn Val Asp Gln
                725                 730                 735

Arg Asp Thr Asp Met Asp Gly Val Gly Asp Gln Cys Asp Asn Cys Pro
            740                 745                 750

Leu Glu His Asn Pro Asp Gln Leu Asp Ser Asp Ser Asp Arg Ile Gly
        755                 760                 765

Asp Thr Cys Asp Asn Asn Gln Asp Ile Asp Glu Asp Gly His Gln Asn
    770                 775                 780

Asn Leu Asp Asn Cys Pro Tyr Val Pro Asn Ala Asn Gln Ala Asp His
785                 790                 795                 800

Asp Lys Asp Gly Lys Gly Asp Ala Cys Asp His Asp Asp Asp Asn Asp
                805                 810                 815

Gly Ile Pro Asp Asp Lys Asp Asn Cys Arg Leu Val Pro Asn Pro Asp
            820                 825                 830

Gln Lys Asp Ser Asp Gly Asp Gly Arg Gly Asp Ala Cys Lys Asp Asp
        835                 840                 845

Phe Asp His Asp Ser Val Pro Asp Ile Asp Asp Ile Cys Pro Glu Asn
    850                 855                 860

Val Asp Ile Ser Glu Thr Asp Phe Arg Arg Phe Gln Met Ile Pro Leu
865                 870                 875                 880

Asp Pro Lys Gly Thr Ser Gln Asn Asp Pro Asn Trp Val Val Arg His
                885                 890                 895

Gln Gly Lys Glu Leu Val Gln Thr Val Asn Cys Asp Pro Gly Leu Ala
            900                 905                 910

Val Gly Tyr Asp Glu Phe Asn Ala Val Asp Phe Ser Gly Thr Phe Phe
        915                 920                 925

Ile Asn Thr Glu Arg Asp Asp Asp Tyr Ala Gly Phe Val Phe Gly Tyr
    930                 935                 940

Gln Ser Ser Ser Arg Phe Tyr Val Val Met Trp Lys Gln Val Thr Gln
945                 950                 955                 960

Ser Tyr Trp Asp Thr Asn Pro Thr Arg Ala Gln Gly Tyr Ser Gly Leu
                965                 970                 975

Ser Val Lys Val Val Asn Ser Thr Thr Gly Pro Gly Glu His Leu Arg
            980                 985                 990

Asn Ala Leu Trp His Thr Gly Asn Thr Pro Gly Gln Val Arg Thr Leu
        995                 1000                1005

Trp His Asp Pro Arg His Ile Gly Trp Lys Asp Phe Thr Ala Tyr Arg
    1010                1015                1020

Trp Arg Leu Ser His Arg Pro Lys Thr Gly Phe Ile Arg Val Val Met
1025                1030                1035                1040

Tyr Glu Gly Lys Lys Ile Met Ala Asp Ser Gly Pro Ile Tyr Asp Lys
                1045                1050                1055

Thr Tyr Ala Gly Gly Arg Leu Gly Leu Phe Val Phe Ser Gln Glu Met
            1060                1065                1070
```

Val Phe Phe Ser Asp Leu Lys Tyr Glu Cys Arg Asp Pro
1075 1080 1085

<210> SEQ ID NO 12
<211> LENGTH: 1066
<212> TYPE: PRT
<213> ORGANISM: Homo sapiens
<220> FEATURE:
<223> OTHER INFORMATION: Vinculin (VCL)

<400> SEQUENCE: 12

Met Pro Val Phe His Thr Arg Thr Ile Glu Ser Ile Leu Glu Pro Val
1 5 10 15

Ala Gln Gln Ile Ser His Leu Val Ile Met His Glu Glu Gly Glu Val
20 25 30

Asp Gly Lys Ala Ile Pro Asp Leu Thr Ala Pro Val Ala Ala Val Gln
35 40 45

Ala Ala Val Ser Asn Leu Val Arg Val Gly Lys Glu Thr Val Gln Thr
50 55 60

Thr Glu Asp Gln Ile Leu Lys Arg Asp Met Pro Pro Ala Phe Ile Lys
65 70 75 80

Val Glu Asn Ala Cys Thr Lys Leu Val Gln Ala Ala Gln Met Leu Gln
85 90 95

Ser Asp Pro Tyr Ser Val Pro Ala Arg Asp Tyr Leu Ile Asp Gly Ser
100 105 110

Arg Gly Ile Leu Ser Gly Thr Ser Asp Leu Leu Leu Thr Phe Asp Glu
115 120 125

Ala Glu Val Arg Lys Ile Ile Arg Val Cys Lys Gly Ile Leu Glu Tyr
130 135 140

Leu Thr Val Ala Glu Val Val Glu Thr Met Glu Asp Leu Val Thr Tyr
145 150 155 160

Thr Lys Asn Leu Gly Pro Gly Met Thr Lys Met Ala Lys Met Ile Asp
165 170 175

Glu Arg Gln Gln Glu Leu Thr His Gln Glu His Arg Val Met Leu Val
180 185 190

Asn Ser Met Asn Thr Val Lys Glu Leu Leu Pro Val Leu Ile Ser Ala
195 200 205

Met Lys Ile Phe Val Thr Thr Lys Asn Ser Lys Asn Gln Gly Ile Glu
210 215 220

Glu Ala Leu Lys Asn Arg Asn Phe Thr Val Glu Lys Met Ser Ala Glu
225 230 235 240

Ile Asn Glu Ile Ile Arg Val Leu Gln Leu Thr Ser Trp Asp Glu Asp
245 250 255

Ala Trp Ala Ser Lys Asp Thr Glu Ala Met Lys Arg Ala Leu Ala Ser
260 265 270

Ile Asp Ser Lys Leu Asn Gln Ala Lys Gly Trp Leu Arg Asp Pro Ser
275 280 285

Ala Ser Pro Gly Asp Ala Gly Glu Gln Ala Ile Arg Gln Ile Leu Asp
290 295 300

Glu Ala Gly Lys Val Gly Glu Leu Cys Ala Gly Lys Glu Arg Arg Glu
305 310 315 320

Ile Leu Gly Thr Cys Lys Met Leu Gly Gln Met Thr Asp Gln Val Ala
325 330 335

Asp Leu Arg Ala Arg Gly Gln Gly Ser Ser Pro Val Ala Met Gln Lys
340 345 350

```
Ala Gln Gln Val Ser Gln Gly Leu Asp Val Leu Thr Ala Lys Val Glu
        355                 360                 365

Asn Ala Ala Arg Lys Leu Glu Ala Met Thr Asn Ser Lys Gln Ser Ile
    370                 375                 380

Ala Lys Lys Ile Asp Ala Ala Gln Asn Trp Leu Ala Asp Pro Asn Gly
385                 390                 395                 400

Gly Pro Glu Gly Glu Glu Gln Ile Arg Gly Ala Leu Ala Glu Ala Arg
                405                 410                 415

Lys Ile Ala Glu Leu Cys Asp Asp Pro Lys Glu Arg Asp Asp Ile Leu
            420                 425                 430

Arg Ser Leu Gly Glu Ile Ser Ala Leu Thr Ser Lys Leu Ala Asp Leu
        435                 440                 445

Arg Arg Gln Gly Lys Gly Asp Ser Pro Glu Ala Arg Ala Leu Ala Lys
    450                 455                 460

Gln Val Ala Thr Ala Leu Gln Asn Leu Gln Thr Lys Thr Asn Arg Ala
465                 470                 475                 480

Val Ala Asn Ser Arg Pro Ala Lys Ala Ala Val His Leu Glu Gly Lys
                485                 490                 495

Ile Glu Gln Ala Gln Arg Trp Ile Asp Asn Pro Thr Val Asp Asp Arg
            500                 505                 510

Gly Val Gly Gln Ala Ala Ile Arg Gly Leu Val Ala Glu Gly His Arg
        515                 520                 525

Leu Ala Asn Val Met Met Gly Pro Tyr Arg Gln Asp Leu Leu Ala Lys
    530                 535                 540

Cys Asp Arg Val Asp Gln Leu Thr Ala Gln Leu Ala Asp Leu Ala Ala
545                 550                 555                 560

Arg Gly Glu Gly Glu Ser Pro Gln Ala Arg Ala Leu Ala Ser Gln Leu
                565                 570                 575

Gln Asp Ser Leu Lys Asp Leu Lys Ala Arg Met Gln Glu Ala Met Thr
            580                 585                 590

Gln Glu Val Ser Asp Val Phe Ser Asp Thr Thr Thr Pro Ile Lys Leu
        595                 600                 605

Leu Ala Val Ala Ala Thr Ala Pro Pro Asp Ala Pro Asn Arg Glu Glu
    610                 615                 620

Val Phe Asp Glu Arg Ala Ala Asn Phe Glu Asn His Ser Gly Lys Leu
625                 630                 635                 640

Gly Ala Thr Ala Glu Lys Ala Ala Ala Val Gly Thr Ala Asn Lys Ser
                645                 650                 655

Thr Val Glu Gly Ile Gln Ala Ser Val Lys Thr Ala Arg Glu Leu Thr
            660                 665                 670

Pro Gln Val Val Ser Ala Ala Arg Ile Leu Leu Arg Asn Pro Gly Asn
        675                 680                 685

Gln Ala Ala Tyr Glu His Phe Glu Thr Met Lys Asn Gln Trp Ile Asp
    690                 695                 700

Asn Val Glu Lys Met Thr Gly Leu Val Asp Glu Ala Ile Asp Thr Lys
705                 710                 715                 720

Ser Leu Leu Asp Ala Ser Glu Glu Ala Ile Lys Lys Asp Leu Asp Lys
                725                 730                 735

Cys Lys Val Ala Met Ala Asn Ile Gln Pro Gln Met Leu Val Ala Gly
            740                 745                 750

Ala Thr Ser Ile Ala Arg Arg Ala Asn Arg Ile Leu Leu Val Ala Lys
        755                 760                 765
```

```
Arg Glu Val Glu Asn Ser Glu Asp Pro Lys Phe Arg Glu Ala Val Lys
    770                 775                 780

Ala Ala Ser Asp Glu Leu Ser Lys Thr Ile Ser Pro Met Val Met Asp
785                 790                 795                 800

Ala Lys Ala Val Ala Gly Asn Ile Ser Asp Pro Gly Leu Gln Lys Ser
                805                 810                 815

Phe Leu Asp Ser Gly Tyr Arg Ile Leu Gly Ala Val Ala Lys Val Arg
            820                 825                 830

Glu Ala Phe Gln Pro Gln Glu Pro Asp Phe Pro Pro Pro Pro Pro Asp
        835                 840                 845

Leu Glu Gln Leu Arg Leu Thr Asp Glu Leu Ala Pro Pro Lys Pro Pro
    850                 855                 860

Leu Pro Glu Gly Glu Val Pro Pro Pro Arg Pro Pro Pro Pro Glu Glu
865                 870                 875                 880

Lys Asp Glu Glu Phe Pro Glu Gln Lys Ala Gly Glu Val Ile Asn Gln
                885                 890                 895

Pro Met Met Met Ala Ala Arg Gln Leu His Asp Glu Ala Arg Lys Trp
            900                 905                 910

Ser Ser Lys Gly Asn Asp Ile Ile Ala Ala Ala Lys Arg Met Ala Leu
        915                 920                 925

Leu Met Ala Glu Met Ser Arg Leu Val Arg Gly Gly Ser Gly Thr Lys
    930                 935                 940

Arg Ala Leu Ile Gln Cys Ala Lys Asp Ile Ala Lys Ala Ser Asp Glu
945                 950                 955                 960

Val Thr Arg Leu Ala Lys Glu Val Ala Lys Gln Cys Thr Asp Lys Arg
                965                 970                 975

Ile Arg Thr Asn Leu Leu Gln Val Cys Glu Arg Ile Pro Thr Ile Ser
            980                 985                 990

Thr Gln Leu Lys Ile Leu Ser Thr Val Lys Ala Thr Met Leu Gly Arg
        995                 1000                1005

Thr Asn Ile Ser Asp Glu Glu Ser Glu Gln Ala Thr Glu Met Leu Val
    1010                1015                1020

His Asn Ala Gln Asn Leu Met Gln Ser Val Lys Glu Thr Val Arg Glu
1025                1030                1035                1040

Ala Glu Ala Ala Ser Ile Lys Ile Arg Thr Asp Ala Gly Phe Thr Leu
                1045                1050                1055

Arg Trp Val Arg Lys Thr Pro Trp Tyr Gln
            1060                1065


<210> SEQ ID NO 13
<211> LENGTH: 1134
<212> TYPE: PRT
<213> ORGANISM: Homo sapiens
<220> FEATURE:
<223> OTHER INFORMATION: Vinculin (VCL)

<400> SEQUENCE: 13

Met Pro Val Phe His Thr Arg Thr Ile Glu Ser Ile Leu Glu Pro Val
1               5                   10                  15

Ala Gln Gln Ile Ser His Leu Val Ile Met His Glu Glu Gly Glu Val
            20                  25                  30

Asp Gly Lys Ala Ile Pro Asp Leu Thr Ala Pro Val Ala Ala Val Gln
        35                  40                  45

Ala Ala Val Ser Asn Leu Val Arg Val Gly Lys Glu Thr Val Gln Thr
    50                  55                  60
```

```
Thr Glu Asp Gln Ile Leu Lys Arg Asp Met Pro Pro Ala Phe Ile Lys
65                  70                  75                  80

Val Glu Asn Ala Cys Thr Lys Leu Val Gln Ala Ala Gln Met Leu Gln
                85                  90                  95

Ser Asp Pro Tyr Ser Val Pro Ala Arg Asp Tyr Leu Ile Asp Gly Ser
            100                 105                 110

Arg Gly Ile Leu Ser Gly Thr Ser Asp Leu Leu Leu Thr Phe Asp Glu
        115                 120                 125

Ala Glu Val Arg Lys Ile Ile Arg Val Cys Lys Gly Ile Leu Glu Tyr
    130                 135                 140

Leu Thr Val Ala Glu Val Val Glu Thr Met Glu Asp Leu Val Thr Tyr
145                 150                 155                 160

Thr Lys Asn Leu Gly Pro Gly Met Thr Lys Met Ala Lys Met Ile Asp
                165                 170                 175

Glu Arg Gln Gln Glu Leu Thr His Gln Glu His Arg Val Met Leu Val
            180                 185                 190

Asn Ser Met Asn Thr Val Lys Glu Leu Leu Pro Val Leu Ile Ser Ala
        195                 200                 205

Met Lys Ile Phe Val Thr Thr Lys Asn Ser Lys Asn Gln Gly Ile Glu
    210                 215                 220

Glu Ala Leu Lys Asn Arg Asn Phe Thr Val Glu Lys Met Ser Ala Glu
225                 230                 235                 240

Ile Asn Glu Ile Ile Arg Val Leu Gln Leu Thr Ser Trp Asp Glu Asp
                245                 250                 255

Ala Trp Ala Ser Lys Asp Thr Glu Ala Met Lys Arg Ala Leu Ala Ser
            260                 265                 270

Ile Asp Ser Lys Leu Asn Gln Ala Lys Gly Trp Leu Arg Asp Pro Ser
        275                 280                 285

Ala Ser Pro Gly Asp Ala Gly Glu Gln Ala Ile Arg Gln Ile Leu Asp
    290                 295                 300

Glu Ala Gly Lys Val Gly Glu Leu Cys Ala Gly Lys Glu Arg Arg Glu
305                 310                 315                 320

Ile Leu Gly Thr Cys Lys Met Leu Gly Gln Met Thr Asp Gln Val Ala
                325                 330                 335

Asp Leu Arg Ala Arg Gly Gln Gly Ser Ser Pro Val Ala Met Gln Lys
            340                 345                 350

Ala Gln Gln Val Ser Gln Gly Leu Asp Val Leu Thr Ala Lys Val Glu
        355                 360                 365

Asn Ala Ala Arg Lys Leu Glu Ala Met Thr Asn Ser Lys Gln Ser Ile
    370                 375                 380

Ala Lys Lys Ile Asp Ala Ala Gln Asn Trp Leu Ala Asp Pro Asn Gly
385                 390                 395                 400

Gly Pro Glu Gly Glu Glu Gln Ile Arg Gly Ala Leu Ala Glu Ala Arg
                405                 410                 415

Lys Ile Ala Glu Leu Cys Asp Asp Pro Lys Glu Arg Asp Asp Ile Leu
            420                 425                 430

Arg Ser Leu Gly Glu Ile Ser Ala Leu Thr Ser Lys Leu Ala Asp Leu
        435                 440                 445

Arg Arg Gln Gly Lys Gly Asp Ser Pro Glu Ala Arg Ala Leu Ala Lys
    450                 455                 460

Gln Val Ala Thr Ala Leu Gln Asn Leu Gln Thr Lys Thr Asn Arg Ala
465                 470                 475                 480

Val Ala Asn Ser Arg Pro Ala Lys Ala Ala Val His Leu Glu Gly Lys
```

-continued

```
                485                 490                 495

Ile Glu Gln Ala Gln Arg Trp Ile Asp Asn Pro Thr Val Asp Asp Arg
            500                 505                 510

Gly Val Gly Gln Ala Ala Ile Arg Gly Leu Val Ala Glu Gly His Arg
        515                 520                 525

Leu Ala Asn Val Met Met Gly Pro Tyr Arg Gln Asp Leu Leu Ala Lys
    530                 535                 540

Cys Asp Arg Val Asp Gln Leu Thr Ala Gln Leu Ala Asp Leu Ala Ala
545                 550                 555                 560

Arg Gly Glu Gly Glu Ser Pro Gln Ala Arg Ala Leu Ala Ser Gln Leu
                565                 570                 575

Gln Asp Ser Leu Lys Asp Leu Lys Ala Arg Met Gln Glu Ala Met Thr
            580                 585                 590

Gln Glu Val Ser Asp Val Phe Ser Asp Thr Thr Thr Pro Ile Lys Leu
        595                 600                 605

Leu Ala Val Ala Ala Thr Ala Pro Pro Asp Ala Pro Asn Arg Glu Glu
    610                 615                 620

Val Phe Asp Glu Arg Ala Ala Asn Phe Glu Asn His Ser Gly Lys Leu
625                 630                 635                 640

Gly Ala Thr Ala Glu Lys Ala Ala Ala Val Gly Thr Ala Asn Lys Ser
                645                 650                 655

Thr Val Glu Gly Ile Gln Ala Ser Val Lys Thr Ala Arg Glu Leu Thr
            660                 665                 670

Pro Gln Val Val Ser Ala Ala Arg Ile Leu Leu Arg Asn Pro Gly Asn
        675                 680                 685

Gln Ala Ala Tyr Glu His Phe Glu Thr Met Lys Asn Gln Trp Ile Asp
    690                 695                 700

Asn Val Glu Lys Met Thr Gly Leu Val Asp Glu Ala Ile Asp Thr Lys
705                 710                 715                 720

Ser Leu Leu Asp Ala Ser Glu Glu Ala Ile Lys Lys Asp Leu Asp Lys
                725                 730                 735

Cys Lys Val Ala Met Ala Asn Ile Gln Pro Gln Met Leu Val Ala Gly
            740                 745                 750

Ala Thr Ser Ile Ala Arg Arg Ala Asn Arg Ile Leu Leu Val Ala Lys
        755                 760                 765

Arg Glu Val Glu Asn Ser Glu Asp Pro Lys Phe Arg Glu Ala Val Lys
    770                 775                 780

Ala Ala Ser Asp Glu Leu Ser Lys Thr Ile Ser Pro Met Val Met Asp
785                 790                 795                 800

Ala Lys Ala Val Ala Gly Asn Ile Ser Asp Pro Gly Leu Gln Lys Ser
                805                 810                 815

Phe Leu Asp Ser Gly Tyr Arg Ile Leu Gly Ala Val Ala Lys Val Arg
            820                 825                 830

Glu Ala Phe Gln Pro Gln Glu Pro Asp Phe Pro Pro Pro Pro Pro Asp
        835                 840                 845

Leu Glu Gln Leu Arg Leu Thr Asp Glu Leu Ala Pro Pro Lys Pro Pro
    850                 855                 860

Leu Pro Glu Gly Glu Val Pro Pro Pro Arg Pro Pro Pro Pro Glu Glu
865                 870                 875                 880

Lys Asp Glu Glu Phe Pro Glu Gln Lys Ala Gly Glu Val Ile Asn Gln
                885                 890                 895

Pro Met Met Met Ala Ala Arg Gln Leu His Asp Glu Ala Arg Lys Trp
            900                 905                 910
```

```
Ser Ser Lys Pro Gly Ile Pro Ala Ala Glu Val Gly Ile Gly Val Val
        915                 920                 925

Ala Glu Ala Asp Ala Ala Asp Ala Ala Gly Phe Pro Val Pro Pro Asp
    930                 935                 940

Met Glu Asp Asp Tyr Glu Pro Glu Leu Leu Leu Met Pro Ser Asn Gln
945                 950                 955                 960

Pro Val Asn Gln Pro Ile Leu Ala Ala Ala Gln Ser Leu His Arg Glu
                965                 970                 975

Ala Thr Lys Trp Ser Ser Lys Gly Asn Asp Ile Ile Ala Ala Ala Lys
            980                 985                 990

Arg Met Ala Leu Leu Met Ala Glu Met Ser Arg Leu Val Arg Gly Gly
        995                 1000                1005

Ser Gly Thr Lys Arg Ala Leu Ile Gln Cys Ala Lys Asp Ile Ala Lys
    1010                1015                1020

Ala Ser Asp Glu Val Thr Arg Leu Ala Lys Glu Val Ala Lys Gln Cys
1025                1030                1035                1040

Thr Asp Lys Arg Ile Arg Thr Asn Leu Leu Gln Val Cys Glu Arg Ile
                1045                1050                1055

Pro Thr Ile Ser Thr Gln Leu Lys Ile Leu Ser Thr Val Lys Ala Thr
            1060                1065                1070

Met Leu Gly Arg Thr Asn Ile Ser Asp Glu Glu Ser Glu Gln Ala Thr
        1075                1080                1085

Glu Met Leu Val His Asn Ala Gln Asn Leu Met Gln Ser Val Lys Glu
    1090                1095                1100

Thr Val Arg Glu Ala Glu Ala Ala Ser Ile Lys Ile Arg Thr Asp Ala
1105                1110                1115                1120

Gly Phe Thr Leu Arg Trp Val Arg Lys Thr Pro Trp Tyr Gln
                1125                1130


<210> SEQ ID NO 14
<211> LENGTH: 222
<212> TYPE: PRT
<213> ORGANISM: Homo sapiens
<220> FEATURE:
<223> OTHER INFORMATION: Vinculin (VCL)

<400> SEQUENCE: 14

Met Pro Pro Ala Phe Ile Lys Val Glu Asn Ala Cys Thr Lys Leu Val
1               5                   10                  15

Gln Ala Ala Gln Met Leu Gln Ser Asp Pro Tyr Ser Val Pro Ala Arg
            20                  25                  30

Asp Tyr Leu Ile Asp Gly Ser Arg Gly Ile Leu Ser Gly Thr Ser Asp
        35                  40                  45

Leu Leu Leu Thr Phe Asp Glu Ala Glu Val Arg Lys Ile Ile Arg Val
    50                  55                  60

Cys Lys Gly Ile Leu Glu Tyr Leu Thr Val Ala Glu Val Val Glu Thr
65                  70                  75                  80

Met Glu Asp Leu Val Thr Tyr Thr Lys Asn Leu Gly Pro Gly Met Thr
                85                  90                  95

Lys Met Ala Lys Met Ile Asp Glu Arg Gln Gln Glu Leu Thr His Gln
            100                 105                 110

Glu His Arg Val Met Leu Val Asn Ser Met Asn Thr Val Lys Glu Leu
        115                 120                 125

Leu Pro Val Leu Ile Ser Ala Met Lys Ile Phe Val Thr Thr Lys Asn
    130                 135                 140
```

```
Ser Lys Asn Gln Gly Ile Glu Glu Ala Leu Lys Asn Arg Asn Phe Thr
145                 150                 155                 160

Val Glu Lys Met Ser Ala Glu Ile Asn Glu Ile Ile Arg Val Leu Gln
                165                 170                 175

Leu Thr Ser Trp Asp Glu Asp Ala Trp Ala Ser Lys Val Arg Val Leu
            180                 185                 190

Ser Gly Glu Ile Ser Lys Ile Pro Asn Ser Pro Trp Leu Gly Val Leu
        195                 200                 205

Ile Gly Thr Cys Leu Ile Leu Tyr Leu Val Ile Phe Val Ala
    210                 215                 220


<210> SEQ ID NO 15
<211> LENGTH: 212
<212> TYPE: PRT
<213> ORGANISM: Homo sapiens
<220> FEATURE:
<223> OTHER INFORMATION: Pre-pro Endothelin 1 (ET-1)

<400> SEQUENCE: 15

Met Asp Tyr Leu Leu Met Ile Phe Ser Leu Leu Phe Val Ala Cys Gln
1               5                   10                  15

Gly Ala Pro Glu Thr Ala Val Leu Gly Ala Glu Leu Ser Ala Val Gly
            20                  25                  30

Glu Asn Gly Gly Glu Lys Pro Thr Pro Ser Pro Pro Trp Arg Leu Arg
        35                  40                  45

Arg Ser Lys Arg Cys Ser Cys Ser Ser Leu Met Asp Lys Glu Cys Val
    50                  55                  60

Tyr Phe Cys His Leu Asp Ile Ile Trp Val Asn Thr Pro Glu His Val
65                  70                  75                  80

Val Pro Tyr Gly Leu Gly Ser Pro Arg Ser Lys Arg Ala Leu Glu Asn
                85                  90                  95

Leu Leu Pro Thr Lys Ala Thr Asp Arg Glu Asn Arg Cys Gln Cys Ala
            100                 105                 110

Ser Gln Lys Asp Lys Lys Cys Trp Asn Phe Cys Gln Ala Gly Lys Glu
        115                 120                 125

Leu Arg Ala Glu Asp Ile Met Glu Lys Asp Trp Asn Asn His Lys Lys
    130                 135                 140

Gly Lys Asp Cys Ser Lys Leu Gly Lys Lys Cys Ile Tyr Gln Gln Leu
145                 150                 155                 160

Val Arg Gly Arg Lys Ile Arg Arg Ser Ser Glu Glu His Leu Arg Gln
                165                 170                 175

Thr Arg Ser Glu Thr Met Arg Asn Ser Val Lys Ser Ser Phe His Asp
            180                 185                 190

Pro Lys Leu Lys Gly Lys Pro Ser Arg Glu Arg Tyr Val Thr His Asn
        195                 200                 205

Arg Ala His Trp
    210


<210> SEQ ID NO 16
<211> LENGTH: 195
<212> TYPE: PRT
<213> ORGANISM: Homo sapiens
<220> FEATURE:
<223> OTHER INFORMATION: Pre-pro Endothelin 1 (ET-1)

<400> SEQUENCE: 16

Ala Pro Glu Thr Ala Val Leu Gly Ala Glu Leu Ser Ala Val Gly Glu
```

```
1               5                   10                  15

Asn Gly Gly Glu Lys Pro Thr Pro Ser Pro Pro Trp Arg Leu Arg Arg
            20                  25                  30

Ser Lys Arg Cys Ser Cys Ser Ser Leu Met Asp Lys Glu Cys Val Tyr
        35                  40                  45

Phe Cys His Leu Asp Ile Ile Trp Val Asn Thr Pro Glu His Val Val
    50                  55                  60

Pro Tyr Gly Leu Gly Ser Pro Arg Ser Lys Arg Ala Leu Glu Asn Leu
65                  70                  75                  80

Leu Pro Thr Lys Ala Thr Asp Arg Glu Asn Arg Cys Gln Cys Ala Ser
                85                  90                  95

Gln Lys Asp Lys Lys Cys Trp Asn Phe Cys Gln Ala Gly Lys Glu Leu
            100                 105                 110

Arg Ala Glu Asp Ile Met Glu Lys Asp Trp Asn Asn His Lys Lys Gly
        115                 120                 125

Lys Asp Cys Ser Lys Leu Gly Lys Lys Cys Ile Tyr Gln Gln Leu Val
    130                 135                 140

Arg Gly Arg Lys Ile Arg Arg Ser Ser Glu Glu His Leu Arg Gln Thr
145                 150                 155                 160

Arg Ser Glu Thr Met Arg Asn Ser Val Lys Ser Ser Phe His Asp Pro
                165                 170                 175

Lys Leu Lys Gly Lys Pro Ser Arg Glu Arg Tyr Val Thr His Asn Arg
            180                 185                 190

Ala His Trp
        195


<210> SEQ ID NO 17
<211> LENGTH: 21
<212> TYPE: PRT
<213> ORGANISM: Homo sapiens
<220> FEATURE:
<223> OTHER INFORMATION: Pre-pro Endothelin 1 (ET-1)

<400> SEQUENCE: 17

Cys Ser Cys Ser Ser Leu Met Asp Lys Glu Cys Val Tyr Phe Cys His
1               5                   10                  15

Leu Asp Ile Ile Trp
            20


<210> SEQ ID NO 18
<211> LENGTH: 45
<212> TYPE: PRT
<213> ORGANISM: Homo sapiens
<220> FEATURE:
<223> OTHER INFORMATION: Pre-pro Endothelin 1 (ET-1)

<400> SEQUENCE: 18

Arg Ser Ser Glu Glu His Leu Arg Gln Thr Arg Ser Glu Thr Met Arg
1               5                   10                  15

Asn Ser Val Lys Ser Ser Phe His Asp Pro Lys Leu Lys Gly Lys Pro
            20                  25                  30

Ser Arg Glu Arg Tyr Val Thr His Asn Arg Ala His Trp
        35                  40                  45


<210> SEQ ID NO 19
<211> LENGTH: 38
<212> TYPE: PRT
<213> ORGANISM: Homo sapiens
<220> FEATURE:
```

<223> OTHER INFORMATION: Pre-pro Endothelin 1 (ET-1)

<400> SEQUENCE: 19

```
Cys Ser Cys Ser Ser Leu Met Asp Lys Glu Cys Val Tyr Phe Cys His
1               5                   10                  15

Leu Asp Ile Ile Trp Val Asn Thr Pro Glu His Val Val Pro Tyr Gly
            20                  25                  30

Leu Gly Ser Pro Arg Ser
        35
```

<210> SEQ ID NO 20
<211> LENGTH: 116
<212> TYPE: PRT
<213> ORGANISM: Homo sapiens
<220> FEATURE:
<223> OTHER INFORMATION: Procalcitonin (PCT)

<400> SEQUENCE: 20

```
Ala Pro Phe Arg Ser Ala Leu Glu Ser Ser Pro Ala Asp Pro Ala Thr
1               5                   10                  15

Leu Ser Glu Asp Glu Ala Arg Leu Leu Leu Ala Ala Leu Val Gln Asp
            20                  25                  30

Tyr Val Gln Met Lys Ala Ser Glu Leu Glu Gln Glu Gln Glu Arg Glu
        35                  40                  45

Gly Ser Ser Leu Asp Ser Pro Arg Ser Lys Arg Cys Gly Asn Leu Ser
    50                  55                  60

Thr Cys Met Leu Gly Thr Tyr Thr Gln Asp Phe Asn Lys Phe His Thr
65                  70                  75                  80

Phe Pro Gln Thr Ala Ile Gly Val Gly Ala Pro Gly Lys Lys Arg Asp
                85                  90                  95

Met Ser Ser Asp Leu Glu Arg Asp His Arg Pro His Val Ser Met Pro
            100                 105                 110

Gln Asn Ala Asn
        115
```

<210> SEQ ID NO 21
<211> LENGTH: 10
<212> TYPE: PRT
<213> ORGANISM: Homo sapiens
<220> FEATURE:
<223> OTHER INFORMATION: SRM peptide of ICAM1

<400> SEQUENCE: 21

```
Leu Leu Gly Ile Glu Thr Pro Leu Pro Lys
1               5                   10
```

<210> SEQ ID NO 22
<211> LENGTH: 7
<212> TYPE: PRT
<213> ORGANISM: Homo sapiens
<220> FEATURE:
<223> OTHER INFORMATION: SRM peptide of AHSG

<400> SEQUENCE: 22

```
Phe Ser Val Val Tyr Ala Lys
1               5
```

<210> SEQ ID NO 23
<211> LENGTH: 10
<212> TYPE: PRT
<213> ORGANISM: Homo sapiens
<220> FEATURE:

<223> OTHER INFORMATION: SRM peptide of CPN1

<400> SEQUENCE: 23

Val Gln Asn Glu Cys Pro Gly Ile Thr Arg
1               5                   10

<210> SEQ ID NO 24
<211> LENGTH: 11
<212> TYPE: PRT
<213> ORGANISM: Homo sapiens
<220> FEATURE:
<223> OTHER INFORMATION: SRM peptide of FABP1

<400> SEQUENCE: 24

Ala Ile Gly Leu Pro Glu Glu Leu Ile Gln Lys
1               5                   10

<210> SEQ ID NO 25
<211> LENGTH: 9
<212> TYPE: PRT
<213> ORGANISM: Homo sapiens
<220> FEATURE:
<223> OTHER INFORMATION: SRM peptide of HRG

<400> SEQUENCE: 25

Asp Gly Tyr Leu Phe Gln Leu Leu Arg
1               5

<210> SEQ ID NO 26
<211> LENGTH: 8
<212> TYPE: PRT
<213> ORGANISM: Homo sapiens
<220> FEATURE:
<223> OTHER INFORMATION: SRM peptide of PIGR

<400> SEQUENCE: 26

Cys Gly Leu Gly Ile Asn Ser Arg
1               5

<210> SEQ ID NO 27
<211> LENGTH: 8
<212> TYPE: PRT
<213> ORGANISM: Homo sapiens
<220> FEATURE:
<223> OTHER INFORMATION: SRM peptide of RAP1A/RAP1B/RAPBL

<400> SEQUENCE: 27

Glu Gln Gly Gln Asn Leu Ala Arg
1               5

<210> SEQ ID NO 28
<211> LENGTH: 12
<212> TYPE: PRT
<213> ORGANISM: Homo sapiens
<220> FEATURE:
<223> OTHER INFORMATION: SRM peptide of THBS1

<400> SEQUENCE: 28

Phe Val Phe Gly Thr Thr Pro Glu Asp Ile Leu Arg
1               5                   10

<210> SEQ ID NO 29
<211> LENGTH: 9
<212> TYPE: PRT
<213> ORGANISM: Homo sapiens
<220> FEATURE:
<223> OTHER INFORMATION: SRM peptide of VCL

<400> SEQUENCE: 29

```
Gly Asn Asp Ile Ile Ala Ala Ala Lys
1               5
```